United States Patent
Nakatani et al.

(10) Patent No.: US 7,238,689 B2
(45) Date of Patent: Jul. 3, 2007

(54) ISOXAZOLINE DERIVATIVE AND HERBICIDE COMPRISING THE SAME AS ACTIVE INGREDIENT

(75) Inventors: Masao Nakatani, Shizuoka (JP); Ryotaro Kugo, Osaka (JP); Masahiro Miyazaki, Shizuoka (JP); Koichiro Kaku, Shizuoka (JP); Makoto Fujinami, Shizuoka (JP); Ryohei Ueno, Shizuoka (JP); Satoru Takahashi, Shizuoka (JP)

(73) Assignees: Ihara Chemical Industry Co., Ltd. (JP); Japan and Kumiai Chemical Industry (JP)

( * ) Notice: Subject to any disclaimer, the term of this patent is extended or adjusted under 35 U.S.C. 154(b) by 432 days.

(21) Appl. No.: 10/250,937

(22) PCT Filed: Feb. 7, 2002

(86) PCT No.: PCT/JP02/01015

§ 371 (c)(1),
(2), (4) Date: Dec. 22, 2003

(87) PCT Pub. No.: WO02/062770

PCT Pub. Date: Aug. 15, 2002

(65) Prior Publication Data

US 2004/0110749 A1    Jun. 10, 2004

(30) Foreign Application Priority Data

Feb. 8, 2001    (JP) .............................. 2001-031784

(51) Int. Cl.
| | |
|---|---|
| *C07D 417/02* | (2006.01) |
| *C07D 413/02* | (2006.01) |
| *A61K 31/541* | (2006.01) |
| *A61K 31/5377* | (2006.01) |
| *A61K 31/496* | (2006.01) |

(52) U.S. Cl. ................. 514/227.8; 514/235.5; 514/254.02; 514/326; 514/380; 544/137; 544/367; 546/209; 548/243

(58) Field of Classification Search ............ 514/227.8, 514/235.5, 254.02, 326, 380; 544/60, 137, 544/367; 546/209; 548/243
See application file for complete search history.

(56) References Cited

U.S. PATENT DOCUMENTS 6,147,031 A    11/2000    Adachi et al. .............. 504/271

FOREIGN PATENT DOCUMENTS

| JP | 9-328483 | 12/1997 |
|---|---|---|
| WO | 99/23094 | 5/1999 |
| WO | 00/50410 | 8/2000 |

*Primary Examiner*—Kamal A. Saeed
(74) *Attorney, Agent, or Firm*—Bacon & Thomas, PLLC

(57) ABSTRACT

An isoxazoline derivative represented by the following general formula [I]:

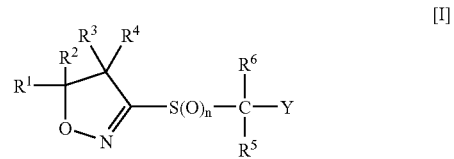

wherein $R^1$ and $R^2$ may be the same or different and are each an alkyl group;
$R^3$, $R^4$, $R^5$ and $R^6$ are each a hydrogen atom;
Y is an optionally substituted 5- to 6-membered aromatic heterocyclic group or fused aromatic heterocyclic group having a hetero atom selected from a nitrogen atom, a oxygen atom and a sulfur atom; and
n is an integer: of 0 to 2.

The isoxazoline derivative has an excellent herbicidal effect and an excellent selectivity between crop and weed.

18 Claims, No Drawings

ISOXAZOLINE DERIVATIVE AND HERBICIDE COMPRISING THE SAME AS ACTIVE INGREDIENT

CROSS-REFERENCE TO RELATED APPLICATIONS

This application is a National Phase Application (35 USC 371) of PCT/JP02/01015 and claims priority of Japanese Application No. 2001-031784 filed Feb. 8, 2001.

BACKGROUND OF THE INVENTION

1. Field of the Invention

The present invention relates to a novel isoxazoline derivative and a herbicide containing the isoxazoline derivative as the active ingredient.

2. Description of the Prior Art

The herbicidal activity of isoxazoline derivatives are reported in, for example, JP-A-8-22558, JP-A-9-328477 and JP-A-9-328483. The compound of the present invention described in detail later, however, is not described in these literatures.

Herbicides applied to useful crops are desired to (a) be applicable to soil or foliage, (b) show a sufficient herbicidal effect at a low ingredient amount, and (c) show a high selectivity between crop and weed. In these respects, the compounds described in the above literatures are not fully satisfactory.

SUMMARY OF THE INVENTION

In view of the above situation, the present inventors made a study on the herbicidal effect and selectivity between crop and weed of various compounds. As a result, the present inventors found out that a novel isoxazoline derivative has an excellent herbicidal effect and an excellent selectivity between crop and weed. The above finding has led to the completion of the present invention.

The present invention provides the followings.

(1) An isoxazoline derivative represented by the following general formula [I] or a pharmaceutically acceptable salt thereof:

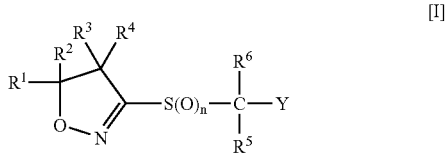

[I]

wherein $R^1$ and $R^2$ may be the same or different and are each a hydrogen atom, a C1 to C10 alkyl group, a C3 to C8 cycloalkyl group or a C3 to C8 cycloalkyl C1 to C3 alkyl group, or $R^1$ and $R^2$ may be bonded to each other to form a C3 to C7 spiro ring together with the carbon atoms to which they bond;

$R^3$ and $R^4$ may be the same or different and are each a hydrogen atom, a C1 to C10 alkyl group or a C3 to C8 cycloalkyl group; or $R^3$ and $R^4$ may be bonded to each other to form a C3 to C7 spiro ring together with the carbon atoms to which they bond; or $R^1$, $R^2$, $R^3$ and $R^4$ may form a 5- to 8-membered ring together with the carbon atoms to which they bond;

$R^5$ and $R^6$ may be the same or different and are each a hydrogen atom or a C1 to C10 alkyl group;

Y is a 5- to 6-membered aromatic heterocyclic group or condensed aromatic heterocyclic group having one or more hetero atoms selected from a nitrogen atom, an oxygen atom and a sulfur atom; the heterocyclic group may be substituted with 0 to 6 same or different groups selected from the following substituent group α; when the heterocyclic group is substituted at the two adjacent positions with two alkyl groups, two alkoxy groups, an alkyl group and an alkoxy group, an alkyl group and an alkylthio group, an alkyl group and an alkylsulfonyl group, an alkyl group and a monoalkylamino group, or an alkyl group and a dialkylamino group, all selected from the substituent group α, the two groups may form, together with the atoms to which they bond, a 5- to 8-membered ring which may be substituted with 1 to 4 halogen atoms; the hetero atom of the heterocyclic group, when it is a nitrogen atom, may be oxidized to become N-oxide;

n is an integer of 0 to 2.

[Substituent Group α]

Hydroxyl group; thiol group; halogen atoms; C1 to C10 alkyl groups; C1 to C10 alkyl groups each mono-substituted with a group selected from the following substituent group β, C1 to C4 haloalkyl groups; C3 to C8 cycloalkyl groups; C1 to C10 alkoxy groups; C1 to C10 alkoxy groups each mono-substituted with a group selected from the following substituent group γ; C1 to C4 haloalkoxy groups; C3 to C8 cycloalkyloxy groups; C3 to C8 cycloalkyl C1 to C3 alkyloxy groups; C1 to C10 alkylthio groups; C1 to C10 alkylthio groups each mono-substituted with a group selected from the substituent group γ; C1 to C4 haloalkylthio groups; C2 to C6 alkenyl groups; C2 to C6 alkenyloxy groups; C2 to C6 alkynyl groups; C2 to C6 alkynyloxy groups; C1 to C10 alkylsulfinyl groups; C1 to C10 alkylsulfinyl groups each mono-substituted with a group selected from the substituent group γ; C1 to C10 alkylsulfonyl groups; C1 to C10 alkylsulfonyl groups each mono-substituted with a group selected from the substituent group γ; C1 to C4 haloalkylsulfinyl groups; C1 to C10 alkylsulfonyloxy groups each mono-substituted with a group selected from the substituent group γ; C1 to C4 haloalkylsulfonyl groups; C1 to C10 alkylsulfonyloxy groups; C1 to C4 haloalkylsulfonyloxy groups; optionally substituted phenyl group; optionally substituted phenoxy group; optionally substituted phenylthio group; optionally substituted aromatic heterocyclic groups; optionally substituted aromatic heterocyclic oxy groups; optionally substituted aromatic heterocyclic thio groups; optionally substituted phenylsulfinyl groups; optionally substituted phenylsulfonyl groups; optionally substituted aromatic heterocyclic sulfonyl groups; optionally substituted phenylsulfonyloxy groups; acyl groups; C1 to C4 haloalkylcarbonyl groups; optionally substituted benzylcarbonyl group; optionally substituted benzoyl group; carboxyl group; C1 to C10 alkoxycarbonyl groups; optionally substituted benzyloxycarbonyl group; optionally substituted phenoxycarbonyl group; cyano group; carbamoyl group (its nitrogen atom may be substituted with same or different groups selected from C1 to C10 alkyl groups and optionally substituted phenyl group); C1 to C6 acyloxy groups; C1 to C4 haloalkylcarbonyloxy groups; optionally substituted benzylcarbonyloxy group; optionally substituted benzoyloxy group; nitro group; and amino group (its nitrogen atom may be substituted with same or different: groups selected from C1 to C10 alkyl groups, optionally substituted phenyl group, C1 to C6 acyl groups, C1 to C4 haloalkylcarbonyl groups, optionally substituted benzylcarbonyl group, optionally substituted benzoyl group, C1 to C10 alkylsulfonyl group, C1 to C4 haloalkylsulfonyl groups, optionally substituted benzylsulfonyl group, and optionally substituted phenylsulfonyl group).

[Substituent Group β]

Hydroxyl group; C3 to C8 cycloalkyl groups which may be substituted with halogen atom or alky group); C1 to C10 alkoxy groups; C1 to C10 alkylthio groups; C1 to C10 alkylsulfonyl groups; C1 to C10 alkoxycarbonyl groups; C2 to C6 haloalkenyl groups; amino group (its nitrogen atom may be substituted with same or different groups selected from C1 to C10 alkyl groups, C1 to C6 acyl groups; C1 to C4 haloalkylcarbonyl groups, C1 to C10 alkylsulfonyl groups and C1 to C4 haloalkylsulfonyl groups); carbamoyl group (its nitrogen atom may be substituted with same or different C1 to C10 alkyl groups); C1 to C6 acyl groups; C1 to C4 haloalkylcarbonyl groups; C1 to C10 alkoxyimino groups; cyano group; optionally substituted phenyl group; and optionally substituted phenoxy group.

[Substituent Group γ]

C1 to C10 alkoxycarbonyl groups; optionally substituted phenyl group; optionally substituted aromatic heterocyclic groups; cyano group; and carbamoyl group (its nitrogen atom may be substituted with same or different C1 to C10 alkyl groups).

(2) An isoxazoline derivative-according to (1), wherein the substituent group α on the heterocycle which may be substituted with 0 to 6 same or different groups, includes hydroxyl group; halogen atoms; C1 to C10 alkyl groups; C1 to C10 alkyl groups each mono-substituted with a group selected from the substituent group β, C1 to C4 haloalkyl groups; C3 to C8 cycloalkyl groups; C1 to C10 alkoxy groups; C1 to C10 alkoxy groups each mono-substituted with a group selected from the substituent group γ; C1 to C4 haloalkoxy groups; C3 to C8 cycloalkyloxy groups; C3 to C8 cycloalkyl C1 to C3 alkyloxy groups; C1 to C10 alkylthio groups; C1 to C10 alkylthio groups each mono-substituted with a group selected from the substituent group γ; C1 to C4 haloalkylthio groups; C2 to C6 alkenyl groups; C2 to C6 alkenyloxy groups; C2 to C6 alkynyl groups; C2 to C6 alkynyloxy groups; C1 to C10 alkylsulfonyl groups; C1 to C4 haloalkylsulfonyl groups; optionally substituted phenyl group; optionally substituted phenoxy group; optionally substituted phenylthio group; optionally substituted aromatic heterocyclic groups; optionally substituted aromatic heterocyclic oxy groups; optionally substituted aromatic heterocyclic thio groups; optionally substituted phenylsulfonyl groups; optionally substituted aromatic heterocyclic sulfonyl groups; C1 to C6 acyl groups; C1 to C4 haloalkylcarbonyl groups; optionally substituted benzylcarbonyl group; optionally substituted benzoyl group; carboxyl group; C1 to C10 alkoxycarbonyl groups; cyano group; carbamoyl group (its nitrogen atom may be substituted with same or different groups selected from C1 to C10 alkyl groups and optionally substituted phenyl group); nitro group; and amino group (its nitrogen atom may be substituted with same or different groups selected from C1 to C10 alkyl groups, optionally substituted phenyl group, C1 to C6 acyl groups, C1 to C4 haloalkylcarbonyl groups, optionally substituted benzylcarbonyl group, optionally substituted benzoyl group, C1 to C10 alkylsulfonyl groups, C1 to C4 haloalkylsulfonyl groups, optionally substituted benzylsulfonyl group, and optionally substituted phenylsulfonyl group); when the heterocyclic group is substituted at the two adjacent positions with two alkyl groups, two alkoxy groups, an alkyl group and an alkoxy group, an alkyl group and an alkylthio group, an alkyl group and an alkylsulfonyl group, an alkyl group and a monoalkylamino group, or an alkyl group and a dialkylamino group, all selected from the substituent group α, the two groups may form, together with the atoms to which they bond, a 5- to 8-membered ring which may be substituted with 1 to 4 halogen atoms.

(3) An isoxazoline derivative according to (2), wherein the substituent group α on the heterocycle which may be substituted with 0 to 6 same or different groups, includes halogen atoms; C1 to C10 alkyl groups; C1 to C4 haloalkyl groups; C1 to C10 alkoxy C1 to C3 alkyl groups; C3 to C8 cycloalkyl groups which may be substituted with halogen atom or alkyl group; C1 to C10 alkoxy groups; C1 to C4 haloalkoxy groups; C3 to C8 cycloalkyl C1 to C3 alkyloxy groups; optionally substituted phenoxy group; C1 to C10 alkylthio groups; C1 to C10 alkylsulfonyl groups; acyl groups; C1 to C4 haloalkylcarbonyl groups; C1 to C10 alkoxycarbonyl groups; cyano group and carbamoyl group (its nitrogen atom may be substituted with same or different C1 to C10 alkyl groups).

(4) An isoxazoline derivative according to any of (1), (2) or (3), wherein $R^1$ and $R^2$ may be the same or different and are each a methyl group or an ethyl group; and $R^3$, $R^4$, $R^5$ and $R^6$ are each a hydrogen atom.

(5) An isoxazoline derivative according to any of (1), (2), (3) or (4) wherein Y is a 5- or 6-membered aromatic heterocyclic group having a hetero atom selected from a nitrogen atom, an oxygen atom and a sulfur atom.

(6) An isoxazoline derivative according to (5), wherein Y is a thienyl group, a pyrazolyl group, an isoxazolyl group, an isothiazolyl group, a pyridyl group or a pyrimidinyl group.

(7) An isoxazoline derivative according to (6), wherein Y is a thiophen-3-yl group, a pyrazol-4-yl group, a pyrazol-5-yl group, an isoxazol-4-yl group, an isothiazol-4-yl group, a pyridyn-3-yl group or a pyrimidin-5-yl group.

(8) An isoxazoline derivative according to (7), wherein Y is a thiophen-3-yl group and the thiophene ring is substituted with the substituent group α at the 2- and 4-positions.

(9) An isoxazoline derivative according to (7), wherein Y is a pyrazol-4-yl group and the pyrazole ring is substituted at the 3- and 5-positions with the substituent group α and at the 1-position with a hydrogen atom, a C1 to C10 alkyl group, a C1 to C10 alkyl group mono-substituted with a group selected from the substituent group β, a C1 to C4 haloalkyl group, a C3 to C8 cycloalkyl group, a C2 to C6 alkenyl group, a C2 to C6 alkynyl group, a C1 to C10 alkylsulfinyl group, a C1 to C10 alkylsulfonyl group, a C1 to C10 alkylsulfonyl group mono-substituted with a group selected from the substituent group γ, a C1 to C4 haloalkylsulfonyl group, an optionally substituted phenyl group, an optionally substituted aromatic heterocyclic group, an optionally substituted phenylsulfonyl group, an optionally substituted aromatic heterocyclic sulfonyl group, an acyl group, a C1 to C4 haloalkylcarbonyl group, an optionally substituted benzylcarbonyl group, an optionally substituted benzoyl group, a C1 to C10 alkoxycarbonyl group, an optionally substituted benzyloxycarbonyl group, an optionally substituted phenoxycarbonyl group, a carbamoyl group (its nitrogen atom may be substituted with same or different groups selected from C1 to C10 alkyl groups and optionally substituted phenyl group), or an amino group (its nitrogen atom may be substituted with same or different groups selected from C1 to C10 alkyl groups, optionally substituted phenyl group, acyl groups, C1 to C4 haloalkylcarbonyl groups, optionally substituted benzylcarbonyl group, optionally substituted benzoyl group, C1 to C10 alkylsulfonyl groups, C1 to C4 haloalkylsulfonyl groups, optionally substituted benzylsulfonyl group and optionally substituted phenylsulfonyl group).

(10) An isoxazoline derivative according to (7), wherein Y is a pyrazol-5-yl group and the pyrazole ring is substituted at the 4-position with the substituent group α and at the 1-position with a hydrogen atom, a C1 to C10 alkyl group, a C1 to C10 alkyl group mono-substituted with a group selected from the substituent group β, a C1 to C4 haloalkyl group, a C3 to C8 cycloalkyl group, a C2 to C6 alkenyl group, a C2 to C6 alkynyl group, a C1 to C10 alkylsulfinyl group, a C1 to C10 alkylsulfonyl group, a C1 to C10alkylsulfonyl group mono-substituted with a group selected from the substituent group γ, a C1 to C4 haloalkylsulfonyl group, an optionally substituted phenyl group, an optionally substituted aromatic heterocyclic group, an optionally substituted phenylsulfonyl group, an optionally substituted aromatic heterocyclic sulfonyl group, an acyl group, a C1 to C4 haloalkylcarbonyl group, an optionally substituted benzylcarbonyl group, an optionally substituted benzoyl group, a C1 to C10 alkoxycarbonyl group, an optionally substituted benzyloxycarbonyl group, an optionally substituted phenoxycarbonyl group, a carbamoyl group (its nitrogen atom may be substituted with same or different groups selected from C1 to C10 alkyl groups and optionally substituted phenyl group), or an amino group (its nitrogen atom may be substituted with same or different groups selected from C1 to C10 alkyl groups, optionally substituted phenyl group; acyl groups, C1 to C4 haloalkylcarbonyl groups, optionally substituted benzylcarbonyl group, optionally substituted benzoyl group, C1 to C10 alkylsulfonyl groups, C1 to C4 haloalkylsulfonyl groups, optionally substituted benzylsulfonyl group and optionally substituted phenylsulfonyl group).

(11) An, isoxazoline derivative according to (7), wherein Y is an isoxazol-4-yl group and the isoxazole ring is substituted with the substituent group α at the 3- and 5-positions.

(12) An isoxazoline derivative according to (7), wherein Y is an isothiazol-4-yl group and the isothiazole ring is substituted with the substituent group α at the 3- and 5-positions.

(13) An isoxazoline derivative according to (7), wherein Y is a pyridin-3-yl group and the pyridine ring is substituted with the substituent group α at the 2- and 4-positions.

(14) An isoxazoline derivative according to (7), wherein Y is a pyrimidin-5-yl group and the pyrimidine ring is substituted with the substituent group α at the 4- and 6-positions.

(15) An isoxazoline derivative according to any of (1) to (14), wherein n is an integer of 2.

(16) An isoxazoline derivative according to any of (1) to (14), wherein n is an integer of 1.

(17) An isoxazoline derivative according to any of (1) to (14), wherein n is an integer of 0.

(18) A herbicide containing, as the active ingredient, an isoxazoline derivative set forth in any of (1) to (17) or a pharmaceutically acceptable salt thereof.

DETAILED DESCRIPTION OF THE INVENTION

The definitions of the terms used in the present specification are given below.

The expression of "C1 to C10", etc. indicates that the substituent appearing after the expression has 1 to 10 carbon atoms in the case of "C1 to C10".

Halogen atom refers to a fluorine atom, a chlorine atom, a bromine atom or an iodine atom.

C1 to C10 alkyl group refers to a straight or branched chain alkyl group of 1 to 10 carbon atoms unless other wise specified; and there can be mentioned, for example, methyl group, ethyl group, n-propyl group, isopropyl group, n-butyl group, isobutyl group, sec-butyl group, tert-butyl group, n-pentyl group, isopentyl group, neopentyl group, n-hexyl group, isohexyl group, 3,3-dimethylbutyl group, heptyl group and octyl group.

C3 to C8 cycloalkyl group refers to a cycloalkyl group of 3 to 8 carbon atoms; and there can be mentioned, for example, cyclopropyl group, cyclobutyl group, cyclopentyl group and cyclohexyl group.

C3 to C8 cycloalkyl C1 to C3 alkyl group (which may be substituted with halogen atom or alkyl group) refers, unless otherwise specified, to a C1 to C3 alkyl group substituted with a C3 to C8 cycloalkyl group which may be substituted with 1 to 4 same or different halogen atoms or C1 to C3 alkyl group; and there can be mentioned, for example, cyclopropylmethyl group, 1-cyclopropylethyl group, 2-cyclopropylethyl group, 1-cyclopropylpropyl group, 2-cyclopropylpropyl group, 3-cyclopropylpropyl group, cyclobutylmethyl group, cyclopentylmethyl group, cyclohexylmethyl group, 2-chlorocyclopropylmethyl group, 2,2-dichlorocyclopropylmethyl group, 2-fluorocyclopropylmethyl group, 2,2-difluorocyclopropylmethyl group, 2-methylcyclopropylmethyl group, 2,2-dimethylcyclopropylmethyl group and 2-methylcyclopropylethyl group.

C3 to C8 cycloalkyl C1 to C3 alkyl group refers to a alkyl group of 1 to 3 carbon atoms, substituted with a cycloalkyl group of 3 to 8 carbon atoms; and there can be mentioned, for example, cyclopropylmethyl group, 1-cyclopropylethyl group, 2-cyclopropylethyl group, 1-cyclopropylpropyl group, 2-cyclopropylpropyl group, 3-cyclopropylpropyl group, cyclobutylmethyl group, cyclopentylmethyl group and cyclohexylmethyl group.

C1 to C4 haloalkyl group refers, unless otherwise specified, to a straight or branched chain alkyl group of 1 to 4 carbon atoms, substituted with 1 to 9 same or different halogen atoms; and there can be mentioned, for example, fluoromethyl group, chloromethyl group, bromomethyl group, difluoromethyl group, trifluoromethyl group, 2,2-difluoroethyl group, 2,2,2-trifluoroethyl group and pentafluoroethyl group.

C2 to C6 alkenyl group refers to a straight or branched chain alkenyl group of 2 to 6 carbon atoms; and there can be mentioned, for example, ethenyl group, 1-propenyl group, 2-propenyl group, isopropenyl group, 1-butenyl group, 2-butenyl group, 3-butenyl group and 2-pentenyl group.

C2 to C6 alkynyl group refers to a straight or branched chain alkynyl group of 2 to 6 carbon atoms; and there can be mentioned, for example, ethynyl group, 2-propynyl group, 1-methyl-2-propynyl group, 2-butynyl group, 3-butynyl group and 2-methyl-3-butynyl group.

C2 to C6 haloalkenyl group refers, unless otherwise specified, to a straight or branched alkenyl group of 2 to 6 carbon atoms, substituted with 1 to 4 same or different halogen atoms; and there can be mentioned, for example, 3-chloro-2-propenyl group and, 2-chloro-2-propneyl group.

C1 to C10 alkoxy group refers to an (alkyl)-O— group wherein the alkyl moiety has the above definition; and there can be mentioned, for example, methoxy group, ethoxy group, n-propoxy group, isopropoxy group, tert-butoxy group, n-butoxy group, sec-butoxy group and isobutoxy group.

C1 to C4 haloalkoxy group refers to a (haloalkyl)-O— group wherein the haloalkyl moiety has the above definition; and there can be mentioned, for example, difluoromethoxy group, trifluoromethoxy group, 2,2-difluoroethoxy group and 2,2,2-trifluoroethoxy group.

C3 to C8 cycloalkyloxy group refers to a (cycloalkyl)-O— group wherein the cycloalkyl moiety has the above definition; and there can be mentioned, for example, cyclopropyloxy group, cyclobutyloxy group, cyclopentyloxy group and cyclohexyloxy group.

C3 to C8 cycloalkyl C1 to C3 alkyloxy group refers to a (cycloalkylalkyl)-O— group wherein the cycloalkylalkyl moiety has the above definition; and there can be mentioned, for example, cyclopropylmethoxy group, 1-cyclopropylethoxy group, 2-cyclopropylethoxy group, 1-cyclopropylpropoxy group, 2-chclopropylpropoxy group, 3-cyclopropylpropoxy group, cyclobutylmethoxy group, cyclopentylmethoxy group and cyclohexylmethoxy group.

C2 to C6 alkenyloxy group and C2 to C6 alkynyloxy group refer, respectively, to an (alkenyl)-O— group and an (alkynyl)-O— group, in each of which the alkenyl or alkynyl moiety has the above definition; and there can be mentioned, for example, 2-propenyloxy group and 2-propynyloxy group.

C1 to C10 alkoxyimino group refers to an (alkoxy)-N= group wherein the alkoxy moiety has the above definition; and there can be mentioned, for example, methoxyimino group and ethoxyimino group.

C1 to C10 alkylthio group, C1 to C10 alkylsulfinyl group and C1 to C10 alkylsulfonyl group refer, respectively, to an (alkyl)-S— group, an (alkyl)-SO— group and an (alkyl)-SO$_2$— group, in each of which the alkyl moiety has the above definition; and there can be mentioned, for example, methylthio group, ethylthio group, n-propylthio group, isopropylthio group, methylsulfinyl, group, methylsulfonyl group, ethylsulfonyl group, n-propylsulfonyl group and isopropylsulfonyl group.

C1 to C10 alkylsulfonyloxy group refers to an (alkylsulfonyl)-O— group wherein the alkylsulfonyl moiety has the above definition, and there can be mentioned, for example, methylsulfonyloxy group and ethylsulfonyloxy group.

C1 to C10 alkoxycarbonyl group refers to an (alkoxy)-CO— group wherein the alkoxy moiety has the above definition, and there can be mentioned, for, example, methoxycarbonyl group, ethoxycarbonyl group, n-propoxycarbonyl group and isopropoxycarbonyl group.

C1 to C6 acryl group refers to a straight or branched chain aliphatic acyl group of 1 to 6 carbon atoms, and there can be mentioned, for example, formyl group, acetyl group, propionyl group, isopropionyl group, butyryl group and pivaloyl group.

C1 to C10 acyloxy group refers to an (acyl)-O— group wherein the acyl moiety has the above definition; and there can be mentioned, for example, acetoxy group, propionyloxy group, ispropionyloxy group and pivalolyoxy group.

C1 to C4 haloalkylcarbonyl group, C1 to C4 haloalkylthio group and C1 to C4 haloalkylsulfonyl group refers, respectively, to a (haloalkyl)-CO— group, a (haloalkyl)-S— group and a (haloalkyl)-SO$_2$— group, in each of which the haloalkyl moiety has the above definition; and there can be mentioned, for example, chloroacetyl group, trifluoroacetyl group, pentafluoropropyl group, difluoromethylthio group, trifluoromethylthio group, chloromethylsulfonyl group, difluoromethylsulfonyl group and trifluoromethylsulfonyl group.

C1 to C4 haloalkylcarbonyloxy group and C1 to C4 haloalkylsulfonyloxy group refer, respectively, to a (haloalkylcarbonyl)-O— group and a (haloalkylsulfonyl)-O— group, in each of which the haloalkylcarbonyl moiety or the haloalkylsulfonyl moiety has the above definition; and there can be mentioned, for example, chloroacetyloxy group, trifluoroacetyloxy group, chloromethylsulfonyloxy group and trifluoromehtylsulfonyloxy group.

"Optionally substituted" in (optionally substituted) phenyl group, (optionally substituted) aromatic heterocyclic group, (optionally substituted) phenoxy group, (optionally substituted aromatic heterocyclic oxy group, (optionally substituted) phenylthio group, (optionally substituted) aromatic heterocyclic thio group, (optionally substituted) phenylsulfonyl group, (optionally substituted) phenylsulfonyloxi group, (optionally substituted) aromatic heterocyclic sulfonyl group, (optionally substituted) benzylcarbonyl group, (optionally substituted) benzylcarbonyloxy group, (optionally substituted) benzylsulfonyl group, (optionally substituted) benzoyl group, (optionally substituted) benzoyloxy group, (optionally substituted) benzyloxycarbonyl group and (optionally substituted) phenoxycarbonyl group, refers to being optionally substituted with, for example, halogen atom, C1 to C10 alkyl group, C1 to C4haloalkyl group, C1 to C10 alkoxyalkyl group, C1 to C10 alkoxy group, C1 to C10 alkylthio group, C1 to C10 alkylsulfonyl group, acyl group, C1 to C10 alkoxycarbonyl group, cyano group, carbamoyl group (its nitrogen atom may be substituted with same or different C1 to C10 alkyl groups) nitro group or amino group (its nitrogen atom may be substituted with same or different groups selected from C1 to C10 alkyl groups, C1 to C6 acyl groups, C1 to C4 haloalkylcarbonyl groups, C1 to C10 alkylsulfonyl groups and C1 to C4 haloalkylsulfonyl groups).

5- to 6-membered aromatic heterocyclic group having a hetero atom selected from a nitrogen atom, an oxygen atom and a sulfur atom includes, for example, furyl group, thienyl group, pyrrolyl group, pyrazolyl group, isoxazolyl group, isothiazolyl group, oxazolyl group, thiazolyl group, imidazolyl group, pyridyl group, pyridazinyl group, pyrimidinyl group, pyrazinyl group, triazinyl group, triazolyl group, oxadiazolyl group and thiadiazolyl group, each having 1 to 3 hetero atoms.

Fused aromatic heterocyclic group refers to a group having 1 to 3 hetero atoms randomly selected from nitrogen atom, oxygen atom and sulfur atom; and there can be mentioned, for example, benzofuryl group, benzothienyl group, indolyl group, benzoxazolyl group, benzothiazolyl group, benzimidazolyl group, benzisoxazolyl group, benzisothiazolyl group, indazolyl group, quinolyl group, isoquinolyl group, phthalazinyl group, quinoxalinyl group, quinazolinyl group, cinnolinyl group and benzotriazolyl group.

Aromatic heterocycle in (optionally substituted) aromatic heterocyclic group, (optionally, substituted) aromatic heterocyclic oxy group, (optionally substituted) aromatic heterocyclic thio group and (optionally substituted) aromatic heterocyclic sulfonyl group, refers to a 5- to 6-membered group having 1 to 3 hetero atoms randomly selected from nitrogen atom, oxygen atom and sulfur atom; and there can be mentioned, for example, furyl group, thienyl group, pyrrolyl group, pyrazolyl group, isoxazolyl group, isothiazolyl group, oxazolyl group, thiazolyl group, imidazolyl group, pyridyl group, pyridazinyl group, pyrimidinyl group, pyrazinyl group, triazinyl group, triazolyl group, oxadiazolyl group and thiadiazolyl group.

Pharmaceutically acceptable salt is a salt of a compound of the general formula [I] having, in the structure, hydroxyl group, carboxyl group, amino group or the like, with a metal or an organic base or with a mineral acid or an organic acid. As the metal, there can be mentioned alkali metals such as sodium, potassium and the like; and alkaline earth metals such as magnesium, calcium and the like. As the organic base, there can be mentioned triethylamine, diisopropylamine, etc. As the mineral acids, there can be mentioned hydrochloric acid, sulfuric acid, etc. As the organic acid, there can be mentioned acetic acid, methanesulfonic acid, p-toluenesulfonic acid, etc.

In the above-mentioned general formula [I], it is preferred that $R^1$ and $R^2$ may be the same or different and are each a methyl group or an ethyl group;

$R^3$; $R^4$, $R^5$ and $R^6$ are each a hydrogen atom;

n is an integer of 2; and

Y is a thiophen-3-yl group [the 2- and 4-positions of the group are substituted with same or different groups selected from halogen atoms, alkyl groups, haloalkyl groups, alkoxyalkyl groups, cycloalkyl groups, alkoxy groups, haloalkoxy groups, acyl groups, haloalkylcarbonyl groups, alkoxycarbonyl groups, cyano group and carbamoyl group (its nitrogen atom may be substituted with same or different alkyl groups)], or a pyrazol-4-yl group [the 3- and 5-positions of the group are substituted with same or different groups selected from halogen atoms, alkyl groups, haloalkyl groups, alkoxyalkyl groups, cycloalkyl groups, alkoxy groups, haloalkoxy groups, cycloalkylalkyloxy groups, optionally substituted phenoxy group, alkylthio groups, alkylsulfonyl groups, acyl groups, haloalkylcarbonyl groups, alkoxycarbonyl groups, cyano group and carbamoyl group (its nitrogen atom may be substituted with same or different alkyl groups); the 1-position is substituted with hydrogen atom, alkyl group, alkyl group mono-substituted with a group selected from the substituent group β, haloalkyl group, cycloalkyl group, alkenyl group, alkynyl group, alkylsulfonyl group, alkylsulfonyl group mono-substituted with a group selected from the substituent group γ, haloalkylsulfonyl group, optionally substituted phenyl group, optionally substituted aromatic heterocyclic group, optionally substituted phenylsulfonyl group, optionally substituted aromatic heterocyclicsulfonyl group, acyl group, haloalkylcarbonyl group, optionally substituted benzylcarbonyl group, optionally substituted benzoyl group, alkoxycarbonyl group, optionally substituted benzyloxycarbonyl group, optionally substituted phenoxycarbonyl group or carbamoyl group (its nitrogen atom may be substituted with same or different groups selected from alkyl groups and optionally substituted phenyl group)], or a pyrazol-5-yl group [the 4-position of the group is substituted with halogen atom, alkyl group, haloalkyl group, alkoxyalkyl group, haloalkoxy group, acyl group, haloalkylcarbonyl group, alkoxycarbonyl group, cyano group or carbamoyl group (its nitrogen atom maybe substituted with same or different alkyl groups); the 1-position is substituted with hydrogen atom, alkyl group, alkyl group mono-substituted with a group selected from the substituent group β, haloalkyl group, cycloalkyl group; or optionally substituted phenyl group], or an isoxazol-4-yl group [the 3- and 5-positions of the group are substituted with same or different groups selected from halogen atoms, alkyl groups, haloalkyl groups, alkoxyalkyl groups, cycloalkyl groups, alkoxy groups, haloalkoxy groups, alkylthio groups, alkylsulfonyl groups, acyl groups, haloalkylcarbonyl groups, alkoxycarbonyl groups, cyano group and carbamoyl group (its nitrogen atom may be substituted with same or different alkyl groups)], or an isothiazol-4-yl group -[the 3- and 5-positions of the group are substituted with same or different groups selected from halogen atoms, alkyl groups,haloalkyl groups, alkoxyalkyl groups, cycloalkyl groups, alkoxy groups, haloalkoxy groups, optionally substituted phenoxy group, alkylthio groups, alkylsulfonyl groups, acyl groups, haloalkylcarbonyl groups, alkoxycarbonyl groups, cyano group and carbamoyl group (its nitrogen atom may be substituted with same or different alkyl groups)], or a pyridin-3-yl group [the 2- and 4-positions of the group are substituted with same or different groups selected from halogen atoms, alkyl groups, haloalkyl groups, alkoxyalkyl groups, cycloalkyl groups, alkoxy groups, haloalkoxy groups, alkylthio groups, alkylsulfonyl groups, acyl groups, haloalkylcarbonyl groups, alkoxycarbonyl groups, cyano group and carbamoyl group (its nitrogen atom may be substituted with same or different alkyl groups)], or a pyrimidin-5-yl group [the 4- and 6-positions of the group are substituted with same or different groups selected from halogen atoms, alkyl groups, haloalkyl groups, alkoxyalkyl groups, cycloalkyl groups, alkoxy groups, haloalkoxy groups, alkylthio groups, alkylsulfonyl groups, acyl groups, haloalkylcarbonyl groups, alkoxycarbonyl groups, cyano group and carbamoyl group (its nitrogen atom may be substituted with same or different alkyl groups)].

Next, representative examples of the present compound represented by the general formula [I] are shown in Tables 1 to 10. However, the present compound is not restricted to these examples.

The following abbreviated expressions used in the Tables refer to the following groups.

| Me: | methyl group | Et: | ethyl group |
|---|---|---|---|
| Pr: | n-propyl group | Pr-i: | isopropyl group |
| Pr-c: | cyclopropyl roup | Bu: | n-butyl group |
| Bu-i: | isobutyl group | Bu-s: | sec-butyl group |
| Bu-t: | tert-butyl group | Bu-c: | cyclobutyl group |
| Pen: | n-pentyl group | Pen-c: | cyclopentyl group |
| Hex: | n-hexyl group | Hex-c: | cyclohexyl group |
| Ph: | phenyl group | | |

For example, (4-Cl)Ph indicates 4-chlorophenyl group, and 3-Hex indicates 3-hexyl group.

When the present compound contains hydroxyl group as a substituent, there may exist keto-enol tautomers. Any of these tautomers and any mixture of these tautomers are included in the present compound.

TABLE 1

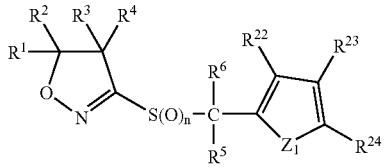

| $R^1$ | $R^2$ | $R^3$ | $R^4$ | n | $R^5$ | $R^6$ | $Z^1$ | $R^{22}$ | $R^{23}$ | $R^{24}$ |
|---|---|---|---|---|---|---|---|---|---|---|
| Me | Me | H | H | 2 | H | H | S | Me | H | H |
| Me | Me | H | H | 2 | H | H | S | Cl | Me | H |
| Me | Me | H | H | 2 | H | H | S | H | H | Me |
| Me | Me | H | H | 2 | H | H | S | Cl | H | H |
| Me | Me | H | H | 2 | H | H | S | H | H | Cl |
| Me | Me | H | H | 2 | H | H | S | Cl | Cl | Cl |
| Me | Me | H | H | 2 | H | H | S | OMe | H | H |
| Me | Me | H | H | 2 | H | H | S | OEt | H | H |
| Me | Me | H | H | 2 | H | H | S | $OCHF_2$ | H | H |
| Me | Me | H | H | 2 | H | H | S | $OCH_2Ph$ | H | H |
| Me | Me | H | H | 2 | H | H | O | H | H | H |
| Me | Me | H | H | 2 | H | H | O | H | H | C(=O)OMe |
| Me | Me | H | H | 2 | H | H | NMe | Me | H | Me |
| Me | Me | H | H | 2 | H | H | NMe | Me | C(=O)OMe | $CH_2C$(=O)OMe |
| Me | Me | H | H | 2 | H | H | NMe | Me | C(=O)OEt | $CH_2C$(=O)OEt |
| Me | Me | H | H | 2 | H | H | NMe | Me | Me | Me |
| Me | Me | H | H | 2 | H | H | NPh | OMe | H | H |
| Me | Me | H | H | 2 | H | H | NPh | OEt | H | H |
| Me | Me | H | H | 2 | H | H | NPh | $OCHF_2$ | H | H |
| H | H | H | H | 2 | H | H | S | $OCHF_2$ | H | H |
| Me | H | H | H | 2 | H | H | S | $OCHF_2$ | H | H |
| Me | H | Me | H | 2 | H | H | S | $OCHF_2$ | H | H |
| Me | Me | H | H | 2 | Me | H | S | $OCHF_2$ | H | H |
| Me | Me | H | H | 2 | Et | H | S | $OCHF_2$ | H | H |
| Me | Me | H | H | 2 | Pr-i | H | S | $OCHF_2$ | H | H |
| Me | Me | H | H | 2 | Me | Me | S | $OCHF_2$ | H | H |
| Me | Et | H | H | 2 | H | H | S | $OCHF_2$ | H | H |
| Et | Et | H | H | 2 | H | H | S | $OCHF_2$ | H | H |
| Me | Pr-i | H | H | 2 | H | H | S | $OCHF_2$ | H | H |
| Me | Pr | H | H | 2 | H | H | S | $OCHF_2$ | H | H |
| Me | Pr-c | H | H | 2 | H | H | S | $OCHF_2$ | H | H |
| Me | $CH_2Pr$-c | H | H | 2 | H | H | S | $OCHF_2$ | H | H |
| —$(CH_2)_2$— | | H | H | 2 | H | H | S | Cl | Cl | Cl |
| —$(CH_2)_3$— | | H | H | 2 | H | H | S | Cl | Cl | Cl |
| —$(CH_2)_4$— | | H | H | 2 | H | H | S | Cl | Cl | Cl |
| —$(CH_2)_5$— | | H | H | 2 | H | H | S | Cl | Cl | Cl |
| H | —$(CH_2)_3$— | | H | 2 | H | H | S | Cl | Cl | Cl |
| H | —$(CH_2)_4$— | | H | 2 | H | H | S | Cl | Cl | Cl |
| H | —$(CH_2)_5$— | | H | 2 | H | H | S | Cl | Cl | Cl |
| H | —$(CH_2)_6$— | | H | 2 | H | H | S | Cl | Cl | Cl |
| Me | Me | H | H | 1 | H | H | S | Me | H | H |
| Me | Me | H | H | 1 | H | H | S | Cl | Me | H |
| Me | Me | H | H | 1 | H | H | S | H | H | Me |
| Me | Me | H | H | 1 | H | H | S | Cl | H | H |
| Me | Me | H | H | 1 | H | H | S | H | H | Cl |
| Me | Me | H | H | 1 | H | H | S | Cl | Cl | Cl |
| Me | Me | H | H | 1 | H | H | S | OMe | H | H |
| Me | Me | H | H | 1 | H | H | S | OEt | H | H |
| Me | Me | H | H | 1 | H | H | S | $OCHF_2$ | H | H |
| Me | Me | H | H | 1 | H | H | S | $OCH_2Ph$ | H | H |
| Me | Me | H | H | 1 | H | H | O | H | H | H |
| Me | Me | H | H | 1 | H | H | O | H | H | C(=O)OMe |
| Me | Me | H | H | 1 | H | H | NMe | Me | H | Me |
| Me | Me | H | H | 1 | H | H | NMe | Me | C(=O)OMe | $CH_2C$(=O)OMe |
| Me | Me | H | H | 1 | H | H | NMe | Me | C(=O)OEt | $CH_2C$(=O)OEt |
| Me | Me | H | H | 1 | H | H | NMe | Me | Me | Me |
| Me | Me | H | H | 1 | H | H | NPh | OMe | H | H |
| Me | Me | H | H | 1 | H | H | NPh | OEt | H | H |
| Me | Me | H | H | 1 | H | H | NPh | $OCHF_2$ | H | H |
| H | H | H | H | 1 | H | H | S | $OCHF_2$ | H | H |
| Me | H | H | H | 1 | H | H | S | $OCHF_2$ | H | H |
| Me | H | Me | H | 1 | H | H | S | $OCHF_2$ | H | H |
| Me | Me | H | H | 1 | Me | H | S | $OCHF_2$ | H | H |
| Me | Me | H | H | 1 | Et | H | S | $OCHF_2$ | H | H |
| Me | Me | H | H | 1 | Pr-i | H | S | $OCHF_2$ | H | H |
| Me | Me | H | H | 1 | Me | Me | S | $OCHF_2$ | H | H |
| Me | Et | H | H | 1 | H | H | S | $OCHF_2$ | H | H |
| Et | Et | H | H | 1 | H | H | S | $OCHF_2$ | H | H |

TABLE 1-continued

| $R^1$ | $R^2$ | $R^3$ | $R^4$ | n | $R^5$ | $R^6$ | $Z^1$ | $R^{22}$ | $R^{23}$ | $R^{24}$ |
|---|---|---|---|---|---|---|---|---|---|---|
| Me | Pr-i | H | H | 1 | H | H | S | $OCHF_2$ | H | H |
| Me | Pr | H | H | 1 | H | H | S | $OCHF_2$ | H | H |
| Me | Pr-c | H | H | 1 | H | H | S | $OCHF_2$ | H | H |
| Me | $CH_2Pr$-c | H | H | 1 | H | H | S | $OCHF_2$ | H | H |
| —$(CH_2)_2$— | | H | H | 1 | H | H | S | Cl | Cl | Cl |
| —$(CH_2)_3$— | | H | H | 1 | H | H | S | Cl | Cl | Cl |
| —$(CH_2)_4$— | | H | H | 1 | H | H | S | Cl | Cl | Cl |
| —$(CH_2)_5$— | | H | H | 1 | H | H | S | Cl | Cl | Cl |
| H | —$(CH_2)_3$— | | H | 1 | H | H | S | Cl | Cl | Cl |
| H | —$(CH_2)_4$— | | H | 1 | H | H | S | Cl | Cl | Cl |
| H | —$(CH_2)_5$— | | H | 1 | H | H | S | Cl | Cl | Cl |
| H | —$(CH_2)_6$— | | H | 1 | H | H | S | Cl | Cl | Cl |
| Me | Me | H | H | 0 | H | H | S | Me | H | H |
| Me | Me | H | H | 0 | H | H | S | Cl | Me | H |
| Me | Me | H | H | 0 | H | H | S | H | H | Me |
| Me | Me | H | H | 0 | H | H | S | Cl | H | H |
| Me | Me | H | H | 0 | H | H | S | H | H | Cl |
| Me | Me | H | H | 0 | H | H | S | Cl | Cl | Cl |
| Me | Me | H | H | 0 | H | H | S | OMe | H | H |
| Me | Me | H | H | 0 | H | H | S | OEt | H | H |
| Me | Me | H | H | 0 | H | H | S | $OCHF_2$ | H | H |
| Me | Me | H | H | 0 | H | H | S | $OCH_2Ph$ | H | H |
| Me | Me | H | H | 0 | H | H | O | H | H | H |
| Me | Me | H | H | 0 | H | H | O | H | H | C(=O)Ome |
| Me | Me | H | H | 0 | H | H | NMe | Me | H | Me |
| Me | Me | H | H | 0 | H | H | NMe | Me | C(=O)OMe | $CH_2C$(=O)OMe |
| Me | Me | H | H | 0 | H | H | NMe | Me | C(=O)OEt | $CH_2C$(=O)OEt |
| Me | Me | H | H | 0 | H | H | NMe | Me | Me | Me |
| Me | Me | H | H | 0 | H | H | NPh | OMe | H | H |
| Me | Me | H | H | 0 | H | H | NPh | OEt | H | H |
| Me | Me | H | H | 0 | H | H | NPh | $OCHF_2$ | H | H |
| H | H | H | H | 0 | H | H | S | $OCHF_2$ | H | H |
| Me | H | H | H | 0 | H | H | S | $OCHF_2$ | H | H |
| Me | H | Me | H | 0 | H | H | S | $OCHF_2$ | H | H |
| Me | Me | H | H | 0 | Me | H | S | $OCHF_2$ | H | H |
| Me | Me | H | H | 0 | Et | H | S | $OCHF_2$ | H | H |
| Me | Me | H | H | 0 | Pr-i | H | S | $OCHF_2$ | H | H |
| Me | Me | H | H | 0 | Me | Me | S | $OCHF_2$ | H | H |
| Me | Et | H | H | 0 | H | H | S | $OCHF_2$ | H | H |
| Et | Et | H | H | 0 | H | H | S | $OCHF_2$ | H | H |
| Me | Pr-i | H | H | 0 | H | H | S | $OCHF_2$ | H | H |
| Me | Pr | H | H | 0 | H | H | S | $OCHF_2$ | H | H |
| Me | Pr-c | H | H | 0 | H | H | S | $OCHF_2$ | H | H |
| Me | $CH_2Pr$-c | H | H | 0 | H | H | S | $OCHF_2$ | H | H |
| —$(CH_2)_2$— | | H | H | 0 | H | H | S | Cl | Cl | Cl |
| —$(CH_2)_3$— | | H | H | 0 | H | H | S | Cl | Cl | Cl |
| —$(CH_2)_4$— | | H | H | 0 | H | H | S | Cl | Cl | Cl |
| —$(CH_2)_5$— | | H | H | 0 | H | H | S | Cl | Cl | Cl |
| H | —$(CH_2)_3$— | | H | 0 | H | H | S | Cl | Cl | Cl |
| H | —$(CH_2)_4$— | | H | 0 | H | H | S | Cl | Cl | Cl |
| H | —$(CH_2)_5$— | | H | 0 | H | H | S | Cl | Cl | Cl |
| H | —$(CH_2)_6$— | | H | 0 | H | H | S | Cl | Cl | Cl |
| Me | Et | H | H | 2 | H | H | S | H | H | H |
| Me | Et | H | H | 2 | H | H | O | H | H | H |
| Me | Et | H | H | 2 | H | H | NH | H | H | H |

TABLE 2

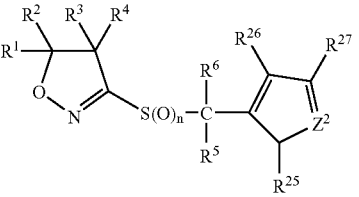

| R¹ | R² | R³ | R⁴ | n | R⁵ | R⁶ | Z² | R²⁵ | R²⁶ | R²⁷ |
|----|----|----|----|---|----|----|----|-----|-----|-----|
| Me | Me | H | H | 2 | H | H | S | H | H | H |
| Me | Me | H | H | 2 | H | H | S | H | OMe | H |
| Me | Me | H | H | 2 | H | H | S | Cl | H | Cl |
| Me | Me | H | H | 2 | H | H | S | Cl | Cl | Cl |
| Me | Me | H | H | 2 | H | H | S | Cl | Me | H |
| Me | Me | H | H | 2 | H | H | S | NHMe | Me | H |
| Me | Me | H | H | 2 | H | H | S | N(Me)₂ | Me | H |
| Me | Me | H | H | 2 | H | H | S | NHC(=O)Me | Me | H |
| Me | Me | H | H | 2 | H | H | S | NHC(=O)Ph | Me | H |
| Me | Me | H | H | 2 | H | H | S | NHSO₂Me | Me | H |
| Me | Me | H | H | 2 | H | H | S | NHSO₂Ph | Me | H |
| Me | Me | H | H | 2 | H | H | S | Me | Me | Me |
| Me | Me | H | H | 2 | H | H | S | Me | C(=O)OMe | Me |
| Me | Me | H | H | 2 | H | H | S | Me | C(=O)OEt | Me |
| Me | Me | H | H | 2 | H | H | S | Me | C(=O)OPh | Me |
| Me | Me | H | H | 2 | H | H | S | Me | CN | Me |
| Me | Me | H | H | 2 | H | H | S | Me | C(=O)NHMe | Me |
| Me | Me | H | H | 2 | H | H | S | Me | C(=O)Me | Me |
| Me | Me | H | H | 2 | H | H | S | Me | C(=O)Et | Me |
| Me | Me | H | H | 2 | H | H | S | Me | C(=O)Pr-i | Me |
| Me | Me | H | H | 2 | H | H | S | Me | C(=O)Pr | Me |
| Me | Me | H | H | 2 | H | H | S | Me | C(=O)CF₃ | Me |
| Me | Me | H | H | 2 | H | H | S | Me | C(NOMe)Me | Me |
| Me | Me | H | H | 2 | H | H | S | Ph | C(=O)Me | Me |
| Me | Me | H | H | 2 | H | H | S | Ph | C(=NOMe)Me | Me |
| Me | Me | H | H | 2 | H | H | S | CF₃ | OMe | H |
| Me | Me | H | H | 2 | H | H | S | CF₃ | OEt | H |
| Me | Me | H | H | 2 | H | H | S | CF₃ | OPr-i | H |
| Me | Me | H | H | 2 | H | H | S | CF₃ | OPr-i | H |
| Me | Me | H | H | 2 | H | H | S | CF₃ | OCHF₂ | H |
| Me | Me | H | H | 2 | H | H | S | Cl | Me | H |
| Me | Me | H | H | 2 | H | H | S | Cl | Me | Me |
| Me | Me | H | H | 2 | H | H | S | Cl | C(=O)OMe | Cl |
| Me | Me | H | H | 2 | H | H | S | Cl | CN | Cl |
| Me | Me | H | H | 2 | H | H | S | Cl | C(=O)NHMe | Cl |
| Me | Me | H | H | 2 | H | H | S | Cl | C(=O)N(Me)₂ | Cl |
| Me | Me | H | H | 2 | H | H | S | Cl | C(=O)Me | Cl |
| Me | Me | H | H | 2 | H | H | S | Cl | C(=O)Et | Cl |
| Me | Me | H | H | 2 | H | H | S | Cl | C(=O)Pr-i | Cl |
| Me | Me | H | H | 2 | H | H | S | Cl | C(=O)Pr | Cl |
| Me | Me | H | H | 2 | H | H | S | Cl | C(=O)CF₃ | Cl |
| Me | Me | H | H | 2 | H | H | S | Cl | C(=NOMe)Me | Cl |
| Me | Me | H | H | 2 | H | H | O | H | H | H |
| Me | Me | H | H | 2 | H | H | O | Me | H | Cl |
| H | H | H | H | 2 | H | H | S | Cl | Cl | Cl |
| Me | H | H | H | 2 | H | H | S | Cl | Cl | Cl |
| Me | H | Me | H | 2 | H | H | S | Cl | Cl | Cl |
| Me | Me | H | H | 2 | Me | H | S | Cl | Cl | Cl |
| Me | Me | H | H | 2 | Et | H | S | Cl | Cl | Cl |
| Me | Me | H | H | 2 | Pr-i | H | S | Cl | Cl | Cl |
| Me | Me | H | H | 2 | Me | Me | S | Cl | Cl | Cl |
| Me | Et | H | H | 2 | H | H | S | Cl | Cl | Cl |
| Et | Ft | H | H | 2 | H | H | S | Cl | Cl | Cl |
| Me | Pr-i | H | H | 2 | H | H | S | Cl | Cl | Cl |
| Me | Pr | H | H | 2 | H | H | S | Cl | Cl | Cl |
| Me | Pr-c | H | H | 2 | H | H | S | Cl | Cl | Cl |
| Me | CH₂Pr-c | H | H | 2 | H | H | S | Cl | Cl | Cl |
| —(CH₂)₂— | | H | H | 2 | H | H | S | Cl | Cl | Cl |
| —(CH₂)₃— | | H | H | 2 | H | H | S | Cl | Cl | Cl |
| —(CH₂)₄— | | H | H | 2 | H | H | S | Cl | Cl | Cl |
| —(CH₂)₅— | | H | H | 2 | H | H | S | Cl | Cl | Cl |
| H | —(CH₂)₃— | | H | 2 | H | H | S | Cl | Cl | Cl |
| H | —(CH₂)₄— | | H | 2 | H | H | S | Cl | Cl | Cl |
| H | —(CH₂)₅— | | H | 2 | H | H | S | Cl | Cl | Cl |
| H | —(CH₂)₆— | | H | 2 | H | H | S | Cl | Cl | Cl |
| Me | Me | H | H | 1 | H | H | S | H | H | H |

TABLE 2-continued

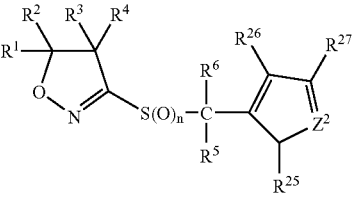

| R¹ | R² | R³ | R⁴ | n | R⁵ | R⁶ | Z² | R²⁵ | R²⁶ | R²⁷ |
|----|----|----|----|---|----|----|----|------|------|------|
| Me | Me | H | H | 1 | H | H | S | H | OMe | H |
| Me | Me | H | H | 1 | H | H | S | Cl | H | Cl |
| Me | Me | H | H | 1 | H | H | S | Cl | Cl | Cl |
| Me | Me | H | H | 1 | H | H | S | Cl | Me | H |
| Me | Me | H | H | 1 | H | H | S | NHMe | Me | H |
| Me | Me | H | H | 1 | H | H | S | N(Me)$_2$ | Me | H |
| Me | Me | H | H | 1 | H | H | S | NHC(=O)Me | Me | H |
| Me | Me | H | H | 1 | H | H | S | NHC(=O)Ph | Me | H |
| Me | Me | H | H | 1 | H | H | S | NHSO$_2$Me | Me | H |
| Me | Me | H | H | 1 | H | H | S | NHSO$_2$Ph | Me | H |
| Me | Me | H | H | 1 | H | H | S | Me | Me | Me |
| Me | Me | H | H | 1 | H | H | S | Me | C(=O)OMe | Me |
| Me | Me | H | H | 1 | H | H | S | Me | C(=O)OEt | Me |
| Me | Me | H | H | 1 | H | H | S | Me | C(=O)OPh | Me |
| Me | Me | H | H | 1 | H | H | S | Me | CN | Me |
| Me | Me | H | H | 1 | H | H | S | Me | C(=O)NHMe | Me |
| Me | Me | H | H | 1 | H | H | S | Me | C(=O)Me | Me |
| Me | Me | H | H | 1 | H | H | S | Me | C(=O)Et | Me |
| Me | Me | H | H | 1 | H | H | S | Me | C(=O)Pr-i | Me |
| Me | Me | H | H | 1 | H | H | S | Me | C(=O)Pr | Me |
| Me | Me | H | H | 1 | H | H | S | Me | C(=O)CF$_3$ | Me |
| Me | Me | H | H | 1 | H | H | S | Me | C(=NOMe)Me | Me |
| Me | Me | H | H | 1 | H | H | S | Ph | C(=O)Me | Me |
| Me | Me | H | H | 1 | H | H | S | Ph | C(=NOMe)Me | Me |
| Me | Me | H | H | 1 | H | H | S | CF$_3$ | OMe | H |
| Me | Me | H | H | 1 | H | H | S | CF$_3$ | OEt | H |
| Me | Me | H | H | 1 | H | H | S | CF$_3$ | OPr-i | H |
| Me | Me | H | H | 1 | H | H | S | CF$_3$ | OPr-i | H |
| Me | Me | H | H | 1 | H | H | S | CF$_3$ | OCHF$_2$ | H |
| Me | Me | H | H | 1 | H | H | S | Cl | Me | H |
| Me | Me | H | H | 1 | H | H | S | Cl | Me | Me |
| Me | Me | H | H | 1 | H | H | S | Cl | C(=O)OMe | Cl |
| Me | Me | H | H | 1 | H | H | S | Cl | CN | Cl |
| Me | Me | H | H | 1 | H | H | S | Cl | C(=O)NHMe | Cl |
| Me | Me | H | H | 1 | H | H | S | Cl | C(=O)N(Me)$_2$ | Cl |
| Me | Me | H | H | 1 | H | H | S | Cl | C(=O)Me | Cl |
| Me | Me | H | H | 1 | H | H | S | Cl | C(=O)Et | Cl |
| Me | Me | H | H | 1 | H | H | S | Cl | C(=O)Pr-i | Cl |
| Me | Me | H | H | 1 | H | H | S | Cl | C(=O)Pr | Cl |
| Me | Me | H | H | 1 | H | H | S | Cl | C(=O)CF$_3$ | Cl |
| Me | Me | H | H | 1 | H | H | S | Cl | C(=NOMe)Me | Cl |
| Me | Me | H | H | 1 | H | H | O | H | H | H |
| Me | Me | H | H | 1 | H | H | O | Me | H | Cl |
| H | H | H | H | 1 | H | H | S | Cl | Cl | Cl |
| Me | H | H | H | 1 | H | H | S | Cl | Cl | Cl |
| Me | H | Me | H | 1 | H | H | S | Cl | Cl | Cl |
| Me | Me | H | H | 1 | Me | H | S | Cl | Cl | Cl |
| Me | Me | H | H | 1 | Et | H | S | Cl | Cl | Cl |
| Me | Me | H | H | 1 | Pr-i | H | S | Cl | Cl | Cl |
| Me | Me | H | H | 1 | Me | Me | S | Cl | Cl | Cl |
| Me | Et | H | H | 1 | H | H | S | Cl | Cl | Cl |
| Et | Et | H | H | 1 | H | H | S | Cl | Cl | Cl |
| Me | Pr-i | H | H | 1 | H | H | S | Cl | Cl | Cl |
| Me | Pr | H | H | 1 | H | H | S | Cl | Cl | Cl |
| Me | Pr-c | H | H | 1 | H | H | S | Cl | Cl | Cl |
| Me | CH$_2$Pr-c | H | H | 1 | H | H | S | Cl | Cl | Cl |
| —(CH$_2$)$_2$— | | H | H | 1 | H | H | S | Cl | Cl | Cl |
| —(CH$_2$)$_3$— | | H | H | 1 | H | H | S | Cl | Cl | Cl |
| —(CH$_2$)$_4$— | | H | H | 1 | H | H | S | Cl | Cl | Cl |
| —(CH$_2$)$_5$— | | H | H | 1 | H | H | S | Cl | Cl | Cl |
| H | —(CH$_2$)$_3$— | | H | 1 | H | H | S | Cl | Cl | Cl |
| H | —(CH$_2$)$_4$— | | H | 1 | H | H | S | Cl | Cl | Cl |
| H | —(CH$_2$)$_5$— | | H | 1 | H | H | S | Cl | Cl | Cl |
| H | —(CH$_2$)$_6$— | | H | 1 | H | H | S | Cl | Cl | Cl |
| Me | Me | H | H | 0 | H | H | S | H | H | H |
| Me | Me | H | H | 0 | H | H | S | H | OMe | H |

TABLE 2-continued

| R¹ | R² | R³ | R⁴ | n | R⁵ | R⁶ | Z² | R²⁵ | R²⁶ | R²⁷ |
|---|---|---|---|---|---|---|---|---|---|---|
| Me | Me | H | H | 0 | H | H | S | Cl | H | Cl |
| Me | Me | H | H | 0 | H | H | S | Cl | Cl | Cl |
| Me | Me | H | H | 0 | H | H | S | Cl | Me | H |
| Me | Me | H | H | 0 | H | H | S | NHMe | Me | H |
| Me | Me | H | H | 0 | H | H | S | N(Me)₂ | Me | H |
| Me | Me | H | H | 0 | H | H | S | NHC(=O)Me | Me | H |
| Me | Me | H | H | 0 | H | H | S | NHC(=O)Ph | Me | H |
| Me | Me | R | H | 0 | H | H | S | NHSO₂Me | Me | H |
| Me | Me | H | H | 0 | H | H | S | NHSO₂Ph | Me | H |
| Me | Me | H | H | 0 | H | H | S | Me | Me | Me |
| Me | Me | H | H | 0 | H | H | S | Me | C(=O)OMe | Me |
| Me | Me | H | H | 0 | H | H | S | Me | C(=O)OEt | Me |
| Me | Me | H | H | 0 | H | H | S | Me | C(=O)OPh | Me |
| Me | Me | H | H | 0 | H | H | S | Me | CN | Me |
| Me | Me | H | H | 0 | H | H | S | Me | C(=O)NHMe | Me |
| Me | Me | H | H | 0 | H | H | S | Me | C(=O)Me | Me |
| Me | Me | H | H | 0 | H | H | S | Me | C(=O)Et | Me |
| Me | Me | H | H | 0 | H | H | S | Me | C(=O)Pr-i | Me |
| Me | Me | H | H | 0 | H | H | S | Me | C(=O)Pr | Me |
| Me | Me | H | H | 0 | H | H | S | Me | C(=O)CF₃ | Me |
| Me | Me | H | H | 0 | H | H | S | Me | C(=NOMe)Me | Me |
| Me | Me | H | H | 0 | H | H | S | Ph | C(=O)Me | Me |
| Me | Me | H | H | 0 | H | H | S | Ph | C(=NOMe)Me | Me |
| Me | Me | H | H | 0 | H | H | S | CF₃ | OMe | H |
| Me | Me | H | H | 0 | H | H | S | CF₃ | OEt | H |
| Me | Me | H | H | 0 | H | H | S | CF₃ | OPr-i | H |
| Me | Me | H | H | 0 | H | H | S | CF₃ | OPr-i | H |
| Me | Me | H | H | 0 | H | H | S | CF₃ | OCHF₂ | H |
| Me | Me | H | H | 0 | H | H | S | Cl | Me | H |
| Me | Me | H | H | 0 | H | H | S | Cl | Me | Me |
| Me | Me | H | H | 0 | H | H | S | Cl | C(=O)OMe | Cl |
| Me | Me | H | H | 0 | H | H | S | Cl | CN | Cl |
| Me | Me | H | H | 0 | H | H | S | Cl | C(=O)NHMe | Cl |
| Me | Me | H | H | 0 | H | H | S | Cl | C(=O)N(Me)₂ | Cl |
| Me | Me | H | H | 0 | H | H | S | Cl | C(=O)Me | Cl |
| Me | Me | H | H | 0 | H | H | S | Cl | C(=O)Et | Cl |
| Me | Me | H | H | 0 | H | H | S | Cl | C(=O)Pr-i | Cl |
| Me | Me | H | H | 0 | H | H | S | Cl | C(=O)Pr | Cl |
| Me | Me | H | H | 0 | H | H | S | Cl | C(=O)CF₃ | Cl |
| Me | Me | H | H | 0 | H | H | S | Cl | C(=NOMe)Me | Cl |
| Me | Me | H | H | 0 | H | H | O | H | H | H |
| Me | Me | H | H | 0 | H | H | O | Me | H | Cl |
| H | H | H | H | 0 | H | H | S | Cl | Cl | Cl |
| Me | H | H | H | 0 | H | H | S | Cl | Cl | Cl |
| Me | H | Me | H | 0 | H | H | S | Cl | Cl | Cl |
| Me | Me | H | H | 0 | Me | H | S | Cl | Cl | Cl |
| Me | Me | H | H | 0 | Et | H | S | Cl | Cl | Cl |
| Me | Me | H | H | 0 | Pr-i | H | S | Cl | Cl | Cl |
| Me | Me | H | H | 0 | Me | Me | S | Cl | Cl | Cl |
| Me | Et | H | H | 0 | H | H | S | Cl | Cl | Cl |
| Et | Et | H | H | 0 | H | H | S | Cl | Cl | Cl |
| Me | Pr-i | H | H | 0 | H | H | S | Cl | Cl | Cl |
| Me | Pr | H | H | 0 | H | H | S | Cl | Cl | Cl |
| Me | Pr-c | H | H | 0 | H | H | S | Cl | Cl | Cl |
| Me | CH₂Pr-c | H | H | 0 | H | H | S | Cl | Cl | Cl |
| —(CH₂)₂— | | H | H | 0 | H | H | S | Cl | Cl | Cl |
| —(CH₂)₃— | | H | H | 0 | H | H | S | Cl | Cl | Cl |
| —(CH₂)₄— | | H | H | 0 | H | H | S | Cl | Cl | Cl |
| —(CH₂)₅— | | H | H | 0 | H | H | S | Cl | Cl | Cl |
| H | —(CH₂)₃— | | H | 0 | H | H | S | Cl | Cl | Cl |
| H | —(CH₂)₄— | | H | 0 | H | H | S | Cl | Cl | Cl |
| H | —(CH₂)₅— | | H | 0 | H | H | S | Cl | Cl | Cl |
| H | —(CH₂)₆— | | H | 0 | H | H | S | Cl | Cl | Cl |

TABLE 3

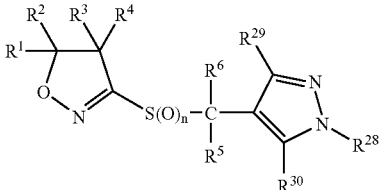

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 2 | H | H | Cl | H | Cl |
| Me | Me | H | H | 2 | H | H | OCHF₂ | H | Cl |
| Me | Me | H | H | 2 | H | H | OCHF₂ | H | OCHF₂ |
| Me | Me | H | H | 2 | H | H | Me | H | Cl |
| Me | Me | H | H | 2 | H | H | Me | H | OCHF₂ |
| Me | Me | H | H | 2 | H | H | CHF₂ | H | Cl |
| Me | Me | H | H | 2 | H | H | CHF₂ | H | OCHF₂ |
| Me | Me | H | H | 2 | H | H | CF₃ | H | F |
| Me | Me | H | H | 2 | H | H | CF₃ | H | Cl |
| Me | Me | H | H | 2 | H | H | CF₃ | H | OMe |
| Me | Me | H | H | 2 | H | H | CF₃ | H | OEt |
| Me | Me | H | H | 2 | H | H | CF₃ | H | OCHF₂ |
| Me | Me | H | H | 2 | H | H | CF₃ | H | CN |
| Me | Me | H | H | 2 | H | H | CF₃ | H | Me |
| Me | Me | H | H | 2 | H | H | H | Me | Cl |
| Me | Me | H | H | 2 | H | H | Me | Me | Me |
| Me | Me | H | H | 2 | H | H | Me | Me | F |
| Me | Me | H | H | 2 | H | H | F | Me | Me |
| Me | Me | H | H | 2 | H | H | Me | Me | Cl |
| Me | Me | H | H | 2 | H | H | Cl | Me | Me |
| Me | Me | H | H | 2 | H | H | Me | Me | OMe |
| Me | Me | H | H | 2 | H | H | OMe | Me | Me |
| Me | Me | H | H | 2 | H | H | Me | Me | OCHF₂ |
| Me | Me | H | H | 2 | H | H | OCHF₂ | Me | Me |
| Me | Me | H | H | 2 | H | H | Me | Me | CN |
| Me | Me | H | H | 2 | H | H | CN | Me | Me |
| Me | Me | H | H | 2 | H | H | Et | Me | F |
| Me | Me | H | H | 2 | H | H | F | Me | Et |
| Me | Me | H | H | 2 | H | H | Et | Me | Cl |
| Me | Me | H | H | 2 | H | H | Cl | Me | Et |
| Me | Me | H | H | 2 | H | H | Et | Me | OMe |
| Me | Me | H | H | 2 | H | H | OMe | Me | Et |
| Me | Me | H | H | 2 | H | H | Et | Me | OCHF₂ |
| Me | Me | H | H | 2 | H | H | OCHF₂ | Me | Et |
| Me | Me | H | H | 2 | H | H | Et | Me | CN |
| Me | Me | H | H | 2 | H | H | CN | Me | Et |
| Me | Me | H | H | 2 | H | H | Pr-i | Me | F |
| Me | Me | H | H | 2 | H | H | F | Me | Pr-i |
| Me | Me | H | H | 2 | H | H | Pr-i | Me | Cl |
| Me | Me | H | H | 2 | H | H | Cl | Me | Pr-i |
| Me | Me | H | H | 2 | H | H | Pr-i | Me | OMe |
| Me | Me | H | H | 2 | H | H | OMe | Me | Pr-i |
| Me | Me | H | H | 2 | H | H | Pr-i | Me | OCHF₂ |
| Me | Me | H | H | 2 | H | H | OCHF₂ | Me | Pr-i |
| Me | Me | H | H | 2 | H | H | Pr-i | Me | CN |
| Me | Me | H | H | 2 | H | H | CN | Me | Pr-i |
| Me | Me | H | H | 2 | H | H | Bu-t | Me | F |
| Me | Me | H | H | 2 | H | H | F | Me | Bu-t |
| Me | Me | H | H | 2 | H | H | Bu-t | Me | Cl |
| Me | Me | H | H | 2 | H | H | Cl | Me | Bu-t |
| Me | Me | H | H | 2 | H | H | Bu-t | Me | OMe |
| Me | Me | H | H | 2 | H | H | OMe | Me | Bu-t |
| Me | Me | H | H | 2 | H | H | Bu-t | Me | OCHF₂ |
| Me | Me | H | H | 2 | H | H | OCHF₂ | Me | Bu-t |
| Me | Me | H | H | 2 | H | H | Bu-t | Me | CN |
| Me | Me | H | H | 2 | H | H | CN | Me | Bu-t |
| Me | Me | H | H | 2 | H | H | CH₂OMe | Me | F |
| Me | Me | H | H | 2 | H | H | F | Me | CH₂OMe |
| Me | Me | H | H | 2 | H | H | CH₂OMe | Me | Cl |
| Me | Me | H | H | 2 | H | H | Cl | Me | CH₂OMe |
| Me | Me | H | H | 2 | H | H | CH₂OMe | Me | OMe |
| Me | Me | H | H | 2 | H | H | OMe | Me | CH₂OMe |
| Me | Me | H | H | 2 | H | H | CH₂OMe | Me | OCHF₂ |
| Me | Me | H | H | 2 | H | H | OCHF₂ | Me | CH₂OMe |
| Me | Me | H | H | 2 | H | H | CH₂OMe | Me | CN |
| Me | Me | H | H | 2 | H | H | CN | Me | CH₂OMe |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 2 | H | H | Cl | Me | Cl |
| Me | Me | H | H | 2 | H | H | CHF₂ | Me | Cl |
| Me | Me | H | H | 2 | H | H | Cl | Me | CHF₂ |
| Me | Me | H | H | 2 | H | H | OCHF₂ | Me | H |
| Me | Me | H | H | 2 | H | H | OCHF₂ | Me | F |
| Me | Me | H | H | 2 | H | H | F | Me | OCHF₂ |
| Me | Me | H | H | 2 | H | H | OCHF₂ | Me | Cl |
| Me | Me | H | H | 2 | H | H | Cl | Me | OCHF₂ |
| Me | Me | H | H | 2 | H | H | OCHF₂ | Me | OMe |
| Me | Me | H | H | 2 | H | H | OMe | Me | OCHF₂ |
| Me | Me | H | H | 2 | H | H | OCHF₂ | Me | OCHF₂ |
| Me | Me | H | H | 2 | H | H | OCHF₂ | Me | CN |
| Me | Me | H | H | 2 | H | H | CN | Me | OCHF₂ |
| Me | Me | H | H | 2 | H | H | CF₃ | Me | H |
| Me | Me | H | H | 2 | H | H | CF₃ | Me | Cl |
| Me | Me | H | H | 2 | H | H | Cl | Me | CF₃ |
| Me | Me | H | H | 2 | H | H | CF₃ | Me | Br |
| Me | Me | H | H | 2 | H | H | Br | Me | CF₃ |
| Me | Me | H | H | 2 | H | H | CF₃ | Me | I |
| Me | Me | H | H | 2 | H | H | I | Me | CF₃ |
| Me | Me | H | H | 2 | H | H | CF₃ | Me | F |
| Me | Me | H | H | 2 | H | H | F | Me | CF₃ |
| Me | Me | H | H | 2 | H | H | CF₃ | Me | OH |
| Me | Me | H | H | 2 | H | H | OH | Me | CF₃ |
| Me | Me | H | H | 2 | H | H | CF₃ | Me | OMe |
| Me | Me | H | H | 2 | H | H | OMe | Me | CF₃ |
| Me | Me | H | H | 2 | H | H | CF₃ | Me | OEt |
| Me | Me | H | H | 2 | H | H | OEt | Me | CF₃ |
| Me | Me | H | H | 2 | H | H | CF₃ | Me | OPr-i |
| Me | Me | H | H | 2 | H | H | CF₃ | Me | OPr |
| Me | Me | H | H | 2 | H | H | CF₃ | Me | OBu-t |
| Me | Me | H | H | 2 | H | H | CF₃ | Me | OBu-s |
| Me | Me | H | H | 2 | H | H | CF₃ | Me | OBu-i |
| Me | Me | H | H | 2 | H | H | CF₃ | Me | OBu |
| Me | Me | H | H | 2 | H | H | CF₃ | Me | O(2-Pen) |
| Me | Me | H | H | 2 | H | H | CF₃ | Me | O(3-Pen) |
| Me | Me | H | H | 2 | H | H | CF₃ | Me | OPen-n |
| Me | Me | H | H | 2 | H | H | CF₃ | Me | O(2-Hex) |
| Me | Me | H | H | 2 | H | H | CF₃ | Me | O(3-Hex) |
| Me | Me | H | H | 2 | H | H | CF₃ | Me | OHex-n |
| Me | Me | H | H | 2 | H | H | CF₃ | Me | OPen-c |
| Me | Me | H | H | 2 | H | H | CF₃ | Me | OHex-c |
| Me | Me | H | H | 2 | H | H | CF₃ | Me | OCH₂Pr-c |
| Me | Me | H | H | 2 | H | H | CF₃ | Me | OCH₂Bu-c |
| Me | Me | H | H | 2 | H | H | CF₃ | Me | OCH₂Pen-c |
| Me | Me | H | H | 2 | H | H | CF₃ | Me | OCH₂Hex-c |
| Me | Me | H | H | 2 | H | H | CF₃ | Me | OCH₂CH=CH₂ |
| Me | Me | H | H | 2 | H | H | CF₃ | Me | OCH₂C≡CH |
| Me | Me | H | H | 2 | H | H | CF₃ | Me | OCHF₂ |
| Me | Me | H | H | 2 | H | H | OCHF₂ | Me | CF₃ |
| Me | Me | H | H | 2 | H | H | CF₃ | Me | OCH₂CHF₂ |
| Me | Me | H | H | 2 | H | H | OCH₂CHF₂ | Me | CF₃ |
| Me | Me | H | H | 2 | H | H | CF₃ | Me | OCH₂CF₃ |
| Me | Me | H | H | 2 | H | H | OCH₂CF₃ | Me | CF₃ |
| Me | Me | H | H | 2 | H | H | CF₃ | Me | OCH₂CN |
| Me | Me | H | H | 2 | H | H | CF₃ | Me | OCH₂C(=O)OEt |
| Me | Me | H | H | 2 | H | H | CF₃ | Me | OCH(Me)C(=O)OEt |
| Me | Me | H | H | 2 | H | H | CF₃ | Me | OCH₂C(=O)NH₂ |
| Me | Me | H | H | 2 | H | H | CF₃ | Me | OCH₂C(=O)NHMe |
| Me | Me | H | H | 2 | H | H | CF₃ | Me | OCH₂C(=O)N(Me)₂ |
| Me | Me | H | H | 2 | H | H | CF₃ | Me | OCH₂Ph |
| Me | Me | H | H | 2 | H | H | CF₃ | Me | OPh |
| Me | Me | H | H | 2 | H | H | CF₃ | Me | O(2-Cl)Ph |
| Me | Me | H | H | 2 | H | H | CF₃ | Me | O(2-Br)Ph |
| Me | Me | H | H | 2 | H | H | CF₃ | Me | O(2-F)Ph |
| Me | Me | H | H | 2 | H | H | CF₃ | Me | O(2-Me)Ph |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 2 | H | H | $CF_3$ | Me | O(2-OMe)Ph |
| Me | Me | H | H | 2 | H | H | $CF_3$ | Me | O(2-$NO_2$)Ph |
| Me | Me | H | H | 2 | H | H | $CF_3$ | Me | O(2-CN)Ph |
| Me | Me | H | H | 2 | H | H | $CF_3$ | Me | O(2-C(=O)OMe)Ph |
| Me | Me | H | H | 2 | H | H | $CF_3$ | Me | O(3-Cl)Ph |
| Me | Me | H | H | 2 | H | H | $CF_3$ | Me | O(3-Br)Ph |
| Me | Me | H | H | 2 | H | H | $CF_3$ | Me | O(3-F)Ph |
| Me | Me | H | H | 2 | H | H | $CF_3$ | Me | O(3-Me)Ph |
| Me | Me | H | H | 2 | H | H | $CF_3$ | Me | O(3-OMe)Ph |
| Me | Me | H | H | 2 | H | H | $CF_3$ | Me | O(3-$NO_2$)Ph |
| Me | Me | H | H | 2 | H | H | $CF_3$ | Me | O(3-CN)Ph |
| Me | Me | H | H | 2 | H | H | $CF_3$ | Me | O(3-C(=O)OMe)Ph |
| Me | Me | H | H | 2 | H | H | $CF_3$ | Me | O(4-Cl)Ph |
| Me | Me | H | H | 2 | H | H | $CF_3$ | Me | O(4-Br)Ph |
| Me | Me | H | H | 2 | H | H | $CF_3$ | Me | O(4-F)Ph |
| Me | Me | H | H | 2 | H | H | $CF_3$ | Me | O(4-Me)Ph |
| Me | Me | H | H | 2 | H | H | $CF_3$ | Me | O(4-OMe)Ph |
| Me | Me | H | H | 2 | H | H | $CF_3$ | Me | O(4-$NO_2$)Ph |
| Me | Me | H | H | 2 | H | H | $CF_3$ | Me | O(4-CN)Ph |
| Me | Me | H | H | 2 | H | H | $CF_3$ | Me | O(4-C(=O)OMe)Ph |
| Me | Me | H | H | 2 | H | H | $CF_3$ | Me | OC(=O)Me |
| Me | Me | H | H | 2 | H | H | $CF_3$ | Me | OC(=O)Et |
| Me | Me | H | H | 2 | H | H | $CF_3$ | Me | OC(=O)$CH_2$Ph |
| Me | Me | H | H | 2 | H | H | $CF_3$ | Me | OC(=O)$CF_3$ |
| Me | Me | H | H | 2 | H | H | $CF_3$ | Me | OC(=O)Ph |
| Me | Me | H | H | 2 | H | H | $CF_3$ | Me | $OSO_2$Me |
| Me | Me | H | H | 2 | H | H | $CF_3$ | Me | $OSO_2$Et |
| Me | Me | H | H | 2 | H | H | $CF_3$ | Me | $OSO_2CH_2$Ph |
| Me | Me | H | H | 2 | H | H | $CF_3$ | Me | $OSO_2CF_3$ |
| Me | Me | H | H | 2 | H | H | $CF_3$ | Me | $OSO_2$Ph |
| Me | Me | H | H | 2 | H | H | $CF_3$ | Me | SMe |
| Me | Me | H | H | 2 | H | H | $CF_3$ | Me | SOMe |
| Me | Me | H | H | 2 | H | H | $CF_3$ | Me | $SO_2$Me |
| Me | Me | H | H | 2 | H | H | $CF_3$ | Me | SEt |
| Me | Me | H | H | 2 | H | H | $CF_3$ | Me | SOEt |
| Me | Me | H | H | 2 | H | H | $CF_3$ | Me | $SO_2$Et |
| Me | Me | H | H | 2 | H | H | $CF_3$ | Me | SPr |
| Me | Me | H | H | 2 | H | H | $CF_3$ | Me | SOPr |
| Me | Me | H | H | 2 | H | H | $CF_3$ | Me | $SO_2$Pr |
| Me | Me | H | H | 2 | H | H | $CF_3$ | Me | SPr-i |
| Me | Me | H | H | 2 | H | H | $CF_3$ | Me | SOPr-i |
| Me | Me | H | H | 2 | H | H | $CF_3$ | Me | $SO_2$Pr-i |
| Me | Me | H | H | 2 | H | H | $CF_3$ | Me | SBu-t |
| Me | Me | H | H | 2 | H | H | $CF_3$ | Me | SOBu-t |
| Me | Me | H | H | 2 | H | H | $CF_3$ | Me | $SO_2$Bu-t |
| Me | Me | H | H | 2 | H | H | $CF_3$ | Me | $SCHF_2$ |
| Me | Me | H | H | 2 | H | H | $CF_3$ | Me | $SOCHF_2$ |
| Me | Me | H | H | 2 | H | H | $CF_3$ | Me | $SO_2CHF_2$ |
| Me | Me | H | H | 2 | H | H | $CF_3$ | Me | $SCF_3$ |
| Me | Me | H | H | 2 | H | H | $CF_3$ | Me | $SOCF_3$ |
| Me | Me | H | H | 2 | H | H | $CF_3$ | Me | $SO_2CF_3$ |
| Me | Me | H | H | 2 | H | H | $CF_3$ | Me | SPh |
| Me | Me | H | H | 2 | H | H | $CF_3$ | Me | SOh |
| Me | Me | H | H | 2 | H | H | $CF_3$ | Me | $SO_2$Ph |
| Me | Me | H | H | 2 | H | H | $CF_3$ | Me | $SCH_2$Ph |
| Me | Me | H | H | 2 | H | H | $CF_3$ | Me | $SOCH_2$Ph |
| Me | Me | H | H | 2 | H | H | $CF_3$ | Me | $SO_2CH_2$Ph |
| Me | Me | H | H | 2 | H | H | $CF_3$ | Me | $SCH_2$C(=O)OEt |
| Me | Me | H | H | 2 | H | H | $CF_3$ | Me | $SOCH_2$C(=O)OEt |
| Me | Me | H | H | 2 | H | H | $CF_3$ | Me | $SO_2CH_2$C(=O)OEt |
| Me | Me | H | H | 2 | H | H | $CF_3$ | Me | SCH(Me)C(=O)OEt |
| Me | Me | H | H | 2 | H | H | $CF_3$ | Me | SOCH(Me)C(=O)OEt |
| Me | Me | H | H | 2 | H | H | $CF_3$ | Me | $SO_2$CH(Me)C(=O)OEt |
| Me | Me | H | H | 2 | H | H | $CF_3$ | Me | $SCH_2$C(=O)$NH_2$ |
| Me | Me | H | H | 2 | H | H | $CF_3$ | Me | $SOCH_2$C(=O)$NH_2$ |
| Me | Me | H | H | 2 | H | H | $CF_3$ | Me | $SO_2CH_2$C(=O)$NH_2$ |

TABLE 3-continued

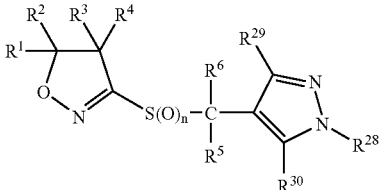

| $R^1$ | $R^2$ | $R^3$ | $R^4$ | n | $R^5$ | $R^6$ | $R^{29}$ | $R^{28}$ | $R^{30}$ |
|---|---|---|---|---|---|---|---|---|---|
| Me | Me | H | H | 2 | H | H | $CF_3$ | Me | $SCH_2C(=O)NHMe$ |
| Me | Me | H | H | 2 | H | H | $CF_3$ | Me | $SOCH_2C(=O)NHMe$ |
| Me | Me | H | H | 2 | H | H | $CF_3$ | Me | $SO_2CH_2C(=O)NHMe$ |
| Me | Me | H | H | 2 | H | H | $CF_3$ | Me | $SCH_2C(=O)N(Me)_2$ |
| Me | Me | H | H | 2 | H | H | $CF_3$ | Me | $SOCH_2C(=O)N(Me)_2$ |
| Me | Me | H | H | 2 | H | H | $CF_3$ | Me | $SO_2CH_2C(=O)N(Me)_2$ |
| Me | Me | H | H | 2 | H | H | $CF_3$ | Me | $NH_2$ |
| Me | Me | H | H | 2 | H | H | $CF_3$ | Me | NHMe |
| Me | Me | H | H | 2 | H | H | $CF_3$ | Me | $N(Me)_2$ |
| Me | Me | H | H | 2 | H | H | $CF_3$ | Me | $NHC(=O)Me$ |
| Me | Me | H | H | 2 | H | H | $CF_3$ | Me | $N(Me)C(=O)Me$ |
| Me | Me | H | H | 2 | H | H | $CF_3$ | Me | $NHSO_2Me$ |
| Me | Me | H | H | 2 | H | H | $CF_3$ | Me | $N(Me)SO_2Me$ |
| Me | Me | H | H | 2 | H | H | $CF_3$ | Me | $NHSO_2CHF_2$ |
| Me | Me | H | H | 2 | H | H | $CF_3$ | Me | $N(Me)SO_2CHF_2$ |
| Me | Me | H | H | 2 | H | H | $CF_3$ | Me | $NHSO_2CF_3$ |
| Me | Me | H | H | 2 | H | H | $CF_3$ | Me | $N(Me)SO_2CF_3$ |
| Me | Me | H | H | 2 | H | H | $CF_3$ | Me | NHPh |
| Me | Me | H | H | 2 | H | H | $CF_3$ | Me | N(Me)Ph |
| Me | Me | H | H | 2 | H | H | $CF_3$ | Me | CN |
| Me | Me | H | H | 2 | H | H | CN | Me | $CF_3$ |
| Me | Me | H | H | 2 | H | H | $CF_3$ | Me | $C(=O)OMe$ |
| Me | Me | H | H | 2 | H | H | $CF_3$ | Me | $C(=O)OPr-i$ |
| Me | Me | H | H | 2 | H | H | $CF_3$ | Me | $C(=O)OCH_2Ph$ |
| Me | Me | H | H | 2 | H | H | $CF_3$ | Me | $C(=O)OPh$ |
| Me | Me | H | H | 2 | H | H | $CF_3$ | Me | $C(=O)NH_2$ |
| Me | Me | H | H | 2 | H | H | $CF_3$ | Me | $C(=O)NHMe$ |
| Me | Me | H | H | 2 | H | H | $CF_3$ | Me | $C(=O)N(Me)_2$ |
| Me | Me | H | H | 2 | H | H | $CF_3$ | Me | $C(=O)Me$ |
| Me | Me | H | H | 2 | H | H | $CF_3$ | Me | $C(=O)CF_3$ |
| Me | Me | H | H | 2 | H | H | $CF_3$ | Me | $C(=O)CH_2Ph$ |
| Me | Me | H | H | 2 | H | H | $CF_3$ | Me | $C(=O)Ph$ |
| Me | Me | H | H | 2 | H | H | $CF_3$ | Me | Me |
| Me | Me | H | H | 2 | H | H | Me | Me | $CF_3$ |
| Me | Me | H | H | 2 | H | H | $CF_3$ | Me | Et |
| Me | Me | H | H | 2 | H | H | $CF_3$ | Me | Pr-i |
| Me | Me | H | H | 2 | H | H | $CF_3$ | Me | Pr |
| Me | Me | H | H | 2 | H | H | $CF_3$ | Me | $CH_2OMe$ |
| Me | Me | H | H | 2 | H | H | $CF_3$ | Me | $CF_3$ |
| Me | Me | H | H | 2 | H | H | $CF_3$ | Me | $CHF_2$ |
| Me | Me | H | H | 2 | H | H | $CF_3$ | Me | Ph |
| Me | Me | H | H | 2 | H | H | $CF_2CF_3$ | Me | Cl |
| Me | Me | H | H | 2 | H | H | CN | Me | F |
| Me | Me | H | H | 2 | H | H | F | Me | CN |
| Me | Me | H | H | 2 | H | H | CN | Me | Cl |
| Me | Me | H | H | 2 | H | H | Cl | Me | CN |
| Me | Me | H | H | 2 | H | H | CN | Me | CN |
| Me | Me | H | H | 2 | H | H | COOMe | Me | F |
| Me | Me | H | H | 2 | H | H | F | Me | COOMe |
| Me | Me | H | H | 2 | H | H | COOMe | Me | Cl |
| Me | Me | H | H | 2 | H | H | Cl | Me | COOMe |
| Me | Me | H | H | 2 | H | H | $SO_2Me$ | Me | Cl |
| Me | Me | H | H | 2 | H | H | Cl | Me | $SO_2Me$ |
| Me | Me | H | H | 2 | H | H | Ph | Me | Me |
| Me | Me | H | H | 2 | H | H | Ph | Me | Cl |
| Me | Me | H | H | 2 | H | H | Ph | Me | QEt |
| Me | Me | H | H | 2 | H | H | Ph | Me | $CF_3$ |
| Me | Me | H | H | 2 | H | H | Ph | Me | Ph |
| Me | Me | H | H | 2 | H | H | Me | Et | $OCHF_2$ |
| Me | Me | H | H | 2 | H | H | $OCHF_2$ | Et | Me |
| Me | Me | H | H | 2 | H | H | Me | Et | CN |
| Me | Me | H | H | 2 | H | H | CN | Et | Me |
| Me | Me | H | H | 2 | H | H | Pr-i | Et | $OCHF_2$ |
| Me | Me | H | H | 2 | H | H | $OCHF_2$ | Et | Pr-i |
| Me | Me | H | H | 2 | H | H | Pr-i | Et | CN |
| Me | Me | H | H | 2 | H | H | CN | Et | Pr-i |

TABLE 3-continued

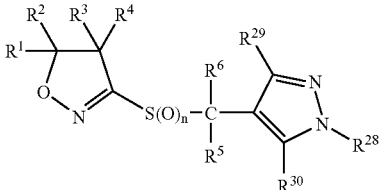

| R¹ | R² | R³ | R⁴ | n | R⁵ | R⁶ | R²⁹ | R²⁸ | R³⁰ |
|----|----|----|----|---|----|----|-----|-----|-----|
| Me | Me | H | H | 2 | H | H | Cl | Et | Cl |
| Me | Me | H | H | 2 | H | H | OCHF₂ | Et | Cl |
| Me | Me | H | H | 2 | H | H | Cl | Et | OCHF₂ |
| Me | Me | H | H | 2 | H | H | OCHF₂ | Et | OCHF₂ |
| Me | Me | H | H | 2 | H | H | CF₃ | Et | F |
| Me | Me | H | H | 2 | H | H | F | Et | CF₃ |
| Me | Me | H | H | 2 | H | H | CF₃ | Et | Cl |
| Me | Me | H | H | 2 | H | H | Cl | Et | CF₃ |
| Me | Me | H | H | 2 | H | H | CF₃ | Et | OMe |
| Me | Me | H | H | 2 | H | H | OMe | Et | CF₃ |
| Me | Me | H | H | 2 | H | H | CF₃ | Et | OEt |
| Me | Me | H | H | 2 | H | H | OEt | Et | CF₃ |
| Me | Me | H | H | 2 | H | H | CF₃ | Et | OCHF₂ |
| Me | Me | H | H | 2 | H | H | OCHF₂ | Et | CF₃ |
| Me | Me | H | H | 2 | H | H | CF₃ | Et | CN |
| Me | Me | H | H | 2 | H | H | CN | Et | CF₃ |
| Me | Me | H | H | 2 | H | H | CF₃ | Et | Me |
| Me | Me | H | H | 2 | H | H | Me | Et | CF₃ |
| Me | Me | H | H | 2 | H | H | Me | Pr-i | OCHF₂ |
| Me | Me | H | H | 2 | H | H | OCHF₂ | Pr-i | Me |
| Me | Me | H | H | 2 | H | H | Me | Pr-i | CN |
| Me | Me | H | H | 2 | H | H | CN | Pr-i | Me |
| Me | Me | H | H | 2 | H | H | Pr-i | Pr-i | OCHF₂ |
| Me | Me | H | H | 2 | H | H | OCHF₂ | Pr-i | Pr-i |
| Me | Me | H | H | 2 | H | H | Pr-i | Pr-i | CN |
| Me | Me | H | H | 2 | H | H | CN | Pr-i | Pr-i |
| Me | Me | H | H | 2 | H | H | Cl | Pr-i | Cl |
| Me | Me | H | H | 2 | H | H | OCHF₂ | Pr-i | Cl |
| Me | Me | H | H | 2 | H | H | Cl | Pr-i | OCHF₂ |
| Me | Me | H | H | 2 | H | H | OCHF₂ | Pr-i | OCHF₂ |
| Me | Me | H | H | 2 | H | H | CF₃ | Pr-i | F |
| Me | Me | H | H | 2 | H | H | F | Pr-i | CF₃ |
| Me | Me | H | H | 2 | H | H | CF₃ | Pr-i | Cl |
| Me | Me | H | H | 2 | H | H | Cl | Pr-i | CF₃ |
| Me | Me | H | H | 2 | H | H | CF₃ | Pr-i | OMe |
| Me | Me | H | H | 2 | H | H | OMe | Pr-i | CF₃ |
| Me | Me | H | H | 2 | H | H | CF₃ | Pr-i | OEt |
| Me | Me | H | H | 2 | H | H | OEt | Pr-i | CF₃ |
| Me | Me | H | H | 2 | H | H | CF₃ | Pr-i | OCHF₂ |
| Me | Me | H | H | 2 | H | H | OCHF₂ | Pr-i | CF₃ |
| Me | Me | H | H | 2 | H | H | CF₃ | Pr-i | CN |
| Me | Me | H | H | 2 | H | H | CN | Pr-i | CF₃ |
| Me | Me | H | H | 2 | H | H | CF₃ | Pr-i | Me |
| Me | Me | H | H | 2 | H | H | Me | Pr-i | CF₃ |
| Me | Me | H | H | 2 | H | H | Me | Pr | OCHF₂ |
| Me | Me | H | H | 2 | H | H | OCHF₂ | Pr | Me |
| Me | Me | H | H | 2 | H | H | Me | Pr | CN |
| Me | Me | H | H | 2 | H | H | CN | Pr | Me |
| Me | Me | H | H | 2 | H | H | Pr-i | Pr | OCHF₂ |
| Me | Me | H | H | 2 | H | H | OCHF₂ | Pr | Pr-i |
| Me | Me | H | H | 2 | H | H | Pr-i | Pr | CN |
| Me | Me | H | H | 2 | H | H | CN | Pr | Pr-i |
| Me | Me | H | H | 2 | H | H | Cl | Pr | Cl |
| Me | Me | H | H | 2 | H | H | OCHF₂ | Pr | Cl |
| Me | Me | H | H | 2 | H | H | Cl | Pr | OCHF₂ |
| Me | Me | H | H | 2 | H | H | OCHF₂ | Pr | OCHF₂ |
| Me | Me | H | H | 2 | H | H | CF₃ | Pr | F |
| Me | Me | H | H | 2 | H | H | F | Pr | CF₃ |
| Me | Me | H | H | 2 | H | H | CF₃ | Pr | Cl |
| Me | Me | H | H | 2 | H | H | Cl | Pr | CF₃ |
| Me | Me | H | H | 2 | H | H | CF₃ | Pr | OMe |
| Me | Me | H | H | 2 | H | H | OMe | Pr | CF₃ |
| Me | Me | H | H | 2 | H | H | CF₃ | Pr | OEt |
| Me | Me | H | H | 2 | H | H | OEt | Pr | CF₃ |
| Me | Me | H | H | 2 | H | H | CF₃ | Pr | OCHF₂ |
| Me | Me | H | H | 2 | H | H | OCHF₂ | Pr | CF₃ |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 2 | H | H | CF$_3$ | Pr | CN |
| Me | Me | H | H | 2 | H | H | CN | Pr | CF$_3$ |
| Me | Me | H | H | 2 | H | H | CF$_3$ | Pr | Me |
| Me | Me | H | H | 2 | H | H | Me | Pr | CF$_3$ |
| Me | Me | H | H | 2 | H | H | Me | Bu-t | F |
| Me | Me | H | H | 2 | H | H | Me | Bu-t | Cl |
| Me | Me | H | H | 2 | H | H | Me | Bu-t | OCHF$_2$ |
| Me | Me | H | H | 2 | H | H | Me | Bu-t | CN |
| Me | Me | H | H | 2 | H | H | Cl | Bu-t | Cl |
| Me | Me | H | H | 2 | H | H | OCHF$_2$ | Bu-t | Cl |
| Me | Me | H | H | 2 | H | H | OCHF$_2$ | Bu-t | OCHF$_2$ |
| Me | Me | H | H | 2 | H | H | CF$_3$ | Bu-t | H |
| Me | Me | H | H | 2 | H | H | CF$_3$ | Bu-t | F |
| Me | Me | H | H | 2 | H | H | CF$_3$ | Bu-t | Cl |
| Me | Me | H | H | 2 | H | H | Cl | Bu-t | CF$_3$ |
| Me | Me | H | H | 2 | H | H | CF$_3$ | Bu-t | OMe |
| Me | Me | H | H | 2 | H | H | OMe | Bu-t | CF$_3$ |
| Me | Me | H | H | 2 | H | H | CF$_3$ | Bu-t | OEt |
| Me | Me | H | H | 2 | H | H | OEt | Bu-t | CF$_3$ |
| Me | Me | H | H | 2 | H | H | CF$_3$ | Bu-t | OCHF$_2$ |
| Me | Me | H | H | 2 | H | H | CF$_3$ | Bu-t | CN |
| Me | Me | H | H | 2 | H | H | CF$_3$ | Bu-t | Me |
| Me | Me | H | H | 2 | H | H | Me | Bu-t | CF$_3$ |
| Me | Me | H | H | 2 | H | H | CF$_3$ | Bu-s | Cl |
| Me | Me | H | H | 2 | H | H | Cl | Bu-s | CF$_3$ |
| Me | Me | H | H | 2 | H | H | CF$_3$ | Bu-i | Cl |
| Me | Me | H | H | 2 | H | H | Cl | Bu-i | CF$_3$ |
| Me | Me | H | H | 2 | H | H | CF$_3$ | Bu | Cl |
| Me | Me | H | H | 2 | H | H | Cl | Bu | CF$_3$ |
| Me | Me | H | H | 2 | H | H | CF$_3$ | 1-Methylbutyl | Cl |
| Me | Me | H | H | 2 | H | H | Cl | 1-Methylbutyl | CF$_3$ |
| Me | Me | H | H | 2 | H | H | CF$_3$ | 1-Ethylpropyl | Cl |
| Me | Me | H | H | 2 | H | H | Cl | 1-Ethylpropyl | CF$_3$ |
| Me | Me | H | H | 2 | H | H | CF$_3$ | 1-Pentyl | Cl |
| Me | Me | H | H | 2 | H | H | Cl | 1-Pentyl | CF$_3$ |
| Me | Me | H | H | 2 | H | H | CF$_3$ | 1-Methylpentyl | Cl |
| Me | Me | H | H | 2 | H | H | Cl | 1-Methylpentyl | CF$_3$ |
| Me | Me | H | H | 2 | H | H | CF$_3$ | 2-Ethylbutyl | Cl |
| Me | Me | H | H | 2 | H | H | Cl | 2-Ethylbutyl | CF$_3$ |
| Me | Me | H | H | 2 | H | H | CF$_3$ | 3,3-Dimethylbutyl | Cl |
| Me | Me | H | H | 2 | H | H | Cl | 3,3-Dimethylbutyl | CF$_3$ |
| Me | Me | H | H | 2 | H | H | CF$_3$ | 1-Hexyl | Cl |
| Me | Me | H | H | 2 | H | H | Cl | 1-Hexyl | CF$_3$ |
| Me | Me | H | H | 2 | H | H | CF$_3$ | 1-Heptyl | Cl |
| Me | Me | H | H | 2 | H | H | Cl | 1-Heptyl | CF$_3$ |
| Me | Me | H | H | 2 | H | H | CF$_3$ | 1-Octyl | Cl |
| Me | Me | H | H | 2 | H | H | Cl | 1-Octyl | CF$_3$ |
| Me | Me | H | H | 2 | H | H | CF$_3$ | CH$_2$Ph | Cl |
| Me | Me | H | H | 2 | H | H | Cl | CH$_2$Ph | CF$_3$ |
| Me | Me | H | H | 2 | H | H | CF$_3$ | Pr-c | F |
| Me | Me | H | H | 2 | H | H | CF$_3$ | Pr-c | Cl |
| Me | Me | H | H | 2 | H | H | CF$_3$ | Pr-c | OMe |
| Me | Me | H | H | 2 | H | H | CF$_3$ | Pr-c | OCHF$_2$ |
| Me | Me | H | H | 2 | H | H | CF$_3$ | Pr-c | CN |
| Me | Me | H | H | 2 | H | H | CF$_3$ | Pen-c | Cl |
| Me | Me | H | H | 2 | H | H | Cl | Pen-c | CF$_3$ |
| Me | Me | H | H | 2 | H | H | CF$_3$ | Hex-c | Cl |
| Me | Me | H | H | 2 | H | H | Cl | Hex-c | CF$_3$ |
| Me | Me | H | H | 2 | H | H | Me | CH$_2$Pr-c | OCHF$_2$ |
| Me | Me | H | H | 2 | H | H | OCHF$_2$ | CH$_2$Pr-c | Me |
| Me | Me | H | H | 2 | H | H | Cl | CH$_2$Pr-c | Cl |
| Me | Me | H | H | 2 | H | H | OCHF$_2$ | CH$_2$Pr-c | Cl |
| Me | Me | H | H | 2 | H | H | Cl | CH$_2$Pr-c | OCHF$_2$ |
| Me | Me | H | H | 2 | H | H | OCHF$_2$ | CH$_2$Pr-c | OCHF$_2$ |
| Me | Me | H | H | 2 | H | H | CF$_3$ | CH$_2$Pr-c | F |
| Me | Me | H | H | 2 | H | H | F | CH$_2$Pr-c | CF$_3$ |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 2 | H | H | CF₃ | CH₂Pr-c | Cl |
| Me | Me | H | H | 2 | H | H | Cl | CH₂Pr-c | CF₃ |
| Me | Me | H | H | 2 | H | H | CF₃ | CH₂Pr-c | OH |
| Me | Me | H | H | 2 | H | H | CF₃ | CH₂Pr-c | OMe |
| Me | Me | H | H | 2 | H | H | OMe | CH₂Pr-c | CF₃ |
| Me | Me | H | H | 2 | H | H | CF₃ | CH₂Pr-c | OEt |
| Me | Me | H | H | 2 | H | H | OEt | CH₂Pr-c | CF₃ |
| Me | Me | H | H | 2 | H | H | CF₃ | CH₂Pr-c | OPr-i |
| Me | Me | H | H | 2 | H | H | CF₃ | CH₂Pr-c | OPr |
| Me | Me | H | H | 2 | H | H | CF₃ | CH₂Pr-c | OBu-t |
| Me | Me | H | H | 2 | H | H | CF₃ | CH₂Pr-c | OCH₂Pr-c |
| Me | Me | H | H | 2 | H | H | CF₃ | CH₂Pr-c | OCH₂Bu-c |
| Me | Me | H | H | 2 | H | H | CF₃ | CH₂Pr-c | OPen-c |
| Me | Me | H | H | 2 | H | H | CF₃ | CH₂Pr-c | OCHF₂ |
| Me | Me | H | H | 2 | H | H | OCHF₂ | CH₂Pr-c | CF₃ |
| Me | Me | H | H | 2 | H | H | CF₃ | CH₂Pr-c | CN |
| Me | Me | H | H | 2 | H | H | CN | CH₂Pr-c | CF₃ |
| Me | Me | H | H | 2 | H | H | CF₃ | CH₂Pr-c | Me |
| Me | Me | H | H | 2 | H | H | Me | CH₂Pr-c | CF₃ |
| Me | Me | H | H | 2 | H | H | CF₃ | 1-cyclopropylethyl | Cl |
| Me | Me | H | H | 2 | H | H | Cl | 1-cyclopropylethyl | CF₃ |
| Me | Me | H | H | 2 | H | H | CF₃ | CH₂(2-Methyl-cyclopropyl) | Cl |
| Me | Me | H | H | 2 | H | H | Cl | CH₂(2-Methyl-cyclopropyl) | CF₃ |
| Me | Me | H | H | 2 | H | H | CF₃ | CH₂(2,2-Dimethyl-cyclopropyl) | Cl |
| Me | Me | H | H | 2 | H | H | Cl | CH₂(2,2-Dimethyl-cyclopropyl) | CF₃ |
| Me | Me | H | H | 2 | H | H | CF₃ | CH₂(2-Chloro-cyclopropyl) | Cl |
| Me | Me | H | H | 2 | H | H | Cl | CH₂(2-Chloro-cyclopropyl) | CF₃ |
| Me | Me | H | H | 2 | H | H | CF₃ | CH₂(2,2-Dichloro-cyclopropyl) | Cl |
| Me | Me | H | H | 2 | H | H | Cl | CH₂(2,2-Dichloro-cyclopropyl) | CF₃ |
| Me | Me | H | H | 2 | H | H | CF₃ | CH₂(2-Fluoro-cyclopropyl) | Cl |
| Me | Me | H | H | 2 | H | H | Cl | CH₂(2-Fluoro-cyclopropyl) | CF₃ |
| Me | Me | H | H | 2 | H | H | CF₃ | CH₂(2,2-Difluoro-cyclopropyl) | Cl |
| Me | Me | H | H | 2 | H | H | Cl | CH₂(2,2-Difluoro-cyclopropyl) | CF₃ |
| Me | Me | H | H | 2 | H | H | CF₃ | CH₂Bu-c | Cl |
| Me | Me | H | H | 2 | H | H | Cl | CH₂Bu-c | CF₃ |
| Me | Me | H | H | 2 | H | H | CF₃ | CH₂Pen-c | Cl |
| Me | Me | H | H | 2 | H | H | Cl | CH₂Pen-c | CF₃ |
| Me | Me | H | H | 2 | H | H | CF₃ | CH₂Hex-c | Cl |
| Me | Me | H | H | 2 | H | H | Cl | CH₂Hex-c | CF₃ |
| Me | Me | H | H | 2 | H | H | CF₃ | CH₂CH₂Pr-c | Cl |
| Me | Me | H | H | 2 | H | H | Cl | CH₂CH₂Pr-c | CF₃ |
| Me | Me | H | H | 2 | H | H | CF₃ | CH₂CH=CH₂ | Cl |
| Me | Me | H | H | 2 | H | H | Cl | CH₂CH=CH₂ | CF₃ |
| Me | Me | H | H | 2 | H | H | CF₃ | CH₂CH=CHCl | Cl |
| Me | Me | H | H | 2 | H | H | Cl | CH₂CH=CHCl | CF₃ |
| Me | Me | H | H | 2 | H | H | Me | CH₂C≡CH | OCHF₂ |
| Me | Me | H | H | 2 | H | H | OCHF₂ | CH₂C≡CH | Me |
| Me | Me | H | H | 2 | H | H | Cl | CH₂CCH | Cl |
| Me | Me | H | H | 2 | H | H | OCHF₂ | CH₂C≡CH | Cl |
| Me | Me | H | H | 2 | H | H | Cl | CH₂C≡CH | OCHF₂ |
| Me | Me | H | H | 2 | H | H | OCHF₂ | CH₂C≡CH | OCHF₂ |
| Me | Me | H | H | 2 | H | H | CF₃ | CH₂C≡CH | F |
| Me | Me | H | H | 2 | H | H | F | CH₂C≡CH | CF₃ |
| Me | Me | H | H | 2 | H | H | CF₃ | CH₂C≡CH | Cl |
| Me | Me | H | H | 2 | H | H | Cl | CH₂C≡CH | CF₃ |
| Me | Me | H | H | 2 | H | H | CF₃ | CH₂C≡CH | OMe |
| Me | Me | H | H | 2 | H | H | OMe | CH₂C≡CH | CF₃ |
| Me | Me | H | H | 2 | H | H | CF₃ | CH₂C≡CH | OEt |
| Me | Me | H | H | 2 | H | H | OEt | CH₂C≡CH | CF₃ |
| Me | Me | H | H | 2 | H | H | CF₃ | CH₂C≡CH | OCHF₂ |
| Me | Me | H | H | 2 | H | H | OCHF₂ | CH₂C≡CH | CF₃ |
| Me | Me | H | H | 2 | H | H | CF₃ | CH₂C≡CH | CN |
| Me | Me | H | H | 2 | H | H | CN | CH₂C≡CH | CF₃ |
| Me | Me | H | H | 2 | H | H | CF₃ | CH₂C≡CH | Me |
| Me | Me | H | H | 2 | H | H | Me | CH₂C≡CH | CF₃ |
| Me | Me | H | H | 2 | H | H | CF₃ | CHMeC≡CH | Cl |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 2 | H | H | Cl | CHMeC≡CH | CF₃ |
| Me | Me | H | H | 2 | H | H | CF₃ | CH₂C≡CMe | Cl |
| Me | Me | H | H | 2 | H | H | Cl | CH₂C≡CMe | CF₃ |
| Me | Me | H | H | 2 | H | H | Me | CHF₂ | F |
| Me | Me | H | H | 2 | H | H | F | CHF₂ | Me |
| Me | Me | H | H | 2 | H | H | Me | CHF₂ | Cl |
| Me | Me | H | H | 2 | H | H | Cl | CHF₂ | Me |
| Me | Me | H | H | 2 | H | H | Me | CHF₂ | OMe |
| Me | Me | H | H | 2 | H | H | OMe | CHF₂ | Me |
| Me | Me | H | H | 2 | H | H | Me | CHF₂ | OCHF₂ |
| Me | Me | H | H | 2 | H | H | OCHF₂ | CHF₂ | Me |
| Me | Me | H | H | 2 | H | H | Me | CHF₂ | CN |
| Me | Me | H | H | 2 | H | H | CN | CHF₂ | Me |
| Me | Me | H | H | 2 | H | H | Me | CHF₂ | Me |
| Me | Me | H | H | 2 | H | H | Et | CHF₂ | Cl |
| Me | Me | H | H | 2 | H | H | Cl | CHF₂ | Et |
| Me | Me | H | H | 2 | H | H | Et | CHF₂ | Et |
| Me | Me | H | H | 2 | H | H | Pr-i | CHF₂ | Cl |
| Me | Me | H | H | 2 | H | H | Cl | CHF₂ | Pr-i |
| Me | Me | H | H | 2 | H | H | Cl | CHF₂ | Cl |
| Me | Me | H | H | 2 | H | H | OCHF₂ | CHF₂ | Cl |
| Me | Me | H | H | 2 | H | H | Cl | CHF₂ | OCHF₂ |
| Me | Me | H | H | 2 | H | H | OCHF₂ | CHF₂ | OCHF₂ |
| Me | Me | H | H | 2 | H | H | CF₃ | CHF₂ | Cl |
| Me | Me | H | H | 2 | H | H | Cl | CHF₂ | CF₃ |
| Me | Me | H | H | 2 | H | H | CF₃ | CHF₂ | F |
| Me | Me | H | H | 2 | H | H | F | CHF₂ | CF₃ |
| Me | Me | H | H | 2 | H | H | CF₃ | CHF₂ | OMe |
| Me | Me | H | H | 2 | H | H | OMe | CHF₂ | CF₃ |
| Me | Me | H | H | 2 | H | H | CF₃ | CHF₂ | OEt |
| Me | Me | H | H | 2 | H | H | OEt | CHF₂ | CF₃ |
| Me | Me | H | H | 2 | H | H | CF₃ | CHF₂ | OCHF₂ |
| Me | Me | H | H | 2 | H | H | OCHF₂ | CHF₂ | CF₃ |
| Me | Me | H | H | 2 | H | H | CF₃ | CHF₂ | CN |
| Me | Me | H | H | 2 | H | H | CN | CHF₂ | CF₃ |
| Me | Me | H | H | 2 | H | H | CF₃ | CHF₂ | Me |
| Me | Me | H | H | 2 | H | H | Me | CHF₂ | CF₃ |
| Me | Me | H | H | 2 | H | H | CF₃ | CH₂CHF₂ | Cl |
| Me | Me | H | H | 2 | H | H | Cl | CH₂CHF₂ | CF₃ |
| Me | Me | H | H | 2 | H | H | CF₃ | CH₂CF₃ | Cl |
| Me | Me | H | H | 2 | H | H | Cl | CH₂CF₃ | CF₃ |
| Me | Me | H | H | 2 | H | H | CF₃ | CH₂OH | Cl |
| Me | Me | H | H | 2 | H | H | Cl | CH₂OH | CF₃ |
| Me | Me | H | H | 2 | H | H | Me | CH₂OMe | OCHF₂ |
| Me | Me | H | H | 2 | H | H | OCHF₂ | CH₂OMe | Me |
| Me | Me | H | H | 2 | H | H | Cl | CH₂OMe | Cl |
| Me | Me | H | H | 2 | H | H | OCHF₂ | CH₂OMe | Cl |
| Me | Me | H | H | 2 | H | H | Cl | CH₂OMe | OCHF₂ |
| Me | Me | H | H | 2 | H | H | OCHF₂ | CH₂OMe | OCHF₂ |
| Me | Me | H | H | 2 | H | H | CF₃ | CH₂OMe | F |
| Me | Me | H | H | 2 | H | H | F | CH₂OMe | CF₃ |
| Me | Me | H | H | 2 | H | H | CF₃ | CH₂OMe | Cl |
| Me | Me | H | H | 2 | H | H | Cl | CH₂OMe | CF₃ |
| Me | Me | H | H | 2 | H | H | CF₃ | CH₂OMe | OMe |
| Me | Me | H | H | 2 | H | H | OMe | CH₂OMe | CF₃ |
| Me | Me | H | H | 2 | H | H | CF₃ | CH₂OMe | OEt |
| Me | Me | H | H | 2 | H | H | OEt | CH₂OMe | CF₃ |
| Me | Me | H | H | 2 | H | H | CF₃ | CH₂OMe | OCHF₂ |
| Me | Me | H | H | 2 | H | H | OCHF₂ | CH₂OMe | CF₃ |
| Me | Me | H | H | 2 | H | H | CF₃ | CH₂OMe | CN |
| Me | Me | H | H | 2 | H | H | CN | CH₂OMe | CF₃ |
| Me | Me | H | H | 2 | H | H | CF₃ | CH₂OMe | Me |
| Me | Me | H | H | 2 | H | H | Me | CH₂OMe | CF₃ |
| Me | Me | H | H | 2 | H | H | CF₃ | CH₂OEt | Cl |
| Me | Me | H | H | 2 | H | H | Cl | CH₂OEt | CF₃ |
| Me | Me | H | H | 2 | H | H | CF₃ | CH₂CH₂OH | Cl |

TABLE 3-continued

| $R^1$ | $R^2$ | $R^3$ | $R^4$ | n | $R^5$ | $R^6$ | $R^{29}$ | $R^{28}$ | $R^{30}$ |
|---|---|---|---|---|---|---|---|---|---|
| Me | Me | H | H | 2 | H | H | Cl | $CH_2CH_2OH$ | $CF_3$ |
| Me | Me | H | H | 2 | H | H | $CF_3$ | $CH_2CH_2OMe$ | Cl |
| Me | Me | H | H | 2 | H | H | Cl | $CH_2CH_2OMe$ | $CF_3$ |
| Me | Me | H | H | 2 | H | H | $CF_3$ | $CH_2CH_2OEt$ | Cl |
| Me | Me | H | H | 2 | H | H | Cl | $CH_2CH_2OEt$ | $CF_3$ |
| Me | Me | H | H | 2 | H | H | $CF_3$ | $CH_2NHMe$ | Cl |
| Me | Me | H | H | 2 | H | H | Cl | $CH_2NHMe$ | $CF_3$ |
| Me | Me | H | H | 2 | H | H | $CF_3$ | $CH_2N(Me)_2$ | Cl |
| Me | Me | H | H | 2 | H | H | Cl | $CH_2N(Me)_2$ | $CF_3$ |
| Me | Me | H | H | 2 | H | H | $CF_3$ | $CH_2N(Me)C(=O)Me$ | Cl |
| Me | Me | H | H | 2 | H | H | Cl | $CH_2N(Me)C(=O)Me$ | $CF_3$ |
| Me | Me | H | H | 2 | H | H | $CF_3$ | $CH_2N(Me)C(=O)CF_3$ | Cl |
| Me | Me | H | H | 2 | H | H | Cl | $CH_2N(Me)C(=O)CF_3$ | |
| Me | Me | H | H | 2 | H | H | $CF_3$ | $CH_2N(Me)SO_2Me$ | Cl |
| Me | Me | H | H | 2 | H | H | Cl | $CH_2N(Me)SO_2Me$ | $CF_3$ |
| Me | Me | H | H | 2 | H | H | $CF_3$ | $CH_2N(Me)SO_2CHF_2$ | Cl |
| Me | Me | H | H | 2 | H | H | Cl | $CH_2N(Me)SO_2CHF_2$ | $CF_3$ |
| Me | Me | H | H | 2 | H | H | $CF_3$ | $CH_2N(Me)SO_2CF_3$ | Cl |
| Me | Me | H | H | 2 | H | H | Cl | $CH_2N(Me)SO_2CF_3$ | $CF_3$ |
| Me | Me | H | H | 2 | H | H | $CF_3$ | $CH_2SMe$ | Cl |
| Me | Me | H | H | 2 | H | H | Cl | $CH_2SMe$ | $CF_3$ |
| Me | Me | H | H | 2 | H | H | $CF_3$ | $CH_2SO_2Me$ | Cl |
| Me | Me | H | H | 2 | H | H | Cl | $CH_2SO_2Me$ | $CF_3$ |
| Me | Me | H | H | 2 | H | H | $CF_3$ | $CH_2CH_2SMe$ | Cl |
| Me | Me | H | H | 2 | H | H | Cl | $CH_2CH_2SMe$ | $CF_3$ |
| Me | Me | H | H | 2 | H | H | $CF_3$ | $CH_2CH_2SO_2Me$ | Cl |
| Me | Me | H | H | 2 | H | H | Cl | $CH_2CH_2SO_2Me$ | $CF_3$ |
| Me | Me | H | H | 2 | H | H | $CF_3$ | $CH_2CN$ | Cl |
| Me | Me | H | H | 2 | H | H | Cl | $CH_2CN$ | $CF_3$ |
| Me | Me | H | H | 2 | H | H | $CF_3$ | $CH_2C(=O)OMe$ | Cl |
| Me | Me | H | H | 2 | H | H | Cl | $CH_2C(=O)OMe$ | $CF_3$ |
| Me | Me | H | H | 2 | H | H | $CF_3$ | $CH_2C(=O)OEt$ | Cl |
| Me | Me | H | H | 2 | H | H | Cl | $CH_2C(=O)OEt$ | $CF_3$ |
| Me | Me | H | H | 2 | H | H | $CF_3$ | $CH(Me)C(=O)OMe$ | Cl |
| Me | Me | H | H | 2 | H | H | Cl | $CH(Me)C(=O)OMe$ | $CF_3$ |
| Me | Me | H | H | 2 | H | H | $CF_3$ | $C(Me)_2C(=O)OMe$ | Cl |
| Me | Me | H | H | 2 | H | H | Cl | $C(Me)_2C(=O)OMe$ | $CF_3$ |
| Me | Me | H | H | 2 | H | H | $CF_3$ | $CH_2C(=O)NH_2$ | Cl |
| Me | Me | H | H | 2 | H | H | Cl | $CH_2C(=O)NH_2$ | $CF_3$ |
| Me | Me | H | H | 2 | H | H | $CF_3$ | $CH_2C(=O)NHMe$ | Cl |
| Me | Me | H | H | 2 | H | H | Cl | $CH_2C(=O)NHMe$ | $CF_3$ |
| Me | Me | H | H | 2 | H | H | $CF_3$ | $CH_2C(=O)N(Me)_2$ | Cl |
| Me | Me | H | H | 2 | H | H | Cl | $CH_2C(=O)N(Me)_2$ | $CF_3$ |
| Me | Me | H | H | 2 | H | H | $CF_3$ | $CH_2C(=O)Me$ | Cl |
| Me | Me | H | H | 2 | H | H | Cl | $CH_2C(=O)Me$ | $CF_3$ |
| Me | Me | H | H | 2 | H | H | $CF_3$ | $CH_2C(=NOMe)Me$ | Cl |
| Me | Me | H | H | 2 | H | H | Cl | $CH_2C(=NOMe)Me$ | $CF_3$ |
| Me | Me | H | H | 2 | H | H | $CF_3$ | $CH_2C(=O)CF_3$ | Cl |
| Me | Me | H | H | 2 | H | H | Cl | $CH_2C(=O)CF_3$ | $CF_3$ |
| Me | Me | H | H | 2 | H | H | $CF_3$ | $CH_2CH_2C(=O)Me$ | Cl |
| Me | Me | H | H | 2 | H | H | Cl | $CH_2CH_2C(=O)Me$ | $CF_3$ |
| Me | Me | H | H | 2 | H | H | Me | Ph | Me |
| Me | Me | H | H | 2 | H | H | Me | Ph | F |
| Me | Me | H | H | 2 | H | H | Me | Ph | Cl |
| Me | Me | H | H | 2 | H | H | Me | Ph | $OCHF_2$ |
| Me | Me | H | H | 2 | H | H | Me | Ph | CN |
| Me | Me | H | H | 2 | H | H | Et | Ph | F |
| Me | Me | H | H | 2 | H | H | Et | Ph | Cl |
| Me | Me | H | H | 2 | H | H | Et | Ph | $OCHF_2$ |
| Me | Me | H | H | 2 | H | H | Et | Ph | CN |
| Me | Me | H | H | 2 | H | H | Pr | Ph | F |
| Me | Me | H | H | 2 | H | H | Pr | Ph | Cl |
| Me | Me | H | H | 2 | H | H | Pr | Ph | $OCHF_2$ |
| Me | Me | H | H | 2 | H | H | Pr | Ph | CN |
| Me | Me | H | H | 2 | H | H | Pr-i | Ph | F |
| Me | Me | H | H | 2 | H | H | Pr-i | Ph | Cl |

TABLE 3-continued

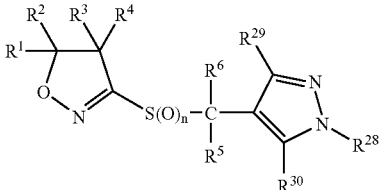

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 2 | H | H | Pr-i | Ph | OCHF₂ |
| Me | Me | H | H | 2 | H | H | Pr-i | Ph | CN |
| Me | Me | H | H | 2 | H | H | Bu-t | Ph | Cl |
| Me | Me | H | H | 2 | H | H | CH₂OMe | Ph | Cl |
| Me | Me | H | H | 2 | H | H | Cl | Ph | Cl |
| Me | Me | H | H | 2 | H | H | OCHF₂ | Ph | Cl |
| Me | Me | H | H | 2 | H | H | OCHF₂ | Ph | OCHF₂ |
| Me | Me | H | H | 2 | H | H | CHF₂ | Ph | Cl |
| Me | Me | H | H | 2 | H | H | CF₃ | Ph | H |
| Me | Me | H | H | 2 | H | H | CF₃ | Ph | Me |
| Me | Me | H | H | 2 | H | H | Me | Ph | CF₃ |
| Me | Me | H | H | 2 | H | H | CF₃ | Ph | Et |
| Me | Me | H | H | 2 | H | H | CF₃ | Ph | Pr-i |
| Me | Me | H | H | 2 | H | H | CF₃ | Ph | CHF₂ |
| Me | Me | H | H | 2 | H | H | CF₃ | Ph | CF₃ |
| Me | Me | H | H | 2 | H | H | CF₃ | Ph | F |
| Me | Me | H | H | 2 | H | H | CF₃ | Ph | Cl |
| Me | Me | H | H | 2 | H | H | Cl | Ph | CF₃ |
| Me | Me | H | H | 2 | H | H | CF₃ | Ph | OH |
| Me | Me | H | H | 2 | H | H | OH | Ph | CF₃ |
| Me | Me | H | H | 2 | H | H | CF₃ | Ph | OMe |
| Me | Me | H | H | 2 | H | H | OMe | Ph | CF₃ |
| Me | Me | H | H | 2 | H | H | CF₃ | Ph | OEt |
| Me | Me | H | H | 2 | H | H | OEt | Ph | CF₃ |
| Me | Me | H | H | 2 | H | H | CF₃ | Ph | OPr-i |
| Me | Me | H | H | 2 | H | H | CF₃ | Ph | OPr |
| Me | Me | H | H | 2 | H | H | CF₃ | Ph | OBu-t |
| Me | Me | H | H | 2 | H | H | CF₃ | Ph | OCH₂Pr-c |
| Me | Me | H | H | 2 | H | H | CF₃ | Ph | OCH₂CH=CH₂ |
| Me | Me | H | H | 2 | H | H | CF₃ | Ph | OCH₂C≡CH |
| Me | Me | H | H | 2 | H | H | CF₃ | Ph | OCHF₂ |
| Me | Me | H | H | 2 | H | H | OCHF₂ | Ph | CF₃ |
| Me | Me | H | H | 2 | H | H | CF₃ | Ph | OCH₂CHF₂ |
| Me | Me | H | H | 2 | H | H | CF₃ | Ph | OCH₂CF₃ |
| Me | Me | H | H | 2 | H | H | CF₃ | Ph | OCH₂C(=O)OMe |
| Me | Me | H | H | 2 | H | H | CF₃ | Ph | OCH(Me)C(=O)OMe |
| Me | Me | H | H | 2 | H | H | CF₃ | Ph | OC(Me)₂C(=O)OMe |
| Me | Me | H | H | 2 | H | H | CF₃ | Ph | OC(=O)Me |
| Me | Me | H | H | 2 | H | H | CF₃ | Ph | OC(=O)Et |
| Me | Me | H | H | 2 | H | H | CF₃ | Ph | OC(=O)CH₂Ph |
| Me | Me | H | H | 2 | H | H | CF₃ | Ph | OC(=O)CF₃ |
| Me | Me | H | H | 2 | H | H | CF₃ | Ph | OC(=O)Ph |
| Me | Me | H | H | 2 | H | H | CF₃ | Ph | OSO₂Me |
| Me | Me | H | H | 2 | H | H | CF₃ | Ph | OSO₂Et |
| Me | Me | H | H | 2 | H | H | CF₃ | Ph | OSO₂CH₂Ph |
| Me | Me | H | H | 2 | H | H | CF₃ | Ph | OSO₂CF₃ |
| Me | Me | H | H | 2 | H | H | CF₃ | Ph | OSO₂Ph |
| Me | Me | H | H | 2 | H | H | CF₃ | Ph | SMe |
| Me | Me | H | H | 2 | H | H | CF₃ | Ph | SOMe |
| Me | Me | H | H | 2 | H | H | CF₃ | Ph | SO₂Me |
| Me | Me | H | H | 2 | H | H | CF₃ | Ph | SEt |
| Me | Me | H | H | 2 | H | H | CF₃ | Ph | SOEt |
| Me | Me | H | H | 2 | H | H | CF₃ | Ph | SO₂Et |
| Me | Me | H | H | 2 | H | H | CF₃ | Ph | SPr-i |
| Me | Me | H | H | 2 | H | H | CF₃ | Ph | SOPr-i |
| Me | Me | H | H | 2 | H | H | CF₃ | Ph | SO₂Pr-i |
| Me | Me | H | H | 2 | H | H | CF₃ | Ph | SPr |
| Me | Me | H | H | 2 | H | H | CF₃ | Ph | SOPr |
| Me | Me | H | H | 2 | H | H | CF₃ | Ph | SO₂Pr |
| Me | Me | H | H | 2 | H | H | CF₃ | Ph | SBu-t |
| Me | Me | H | H | 2 | H | H | CF₃ | Ph | SOBu-t |
| Me | Me | H | H | 2 | H | H | CF₃ | Ph | SO₂Bu-t |
| Me | Me | H | H | 2 | H | H | CF₃ | Ph | SCHF₂ |
| Me | Me | H | H | 2 | H | H | CF₃ | Ph | SOCHF₂ |
| Me | Me | H | H | 2 | H | H | CF₃ | Ph | SO₂CHF₂ |
| Me | Me | H | H | 2 | H | H | CF₃ | Ph | NH₂ |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 2 | H | H | CF₃ | Ph | NHMe |
| Me | Me | H | H | 2 | H | H | CF₃ | Ph | N(Me)₂ |
| Me | Me | H | H | 2 | H | H | CF₃ | Ph | NHC(=O)Me |
| Me | Me | H | H | 2 | H | H | CF₃ | Ph | N(Me)C(=O)Me |
| Me | Me | H | H | 2 | H | H | CF₃ | Ph | NHSO₂Me |
| Me | Me | H | H | 2 | H | H | CF₃ | Ph | N(Me)SO₂Me |
| Me | Me | H | H | 2 | H | H | CF₃ | Ph | NHSO₂CF₃ |
| Me | Me | H | H | 2 | H | H | CF₃ | Ph | N(Me)SO₂CF₃ |
| Me | Me | H | H | 2 | H | H | CF₃ | Ph | NHPh |
| Me | Me | H | H | 2 | H | H | CF₃ | Ph | N(Me)Ph |
| Me | Me | H | H | 2 | H | H | CF₃ | Ph | CN |
| Me | Me | H | H | 2 | H | H | CF₃ | Ph | C(=O)Me |
| Me | Me | H | H | 2 | H | H | CF₃ | Ph | C(=O)OMe |
| Me | Me | H | H | 2 | H | H | CF₃ | Ph | C(=O)NH₂ |
| Me | Me | H | H | 2 | H | H | CF₃ | Ph | C(=O)NHMe |
| Me | Me | H | H | 2 | H | H | CF₃ | Ph | C(=O)N(Me)₂ |
| Me | Me | H | H | 2 | H | H | CF₃ | Ph | Imidazol-1-yl |
| Me | Me | H | H | 2 | H | H | CF₃ | Ph | Pyrazol-1-yl |
| Me | Me | H | H | 2 | H | H | CF₃ | Ph | 1,2,4-Triazol-1-yl |
| Me | Me | H | H | 2 | H | H | CF₃ | Ph | 1,2,4-Triazol-4-yl |
| Me | Me | H | H | 2 | H | H | CF₃ | Ph | Tetrazol-1-yl |
| Me | Me | H | H | 2 | H | H | CF₃ | Ph | Tetrazol-5-yl |
| Me | Me | H | H | 2 | H | H | CF₃ | Ph | (4,6-Dimethoxypyrimidin-2-yl)oxy |
| Me | Me | H | H | 2 | H | H | CF₃ | Ph | (4,6-Dimethoxypyrimidin-2-yl)sulfonyl |
| Me | Me | H | H | 2 | H | H | CF₂CF₃ | Ph | Cl |
| Me | Me | H | H | 2 | H | H | CF₃ | (2-Cl)Ph | Cl |
| Me | Me | H | H | 2 | H | H | CF₃ | (2-F)Ph | Cl |
| Me | Me | H | H | 2 | H | H | CF₃ | (2-OMe)Ph | Cl |
| Me | Me | H | H | 2 | H | H | CF₃ | (2-Me)Ph | Cl |
| Me | Me | H | H | 2 | H | H | CF₃ | (2-NO₂)Ph | Cl |
| Me | Me | H | H | 2 | H | H | CF₃ | (2-CN)Ph | Cl |
| Me | Me | H | H | 2 | H | H | CF₃ | (2-C(=O)Me)Ph | Cl |
| Me | Me | H | H | 2 | H | H | CF₃ | (2-C(=O)OMe)Ph | Cl |
| Me | Me | H | H | 2 | H | H | CF₃ | (2-C(=O)OEt)Ph | Cl |
| Me | Me | H | H | 2 | H | H | CF₃ | (2-C(=O)OPr-i)Ph | Cl |
| Me | Me | H | H | 2 | H | H | CF₃ | (2-C(=O)NH₂)Ph | Cl |
| Me | Me | H | H | 2 | H | H | CF₃ | (2-C(=O)NHMe)Ph | Cl |
| Me | Me | H | H | 2 | H | H | CF₃ | (2-C(=O)NMe₂)Ph | Cl |
| Me | Me | H | H | 2 | H | H | CF₃ | (3-Cl)Ph | Cl |
| Me | Me | H | H | 2 | H | H | CF₃ | (3-F)Ph | Cl |
| Me | Me | H | H | 2 | H | H | CF₃ | (3-OMe)Ph | Cl |
| Me | Me | H | H | 2 | H | H | CF₃ | (3-Me)Ph | Cl |
| Me | Me | H | H | 2 | H | H | CF₃ | (3-NO₂)Ph | Cl |
| Me | Me | H | H | 2 | H | H | CF₃ | (3-CN)Ph | Cl |
| Me | Me | H | H | 2 | H | H | CF₃ | (3-C(=O)Me)Ph | Cl |
| Me | Me | H | H | 2 | H | H | CF₃ | (3-C(=O)OMe)Ph | Cl |
| Me | Me | H | H | 2 | H | H | CF₃ | (3-C(=)OEt)Ph | Cl |
| Me | Me | H | H | 2 | H | H | CF₃ | (3-C(=O)OPr-i)Ph | Cl |
| Me | Me | H | H | 2 | H | H | CF₃ | (3-C(=O)NH₂)Ph | Cl |
| Me | Me | H | H | 2 | H | H | CF₃ | (3-C(=O)NHMe)Ph | Cl |
| Me | Me | H | H | 2 | H | H | CF₃ | (3-C(=O)NMe₂)Ph | Cl |
| Me | Me | H | H | 2 | H | H | CF₃ | (4-Cl)Ph | Cl |
| Me | Me | H | H | 2 | H | H | CF₃ | (4-F)Ph | Cl |
| Me | Me | H | H | 2 | H | H | CF₃ | (4-OMe)Ph | Cl |
| Me | Me | H | H | 2 | H | H | CF₃ | (4-Me)Ph | Cl |
| Me | Me | H | H | 2 | H | H | CF₃ | (4-NO₂)Ph | Cl |
| Me | Me | H | H | 2 | H | H | CF₃ | (4-CN)Ph | Cl |
| Me | Me | H | H | 2 | H | H | CF₃ | (4-C(=O)MePh | Cl |
| Me | Me | H | H | 2 | H | H | CF₃ | (4-C(=O)OMe)Ph | Cl |
| Me | Me | H | H | 2 | H | H | CF₃ | (4-C(=O)OEt)Ph | Cl |
| Me | Me | H | H | 2 | H | H | CF₃ | (4-C(=O)OPr-i)Ph | Cl |
| Me | Me | H | H | 2 | H | H | CF₃ | (4-C(=O)NH₂)Ph | Cl |
| Me | Me | H | H | 2 | H | H | CF₃ | (4-C(=O)NHMe)Ph | Cl |
| Me | Me | H | H | 2 | H | H | CF₃ | (4-C(=O)NMe₂)Ph | Cl |
| Me | Me | H | H | 2 | H | H | CF₃ | Pyrmidin-2-yl | Cl |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 2 | H | H | CF₃ | 4,6-Dimethoxypyrimidin-2-yl | Cl |
| Me | Me | H | H | 2 | H | H | CF₃ | Thiophen-2-yl | Cl |
| Me | Me | H | H | 2 | H | H | CF₃ | Furan-2-yl | Cl |
| Me | Me | H | H | 2 | H | H | CF₃ | SO₂Me | Cl |
| Me | Me | H | H | 2 | H | H | CF₃ | SO₂Et | Cl |
| Me | Me | H | H | 2 | H | H | CF₃ | SO₂Pr-i | Cl |
| Me | Me | H | H | 2 | H | H | CF₃ | SO₂CH₂Ph | Cl |
| Me | Me | H | H | 2 | H | H | CF₃ | SO₂CHF₂ | Cl |
| Me | Me | H | H | 2 | H | H | CF₃ | SO₂CF₃ | Cl |
| Me | Me | H | H | 2 | H | H | CF₃ | SO₂Ph | Cl |
| Me | Me | H | H | 2 | H | H | CF₃ | C(=O)Me | Cl |
| Me | Me | H | H | 2 | H | H | CF₃ | C(=O)Et | Cl |
| Me | Me | H | H | 2 | H | H | CF₃ | C(=O)Pr-i | Cl |
| Me | Me | H | H | 2 | H | H | CF₃ | C(=O)Bu-t | Cl |
| Me | Me | H | H | 2 | H | H | CF₃ | C(=O)Ph | Cl |
| Me | Me | H | H | 2 | H | H | CF₃ | C(=O)CH₂Ph | Cl |
| Me | Me | H | H | 2 | H | H | CF₃ | C(=O)CH₂Cl | Cl |
| Me | Me | H | H | 2 | H | H | CF₃ | C(=O)CHCl₂ | Cl |
| Me | Me | H | H | 2 | H | H | CF₃ | C(=O)CF₃ | Cl |
| Me | Me | H | H | 2 | H | H | CF₃ | C(=O)OMe | Cl |
| Me | Me | H | H | 2 | H | H | CF₃ | C(=O)OPh | Cl |
| Me | Me | H | H | 2 | H | H | CF₃ | C(=O)OCH₂Ph | Cl |
| Me | Me | H | H | 2 | H | H | CF₃ | C(=O)NHMe | Cl |
| Me | Me | H | H | 2 | H | H | CF₃ | C(=O)N(Me)₂ | Cl |
| Me | Me | H | H | 2 | H | H | CF₃ | C(=O)NHPh | Cl |
| Me | Me | H | H | 2 | H | H | CF₃ | NH₂ | Cl |
| Me | Me | H | H | 2 | H | H | Cl | —(CH₂)₂O— | |
| Me | Me | H | H | 2 | H | H | Cl | —(CH₂)₃O— | |
| Me | Me | H | H | 2 | H | H | Cl | —(CH₂)₃S— | |
| Me | Me | H | H | 2 | H | H | Cl | —(CH₂)₃SO₂— | |
| Me | Me | H | H | 2 | H | H | CF₃ | —(CH₂)₂O— | |
| Me | Me | H | H | 2 | H | H | CF₃ | —(CH₂)₃O— | |
| Me | Me | H | H | 2 | H | H | CF₃ | —(CH₂)₃S— | |
| Me | Me | H | H | 2 | H | H | CF₃ | —(CH₂)₃SO₂— | |
| Me | Me | H | H | 2 | H | H | OMe | —(CH₂)₄— | |
| Me | Me | H | H | 2 | H | H | OCHF₂ | —(CH₂)₄— | |
| H | H | H | H | 2 | H | H | CF₃ | Me | Cl |
| Me | H | H | H | 2 | H | H | CF₃ | Me | Cl |
| Me | H | Me | H | 2 | H | H | CF₃ | Me | Cl |
| Me | Me | Me | H | 2 | H | H | CF₃ | Me | Cl |
| Me | Me | H | H | 2 | Me | H | CF₃ | Me | Cl |
| Me | Me | H | H | 2 | Et | H | CF₃ | Me | Cl |
| Me | Me | H | H | 2 | Pr-i | H | CF₃ | Me | Cl |
| Me | Me | H | H | 2 | Me | Me | CF₃ | Me | Cl |
| Me | Et | H | H | 2 | H | H | CF₃ | Me | Cl |
| Et | Et | H | H | 2 | H | H | CF₃ | Me | Cl |
| Me | Pr-i | H | H | 2 | H | H | CF₃ | Me | Cl |
| Me | Pr | H | H | 2 | H | H | CF₃ | Me | Cl |
| Me | Pr-c | H | H | 2 | H | H | CF₃ | Me | Cl |
| Me | CH₂Pr-c | H | H | 2 | H | H | CF₃ | Me | Cl |
| —(CH₂)₂— | | H | H | 2 | H | H | CF₃ | Me | Cl |
| —(CH₂)₃— | | H | H | 2 | H | H | CF₃ | Me | Cl |
| —(CH₂)₄— | | H | H | 2 | H | H | CF₃ | Me | Cl |
| —(CH₂)₅— | | H | H | 2 | H | H | CF₃ | Me | Cl |
| H | —(CH₂)₃— | | H | 2 | H | H | CF₃ | Me | Cl |
| H | —(CH₂)₄— | | H | 2 | H | H | CF₃ | Me | Cl |
| H | —(CH₂)₅— | | H | 2 | H | H | CF₃ | Me | Cl |
| H | —(CH₂)₆— | | H | 2 | H | H | CF₃ | Me | Cl |
| Me | Me | H | H | 1 | H | H | Cl | H | Cl |
| Me | Me | H | H | 1 | H | H | OCHF₂ | H | Cl |
| Me | Me | H | H | 1 | H | H | OCHF₂ | H | OCHF₂ |
| Me | Me | H | H | 1 | H | H | CHF₂ | H | Cl |
| Me | Me | H | H | 1 | H | H | CF₃ | H | F |
| Me | Me | H | H | 1 | H | H | CF₃ | H | Cl |
| Me | Me | H | H | 1 | H | H | CF₃ | H | OMe |
| Me | Me | H | H | 1 | H | H | CF₃ | H | OEt |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 1 | H | H | CF₃ | H | OCHF₂ |
| Me | Me | H | H | 1 | H | H | CF₃ | H | CN |
| Me | Me | H | H | 1 | H | H | CF₃ | H | Me |
| Me | Me | H | H | 1 | H | H | H | Me | Cl |
| Me | Me | H | H | 1 | H | H | Me | Me | Me |
| Me | Me | H | H | 1 | H | H | Me | Me | Cl |
| Me | Me | H | H | 1 | H | H | Cl | Me | Me |
| Me | Me | H | H | 1 | H | H | Et | Me | Cl |
| Me | Me | H | H | 1 | H | H | Cl | Me | Et |
| Me | Me | H | H | 1 | H | H | Pr-i | Me | Cl |
| Me | Me | H | H | 1 | H | H | Cl | Me | Pr-i |
| Me | Me | H | H | 1 | H | H | Bu-t | Me | Cl |
| Me | Me | H | H | 1 | H | H | Cl | Me | Bu-t |
| Me | Me | H | H | 1 | H | H | Cl | Me | Cl |
| Me | Me | H | H | 1 | H | H | CHF₂ | Me | Cl |
| Me | Me | H | H | 1 | H | H | Cl | Me | CHF₂ |
| Me | Me | H | H | 1 | H | H | OCHF₂ | Me | H |
| Me | Me | H | H | 1 | H | H | OCHF₂ | Me | Cl |
| Me | Me | H | H | 1 | H | H | Cl | Me | OCHF₂ |
| Me | Me | H | H | 1 | H | H | OCHF₂ | Me | OCHF₂ |
| Me | Me | H | H | 1 | H | H | CF₃ | Me | H |
| Me | Me | H | H | 1 | H | H | CF₃ | Me | Cl |
| Me | Me | H | H | 1 | H | H | Cl | Me | CF₃ |
| Me | Me | H | H | 1 | H | H | CF₃ | Me | F |
| Me | Me | H | H | 1 | H | H | F | Me | CF₃ |
| Me | Me | H | H | 1 | H | H | CF₃ | Me | OH |
| Me | Me | H | H | 1 | H | H | OH | Me | CF₃ |
| Me | Me | H | H | 1 | H | H | CF₃ | Me | OMe |
| Me | Me | H | H | 1 | H | H | OMe | Me | CF₃ |
| Me | Me | H | H | 1 | H | H | CF₃ | Me | OEt |
| Me | Me | H | H | 1 | H | H | OEt | Me | CF₃ |
| Me | Me | H | H | 1 | H | H | CF₃ | Me | OPr-i |
| Me | Me | H | H | 1 | H | H | CF₃ | Me | OPr |
| Me | Me | H | H | 1 | H | H | CF₃ | Me | OBu-t |
| Me | Me | H | H | 1 | H | H | CF₃ | Me | OBu-s |
| Me | Me | H | H | 1 | H | H | CF₃ | Me | OBu-i |
| Me | Me | H | H | 1 | H | H | CF₃ | Me | OBu |
| Me | Me | H | H | 1 | H | H | CF₃ | Me | O(2-Pen) |
| Me | Me | H | H | 1 | H | H | CF₃ | Me | O(3-Pen) |
| Me | Me | H | H | 1 | H | H | CF₃ | Me | OPen-n |
| Me | Me | H | H | 1 | H | H | CF₃ | Me | O(2-Hex) |
| Me | Me | H | H | 1 | H | H | CF₃ | Me | O(3-Hex) |
| Me | Me | H | H | 1 | H | H | CF₃ | Me | OHex-n |
| Me | Me | H | H | 1 | H | H | CF₃ | Me | OPen-c |
| Me | Me | H | H | 1 | H | H | CF₃ | Me | OHex-c |
| Me | Me | H | H | 1 | H | H | CF₃ | Me | OCH₂Pr-c |
| Me | Me | H | H | 1 | H | H | CF₃ | Me | OCH₂Bu-c |
| Me | Me | H | H | 1 | H | H | CF₃ | Me | OCH₂Pen-c |
| Me | Me | H | H | 1 | H | H | CF₃ | Me | OCH₂Hex-c |
| Me | Me | H | H | 1 | H | H | CF₃ | Me | OCH₂CH=CH₂ |
| Me | Me | H | H | 1 | H | H | CF₃ | Me | OCH₂C≡CH |
| Me | Me | H | H | 1 | H | H | CF₃ | Me | OCHF₂ |
| Me | Me | H | H | 1 | H | H | OCHF₂ | Me | CF₃ |
| Me | Me | H | H | 1 | H | H | CF₃ | Me | OCH₂CHF₂ |
| Me | Me | H | H | 1 | H | H | OCH₂CHF₂ | Me | CF₃ |
| Me | Me | H | H | 1 | H | H | CF₃ | Me | OCH₂CF₃ |
| Me | Me | H | H | 1 | H | H | OCH₂CF₃ | Me | CF₃ |
| Me | Me | H | H | 1 | H | H | CF₃ | Me | OCH₂CN |
| Me | Me | H | H | 1 | H | H | CF₃ | Me | OCH₂C(=O)OEt |
| Me | Me | H | H | 1 | H | H | CF₃ | Me | OCH(Me)C(=O)OEt |
| Me | Me | H | H | 1 | H | H | CF₃ | Me | OCH₂C(=O)NH₂ |
| Me | Me | H | H | 1 | H | H | CF₃ | Me | OCH₂C(=O)NHMe |
| Me | Me | H | H | 1 | H | H | CF₃ | Me | OCH₂C(=O)N(Me)₂ |
| Me | Me | H | H | 1 | H | H | CF₃ | Me | OCH₂Ph |
| Me | Me | H | H | 1 | H | H | CF₃ | Me | OPh |
| Me | Me | H | H | 1 | H | H | CF₃ | Me | O(2-Cl)Ph |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 1 | H | H | CF₃ | Me | O(2-Br)Ph |
| Me | Me | H | H | 1 | H | H | CF₃ | Me | O(2-F)Ph |
| Me | Me | H | H | 1 | H | H | CF₃ | Me | O(2-Me)Ph |
| Me | Me | H | H | 1 | H | H | CF₃ | Me | O(2-OMe)Ph |
| Me | Me | H | H | 1 | H | H | CF₃ | Me | O(2-NO₂)Ph |
| Me | Me | H | H | 1 | H | H | CF₃ | Me | O(2-CN)Ph |
| Me | Me | H | H | 1 | H | H | CF₃ | Me | O(2-C(=O)OMe)Ph |
| Me | Me | H | H | 1 | H | H | CF₃ | Me | O(3-Cl)Ph |
| Me | Me | H | H | 1 | H | H | CF₃ | Me | O(3-Br)Ph |
| Me | Me | H | H | 1 | H | H | CF₃ | Me | O(3-F)Ph |
| Me | Me | H | H | 1 | H | H | CF₃ | Me | O(3-Me)Ph |
| Me | Me | H | H | 1 | H | H | CF₃ | Me | O(3-OMe)Ph |
| Me | Me | H | H | 1 | H | H | CF₃ | Me | O(3-NO₂)Ph |
| Me | Me | H | H | 1 | H | H | CF₃ | Me | O(3-CN)Ph |
| Me | Me | H | H | 1 | H | H | CF₃ | Me | O(3-C(=O)OMe)Ph |
| Me | Me | H | H | 1 | H | H | CF₃ | Me | O(4-Cl)Ph |
| Me | Me | H | H | 1 | H | H | CF₃ | Me | O(4-Br)Ph |
| Me | Me | H | H | 1 | H | H | CF₃ | Me | O(4-F)Ph |
| Me | Me | H | H | 1 | H | H | CF₃ | Me | O(4-Me)Ph |
| Me | Me | H | H | 1 | H | H | CF₃ | Me | O(4-OMe)Ph |
| Me | Me | H | H | 1 | H | H | CF₃ | Me | O(4-NO₂)Ph |
| Me | Me | H | H | 1 | H | H | CF₃ | Me | O(4-CN)Ph |
| Me | Me | H | H | 1 | H | H | CF₃ | Me | O(4-C(=O)OMe)Ph |
| Me | Me | H | H | 1 | H | H | CF₃ | Me | OC(=O)Me |
| Me | Me | H | H | 1 | H | H | CF₃ | Me | OC(=O)Et |
| Me | Me | H | H | 1 | H | H | CF₃ | Me | OC(=O)CH₂Ph |
| Me | Me | H | H | 1 | H | H | CF₃ | Me | OC(=O)CF₃ |
| Me | Me | H | H | 1 | H | H | CF₃ | Me | OC(=O)Ph |
| Me | Me | H | H | 1 | H | H | CF₃ | Me | OSO₂Me |
| Me | Me | H | H | 1 | H | H | CF₃ | Me | OSO₂Et |
| Me | Me | H | H | 1 | H | H | CF₃ | Me | OSO₂CH₂Ph |
| Me | Me | H | H | 1 | H | H | CF₃ | Me | OSO₂CF₃ |
| Me | Me | H | H | 1 | H | H | CF₃ | Me | OSO₂Ph |
| Me | Me | H | H | 1 | H | H | CF₃ | Me | SMe |
| Me | Me | H | H | 1 | H | H | CF₃ | Me | SO₂Me |
| Me | Me | H | H | 1 | H | H | CF₃ | Me | SEt |
| Me | Me | H | H | 1 | H | H | CF₃ | Me | SO₂Et |
| Me | Me | H | H | 1 | H | H | CF₃ | Me | SPr |
| Me | Me | H | H | 1 | H | H | CF₃ | Me | SO₂Pr |
| Me | Me | H | H | 1 | H | H | CF₃ | Me | SPr-i |
| Me | Me | H | H | 1 | H | H | CF₃ | Me | SO₂Pr-i |
| Me | Me | H | H | 1 | H | H | CF₃ | Me | SBu-t |
| Me | Me | H | H | 1 | H | H | CF₃ | Me | SO₂Bu-t |
| Me | Me | H | H | 1 | H | H | CF₃ | Me | SCHF₂ |
| Me | Me | H | H | 1 | H | H | CF₃ | Me | SO₂CHF₂ |
| Me | Me | H | H | 1 | H | H | CF₃ | Me | SCF₃ |
| Me | Me | H | H | 1 | H | H | CF₃ | Me | SO₂CF₃ |
| Me | Me | H | H | 1 | H | H | CF₃ | Me | SPh |
| Me | Me | H | H | 1 | H | H | CF₃ | Me | SO₂Ph |
| Me | Me | H | H | 1 | H | H | CF₃ | Me | SCH₂Ph |
| Me | Me | H | H | 1 | H | H | CF₃ | Me | SO₂CH₂Ph |
| Me | Me | H | H | 1 | H | H | CF₃ | Me | SCH₂C(=O)OEt |
| Me | Me | H | H | 1 | H | H | CF₃ | Me | SO₂CH₂C(=O)OEt |
| Me | Me | H | H | 1 | H | H | CF₃ | Me | SCH(Me)C(=O)OEt |
| Me | Me | H | H | 1 | H | H | CF₃ | Me | SO₂CH(Me)C(=O)OEt |
| Me | Me | H | H | 1 | H | H | CF₃ | Me | SCH₂C(=O)NH₂ |
| Me | Me | H | H | 1 | H | H | CF₃ | Me | SO₂CH₂C(=O)NH₂ |
| Me | Me | H | H | 1 | H | H | CF₃ | Me | SCH₂C(=O)NHMe |
| Me | Me | H | H | 1 | H | H | CF₃ | Me | SO₂CH₂C(=O)NHMe |
| Me | Me | H | H | 1 | H | H | CF₃ | Me | SCH₂C(=O)N(Me)₂ |
| Me | Me | H | H | 1 | H | H | CF₃ | Me | SO₂CH₂C(=O)N(Me)₂ |
| Me | Me | H | H | 1 | H | H | CF₃ | Me | NH₂ |
| Me | Me | H | H | 1 | H | H | CF₃ | Me | NHMe |
| Me | Me | H | H | 1 | H | H | CF₃ | Me | N(Me)₂ |
| Me | Me | H | H | 1 | H | H | CF₃ | Me | NHC(=O)Me |
| Me | Me | H | H | 1 | H | H | CF₃ | Me | N(Me)C(=O)Me |

TABLE 3-continued

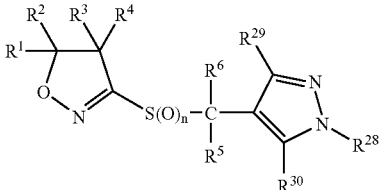

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 1 | H | H | CF₃ | Me | NHSO₂Me |
| Me | Me | H | H | 1 | H | H | CF₃ | Me | N(Me)SO₂Me |
| Me | Me | H | H | 1 | H | H | CF₃ | Me | NHSO₂CHF₂ |
| Me | Me | H | H | 1 | H | H | CF₃ | Me | N(Me)SO₂CHF₂ |
| Me | Me | H | H | 1 | H | H | CF₃ | Me | NHSO₂CF₃ |
| Me | Me | H | H | 1 | H | H | CF₃ | Me | N(Me)SO₂CF₃ |
| Me | Me | H | H | 1 | H | H | CF₃ | Me | NHPh |
| Me | Me | H | H | 1 | H | H | CF₃ | Me | N(Me)Ph |
| Me | Me | H | H | 1 | H | H | CF₃ | Me | CN |
| Me | Me | H | H | 1 | H | H | CN | Me | CF₃ |
| Me | Me | H | H | 1 | H | H | CF₃ | Me | C(=O)OMe |
| Me | Me | H | H | 1 | H | H | CF₃ | Me | C(=O)OCH₂Ph |
| Me | Me | H | H | 1 | H | H | CF₃ | Me | C(=O)OPh |
| Me | Me | H | H | 1 | H | H | CF₃ | Me | C(=O)NH₂ |
| Me | Me | H | H | 1 | H | H | CF₃ | Me | C(=O)NHMe |
| Me | Me | H | H | 1 | H | H | CF₃ | Me | C(=O)N(Me)₂ |
| Me | Me | H | H | 1 | H | H | CF₃ | Me | C(=O)Me |
| Me | Me | H | H | 1 | H | H | CF₃ | Me | C(=O)CF₃ |
| Me | Me | H | H | 1 | H | H | CF₃ | Me | C(=O)CH₂ph |
| Me | Me | H | H | 1 | H | H | CF₃ | Me | C(=O)Ph |
| Me | Me | H | H | 1 | H | H | CF₃ | Me | Me |
| Me | Me | H | H | 1 | H | H | Me | Me | CF₃ |
| Me | Me | H | H | 1 | H | H | CF₃ | Me | Et |
| Me | Me | H | H | 1 | H | H | CF₃ | Me | Pr-i |
| Me | Me | H | H | 1 | H | H | CF₃ | Me | Pr |
| Me | Me | H | H | 1 | H | H | CF₃ | Me | CH₂OMe |
| Me | Me | H | H | 1 | H | H | CF₃ | Me | CF₃ |
| Me | Me | H | H | 1 | H | H | CF₃ | Me | CHF₂ |
| Me | Me | H | H | 1 | H | H | CF₃ | Me | Ph |
| Me | Me | H | H | 1 | H | H | CF₂CF₃ | Me | Cl |
| Me | Me | H | H | 1 | H | H | Ph | Me | Me |
| Me | Me | H | H | 1 | H | H | Ph | Me | Cl |
| Me | Me | H | H | 1 | H | H | Ph | Me | OEt |
| Me | Me | H | H | 1 | H | H | Ph | Me | CF₃ |
| Me | Me | H | H | 1 | H | H | Ph | Me | Ph |
| Me | Me | H | H | 1 | H | H | Cl | Et | Cl |
| Me | Me | H | H | 1 | H | H | OCHF₂ | Et | Cl |
| Me | Me | H | H | 1 | H | H | Cl | Et | OCHF₂ |
| Me | Me | H | H | 1 | H | H | OCHF₂ | Et | OCHF₂ |
| Me | Me | H | H | 1 | H | H | CF₃ | Et | F |
| Me | Me | H | H | 1 | H | H | F | Et | CF₃ |
| Me | Me | H | H | 1 | H | H | CF₃ | Et | Cl |
| Me | Me | H | H | 1 | H | H | Cl | Et | CF₃ |
| Me | Me | H | H | 1 | H | H | CF₃ | Et | OMe |
| Me | Me | H | H | 1 | H | H | OMe | Et | CF₃ |
| Me | Me | H | H | 1 | H | H | CF₃ | Et | OEt |
| Me | Me | H | H | 1 | H | H | OEt | Et | CF₃ |
| Me | Me | H | H | 1 | H | H | CF₃ | Et | OCHF₂ |
| Me | Me | H | H | 1 | H | H | OCHF₂ | Et | CF₃ |
| Me | Me | H | H | 1 | H | H | CF₃ | Et | CN |
| Me | Me | H | H | 1 | H | H | CN | Et | CF₃ |
| Me | Me | H | H | 1 | H | H | CF₃ | Et | Me |
| Me | Me | H | H | 1 | H | H | Me | Et | CF₃ |
| Me | Me | H | H | 1 | H | H | Cl | Pr-i | Cl |
| Me | Me | H | H | 1 | H | H | OCHF₂ | Pr-i | Cl |
| Me | Me | H | H | 1 | H | H | Cl | Pr-i | OCHF₂ |
| Me | Me | H | H | 1 | H | H | OCHF₂ | Pr-i | OCHF₂ |
| Me | Me | H | H | 1 | H | H | CF₃ | Pr-i | F |
| Me | Me | H | H | 1 | H | H | F | Pr-i | CF₃ |
| Me | Me | H | H | 1 | H | H | CF₃ | Pr-i | Cl |
| Me | Me | H | H | 1 | H | H | Cl | Pr-i | CF₃ |
| Me | Me | H | H | 1 | H | H | CF₃ | Pr-i | OMe |
| Me | Me | H | H | 1 | H | H | OMe | Pr-i | CF₃ |
| Me | Me | H | H | 1 | H | H | CF₃ | Pr-i | OEt |
| Me | Me | H | H | 1 | H | H | OEt | Pr-i | CF₃ |
| Me | Me | H | H | 1 | H | H | CF₃ | Pr-i | OCHF₂ |

TABLE 3-continued

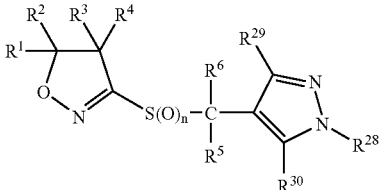

| R$^1$ | R$^2$ | R$^3$ | R$^4$ | n | R$^5$ | R$^6$ | R$^{29}$ | R$^{28}$ | R$^{30}$ |
|---|---|---|---|---|---|---|---|---|---|
| Me | Me | H | H | 1 | H | H | OCHF$_2$ | Pr-i | CF$_3$ |
| Me | Me | H | H | 1 | H | H | CF$_3$ | Pr-i | CN |
| Me | Me | H | H | 1 | H | H | CN | Pr-i | CF$_3$ |
| Me | Me | H | H | 1 | H | H | CF$_3$ | Pr-i | Me |
| Me | Me | H | H | 1 | H | H | Me | Pr-i | CF$_3$ |
| Me | Me | H | H | 1 | H | H | Cl | Pr | Cl |
| Me | Me | H | H | 1 | H | H | OCHF$_2$ | Pr | Cl |
| Me | Me | H | H | 1 | H | H | Cl | Pr | OCHF$_2$ |
| Me | Me | H | H | 1 | H | H | OCHF$_2$ | Pr | OCHF$_2$ |
| Me | Me | H | H | 1 | H | H | CF$_3$ | Pr | F |
| Me | Me | H | H | 1 | H | H | F | Pr | CF$_3$ |
| Me | Me | H | H | 1 | H | H | CF$_3$ | Pr | Cl |
| Me | Me | H | H | 1 | H | H | Cl | Pr | CF$_3$ |
| Me | Me | H | H | 1 | H | H | CF$_3$ | Pr | OMe |
| Me | Me | H | H | 1 | H | H | OMe | Pr | CF$_3$ |
| Me | Me | H | H | 1 | H | H | CF$_3$ | Pr | OEt |
| Me | Me | H | H | 1 | H | H | OEt | Pr | CF$_3$ |
| Me | Me | H | H | 1 | H | H | CF$_3$ | Pr | OCHF$_2$ |
| Me | Me | H | H | 1 | H | H | OCHF$_2$ | Pr | CF$_3$ |
| Me | Me | H | H | 1 | H | H | CF$_3$ | Pr | CN |
| Me | Me | H | H | 1 | H | H | CN | Pr | CF$_3$ |
| Me | Me | H | H | 1 | H | H | CF$_3$ | Pr | Me |
| Me | Me | H | H | 1 | H | H | Me | Pr | CF$_3$ |
| Me | Me | H | H | 1 | H | H | Cl | Bu-t | Cl |
| Me | Me | H | H | 1 | H | H | OCHF$_2$ | Bu-t | Cl |
| Me | Me | H | H | 1 | H | H | OCHF$_2$ | Bu-t | OCHF$_2$ |
| Me | Me | H | H | 1 | H | H | CF$_3$ | Bu-t | H |
| Me | Me | H | H | 1 | H | H | CF$_3$ | Bu-t | F |
| Me | Me | H | H | 1 | H | H | CF$_3$ | Bu-t | Cl |
| Me | Me | H | H | 1 | H | H | Cl | Bu-t | CF$_3$ |
| Me | Me | H | H | 1 | H | H | CF$_3$ | Bu-t | OMe |
| Me | Me | H | H | 1 | H | H | OMe | Bu-t | CF$_3$ |
| Me | Me | H | H | 1 | H | H | CF$_3$ | Bu-t | OEt |
| Me | Me | H | H | 1 | H | H | OEt | Bu-t | CF$_3$ |
| Me | Me | H | H | 1 | H | H | CF$_3$ | Bu-t | OCHF$_2$ |
| Me | Me | H | H | 1 | H | H | CF$_3$ | Bu-t | CN |
| Me | Me | H | H | 1 | H | H | CF$_3$ | Bu-t | Me |
| Me | Me | H | H | 1 | H | H | Me | Bu-t | CF$_3$ |
| Me | Me | H | H | 1 | H | H | CF$_3$ | Bu-s | Cl |
| Me | Me | H | H | 1 | H | H | Cl | Bu-s | CF$_3$ |
| Me | Me | H | H | 1 | H | H | CF$_3$ | Bu-i | Cl |
| Me | Me | H | H | 1 | H | H | Cl | Bu-i | CF$_3$ |
| Me | Me | H | H | 1 | H | H | CF$_3$ | Bu | Cl |
| Me | Me | H | H | 1 | H | H | Cl | Bu | CF$_3$ |
| Me | Me | H | H | 1 | H | H | CF$_3$ | 1-Methylbutyl | Cl |
| Me | Me | H | H | 1 | H | H | Cl | 1-Methylbutyl | CF$_3$ |
| Me | Me | H | H | 1 | H | H | CF$_3$ | 1-Ethylpropyl | Cl |
| Me | Me | H | H | 1 | H | H | Cl | 1-Ethylpropyl | CF$_3$ |
| Me | Me | H | H | 1 | H | H | CF$_3$ | 1-Pentyl | Cl |
| Me | Me | H | H | 1 | H | H | Cl | 1-Pentyl | CF$_3$ |
| Me | Me | H | H | 1 | H | H | CF$_3$ | 1-Methylpentyl | Cl |
| Me | Me | H | H | 1 | H | H | Cl | 1-Methylpentyl | CF$_3$ |
| Me | Me | H | H | 1 | H | H | CF$_3$ | 2-Ethylbutyl | Cl |
| Me | Me | H | H | 1 | H | H | Cl | 2-Ethylbutyl | CF$_3$ |
| Me | Me | H | H | 1 | H | H | CF$_3$ | 3,3-Dimethylbutyl | Cl |
| Me | Me | H | H | 1 | H | H | Cl | 3,3-Diniethylbutyl | CF$_3$ |
| Me | Me | H | H | 1 | H | H | CF$_3$ | 1-Hexyl | Cl |
| Me | Me | H | H | 1 | H | H | Cl | 1-Hexyl | CF$_3$ |
| Me | Me | H | H | 1 | H | H | CF$_3$ | 1-Heptyl | Cl |
| Me | Me | H | H | 1 | H | H | Cl | 1-Heptyl | CF$_3$ |
| Me | Me | H | H | 1 | H | H | CF$_3$ | 1-Octyl | Cl |
| Me | Me | H | H | 1 | H | H | Cl | 1-Octyl | CF$_3$ |
| Me | Me | H | H | 1 | H | H | CF$_3$ | CH$_2$Ph | Cl |
| Me | Me | H | H | 1 | H | H | Cl | CH$_2$Ph | CF$_3$ |
| Me | Me | H | H | 1 | H | H | CF$_3$ | Pr-c | Cl |
| Me | Me | H | H | 1 | H | H | CF$_3$ | Pen-c | Cl |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 1 | H | H | Cl | Pen-c | CF₃ |
| Me | Me | H | H | 1 | H | H | CF₃ | Hex-c | Cl |
| Me | Me | H | H | 1 | H | H | Cl | Hex-c | CF₃ |
| Me | Me | H | H | 1 | H | H | Cl | CH₂Pr-c | Cl |
| Me | Me | H | H | 1 | H | H | OCHF₂ | CH₂Pr-c | Cl |
| Me | Me | H | H | 1 | H | H | Cl | CH₂Pr-c | OCHF₂ |
| Me | Me | H | H | 1 | H | H | OCHF₂ | CH₂Pr-c | OCHF₂ |
| Me | Me | H | H | 1 | H | H | CF₃ | CH₂Pr-c | F |
| Me | Me | H | H | 1 | H | H | F | CH₂Pr-c | CF₃ |
| Me | Me | H | H | 1 | H | H | CF₃ | CH₂Pr-c | Cl |
| Me | Me | H | H | 1 | H | H | Cl | CH₂Pr-c | CF₃ |
| Me | Me | H | H | 1 | H | H | CF₃ | CH₂Pr-c | CN |
| Me | Me | H | H | 1 | H | H | CF₃ | CH₂Pr-c | OH |
| Me | Me | H | H | 1 | H | H | CF₃ | CH₂Pr-c | OMe |
| Me | Me | H | H | 1 | H | H | OMe | CH₂Pr-c | CF₃ |
| Me | Me | H | H | 1 | H | H | CF₃ | CH₂Pr-c | OEt |
| Me | Me | H | H | 1 | H | H | OEt | CH₂Pr-c | CF₃ |
| Me | Me | H | H | 1 | H | H | CF₃ | CH₂Pr-c | OPr-i |
| Me | Me | H | H | 1 | H | H | CF₃ | CH₂Pr-c | OPr |
| Me | Me | H | H | 1 | H | H | CF₃ | CH₂Pr-c | OBu-t |
| Me | Me | H | H | 1 | H | H | CF₃ | CH₂Pr-c | OCH₂Pr-c |
| Me | Me | H | H | 1 | H | H | CF₃ | CH₂Pr-c | OCH₂Bu-c |
| Me | Me | H | H | 1 | H | H | CF₃ | CH₂Pr-c | OPen-c |
| Me | Me | H | H | 1 | H | H | CF₃ | CH₂Pr-c | OCHF₂ |
| Me | Me | H | H | 1 | H | H | OCHF₂ | CH₂Pr-c | CF₃ |
| Me | Me | H | H | 1 | H | H | CF₃ | CH₂Pr-c | CN |
| Me | Me | H | H | 1 | H | H | CN | CH₂Pr-c | CF₃ |
| Me | Me | H | H | 1 | H | H | CF₃ | CH₂Pr-c | Me |
| Me | Me | H | H | 1 | H | H | Me | CH₂Pr-c | CF₃ |
| Me | Me | H | H | I | H | H | CF₃ | 1-cyclopropylethyl | Cl |
| Me | Me | H | H | 1 | H | H | Cl | 1-cyclopropylethyl | CF₃ |
| Me | Me | H | H | 1 | H | H | CF₃ | CH₂(2-Methyl-cyclopropyl) | Cl |
| Me | Me | H | H | 1 | H | H | Cl | CH₂(2-Methyl-cyclopropyl) | CF₃ |
| Me | Me | H | H | 1 | H | H | CF₃ | CH₂(2,2-Dimethyl-cyclopropyl) | Cl |
| Me | Me | H | H | 1 | H | H | Cl | CH₂(2,2-Dimethyl-cyclopropyl) | CF₃ |
| Me | Me | H | H | 1 | H | H | CF₃ | CH₂(2-Chloro-cyclopropyl) | Cl |
| Me | Me | H | H | 1 | H | H | Cl | CH₂(2-Chloro-cyclopropyl) | CF₃ |
| Me | Me | H | H | 1 | H | H | CF₃ | CH₂(2,2-Dichloro-cyclopropyl) | Cl |
| Me | Me | H | H | 1 | H | H | Cl | CH₂(2,2-Dichloro-cyclopropyl) | CF₃ |
| Me | Me | H | H | 1 | H | H | CF₃ | CH₂(2-Fluoro-cyclopropyl) | Cl |
| Me | Me | H | H | 1 | H | H | Cl | CH₂(2-Fluoro-cyclopropyl) | CF₃ |
| Me | Me | H | H | 1 | H | H | CF₃ | CH₂(2,2-Difluoro-cyclopropyl) | Cl |
| Me | Me | H | H | 1 | H | H | Cl | CH₂(2,2-Difluoro-cyclopropyl) | CF₃ |
| Me | Me | H | H | 1 | H | H | CF₃ | CH₂Bu-c | Cl |
| Me | Me | H | H | 1 | H | H | Cl | CH₂Bu-c | CF₃ |
| Me | Me | H | H | 1 | H | H | CF₃ | CH₂Pen-c | Cl |
| Me | Me | H | H | 1 | H | H | Cl | CH₂Pen-c | CF₃ |
| Me | Me | H | H | 1 | H | H | CF₃ | CH₂Hex-c | Cl |
| Me | Me | H | H | 1 | H | H | Cl | CH₂Hex-c | CF₃ |
| Me | Me | H | H | 1 | H | H | CF₃ | CH₂CH₂Pr-c | Cl |
| Me | Me | H | H | 1 | H | H | Cl | CH₂CH₂Pr-c | CF₃ |
| Me | Me | H | H | 1 | H | H | CF₃ | CH₂CH=CH₂ | Cl |
| Me | Me | H | H | 1 | H | H | Cl | CH₂CH=CH₂ | CF₃ |
| Me | Me | H | H | 1 | H | H | CF₃ | CH₂CH=CH | Cl |
| Me | Me | H | H | 1 | H | H | Cl | CH₂CH=CH | CF₃ |
| Me | Me | H | H | 1 | H | H | CF₃ | CH₂C≡CH | Cl |
| Me | Me | H | H | 1 | H | H | Cl | CH₂C≡CH | Cl |
| Me | Me | H | H | 1 | H | H | OCHF₂ | CH₂C≡CH | Cl |
| Me | Me | H | H | 1 | H | H | Cl | CH₂C≡CH | OCHF₂ |
| Me | Me | H | H | 1 | H | H | OCHF₂ | CH₂C≡CH | OCHF₂ |
| Me | Me | H | H | 1 | H | H | CF₃ | CH₂C≡CH | F |
| Me | Me | H | H | 1 | H | H | F | CH₂C≡CH | CF₃ |
| Me | Me | H | H | 1 | H | H | CF₃ | CH₂C≡CH | Cl |
| Me | Me | H | H | 1 | H | H | Cl | CH₂C≡CH | CF₃ |
| Me | Me | H | H | 1 | H | H | CF₃ | CH₂C≡CH | OMe |
| Me | Me | H | H | 1 | H | H | OMe | CH₂C≡CH | CF₃ |
| Me | Me | H | H | 1 | H | H | CF₃ | CH₂C≡CH | OEt |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 1 | H | H | OEt | CH₂C≡CH | CF₃ |
| Me | Me | H | H | 1 | H | H | CF₃ | CH₂C≡CH | OCHF₂ |
| Me | Me | H | H | 1 | H | H | OCHF₂ | CH₂C≡CH | CF₃ |
| Me | Me | H | H | 1 | H | H | CF₃ | CH₂C≡CH | CN |
| Me | Me | H | H | 1 | H | H | CN | CH₂C≡CH | CF₃ |
| Me | Me | H | H | 1 | H | H | CF₃ | CH₂C≡CH | Me |
| Me | Me | H | H | 1 | H | H | Me | CH₂C≡CH | CF₃ |
| Me | Me | H | H | 1 | H | H | CF₃ | CHMeC≡CH | Cl |
| Me | Me | H | H | 1 | H | H | Cl | CHMeC≡CH | CF₃ |
| Me | Me | H | H | 1 | H | H | CF₃ | CH₂C≡CMe | Cl |
| Me | Me | H | H | 1 | H | H | Cl | CH₂C≡CMe | CF₃ |
| Me | Me | H | H | 1 | H | H | Cl | CHF₂ | Cl |
| Me | Me | H | H | 1 | H | H | OCHF₂ | CHF₂ | Cl |
| Me | Me | H | H | 1 | H | H | Cl | CHF₂ | OCHF₂ |
| Me | Me | H | H | 1 | H | H | OCHF₂ | CHF₂ | OCHF₂ |
| Me | Me | H | H | 1 | H | H | CF₃ | CHF₂ | Cl |
| Me | Me | H | H | 1 | H | H | Cl | CHF₂ | CF₃ |
| Me | Me | H | H | 1 | H | H | CF₃ | CHF₂ | F |
| Me | Me | H | H | 1 | H | H | F | CHF₂ | CF₃ |
| Me | Me | H | H | 1 | H | H | CF₃ | CHF₂ | OMe |
| Me | Me | H | H | 1 | H | H | OMe | CHF₂ | CF₃ |
| Me | Me | H | H | 1 | H | H | CF₃ | CHF₂ | OEt |
| Me | Me | H | H | 1 | H | H | OEt | CHF₂ | CF₃ |
| Me | Me | H | H | 1 | H | H | CF₃ | CHF₂ | OCHF₂ |
| Me | Me | H | H | 1 | H | H | OCHF₂ | CHF₂ | CF₃ |
| Me | Me | H | H | 1 | H | H | CF₃ | CHF₂ | CN |
| Me | Me | H | H | 1 | H | H | CN | CHF₂ | CF₃ |
| Me | Me | H | H | 1 | H | H | CF₃ | CHF₂ | Me |
| Me | Me | H | H | 1 | H | H | Me | CHF₂ | CF₃ |
| Me | Me | H | H | 1 | H | H | Me | CHF₂ | Cl |
| Me | Me | H | H | 1 | H | H | Cl | CHF₂ | Me |
| Me | Me | H | H | 1 | H | H | Et | CHF₂ | Cl |
| Me | Me | H | H | 1 | H | H | Cl | CHF₂ | Et |
| Me | Me | H | H | 1 | H | H | CF₃ | CH₂CHF₂ | Cl |
| Me | Me | H | H | 1 | H | H | Cl | CH₂CHF₂ | CF₃ |
| Me | Me | H | H | 1 | H | H | CF₃ | CH₂CF₃ | Cl |
| Me | Me | H | H | 1 | H | H | Cl | CH₂CF₃ | CF₃ |
| Me | Me | H | H | 1 | H | H | CF₃ | CH₂OH | Cl |
| Me | Me | H | H | 1 | H | H | Cl | CH₂OH | CF₃ |
| Me | Me | H | H | 1 | H | H | Cl | CH₂OMe | Cl |
| Me | Me | H | H | 1 | H | H | OCHF₂ | CH₂OMe | Cl |
| Me | Me | H | H | 1 | H | H | Cl | CH₂OMe | OCHF₂ |
| Me | Me | H | H | 1 | H | H | OCHF₂ | CH₂OMe | OCHF₂ |
| Me | Me | H | H | 1 | H | H | CF₃ | CH₂OMe | F |
| Me | Me | H | H | 1 | H | H | F | CH₂OMe | CF₃ |
| Me | Me | H | H | 1 | H | H | CF₃ | CH₂OMe | Cl |
| Me | Me | H | H | 1 | H | H | Cl | CH₂OMe | CF₃ |
| Me | Me | H | H | 1 | H | H | CF₃ | CH₂OMe | OMe |
| Me | Me | H | H | 1 | H | H | OMe | CH₂OMe | CF₃ |
| Me | Me | H | H | 1 | H | H | CF₃ | CH₂OMe | OEt |
| Me | Me | H | H | 1 | H | H | OEt | CH₂OMe | CF₃ |
| Me | Me | H | H | 1 | H | H | CF₃ | CH₂OMe | OCHF₂ |
| Me | Me | H | H | 1 | H | H | OCHF₂ | CH₂OMe | CF₃ |
| Me | Me | H | H | 1 | H | H | CF₃ | CH₂OMe | CN |
| Me | Me | H | H | 1 | H | H | CN | CH₂OMe | CF₃ |
| Me | Me | H | H | 1 | H | H | CF₃ | CH₂OMe | Me |
| Me | Me | H | H | 1 | H | H | Me | CH₂OMe | CF₃ |
| Me | Me | H | H | 1 | H | H | CF₃ | CH₂OEt | Cl |
| Me | Me | H | H | 1 | H | H | Cl | CH₂OEt | CF₃ |
| Me | Me | H | H | 1 | H | H | CF₃ | CH₂CH₂OH | Cl |
| Me | Me | H | H | 1 | H | H | Cl | CH₂CH₂OH | CF₃ |
| Me | Me | H | H | 1 | H | H | CF₃ | CH₂CH₂OMe | Cl |
| Me | Me | H | H | 1 | H | H | Cl | CH₂CH₂OMe | CF₃ |
| Me | Me | H | H | 1 | H | H | CF₃ | CH₂CH₂OEt | Cl |
| Me | Me | H | H | 1 | H | H | Cl | CH₂CH₂OEt | CF₃ |
| Me | Me | H | H | 1 | H | H | CF₃ | CH₂NHMe | Cl |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 1 | H | H | Cl | CH₂NHMe | CF₃ |
| Me | Me | H | H | 1 | H | H | CF₃ | CH₂N(Me)₂ | Cl |
| Me | Me | H | H | 1 | H | H | Cl | CH₂N(Me)₂ | CF₃ |
| Me | Me | H | H | 1 | H | H | CF₃ | CH₂N(Me)C(=O)Me | Cl |
| Me | Me | H | H | 1 | H | H | Cl | CH₂N(Me)C(=O)Me | CF₃ |
| Me | Me | H | H | 1 | H | H | CF₃ | CH₂N(Me)C(=O)CF₃ | Cl |
| Me | Me | H | H | 1 | H | H | Cl | CH₂N(Me)C(=O)CF₃ | CF₃ |
| Me | Me | H | H | 1 | H | H | CF₃ | CH₂N(Me)SO₂Me | Cl |
| Me | Me | H | H | 1 | H | H | Cl | CH₂N(Me)SO₂Me | CF₃ |
| Me | Me | H | H | 1 | H | H | CF₃ | CH₂N(Me)SO₂CHF₂ | Cl |
| Me | Me | H | H | 1 | H | H | Cl | CH₂N(Me)SO₂CHF₂ | CF₃ |
| Me | Me | H | H | 1 | H | H | CF₃ | CH₂N(Me)SO₂CF₃ | Cl |
| Me | Me | H | H | 1 | H | H | Cl | CH₂N(Me)SO₂CF₃ | CF₃ |
| Me | Me | H | H | 1 | H | H | CF₃ | CH₂SMe | Cl |
| Me | Me | H | H | 1 | H | H | Cl | CH₂SMe | CF₃ |
| Me | Me | H | H | 1 | H | H | CF₃ | CH₂SO₂Me | Cl |
| Me | Me | H | H | 1 | H | H | Cl | CH₂SO₂Me | CF₃ |
| Me | Me | H | H | 1 | H | H | CF₃ | CH₂CH₂SMe | Cl |
| Me | Me | H | H | 1 | H | H | Cl | CH₂CH₂SMe | CF₃ |
| Me | Me | H | H | 1 | H | H | CF₃ | CH₂CH₂SO₂Me | Cl |
| Me | Me | H | H | 1 | H | H | Cl | CH₂CH₂SO₂Me | CF₃ |
| Me | Me | H | H | 1 | H | H | CF₃ | CH₂CN | Cl |
| Me | Me | H | H | 1 | H | H | Cl | CH₂CN | CF₃ |
| Me | Me | H | H | 1 | H | H | CF₃ | CH₂C(=O)OMe | Cl |
| Me | Me | H | H | 1 | H | H | Cl | CH₂C(=O)OMe | CF₃ |
| Me | Me | H | H | 1 | H | H | CF₃ | CH₂C(=O)OEt | Cl |
| Me | Me | H | H | 1 | H | H | Cl | CH₂C(=O)OEt | CF₃ |
| Me | Me | H | H | 1 | H | H | CF₃ | CH(Me)C(=O)OMe | Cl |
| Me | Me | H | H | 1 | H | H | Cl | CH(Me)C(=O)OMe | CF₃ |
| Me | Me | H | H | 1 | H | H | CF₃ | C(Me)₂C(=O)OMe | Cl |
| Me | Me | H | H | 1 | H | H | Cl | C(Me)₂C(=O)OMe | CF₃ |
| Me | Me | H | H | 1 | H | H | CF₃ | CH₂C(=O)NH₂ | Cl |
| Me | Me | H | H | 1 | H | H | Cl | CH₂C(=O)NH₂ | CF₃ |
| Me | Me | H | H | 1 | H | H | CF₃ | CH₂C(=O)NHMe | Cl |
| Me | Me | H | H | 1 | H | H | Cl | CH₂C(=O)NHMe | CF₃ |
| Me | Me | H | H | 1 | H | H | CF₃ | CH₂C(=O)N(Me)₂ | Cl |
| Me | Me | H | H | 1 | H | H | Cl | CH₂C(=O)N(Me)₂ | CF₃ |
| Me | Me | H | H | 1 | H | H | CF₃ | CH₂C(=O)Me | Cl |
| Me | Me | H | H | 1 | H | H | Cl | CH₂C(=O)Me | CF₃ |
| Me | Me | H | H | 1 | H | H | CF₃ | CH₂C(NOMe)Me | Cl |
| Me | Me | H | H | 1 | H | H | Cl | CH₂C(NOMe)Me | CF₃ |
| Me | Me | H | H | 1 | H | H | CF₃ | CH₂C(=O)CF₃ | Cl |
| Me | Me | H | H | 1 | H | H | Cl | CH₂C(=O)CF₃ | CF₃ |
| Me | Me | H | H | 1 | H | H | CF₃ | CH₂CH₂C(=O)Me | Cl |
| Me | Me | H | H | 1 | H | H | Cl | CH₂CH₂C(=O)Me | CF₃ |
| Me | Me | H | H | 1 | H | H | Me | Ph | Me |
| Me | Me | H | H | 1 | H | H | Me | Ph | Cl |
| Me | Me | H | H | 1 | H | H | Et | Ph | Cl |
| Me | Me | H | H | 1 | H | H | Pr | Ph | Cl |
| Me | Me | H | H | 1 | H | H | Pr-i | Ph | Cl |
| Me | Me | H | H | 1 | H | H | Bu-t | Ph | Cl |
| Me | Me | H | H | 1 | H | H | CH₂OMe | Ph | Cl |
| Me | Me | H | H | 1 | H | H | Cl | Ph | Cl |
| Me | Me | H | H | 1 | H | H | OCHF₂ | Ph | Cl |
| Me | Me | H | H | 1 | H | H | OCHF₂ | Ph | OCHF₂ |
| Me | Me | H | H | 1 | H | H | CHF₂ | Ph | Cl |
| Me | Me | H | H | 1 | H | H | CF₃ | Ph | H |
| Me | Me | H | H | 1 | H | H | CF₃ | Ph | Me |
| Me | Me | H | H | 1 | H | H | Me | Ph | CF₃ |
| Me | Me | H | H | 1 | H | H | CF₃ | Ph | Et |
| Me | Me | H | H | 1 | H | H | CF₃ | Ph | Pr-i |
| Me | Me | H | H | 1 | H | H | CF₃ | Ph | CHF₂ |
| Me | Me | H | H | 1 | H | H | CF₃ | Ph | CF₃ |
| Me | Me | H | H | 1 | H | H | CF₃ | Ph | F |
| Me | Me | H | H | 1 | H | H | CF₃ | Ph | Cl |
| Me | Me | H | H | 1 | H | H | Cl | Ph | CF₃ |

TABLE 3-continued

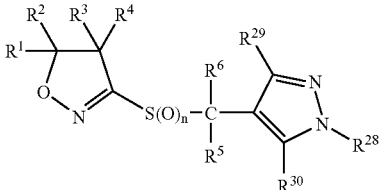

| R¹ | R² | R³ | R⁴ | n | R⁵ | R⁶ | R²⁹ | R²⁸ | R³⁰ |
|----|----|----|----|---|----|----|-----|-----|-----|
| Me | Me | H | H | 1 | H | H | CF₃ | Ph | OH |
| Me | Me | H | H | 1 | H | H | OH | Ph | CF₃ |
| Me | Me | H | H | 1 | H | H | CF₃ | Ph | OMe |
| Me | Me | H | H | 1 | H | H | OMe | Ph | CF₃ |
| Me | Me | H | H | 1 | H | H | CF₃ | Ph | OEt |
| Me | Me | H | H | 1 | H | H | OEt | Ph | CF₃ |
| Me | Me | H | H | 1 | H | H | CF₃ | Ph | OPr-i |
| Me | Me | H | H | 1 | H | H | CF₃ | Ph | OPr |
| Me | Me | H | H | 1 | H | H | CF₃ | Ph | OBu-t |
| Me | Me | H | H | 1 | H | H | CF₃ | Ph | OCH₂Pr-c |
| Me | Me | H | H | 1 | H | H | CF₃ | Ph | OCH₂CH=CH₂ |
| Me | Me | H | H | 1 | H | H | CF₃ | Ph | OCH₂C≡CH |
| Me | Me | H | H | 1 | H | H | CF₃ | Ph | OCHF₂ |
| Me | Me | H | H | 1 | H | H | OCHF₂ | Ph | CF₃ |
| Me | Me | H | H | 1 | H | H | CF₃ | Ph | OCH₂CHF₂ |
| Me | Me | H | H | 1 | H | H | CF₃ | Ph | OCH₂CF₃ |
| Me | Me | H | H | 1 | H | H | CF₃ | Ph | OCH₂C(=O)OMe |
| Me | Me | H | H | 1 | H | H | CF₃ | Ph | OCH(Me)C(=O)OMe |
| Me | Me | H | H | 1 | H | H | CF₃ | Ph | OC(Me)₂C(=O)OMe |
| Me | Me | H | H | 1 | H | H | CF₃ | Ph | OC(=O)Me |
| Me | Me | H | H | 1 | H | H | CF₃ | Ph | OC(=O)Et |
| Me | Me | H | H | 1 | H | H | CF₃ | Ph | OC(=O)CH₂Ph |
| Me | Me | H | H | 1 | H | H | CF₃ | Ph | OC(=O)CF₃ |
| Me | Me | H | H | 1 | H | H | CF₃ | Ph | OC(=O)Ph |
| Me | Me | H | H | 1 | H | H | CF₃ | Ph | OSO₂Me |
| Me | Me | H | H | 1 | H | H | CF₃ | Ph | OSO₂Et |
| Me | Me | H | H | 1 | H | H | CF₃ | Ph | OSO₂CH₂Ph |
| Me | Me | H | H | 1 | H | H | CF₃ | Ph | OSO₂CF₃ |
| Me | Me | H | H | 1 | H | H | CF₃ | Ph | OSO₂Ph |
| Me | Me | H | H | 1 | H | H | CF₃ | Ph | SMe |
| Me | Me | H | H | 1 | H | H | CF₃ | Ph | SO₂Me |
| Me | Me | H | H | 1 | H | H | CF₃ | Ph | SEt |
| Me | Me | H | H | 1 | H | H | CF₃ | Ph | SO₂Et |
| Me | Me | H | H | 1 | H | H | CF₃ | Ph | SPr-i |
| Me | Me | H | H | 1 | H | H | CF₃ | Ph | SO₂Pr-i |
| Me | Me | H | H | 1 | H | H | CF₃ | Ph | SPr |
| Me | Me | H | H | 1 | H | H | CF₃ | Ph | SO₂Pr |
| Me | Me | H | H | 1 | H | H | CF₃ | Ph | SBu-t |
| Me | Me | H | H | 1 | H | H | CF₃ | Ph | SO₂Bu-t |
| Me | Me | H | H | 1 | H | H | CF₃ | Ph | SCHF₂ |
| Me | Me | H | H | 1 | H | H | CF₃ | Ph | SO₂CHF₂ |
| Me | Me | H | H | 1 | H | H | CF₃ | Ph | NH₂ |
| Me | Me | H | H | 1 | H | H | CF₃ | Ph | NHMe |
| Me | Me | H | H | 1 | H | H | CF₃ | Ph | N(Me)₂ |
| Me | Me | H | H | 1 | H | H | CF₃ | Ph | NHC(=O)Me |
| Me | Me | H | H | 1 | H | H | CF₃ | Ph | N(Me)C(=O)Me |
| Me | Me | H | H | 1 | H | H | CF₃ | Ph | NHSO₂Me |
| Me | Me | H | H | 1 | H | H | CF₃ | Ph | N(Me)SO₂Me |
| Me | Me | H | H | 1 | H | H | CF₃ | Ph | NHSO₂CF₃ |
| Me | Me | H | H | 1 | H | H | CF₃ | Ph | N(Me)SO₂CF₃ |
| Me | Me | H | H | 1 | H | H | CF₃ | Ph | NHPh |
| Me | Me | H | H | 1 | H | H | CF₃ | Ph | N(Me)Ph |
| Me | Me | H | H | 1 | H | H | CF₃ | Ph | CN |
| Me | Me | H | H | 1 | H | H | CF₃ | Ph | C(=O)Me |
| Me | Me | H | H | 1 | H | H | CF₃ | Ph | C(=O)OMe |
| Me | Me | H | H | 1 | H | H | CF₃ | Ph | C(=O)NH₂ |
| Me | Me | H | H | 1 | H | H | CF₃ | Ph | C(=O)NHMe |
| Me | Me | H | H | 1 | H | H | CF₃ | Ph | C(=O)N(Me)₂ |
| Me | Me | H | H | 1 | H | H | CF₃ | Ph | Imidazol-1-yl |
| Me | Me | H | H | 1 | H | H | CF₃ | Ph | Pyrazol-yl |
| Me | Me | H | H | 1 | H | H | CF₃ | Ph | 1,2,4-Triazol-1-yl |
| Me | Me | H | H | 1 | H | H | CF₃ | Ph | 1,2,4-Triazol-4-yl |
| Me | Me | H | H | 1 | H | H | CF₃ | Ph | Tetrazol-1-yl |
| Me | Me | H | H | 1 | H | H | CF₃ | Ph | Tetrazol-5-yl |
| Me | Me | H | H | 1 | H | H | CF₃ | Ph | (4,6-Dimethoxypyrimidin-2-yl)oxy |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 1 | H | H | CF₃ | Ph | (4,6-Dimethoxypyrimidin-2-yl) sulfonyl |
| Me | Me | H | H | 1 | H | H | CF₂CF₃ | Ph | Cl |
| Me | Me | H | H | 1 | H | H | CF₃ | (2-Cl)Ph | Cl |
| Me | Me | H | H | 1 | H | H | CF₃ | (2-F)Ph | Cl |
| Me | Me | H | H | 1 | H | H | CF₃ | (2-OMe)Ph | Cl |
| Me | Me | H | H | 1 | H | H | CF₃ | (2-Me)Ph | Cl |
| Me | Me | H | H | 1 | H | H | CF₃ | (2-NO₂)Ph | Cl |
| Me | Me | H | H | 1 | H | H | CF₃ | (2-CN)Ph | Cl |
| Me | Me | H | H | 1 | H | H | CF₃ | (2-C(=O)Me)Ph | Cl |
| Me | Me | H | H | 1 | H | H | CF₃ | (2-C(=O)OMe)Ph | Cl |
| Me | Me | H | H | 1 | H | H | CF₃ | (2-C(=O)OEt)Ph | Cl |
| Me | Me | H | H | 1 | H | H | CF₃ | (2-C(=O)OPr-i)Ph | Cl |
| Me | Me | H | H | 1 | H | H | CF₃ | (2-C(=O)NH₂)Ph | Cl |
| Me | Me | H | H | 1 | H | H | CF₃ | (2-C(=O)NHMe)Ph | Cl |
| Me | Me | H | H | 1 | H | H | CF₃ | (2-C(=O)NMe₂)Ph | Cl |
| Me | Me | H | H | 1 | H | H | CF₃ | (3-Cl)Ph | Cl |
| Me | Me | H | H | 1 | H | H | CF₃ | (3-F)Ph | Cl |
| Me | Me | H | H | 1 | H | H | CF₃ | (3-OMe)Ph | Cl |
| Me | Me | H | H | 1 | H | H | CF₃ | (3-Me)Ph | Cl |
| Me | Me | H | H | 1 | H | H | CF₃ | (3-NO₂)Ph | Cl |
| Me | Me | H | H | 1 | H | H | CF₃ | (3-CN)Ph | Cl |
| Me | Me | H | H | 1 | H | H | CF₃ | (3-C(=O)Me)Ph | Cl |
| Me | Me | H | H | 1 | H | H | CF₃ | (3-C(=O)OMe)Ph | Cl |
| Me | Me | H | H | 1 | H | H | CF₃ | (3-C(=O)OEt)Ph | Cl |
| Me | Me | H | H | 1 | H | H | CF₃ | (3-C(=O)OPr-i)Ph | Cl |
| Me | Me | H | H | 1 | H | H | CF₃ | (3-C(=O)NH₂)Ph | Cl |
| Me | Me | H | H | 1 | H | H | CF₃ | (3-C(=O)NHMe)Ph | Cl |
| Me | Me | H | H | 1 | H | H | CF₃ | (3-C(=O)NMe₂)Ph | Cl |
| Me | Me | H | H | 1 | H | H | CF₃ | (4-Cl)Ph | Cl |
| Me | Me | H | H | 1 | H | H | CF₃ | (4-F)Ph | Cl |
| Me | Me | H | H | 1 | H | H | CF₃ | (4-OMe)Ph | Cl |
| Me | Me | H | H | 1 | H | H | CF₃ | (4-Me)Ph | Cl |
| Me | Me | H | H | 1 | H | H | CF₃ | (4-NO₂)Ph | Cl |
| Me | Me | H | H | 1 | H | H | CF₃ | (4-CN)Ph | Cl |
| Me | Me | H | H | 1 | H | H | CF₃ | (4-C(=O)Me)Ph | Cl |
| Me | Me | H | H | 1 | H | H | CF₃ | (4-C(=O)OMe)Ph | Cl |
| Me | Me | H | H | 1 | H | H | CF₃ | (4-C(=O)OEt)Ph | Cl |
| Me | Me | H | H | 1 | H | H | CF₃ | (4-C(=O)OPr-i)Ph | Cl |
| Me | Me | H | H | 1 | H | H | CF₃ | (4-C(=O)NH₂)Ph | Cl |
| Me | Me | H | H | 1 | H | H | CF₃ | (4-C(=O)NHMe)Ph | Cl |
| Me | Me | H | H | 1 | H | H | CF₃ | (4-C(=O)NMe₂)Ph | Cl |
| Me | Me | H | H | 1 | H | H | CF₃ | Pyrmidin-2-yl | Cl |
| Me | Me | H | H | 1 | H | H | CF₃ | 4,6-Dimethoxypyrmidin-2-yl | Cl |
| Me | Me | H | H | 1 | H | H | CF₃ | Thiophen-2-yl | Cl |
| Me | Me | H | H | 1 | H | H | CF₃ | Furan-2-yl | Cl |
| Me | Me | H | H | 1 | H | H | CF₃ | SO₂Me | Cl |
| Me | Me | H | H | 1 | H | H | CF₃ | SO₂Et | Cl |
| Me | Me | H | H | 1 | H | H | CF₃ | SO₂Pr-i | Cl |
| Me | Me | H | H | 1 | H | H | CF₃ | SO₂CH₂Ph | Cl |
| Me | Me | H | H | 1 | H | H | CF₃ | SO₂CHF₂ | Cl |
| Me | Me | H | H | 1 | H | H | CF₃ | SO₂CF₃ | Cl |
| Me | Me | H | H | 1 | H | H | CF₃ | SO₂Ph | Cl |
| Me | Me | H | H | 1 | H | H | CF₃ | C(=O)Me | Cl |
| Me | Me | H | H | 1 | H | H | CF₃ | C(=O)Et | Cl |
| Me | Me | H | H | 1 | H | H | CF₃ | C(=O)Pr-i | Cl |
| Me | Me | H | H | 1 | H | H | CF₃ | C(=O)Bu-t | Cl |
| Me | Me | H | H | 1 | H | H | CF₃ | C(=O)Ph | Cl |
| Me | Me | H | H | 1 | H | H | CF₃ | C(=O)CH₂Ph | Cl |
| Me | Me | H | H | 1 | H | H | CF₃ | C(=O)CH₂Cl | Cl |
| Me | Me | H | H | 1 | H | H | CF₃ | C(=O)CHCl₂ | Cl |
| Me | Me | H | H | 1 | H | H | CF₃ | C(=O)CF₃ | Cl |
| Me | Me | H | H | 1 | H | H | CF₃ | C(=O)OMe | Cl |
| Me | Me | H | H | 1 | H | H | CF₃ | C(=O)OPh | Cl |
| Me | Me | H | H | 1 | H | H | CF₃ | C(=O)OCH₂Ph | Cl |
| Me | Me | H | H | 1 | H | H | CF₃ | C(=O)NHMe | Cl |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 1 | H | H | CF₃ | C(=O)N(Me)₂ | Cl |
| Me | Me | H | H | 1 | H | H | CF₃ | C(=O)NHPh | Cl |
| Me | Me | H | H | 1 | H | H | CF₃ | NH₂ | Cl |
| Me | Me | H | H | 1 | H | H | Cl | —(CH₂)₂O— | |
| Me | Me | H | H | 1 | H | H | Cl | —(CH₂)₃O— | |
| Me | Me | H | H | 1 | H | H | Cl | —(CH₂)₃S— | |
| Me | Me | H | H | 1 | H | H | Cl | —(CH₂)₃SO₂— | |
| Me | Me | H | H | 1 | H | H | CF₃ | —(CH₂)₂O— | |
| Me | Me | H | H | 1 | H | H | CF₃ | —(CH₂)₃O— | |
| Me | Me | H | H | 1 | H | H | CF₃ | —(CH₂)₃S— | |
| Me | Me | H | H | 1 | H | H | CF₃ | —(CH₂)₃SO₂— | |
| Me | Me | H | H | 1 | H | H | OMe | —(CH₂)₄— | |
| Me | Me | H | H | 1 | H | H | OCHF₂ | —(CH₂)₄— | |
| H | H | H | H | 1 | H | H | CF₃ | Me | Cl |
| Me | H | H | H | 1 | H | H | CF₃ | Me | Cl |
| Me | H | Me | H | 1 | H | H | CF₃ | Me | Cl |
| Me | Me | Me | H | 1 | H | H | CF₃ | Me | Cl |
| Me | Me | H | H | 1 | Me | H | CF₃ | Me | Cl |
| Me | Me | H | H | 1 | Et | H | CF₃ | Me | Cl |
| Me | Me | H | H | 1 | Pr-i | H | CF₃ | Me | Cl |
| Me | Me | H | H | 1 | Me | Me | CF₃ | Me | Cl |
| Me | Et | H | H | 1 | H | H | CF₃ | Me | Cl |
| Et | Et | H | H | 1 | H | H | CF₃ | Me | Cl |
| Me | Pr-i | H | H | 1 | H | H | CF₃ | Me | Cl |
| Me | Pr | H | H | 1 | H | H | CF₃ | Me | Cl |
| Me | Pr-c | H | H | 1 | H | H | CF₃ | Me | Cl |
| Me | CH₂Pr-c | H | H | 1 | H | H | CF₃ | Me | Cl |
| —(CH₂)₂— | | H | H | 1 | H | H | CF₃ | Me | Cl |
| —(CH₂)₃— | | H | H | 1 | H | H | CF₃ | Me | Cl |
| —(CH₂)₄— | | H | H | 1 | H | H | CF₃ | Me | Cl |
| —(CH₂)₅— | | H | H | 1 | H | H | CF₃ | Me | Cl |
| H | —(CH₂)₃— | | H | 1 | H | H | CF₃ | Me | Cl |
| H | —(CH₂)₄— | | H | 1 | H | H | CF₃ | Me | Cl |
| H | —(CH₂)₅— | | H | 1 | H | H | CF₃ | Me | Cl |
| H | —(CH₂)₆— | | H | 1 | H | H | CF₃ | Me | Cl |
| Me | Me | H | H | 0 | H | H | Cl | H | Cl |
| Me | Me | H | H | 0 | H | H | OCHF₂ | H | Cl |
| Me | Me | H | H | 0 | H | H | OCHF₂ | H | OCHF₂ |
| Me | Me | H | H | 0 | H | H | CHF₂ | H | Cl |
| Me | Me | H | H | 0 | H | H | CF₃ | H | F |
| Me | Me | H | H | 0 | H | H | CF₃ | H | Cl |
| Me | Me | H | H | 0 | H | H | CF₃ | H | OMe |
| Me | Me | H | H | 0 | H | H | CF₃ | H | OEt |
| Me | Me | H | H | 0 | H | H | CF₃ | H | OCHF₂ |
| Me | Me | H | H | 0 | H | H | CF₃ | H | CN |
| Me | Me | H | H | 0 | H | H | CF₃ | H | Me |
| Me | Me | H | H | 0 | H | H | H | Me | Cl |
| Me | Me | H | H | 0 | H | H | Me | Me | Me |
| Me | Me | H | H | 0 | H | H | Me | Me | Cl |
| Me | Me | H | H | 0 | H | H | Cl | Me | Me |
| Me | Me | H | H | 0 | H | H | Et | Me | Cl |
| Me | Me | H | H | 0 | H | H | Cl | Me | Et |
| Me | Me | H | H | 0 | H | H | Pr-i | Me | Cl |
| Me | Me | H | H | 0 | H | H | Cl | Me | Pr-i |
| Me | Me | H | H | 0 | H | H | Bu-t | Me | Cl |
| Me | Me | H | H | 0 | H | H | Cl | Me | Bu-t |
| Me | Me | H | H | 0 | H | H | Cl | Me | Cl |
| Me | Me | H | H | 0 | H | H | CHF₂ | Me | Cl |
| Me | Me | H | H | 0 | H | H | Cl | Me | CHF₂ |
| Me | Me | H | H | 0 | H | H | OCHF₂ | Me | H |
| Me | Me | H | H | 0 | H | H | OCHF₂ | Me | Cl |
| Me | Me | H | H | 0 | H | H | Cl | Me | OCHF₂ |
| Me | Me | H | H | 0 | H | H | OCHF₂ | Me | OCHF₂ |
| Me | Me | H | H | 0 | H | H | CF₃ | Me | H |
| Me | Me | H | H | 0 | H | H | CF₃ | Me | Cl |
| Me | Me | H | H | 0 | H | H | Cl | Me | CF₃ |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 0 | H | H | CF₃ | Me | F |
| Me | Me | H | H | 0 | H | H | F | Me | CF₃ |
| Me | Me | H | H | 0 | H | H | CF₃ | Me | OH |
| Me | Me | H | H | 0 | H | H | OH | Me | CF₃ |
| Me | Me | H | H | 0 | H | H | CF₃ | Me | OMe |
| Me | Me | H | H | 0 | H | H | OMe | Me | CF₃ |
| Me | Me | H | H | 0 | H | H | CF₃ | Me | OEt |
| Me | Me | H | H | 0 | H | H | OEt | Me | CF₃ |
| Me | Me | H | H | 0 | H | H | CF₃ | Me | OPr-i |
| Me | Me | H | H | 0 | H | H | CF₃ | Me | OPr |
| Me | Me | H | H | 0 | H | H | CF₃ | Me | OBu-t |
| Me | Me | H | H | 0 | H | H | CF₃ | Me | OBu-s |
| Me | Me | H | H | 0 | H | H | CF₃ | Me | OBu-i |
| Me | Me | H | H | 0 | H | H | CF₃ | Me | OBu |
| Me | Me | H | H | 0 | H | H | CF₃ | Me | O(2-Pen) |
| Me | Me | H | H | 0 | H | H | CF₃ | Me | O(3-Pen) |
| Me | Me | H | H | 0 | H | H | CF₃ | Me | OPen-n |
| Me | Me | H | H | 0 | H | H | CF₃ | Me | O(2-Hex) |
| Me | Me | H | H | 0 | H | H | CF₃ | Me | O(3-Hex) |
| Me | Me | H | H | 0 | H | H | CF₃ | Me | OHex-n |
| Me | Me | H | H | 0 | H | H | CF₃ | Me | OPen-c |
| Me | Me | H | H | 0 | H | H | CF₃ | Me | OHex-c |
| Me | Me | H | H | 0 | H | H | CF₃ | Me | OCH₂Pr-c |
| Me | Me | H | H | 0 | H | H | CF₃ | Me | OCH₂Bu-c |
| Me | Me | H | H | 0 | H | H | CF₃ | Me | OCH₂Pen-c |
| Me | Me | H | H | 0 | H | H | CF₃ | Me | OCH₂Hex-c |
| Me | Me | H | H | 0 | H | H | CF₃ | Me | OCH₂CH=CH₂ |
| Me | Me | H | H | 0 | H | H | CF₃ | Me | OCH₂C*CH |
| Me | Me | H | H | 0 | H | H | CF₃ | Me | OCHF₂ |
| Me | Me | H | H | 0 | H | H | OCHF₂ | Me | CF₃ |
| Me | Me | H | H | 0 | H | H | CF₃ | Me | OCH₂CHF₂ |
| Me | Me | H | H | 0 | H | H | OCH₂CHF₂ | Me | CF₃ |
| Me | Me | H | H | 0 | H | H | CF₃ | Me | OCH₂CF₃ |
| Me | Me | H | H | 0 | H | H | OCH₂CF₃ | Me | CF₃ |
| Me | Me | H | H | 0 | H | H | CF₃ | Me | OCH₂CN |
| Me | Me | H | H | 0 | H | H | CF₃ | Me | OCH₂C(=O)OEt |
| Me | Me | H | H | 0 | H | H | CF₃ | Me | OCH(Me)C(=O)OEt |
| Me | Me | H | H | 0 | H | H | CF₃ | Me | OCH₂C(=O)NH₂ |
| Me | Me | H | H | 0 | H | H | CF₃ | Me | OCH₂C(=O)NHMe |
| Me | Me | H | H | 0 | H | H | CF₃ | Me | OCH₂C(=O)N(Me)₂ |
| Me | Me | H | H | 0 | H | H | CF₃ | Me | OCH₂Ph |
| Me | Me | H | H | 0 | H | H | CF₃ | Me | OPh |
| Me | Me | H | H | 0 | H | H | CF₃ | Me | O(2-CL)Ph |
| Me | Me | H | H | 0 | H | H | CF₃ | Me | O(2-Br)Ph |
| Me | Me | H | H | 0 | H | H | CF₃ | Me | O(2-F)Ph |
| Me | Me | H | H | 0 | H | H | CF₃ | Me | O(2-Me)Ph |
| Me | Me | H | H | 0 | H | H | CF₃ | Me | O(2-OMe)Ph |
| Me | Me | H | H | 0 | H | H | CF₃ | Me | O(2-NO₂)Ph |
| Me | Me | H | H | 0 | H | H | CF₃ | Me | Q(2-CN)Ph |
| Me | Me | H | H | 0 | H | H | CF₃ | Me | O(2-C(=O)OMe)Ph |
| Me | Me | H | H | 0 | H | H | CF₃ | Me | O(3-Cl)Ph |
| Me | Me | H | H | 0 | H | H | CF₃ | Me | O(3-Br)Ph |
| Me | Me | H | H | 0 | H | H | CF₃ | Me | O(3-F)Ph |
| Me | Me | H | H | 0 | H | H | CF₃ | Me | O(3-Me)Ph |
| Me | Me | H | H | 0 | H | H | CF₃ | Me | O(3-OMe)Ph |
| Me | Me | H | H | 0 | H | H | CF₃ | Me | O(3-NO₂)Ph |
| Me | Me | H | H | 0 | H | H | CF₃ | Me | O(3-CN)Ph |
| Me | Me | H | H | 0 | H | H | CF₃ | Me | O(3-C(=O)OMe)Ph |
| Me | Me | H | H | 0 | H | H | CF₃ | Me | O(4-Cl)Ph |
| Me | Me | H | H | 0 | H | H | CF₃ | Me | O(4-Br)Ph |
| Me | Me | H | H | 0 | H | H | CF₃ | Me | O(4-F)Ph |
| Me | Me | H | H | 0 | H | H | CF₃ | Me | O(4-Me)Ph |
| Me | Me | H | H | 0 | H | H | CF₃ | Me | O(4-OMe)Ph |
| Me | Me | H | H | 0 | H | H | CF₃ | Me | O(4-NO₂)Ph |
| Me | Me | H | H | 0 | H | H | CF₃ | Me | O(4-CN)Ph |
| Me | Me | H | H | 0 | H | H | CF₃ | Me | O(4-C(=O)OMe)Ph |

TABLE 3-continued

| R¹ | R² | R³ | R⁴ | n | R⁵ | R⁶ | R²⁹ | R²⁸ | R³⁰ |
|----|----|----|----|---|----|----|-----|-----|-----|
| Me | Me | H | H | 0 | H | H | CF₃ | Me | OC(=O)Me |
| Me | Me | H | H | 0 | H | H | CF₃ | Me | OC(=O)Et |
| Me | Me | H | H | 0 | H | H | CF₃ | Me | OC(=O)CH₂Ph |
| Me | Me | H | H | 0 | H | H | CF₃ | Me | OC(=O)CF₃ |
| Me | Me | H | H | 0 | H | H | CF₃ | Me | OC(=O)Ph |
| Me | Me | H | H | 0 | H | H | CF₃ | Me | OSO₂Me |
| Me | Me | H | H | 0 | H | H | CF₃ | Me | OSO₂Et |
| Me | Me | H | H | 0 | H | H | CF₃ | Me | OSO₂CH₂Ph |
| Me | Me | H | H | 0 | H | H | CF₃ | Me | OSO₂CF₃ |
| Me | Me | H | H | 0 | H | H | CF₃ | Me | OSO₂Ph |
| Me | Me | H | H | 0 | H | H | CF₃ | Me | SMe |
| Me | Me | H | H | 0 | H | H | CF₃ | Me | SO₂Me |
| Me | Me | H | H | 0 | H | H | CF₃ | Me | SEt |
| Me | Me | H | H | 0 | H | H | CF₃ | Me | SO₂Et |
| Me | Me | H | H | 0 | H | H | CF₃ | Me | SPr |
| Me | Me | H | H | 0 | H | H | CF₃ | Me | SO₂Pr |
| Me | Me | H | H | 0 | H | H | CF₃ | Me | SPr-i |
| Me | Me | H | H | 0 | H | H | CF₃ | Me | SO₂Pr-i |
| Me | Me | H | H | 0 | H | H | CF₃ | Me | SBu-t |
| Me | Me | H | H | 0 | H | H | CF₃ | Me | SO₂Bu-t |
| Me | Me | H | H | 0 | H | H | CF₃ | Me | SCHF₂ |
| Me | Me | H | H | 0 | H | H | CF₃ | Me | SO₂CHF₂ |
| Me | Me | H | H | 0 | H | H | CF₃ | Me | SCF₃ |
| Me | Me | H | H | 0 | H | H | CF₃ | Me | SO₂CF₃ |
| Me | Me | H | H | 0 | H | H | CF₃ | Me | SPh |
| Me | Me | H | H | 0 | H | H | CF₃ | Me | SO₂Ph |
| Me | Me | H | H | 0 | H | H | CF₃ | Me | SCH₂Ph |
| Me | Me | H | H | 0 | H | H | CF₃ | Me | SO₂CH₂Ph |
| Me | Me | H | H | 0 | H | H | CF₃ | Me | SCH₂C(=O)OEt |
| Me | Me | H | H | 0 | H | H | CF₃ | Me | SO₂CH₂C(=O)OEt |
| Me | Me | H | H | 0 | H | H | CF₃ | Me | SCH(Me)C(=O)OEt |
| Me | Me | H | H | 0 | H | H | CF₃ | Me | SO₂CH(Me)C(=O)OEt |
| Me | Me | H | H | 0 | H | H | CF₃ | Me | SCH₂C(=O)NH₂ |
| Me | Me | H | H | 0 | H | H | CF₃ | Me | SO₂CH₂C(=O)NH₂ |
| Me | Me | H | H | 0 | H | H | CF₃ | Me | SCH₂C(=O)NHMe |
| Me | Me | H | H | 0 | H | H | CF₃ | Me | SO₂CH₂C(=O)NHMe |
| Me | Me | H | H | 0 | H | H | CF₃ | Me | SCH₂C(=O)N(Me)₂ |
| Me | Me | H | H | 0 | H | H | CF₃ | Me | SO₂CH₂C(=O)N(Me)₂ |
| Me | Me | H | H | 0 | H | H | CF₃ | Me | NH₂ |
| Me | Me | H | H | 0 | H | H | CF₃ | Me | NHMe |
| Me | Me | H | H | 0 | H | H | CF₃ | Me | N(Me)₂ |
| Me | Me | H | H | 0 | H | H | CF₃ | Me | NHC(=O)Me |
| Me | Me | H | H | 0 | H | H | CF₃ | Me | N(Me)C(=O)Me |
| Me | Me | H | H | 0 | H | H | CF₃ | Me | NHSO₂Me |
| Me | Me | H | H | 0 | H | H | CF₃ | Me | N(Me)SO₂Me |
| Me | Me | H | H | 0 | H | H | CF₃ | Me | NHSO₂CHF₂ |
| Me | Me | H | H | 0 | H | H | CF₃ | Me | N(Me)SO₂CHF₂ |
| Me | Me | H | H | 0 | H | H | CF₃ | Me | NHSO₂CF₃ |
| Me | Me | H | H | 0 | H | H | CF₃ | Me | N(Me)SO₂CF₃ |
| Me | Me | H | H | 0 | H | H | CF₃ | Me | NHPh |
| Me | Me | H | H | 0 | H | H | CF₃ | Me | N(Me)Ph |
| Me | Me | H | H | 0 | H | H | CF₃ | Me | CN |
| Me | Me | H | H | 0 | H | H | CN | Me | CF₃ |
| Me | Me | H | H | 0 | H | H | CF₃ | Me | C(=O)OMe |
| Me | Me | H | H | 0 | H | H | CF₃ | Me | C(=O)OCH₂Ph |
| Me | Me | H | H | 0 | H | H | CF₃ | Me | C(=O)OPh |
| Me | Me | H | H | 0 | H | H | CF₃ | Me | C(=O)NH₂ |
| Me | Me | H | H | 0 | H | H | CF₃ | Me | C(=O)NHMe |
| Me | Me | H | H | 0 | H | H | CF₃ | Me | C(=O)N(Me)₂ |
| Me | Me | H | H | 0 | H | H | CF₃ | Me | C(=O)Me |
| Me | Me | H | H | 0 | H | H | CF₃ | Me | C(=O)CF₃ |
| Me | Me | H | H | 0 | H | H | CF₃ | Me | C(=O)CH₂Ph |
| Me | Me | H | H | 0 | H | H | CF₃ | Me | C(=O)Ph |
| Me | Me | H | H | 0 | H | H | CF₃ | Me | Me |
| Me | Me | H | H | 0 | H | H | Me | Me | CF₃ |
| Me | Me | H | H | 0 | H | H | CF₃ | Me | Et |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 0 | H | H | CF₃ | Me | Pr-i |
| Me | Me | H | H | 0 | H | H | CF₃ | Me | Pr |
| Me | Me | H | H | 0 | H | H | CF₃ | Me | CH₂OMe |
| Me | Me | H | H | 0 | H | H | CF₃ | Me | CF₃ |
| Me | Me | H | H | 0 | H | H | CF₃ | Me | CHF₂ |
| Me | Me | H | H | 0 | H | H | CF₃ | Me | Ph |
| Me | Me | H | H | 0 | H | H | CF₂CF₃ | Me | Cl |
| Me | Me | H | H | 0 | H | H | Ph | Me | Me |
| Me | Me | H | H | 0 | H | H | Ph | Me | Cl |
| Me | Me | H | H | 0 | H | H | Ph | Me | OEt |
| Me | Me | H | H | 0 | H | H | Ph | Me | CF₃ |
| Me | Me | H | H | 0 | H | H | Ph | Me | Ph |
| Me | Me | H | H | 0 | H | H | Cl | Et | Cl |
| Me | Me | H | H | 0 | H | H | OCHF₂ | Et | Cl |
| Me | Me | H | H | 0 | H | H | Cl | Et | OCHF₂ |
| Me | Me | H | H | 0 | H | H | OCHF₂ | Et | OCHF₂ |
| Me | Me | H | H | 0 | H | H | CF₃ | Et | F |
| Me | Me | H | H | 0 | H | H | F | Et | CF₃ |
| Me | Me | H | H | 0 | H | H | CF₃ | Et | Cl |
| Me | Me | H | H | 0 | H | H | Cl | Et | CF₃ |
| Me | Me | H | H | 0 | H | H | CF₃ | Et | OMe |
| Me | Me | H | H | 0 | H | H | OMe | Et | CF₃ |
| Me | Me | H | H | 0 | H | H | CF₃ | Et | OEt |
| Me | Me | H | H | 0 | H | H | OEt | Et | CF₃ |
| Me | Me | H | H | 0 | H | H | CF₃ | Et | OCHF₂ |
| Me | Me | H | H | 0 | H | H | OCHF₂ | Et | CF₃ |
| Me | Me | H | H | 0 | H | H | CF₃ | Et | CN |
| Me | Me | H | H | 0 | H | H | CN | Et | CF₃ |
| Me | Me | H | H | 0 | H | H | CF₃ | Et | Me |
| Me | Me | H | H | 0 | H | H | Me | Et | CF₃ |
| Me | Me | H | H | 0 | H | H | Cl | Pr-i | Cl |
| Me | Me | H | H | 0 | H | H | OCHF₂ | Pr-i | Cl |
| Me | Me | H | H | 0 | H | H | Cl | Pr-i | OCHF₂ |
| Me | Me | H | H | 0 | H | H | OCHF₂ | Pr-i | OCHF₂ |
| Me | Me | H | H | 0 | H | H | CF₃ | Pr-i | F |
| Me | Me | H | H | 0 | H | H | F | Pr-i | CF₃ |
| Me | Me | H | H | 0 | H | H | CF₃ | Pr-i | Cl |
| Me | Me | H | H | 0 | H | H | Cl | Pr-i | CF₃ |
| Me | Me | H | H | 0 | H | H | CF₃ | Pr-i | OMe |
| Me | Me | H | H | 0 | H | H | OMe | Pr-i | CF₃ |
| Me | Me | H | H | 0 | H | H | CF₃ | Pr-i | OEt |
| Me | Me | H | H | 0 | H | H | OEt | Pr-i | CF₃ |
| Me | Me | H | H | 0 | H | H | CF₃ | Pr-i | OCHF₂ |
| Me | Me | H | H | 0 | H | H | OCHF₂ | Pr-i | CF₃ |
| Me | Me | H | H | 0 | H | H | CF₃ | Pr-i | CN |
| Me | Me | H | H | 0 | H | H | CN | Pr-i | CF₃ |
| Me | Me | H | H | 0 | H | H | CF₃ | Pr-i | Me |
| Me | Me | H | H | 0 | H | H | Me | Pr-i | CF₃ |
| Me | Me | H | H | 0 | H | H | Cl | Pr | Cl |
| Me | Me | H | H | 0 | H | H | OCHF₂ | Pr | Cl |
| Me | Me | H | H | 0 | H | H | Cl | Pr | OCHF₂ |
| Me | Me | H | H | 0 | H | H | OCHF₂ | Pr | OCHF₂ |
| Me | Me | H | H | 0 | H | H | CF₃ | Pr | F |
| Me | Me | H | H | 0 | H | H | F | Pr | CF₃ |
| Me | Me | H | H | 0 | H | H | CF₃ | Pr | Cl |
| Me | Me | H | H | 0 | H | H | Cl | Pr | CF₃ |
| Me | Me | H | H | 0 | H | H | CF₃ | Pr | OMe |
| Me | Me | H | H | 0 | H | H | OMe | Pr | CF₃ |
| Me | Me | H | H | 0 | H | H | CF₃ | Pr | OEt |
| Me | Me | H | H | 0 | H | H | OEt | Pr | CF₃ |
| Me | Me | H | H | 0 | H | H | CF₃ | Pr | OCHF₂ |
| Me | Me | H | H | 0 | H | H | OCHF₂ | Pr | CF₃ |
| Me | Me | H | H | 0 | H | H | CF₃ | Pr | CN |
| Me | Me | H | H | 0 | H | H | CN | Pr | CF₃ |
| Me | Me | H | H | 0 | H | H | CF₃ | Pr | Me |
| Me | Me | H | H | 0 | H | H | Me | Pr | CF₃ |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 0 | H | H | Cl | Bu-t | Cl |
| Me | Me | H | H | 0 | H | H | OCHF₂ | Bu-t | Cl |
| Me | Me | H | H | 0 | H | H | OCHF₂ | Bu-t | OCHF₂ |
| Me | Me | H | H | 0 | H | H | CF₃ | Bu-t | H |
| Me | Me | H | H | 0 | H | H | CF₃ | Bu-t | F |
| Me | Me | H | H | 0 | H | H | CF₃ | Bu-t | Cl |
| Me | Me | H | H | 0 | H | H | Cl | Bu-t | CF₃ |
| Me | Me | H | H | 0 | H | H | CF₃ | Bu-t | OMe |
| Me | Me | H | H | 0 | H | H | OMe | Bu-t | CF₃ |
| Me | Me | H | H | 0 | H | H | CF₃ | Bu-t | OEt |
| Me | Me | H | H | 0 | H | H | OEt | Bu-t | CF₃ |
| Me | Me | H | H | 0 | H | H | CF₃ | Bu-t | OCHF₂ |
| Me | Me | H | H | 0 | H | H | CF₃ | Bu-t | CN |
| Me | Me | H | H | 0 | H | H | CF₃ | Bu-t | Me |
| Me | Me | H | H | 0 | H | H | Me | Bu-t | CF₃ |
| Me | Me | H | H | 0 | H | H | CF₃ | Bu-s | Cl |
| Me | Me | H | H | 0 | H | H | Cl | Bu-s | CF₃ |
| Me | Me | H | H | 0 | H | H | CF₃ | Bu-i | Cl |
| Me | Me | H | H | 0 | H | H | Cl | Bu-i | CF₃ |
| Me | Me | H | H | 0 | H | H | CF₃ | Bu | Cl |
| Me | Me | H | H | 0 | H | H | Cl | Bu | CF₃ |
| Me | Me | H | H | 0 | H | H | CF₃ | 1-Methylbutyl | Cl |
| Me | Me | H | H | 0 | H | H | Cl | 1-Methylbutyl | CF₃ |
| Me | Me | H | H | 0 | H | H | CF₃ | 1-Ethylpropyl | Cl |
| Me | Me | H | H | 0 | H | H | Cl | 1-Ethylpropyl | CF₃ |
| Me | Me | H | H | 0 | H | H | CF₃ | 1-Pentyl | Cl |
| Me | Me | H | H | 0 | H | H | Cl | 1-Pentyl | CF₃ |
| Me | Me | H | H | 0 | H | H | CF₃ | 1-Methylpentyl | Cl |
| Me | Me | H | H | 0 | H | H | Cl | 1-Methylpentyl | CF₃ |
| Me | Me | H | H | 0 | H | H | CF₃ | 2-Ethylbutyl | Cl |
| Me | Me | H | H | 0 | H | H | Cl | 2-Ethylbutyl | CF₃ |
| Me | Me | H | H | 0 | H | H | CF₃ | 3,3-Dimethylbutyl | Cl |
| Me | Me | H | H | 0 | H | H | Cl | 3,3-Dimethylbutyl | CF₃ |
| Me | Me | H | H | 0 | H | H | CF₃ | 1-Hexyl | Cl |
| Me | Me | H | H | 0 | H | H | Cl | 1-Hexyl | CF₃ |
| Me | Me | H | H | 0 | H | H | CF₃ | 1-Heptyl | Cl |
| Me | Me | H | H | 0 | H | H | Cl | 1-Heptyl | CF₃ |
| Me | Me | H | H | 0 | H | H | CF₃ | 1-Octyl | Cl |
| Me | Me | H | H | 0 | H | H | Cl | 1-Octyl | CF₃ |
| Me | Me | H | H | 0 | H | H | CF₃ | CH₂Ph | Cl |
| Me | Me | H | H | 0 | H | H | Cl | CH₂Ph | CF₃ |
| Me | Me | H | H | 0 | H | H | CF₃ | Pr-c | Cl |
| Me | Me | H | H | 0 | H | H | CF₃ | Pen-c | Cl |
| Me | Me | H | H | 0 | H | H | Cl | Pen-c | CF₃ |
| Me | Me | H | H | 0 | H | H | CF₃ | Hex-c | Cl |
| Me | Me | H | H | 0 | H | H | Cl | Hex-c | CF₃ |
| Me | Me | H | H | 0 | H | H | Cl | CH₂Pr-c | Cl |
| Me | Me | H | H | 0 | H | H | OCHF₂ | CH₂Pr-c | Cl |
| Me | Me | H | H | 0 | H | H | Cl | CH₂Pr-c | OCHF₂ |
| Me | Me | H | H | 0 | H | H | OCHF₂ | CH₂Pr-c | OCHF₂ |
| Me | Me | H | H | 0 | H | H | CF₃ | CH₂Pr-c | F |
| Me | Me | H | H | 0 | H | H | F | CH₂Pr-c | CF₃ |
| Me | Me | H | H | 0 | H | H | CF₃ | CH₂Pr-c | Cl |
| Me | Me | H | H | 0 | H | H | Cl | CH₂Pr-c | CF₃ |
| Me | Me | H | H | 0 | H | H | CF₃ | CH₂Pr-c | CN |
| Me | Me | H | H | 0 | H | H | CF₃ | CH₂Pr-c | OH |
| Me | Me | H | H | 0 | H | H | CF₃ | CH₂Pr-c | OMe |
| Me | Me | H | H | 0 | H | H | OMe | CH₂Pr-c | CF₃ |
| Me | Me | H | H | 0 | H | H | CF₃ | CH₂Pr-c | OEt |
| Me | Me | H | H | 0 | H | H | OEt | CH₂Pr-c | CF₃ |
| Me | Me | H | H | 0 | H | H | CF₃ | CH₂Pr-c | OPr-i |
| Me | Me | H | H | 0 | H | H | CF₃ | CH₂Pr-c | OPr |
| Me | Me | H | H | 0 | H | H | CF₃ | CH₂Pr-c | OBu-t |
| Me | Me | H | H | 0 | H | H | CF₃ | CH₂Pr-c | OCH₂Pr-c |
| Me | Me | H | H | 0 | H | H | CF₃ | CH₂Pr-c | OCH₂Bu-c |
| Me | Me | H | H | 0 | H | H | CF₃ | CH₂Pr-c | OPen-c |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 0 | H | H | $CF_3$ | $CH_2Pr$-c | $OCHF_2$ |
| Me | Me | H | H | 0 | H | H | $OCHF_2$ | $CH_2Pr$-c | $CF_3$ |
| Me | Me | H | H | 0 | H | H | $CF_3$ | $CH_2Pr$-c | CN |
| Me | Me | H | H | 0 | H | H | CN | $CH_2Pr$-o | $CF_3$ |
| Me | Me | H | H | 0 | H | H | $CF_3$ | $CH_2Pr$-c | Me |
| Me | Me | H | H | 0 | H | H | Me | $CH_2Pr$-c | $CF_3$ |
| Me | Me | H | H | 0 | H | H | $CF_3$ | 1-cyclopropylethyl | Cl |
| Me | Me | H | H | 0 | H | H | Cl | 1-cyclopropylethyl | $CF_3$ |
| Me | Me | H | H | 0 | H | H | $CF_3$ | $CH_2$(2-Methyl-cyclopropyl) | Cl |
| Me | Me | H | H | 0 | H | H | Cl | $CH_2$(2-Methyl-cyclopropyl) | $CF_3$ |
| Me | Me | H | H | 0 | H | H | $CF_3$ | $CH_2$(2,2-Dimethyl-cycloproppyl) | Cl |
| Me | Me | H | H | 0 | H | H | Cl | $CH_2$(2,2-Dimethyl-cyclopropyl) | $CF_3$ |
| Me | Me | H | H | 0 | H | H | $CF_3$ | $CH_2$(2-Chloro-cyclopropyl) | Cl |
| Me | Me | H | H | 0 | H | H | Cl | $CH_2$(2-Chloro-cyclopropyl) | $CF_3$ |
| Me | Me | H | H | 0 | H | H | $CF_3$ | $CH_2$(2,2-Dichloro-cyclopropyl) | Cl |
| Me | Me | H | H | 0 | H | H | Cl | $CH_2$(2,2-Dichloro-cyclopropyl) | $CF_3$ |
| Me | Me | H | H | 0 | H | H | $CF_3$ | $CH_2$(2-Fluoro-cyclopropyl) | Cl |
| Me | Me | H | H | 0 | H | H | Cl | $CH_2$(2-Fluoro-cyclopropyl) | $CF_3$ |
| Me | Me | H | H | 0 | H | H | $CF_3$ | $CH_2$(2,2-Difluoro-cyclopropyl) | Cl |
| Me | Me | H | H | 0 | H | H | Cl | $CH_2$(2,2-Difluoro-cyclopropyl) | $CF_3$ |
| Me | Me | H | H | 0 | H | H | $CF_3$ | $CH_2Bu$-c | Cl |
| Me | Me | H | H | 0 | H | H | Cl | $CH_2Bu$-c | $CF_3$ |
| Me | Me | H | H | 0 | H | H | $CF_3$ | $CH_2Pen$-c | Cl |
| Me | Me | H | H | 0 | H | H | Cl | $CH_2Pen$-c | $CF_3$ |
| Me | Me | H | H | 0 | H | H | $CF_3$ | $CH_2Hex$-c | Cl |
| Me | Me | H | H | 0 | H | H | Cl | $CH_2Hex$-c | $CF_3$ |
| Me | Me | H | H | 0 | H | H | $CF_3$ | $CH_2CH_2Pr$-c | Cl |
| Me | Me | H | H | 0 | H | H | Cl | $CH_2CH_2Pr$-c | $CF_3$ |
| Me | Me | H | H | 0 | H | H | $CF_3$ | $CH_2CH=CH_2$ | Cl |
| Me | Me | H | H | 0 | H | H | Cl | $CH_2CH=CH_2$ | $CF_3$ |
| Me | Me | H | H | 0 | H | H | $CF_3$ | $CH_2CH=CHCl$ | Cl |
| Me | Me | H | H | 0 | H | H | Cl | $CH_2CH=CHCl$ | $CF_3$ |
| Me | Me | H | H | 0 | H | H | Cl | $CH_2C\equiv CH$ | Cl |
| Me | Me | H | H | 0 | H | H | $OCHF_2$ | $CH_2C\equiv CH$ | Cl |
| Me | Me | H | H | 0 | H | H | Cl | $CH_2C\equiv CH$ | $OCHF_2$ |
| Me | Me | H | H | 0 | H | H | $OCHF_2$ | $CH_2C\equiv CH$ | OCHF |
| Me | Me | H | H | 0 | H | H | $CF_3$ | $CH_2C\equiv CH$ | F |
| Me | Me | H | H | 0 | H | H | F | $CH_2C\equiv CH$ | $CF_3$ |
| Me | Me | H | H | 0 | H | H | $CF_3$ | $CH_2C\equiv CH$ | Cl |
| Me | Me | H | H | 0 | H | H | Cl | $CH_2C\equiv CH$ | $CF_3$ |
| Me | Me | H | H | 0 | H | H | $CF_3$ | $CH_2C\equiv CH$ | OMe |
| Me | Me | H | H | 0 | H | H | OMe | $CH_2C\equiv CH$ | $CF_3$ |
| Me | Me | H | H | 0 | H | H | $CF_3$ | $CH_2C\equiv CH$ | OEt |
| Me | Me | H | H | 0 | H | H | OEt | $CH_2C\equiv CH$ | $CF_3$ |
| Me | Me | H | H | 0 | H | H | $CF_3$ | $CH_2C\equiv CH$ | $OCHF_2$ |
| Me | Me | H | H | 0 | H | H | $OCHF_2$ | $CH_2C\equiv CH$ | $CF_3$ |
| Me | Me | H | H | 0 | H | H | $CF_3$ | $CH_2C\equiv CH$ | CN |
| Me | Me | H | H | 0 | H | H | CN | $CH_2C\equiv CH$ | $CF_3$ |
| Me | Me | H | H | 0 | H | H | $CF_3$ | $CH_2C\equiv CH$ | Me |
| Me | Me | H | H | 0 | H | H | Me | $CH_2C\equiv CH$ | $CF_3$ |
| Me | Me | H | H | 0 | H | H | $CF_3$ | $CH_2C\equiv CH$ | Cl |
| Me | Me | H | H | 0 | H | H | Cl | $CH_2C\equiv CH$ | $CF_3$ |
| Me | Me | H | H | 0 | H | H | $CF_3$ | $CH_2C\equiv Me$ | Cl |
| Me | Me | H | H | 0 | H | H | Cl | $CH_2C\equiv Me$ | $CF_3$ |
| Me | Me | H | H | 0 | H | H | Cl | $CHF_2$ | Cl |
| Me | Me | H | H | 0 | H | H | $OCHF_2$ | $CHF_2$ | Cl |
| Me | Me | H | H | 0 | H | H | Cl | $CHF_2$ | $OCHF_2$ |
| Me | Me | H | H | 0 | H | H | $OCHF_2$ | $CHF_2$ | $OCHF_2$ |
| Me | Me | H | H | 0 | H | H | $CF_3$ | $CHF_2$ | Cl |
| Me | Me | H | H | 0 | H | H | Cl | $CHF_2$ | $CF_3$ |
| Me | Me | H | H | 0 | H | H | $CF_3$ | $CHF_2$ | F |
| Me | Me | H | H | 0 | H | H | F | $CHF_2$ | $CF_3$ |
| Me | Me | H | H | 0 | H | H | $CF_3$ | $CHF_2$ | OMe |
| Me | Me | H | H | 0 | H | H | OMe | $CHF_2$ | $CF_3$ |
| Me | Me | H | H | 0 | H | H | $CF_3$ | $CHF_2$ | OEt |
| Me | Me | H | H | 0 | H | H | OEt | $CHF_2$ | $CF_3$ |

TABLE 3-continued

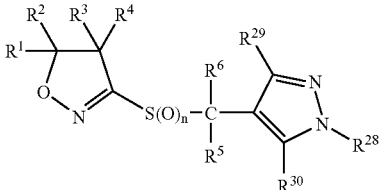

| $R^1$ | $R^2$ | $R^3$ | $R^4$ | n | $R^5$ | $R^6$ | $R^{29}$ | $R^{28}$ | $R^{30}$ |
|---|---|---|---|---|---|---|---|---|---|
| Me | Me | H | H | 0 | H | H | $CF_3$ | $CHF_2$ | $OCHF_2$ |
| Me | Me | H | H | 0 | H | H | $OCHF_2$ | $CHF_2$ | $CF_3$ |
| Me | Me | H | H | 0 | H | H | $CF_3$ | $CHF_2$ | CN |
| Me | Me | H | H | 0 | H | H | CN | $CHF_2$ | $CF_3$ |
| Me | Me | H | H | 0 | H | H | $CF_3$ | $CHF_2$ | Me |
| Me | Me | H | H | 0 | H | H | Me | $CHF_2$ | $CF_3$ |
| Me | Me | H | H | 0 | H | H | Me | $CHF_2$ | Cl |
| Me | Me | H | H | 0 | H | H | Cl | $CHF_2$ | Me |
| Me | Me | H | H | 0 | H | H | Et | $CHF_2$ | Cl |
| Me | Me | H | H | 0 | H | H | Cl | $CHF_2$ | Et |
| Me | Me | H | H | 0 | H | H | $CF_3$ | $CH_2CHF_2$ | Cl |
| Me | Me | H | H | 0 | H | H | Cl | $CH_2CHF_2$ | $CF_3$ |
| Me | Me | H | H | 0 | H | H | $CF_3$ | $CH_2CF_3$ | Cl |
| Me | Me | H | H | 0 | H | H | Cl | $CH_2CF_3$ | $CF_3$ |
| Me | Me | H | H | 0 | H | H | $CF_3$ | $CH_2OH$ | Cl |
| Me | Me | H | H | 0 | H | H | Cl | $CH_2OH$ | $CF_3$ |
| Me | Me | H | H | 0 | H | H | Cl | $CH_2OMe$ | Cl |
| Me | Me | H | H | 0 | H | H | $OCHF_2$ | $CH_2OMe$ | Cl |
| Me | Me | H | H | 0 | H | H | Cl | $CH_2OMe$ | $OCHF_2$ |
| Me | Me | H | H | 0 | H | H | $OCHF_2$ | $CH_2OMe$ | $OCHF_2$ |
| Me | Me | H | H | 0 | H | H | $CF_3$ | $CH_2OMe$ | F |
| Me | Me | H | H | 0 | H | H | F | $CH_2OMe$ | $CF_3$ |
| Me | Me | H | H | 0 | H | H | $CF_3$ | $CH_2OMe$ | Cl |
| Me | Me | H | H | 0 | H | H | Cl | $CH_2OMe$ | $CF_3$ |
| Me | Me | H | H | 0 | H | H | $CF_3$ | $CH_2OMe$ | OMe |
| Me | Me | H | H | 0 | H | H | OMe | $CH_2OMe$ | $CF_3$ |
| Me | Me | H | H | 0 | H | H | $CF_3$ | $CH_2OMe$ | OEt |
| Me | Me | H | H | 0 | H | H | OEt | $CH_2OMe$ | $CF_3$ |
| Me | Me | H | H | 0 | H | H | $CF_3$ | $CH_2OMe$ | $OCHF_2$ |
| Me | Me | H | H | 0 | H | H | $OCHF_2$ | $CH_2OMe$ | $CF_3$ |
| Me | Me | H | H | 0 | H | H | $CF_3$ | $CH_2OMe$ | CN |
| Me | Me | H | H | 0 | H | H | CN | $CH_2OMe$ | $CF_3$ |
| Me | Me | H | H | 0 | H | H | $CF_3$ | $CH_2OMe$ | Me |
| Me | Me | H | H | 0 | H | H | Me | $CH_2OMe$ | $CF_3$ |
| Me | Me | H | H | 0 | H | H | $CF_3$ | $CH_2OEt$ | Cl |
| Me | Me | H | H | 0 | H | H | Cl | $CH_2OEt$ | $CF_3$ |
| Me | Me | H | H | 0 | H | H | $CF_3$ | $CH_2CH_2OH$ | Cl |
| Me | Me | H | H | 0 | H | H | Cl | $CH_2CH_2OH$ | $CF_3$ |
| Me | Me | H | H | 0 | H | H | $CF_3$ | $CH_2CH_2OMe$ | Cl |
| Me | Me | H | H | 0 | H | H | Cl | $CH_2CH_2OMe$ | $CF_3$ |
| Me | Me | H | H | 0 | H | H | $CF_3$ | $CH_2CH_2OEt$ | Cl |
| Me | Me | H | H | 0 | H | H | Cl | $CH_2CH_2OEt$ | $CF_3$ |
| Me | Me | H | H | 0 | H | H | $CF_3$ | $CH_2NHMe$ | Cl |
| Me | Me | H | H | 0 | H | H | Cl | $CH_2NHMe$ | $CF_3$ |
| Me | Me | H | H | 0 | H | H | $CF_3$ | $CH_2N(Me)_2$ | Cl |
| Me | Me | H | H | 0 | H | H | Cl | $CH_2N(Me)_2$ | $CF_3$ |
| Me | Me | H | H | 0 | H | H | $CF_3$ | $CH_2N(Me)C(=O)Me$ | Cl |
| Me | Me | H | H | 0 | H | H | Cl | $CH_2N(Me)C(=O)Me$ | $CF_3$ |
| Me | Me | H | H | 0 | H | H | $CF_3$ | $CH_2N(Me)C(=O)CF_3$ | Cl |
| Me | Me | H | H | 0 | H | H | Cl | $CH_2N(Me)C(=O)CF_3$ | $CF_3$ |
| Me | Me | H | H | 0 | H | H | $CF_3$ | $CH_2N(Me)SO_2Me$ | Cl |
| Me | Me | H | H | 0 | H | H | Cl | $CH_2N(Me)SO_2Me$ | $CF_3$ |
| Me | Me | H | H | 0 | H | H | $CF_3$ | $CH_2N(Me)SO_2CHF_2$ | Cl |
| Me | Me | H | H | 0 | H | H | Cl | $CH_2N(Me)SO_2CHF_2$ | $CF_3$ |
| Me | Me | H | H | 0 | H | H | $CF_3$ | $CH_2N(Me)SO_2CF_3$ | Cl |
| Me | Me | H | H | 0 | H | H | Cl | $CH_2N(Me)SO_2CF_3$ | $CF_3$ |
| Me | Me | H | H | 0 | H | H | $CF_3$ | $CH_2SMe$ | Cl |
| Me | Me | H | H | 0 | H | H | Cl | $CH_2SMe$ | $CF_3$ |
| Me | Me | H | H | 0 | H | H | $CF_3$ | $CH_2SO_2Me$ | Cl |
| Me | Me | H | H | 0 | H | H | Cl | $CH_2SO_2Me$ | $CF_3$ |
| Me | Me | H | H | 0 | H | H | $CF_3$ | $CH_2CH_2SMe$ | Cl |
| Me | Me | H | H | 0 | H | H | Cl | $CH_2CH_2SMe$ | $CF_3$ |
| Me | Me | H | H | 0 | H | H | $CF_3$ | $CH_2CH_2SO_2Me$ | Cl |
| Me | Me | H | H | 0 | H | H | Cl | $CH_2CH_2SO_2Me$ | $CF_3$ |
| Me | Me | H | H | 0 | H | H | $CF_3$ | $CH_2CN$ | Cl |
| Me | Me | H | H | 0 | H | H | Cl | $CH_2CN$ | $CF_3$ |

TABLE 3-continued

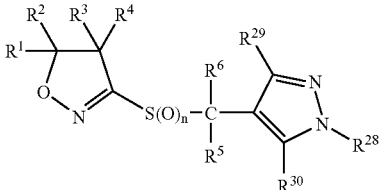

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 0 | H | H | $CF_3$ | $CH_2C(=O)OMe$ | Cl |
| Me | Me | H | H | 0 | H | H | Cl | $CH_2C(=O)OMe$ | $CF_3$ |
| Me | Me | H | H | 0 | H | H | $CF_3$ | $CH_2C(=O)OEt$ | Cl |
| Me | Me | H | H | 0 | H | H | Cl | $CH_2C(=O)OEt$ | $CF_3$ |
| Me | Me | H | H | 0 | H | H | $CF_3$ | $CH(Me)C(=O)OMe$ | Cl |
| Me | Me | H | H | 0 | H | H | Cl | $CH(Me)C(=O)OMe$ | $CF_3$ |
| Me | Me | H | H | 0 | H | H | $CF_3$ | $C(Me)_2C(=O)OMe$ | Cl |
| Me | Me | H | H | 0 | H | H | Cl | $C(Me)_2C(=O)OMe$ | $CF_3$ |
| Me | Me | H | H | 0 | H | H | $CF_3$ | $CH_2C(=O)NH_2$ | Cl |
| Me | Me | H | H | 0 | H | H | Cl | $CH_2C(=O)NH_2$ | $CF_3$ |
| Me | Me | H | H | 0 | H | H | $CF_3$ | $CH_2C(=O)NHMe$ | Cl |
| Me | Me | H | H | 0 | H | H | Cl | $CH_2C(=O)NHMe$ | $CF_3$ |
| Me | Me | H | H | 0 | H | H | $CF_3$ | $CH_2C(=O)N(Me)_2$ | Cl |
| Me | Me | H | H | 0 | H | H | Cl | $CH_2C(=O)N(Me)_2$ | $CF_3$ |
| Me | Me | H | H | 0 | H | H | $CF_3$ | $CH_2C(=O)Me$ | Cl |
| Me | Me | H | H | 0 | H | H | Cl | $CH_2C(=O)Me$ | $CF_3$ |
| Me | Me | H | H | 0 | H | H | $CF_3$ | $CH_2C(=NOMe)Me$ | Cl |
| Me | Me | H | H | 0 | H | H | Cl | $CH_2C(=NOMe)Me$ | $CF_3$ |
| Me | Me | H | H | 0 | H | H | $CF_3$ | $CH_2C(=O)CF_3$ | Cl |
| Me | Me | H | H | 0 | H | H | Cl | $CH_2C(=O)CF_3$ | $CF_3$ |
| Me | Me | H | H | 0 | H | H | $CF_3$ | $CH_2CH_2C(=O)Me$ | Cl |
| Me | Me | H | H | 0 | H | H | Cl | $CH_2CH_2C(=O)Me$ | $CF_3$ |
| Me | Me | H | H | 0 | H | H | Me | Ph | Me |
| Me | Me | H | H | 0 | H | H | Me | Ph | Cl |
| Me | Me | H | H | 0 | H | H | Et | Ph | Cl |
| Me | Me | H | H | 0 | H | H | Pr | Ph | Cl |
| Me | Me | H | H | 0 | H | H | Pr-i | Ph | Cl |
| Me | Me | H | H | 0 | H | H | Bu-t | Ph | Cl |
| Me | Me | H | H | 0 | H | H | $CH_2OMe$ | Ph | Cl |
| Me | Me | H | H | 0 | H | H | Cl | Ph | Cl |
| Me | Me | H | H | 0 | H | H | $OCHF_2$ | Ph | Cl |
| Me | Me | H | H | 0 | H | H | $OCHF_2$ | Ph | $OCHF_2$ |
| Me | Me | H | H | 0 | H | H | $CHF_2$ | Ph | Cl |
| Me | Me | H | H | 0 | H | H | $CF_3$ | Ph | H |
| Me | Me | H | H | 0 | H | H | $CF_3$ | Ph | Me |
| Me | Me | H | H | 0 | H | H | Me | Ph | $CF_3$ |
| Me | Me | H | H | 0 | H | H | $CF_3$ | Ph | Et |
| Me | Me | H | H | 0 | H | H | $CF_3$ | Ph | Pr-i |
| Me | Me | H | H | 0 | H | H | $CF_3$ | Ph | $CHF_2$ |
| Me | Me | H | H | 0 | H | H | $CF_3$ | Ph | $CF_3$ |
| Me | Me | H | H | 0 | H | H | $CF_3$ | Ph | F |
| Me | Me | H | H | 0 | H | H | $CF_3$ | Ph | Cl |
| Me | Me | H | H | 0 | H | H | Cl | Ph | $CF_3$ |
| Me | Me | H | H | 0 | H | H | $CF_3$ | Ph | OH |
| Me | Me | H | H | 0 | H | H | OH | Ph | $CF_3$ |
| Me | Me | H | H | 0 | H | H | $CF_3$ | Ph | OMe |
| Me | Me | H | H | 0 | H | H | OMe | Ph | $CF_3$ |
| Me | Me | H | H | 0 | H | H | $CF_3$ | Ph | OEt |
| Me | Me | H | H | 0 | H | H | OEt | Ph | $CF_3$ |
| Me | Me | H | H | 0 | H | H | $CF_3$ | Ph | OPr-i |
| Me | Me | H | H | 0 | H | H | $CF_3$ | Ph | OPr |
| Me | Me | H | H | 0 | H | H | $CF_3$ | Ph | OBu-t |
| Me | Me | H | H | 0 | H | H | $CF_3$ | Ph | $OCH_2Pr$-c |
| Me | Me | H | H | 0 | H | H | $CF_3$ | Ph | $OCH_2CH=CH_2$ |
| Me | Me | H | H | 0 | H | H | $CF_3$ | Ph | $OCH_2C\equiv CH$ |
| Me | Me | H | H | 0 | H | H | $CF_3$ | Ph | $OCHF_2$ |
| Me | Me | H | H | 0 | H | H | $OCHF_2$ | Ph | $CF_3$ |
| Me | Me | H | H | 0 | H | H | $CF_3$ | Ph | $OCH_2CHF_2$ |
| Me | Me | H | H | 0 | H | H | $CF_3$ | Ph | $OCH_2CF_3$ |
| Me | Me | H | H | 0 | H | H | $CF_3$ | Ph | $OCH_2C(=O)OMe$ |
| Me | Me | H | H | 0 | H | H | $CF_3$ | Ph | $OCH(Me)C(=O)OMe$ |
| Me | Me | H | H | 0 | H | H | $CF_3$ | Ph | $OC(Me)_2C(=O)OMe$ |
| Me | Me | H | H | 0 | H | H | $CF_3$ | Ph | $OC(=O)Me$ |
| Me | Me | H | H | 0 | H | H | $CF_3$ | Ph | $OC(=O)Et$ |
| Me | Me | H | H | 0 | H | H | $CF_3$ | Ph | $OC(=O)CH_2Ph$ |
| Me | Me | H | H | 0 | H | H | $CF_3$ | Ph | $OC(=O)CF_3$ |

TABLE 3-continued

| R¹ | R² | R³ | R⁴ | n | R⁵ | R⁶ | R²⁹ | R²⁸ | R³⁰ |
|---|---|---|---|---|---|---|---|---|---|
| Me | Me | H | H | 0 | H | H | CF₃ | Ph | OC(=O)Ph |
| Me | Me | H | H | 0 | H | H | CF₃ | Ph | OSO₂Me |
| Me | Me | H | H | 0 | H | H | CF₃ | Ph | OSO₂Et |
| Me | Me | H | H | 0 | H | H | CF₃ | Ph | OSO₂CH₂Ph |
| Me | Me | H | H | 0 | H | H | CF₃ | Ph | OSO₂CF₃ |
| Me | Me | H | H | 0 | H | H | CF₃ | Ph | OSO₂Ph |
| Me | Me | H | H | 0 | H | H | CF₃ | Ph | SMe |
| Me | Me | H | H | 0 | H | H | CF₃ | Ph | SO₂Me |
| Me | Me | H | H | 0 | H | H | CF₃ | Ph | SEt |
| Me | Me | H | H | 0 | H | H | CF₃ | Ph | SO₂Et |
| Me | Me | H | H | 0 | H | H | CF₃ | Ph | SPr-i |
| Me | Me | H | H | 0 | H | H | CF₃ | Ph | SO₂Pr-i |
| Me | Me | H | H | 0 | H | H | CF₃ | Ph | SPr |
| Me | Me | H | H | 0 | H | H | CF₃ | Ph | SO₂Pr |
| Me | Me | H | H | 0 | H | H | CF₃ | Ph | SBu-t |
| Me | Me | H | H | 0 | H | H | CF₃ | Ph | SO₂Bu-t |
| Me | Me | H | H | 0 | H | H | CF₃ | Ph | SCHF₂ |
| Me | Me | H | H | 0 | H | H | CF₃ | Ph | SO₂CHF₂ |
| Me | Me | H | H | 0 | H | H | CF₃ | Ph | NH₂ |
| Me | Me | H | H | 0 | H | H | CF₃ | Ph | NHMe |
| Me | Me | H | H | 0 | H | H | CF₃ | Ph | N(Me)₂ |
| Me | Me | H | H | 0 | H | H | CF₃ | Ph | NHC(=O)Me |
| Me | Me | H | H | 0 | H | H | CF₃ | Ph | N(Me)C(=O)Me |
| Me | Me | H | H | 0 | H | H | CF₃ | Ph | NHSO₂Me |
| Me | Me | H | H | 0 | H | H | CF₃ | Ph | N(Me)SO₂Me |
| Me | Me | H | H | 0 | H | H | CF₃ | Ph | NHSO₂CF₃ |
| Me | Me | H | H | 0 | H | H | CF₃ | Ph | N(Me)SO₂CF₃ |
| Me | Me | H | H | 0 | H | H | CF₃ | Ph | NHPh |
| Me | Me | H | H | 0 | H | H | CF₃ | Ph | N(Me)Ph |
| Me | Me | H | H | 0 | H | H | CF₃ | Ph | CN |
| Me | Me | H | H | 0 | H | H | CF₃ | Ph | C(=O)Me |
| Me | Me | H | H | 0 | H | H | CF₃ | Ph | C(=O)OMe |
| Me | Me | H | H | 0 | H | H | CF₃ | Ph | C(=O)NH₂ |
| Me | Me | H | H | 0 | H | H | CF₃ | Ph | C(=O)NHMe |
| Me | Me | H | H | 0 | H | H | CF₃ | Ph | C(=O)N(Me)₂ |
| Me | Me | H | H | 0 | H | H | CF₃ | Ph | Imidazol-1-yl |
| Me | Me | H | H | 0 | H | H | CF₃ | Ph | Pyrazol-1-yl |
| Me | Me | H | H | 0 | H | H | CF₃ | Ph | 1,2,4-Triazol-1-yl |
| Me | Me | H | H | 0 | H | H | CF₃ | Ph | 1,2,4-Triazol-4-yl |
| Me | Me | H | H | 0 | H | H | CF₃ | Ph | Tetrazol-1-yl |
| Me | Me | H | H | 0 | H | H | CF₃ | Ph | Tetrazol-5-yl |
| Me | Me | H | H | 0 | H | H | CF₃ | Ph | (4,6-Dimethoxypyrimidin-2-yl)oxy |
| Me | Me | H | H | 0 | H | H | CF₃ | Ph | (4,6-Dimethoxypyrimidin-2-yl)sulfonyl |
| Me | Me | H | H | 0 | H | H | CF₂CF₃ | Ph | Cl |
| Me | Me | H | H | 0 | H | H | CF₃ | (2-Cl)Ph | Cl |
| Me | Me | H | H | 0 | H | H | CF₃ | (2-F)Ph | Cl |
| Me | Me | H | H | 0 | H | H | CF₃ | (2-OMe)Ph | Cl |
| Me | Me | H | H | 0 | H | H | CF₃ | (2-Me)Ph | Cl |
| Me | Me | H | H | 0 | H | H | CF₃ | (2-NO₂)Ph | Cl |
| Me | Me | H | H | 0 | H | H | CF₃ | (2-CN)Ph | Cl |
| Me | Me | H | H | 0 | H | H | CF₃ | (2-C(=O)Me)Ph | Cl |
| Me | Me | H | H | 0 | H | H | CF₃ | (2-C(=O)OMe)Ph | Cl |
| Me | Me | H | H | 0 | H | H | CF₃ | (2-C(=O)OEt)Ph | Cl |
| Me | Me | H | H | 0 | H | H | CF₃ | (2-C(=O)OPr-i)Ph | Cl |
| Me | Me | H | H | 0 | H | H | CF₃ | (2-C(=O)NH₂)Ph | Cl |
| Me | Me | H | H | 0 | H | H | CF₃ | (2-C(=O)NHMe)Ph | Cl |
| Me | Me | H | H | 0 | H | H | CF₃ | (2-C(=O)NMe₂)Ph | Cl |
| Me | Me | H | H | 0 | H | H | CF₃ | (3-Cl)Ph | Cl |
| Me | Me | H | H | 0 | H | H | CF₃ | (3-F)Ph | Cl |
| Me | Me | H | H | 0 | H | H | CF₃ | (3-OMe)Ph | Cl |
| Me | Me | H | H | 0 | H | H | CF₃ | (3-Me)Ph | Cl |
| Me | Me | H | H | 0 | H | H | CF₃ | (3-NO₂)Ph | Cl |
| Me | Me | H | H | 0 | H | H | CF₃ | (3-CN)Ph | Cl |
| Me | Me | H | H | 0 | H | H | CF₃ | (3-C(=O)Me)Ph | Cl |
| Me | Me | H | H | 0 | H | H | CF₃ | (3-C(=O)OMe)Ph | Cl |

TABLE 3-continued

| R$^1$ | R$^2$ | R$^3$ | R$^4$ | n | R$^5$ | R$^6$ | R$^{29}$ | R$^{28}$ | R$^{30}$ |
|---|---|---|---|---|---|---|---|---|---|
| Me | Me | H | H | 0 | H | H | CF$_3$ | (3-C(=O)OEt)Ph | Cl |
| Me | Me | H | H | 0 | H | H | CF$_3$ | (3-C(=O)OPr-i)Ph | Cl |
| Me | Me | H | H | 0 | H | H | CF$_3$ | (3-C(=O)NH$_2$)Ph | Cl |
| Me | Me | H | H | 0 | H | H | CF$_3$ | (3-C(=O)NHMe)Ph | Cl |
| Me | Me | H | H | 0 | H | H | CF$_3$ | (3-C(=O)NMe$_2$)Ph | Cl |
| Me | Me | H | H | 0 | H | H | CF$_3$ | (4-Cl)Ph | Cl |
| Me | Me | H | H | 0 | H | H | CF$_3$ | (4-F)Ph | Cl |
| Me | Me | H | H | 0 | H | H | CF$_3$ | (4-OMe)Ph | Cl |
| Me | Me | H | H | 0 | H | H | CF$_3$ | (4-Me)Ph | Cl |
| Me | Me | H | H | 0 | H | H | CF$_3$ | (4-NO$_2$)Ph | Cl |
| Me | Me | H | H | 0 | H | H | CF$_3$ | (4-N)Ph | Cl |
| Me | Me | H | H | 0 | H | H | CF$_3$ | (4-C(=O)Me)Ph | Cl |
| Me | Me | H | H | 0 | H | H | CF$_3$ | (4-C(=O)OMe)Ph | Cl |
| Me | Me | H | H | 0 | H | H | CF$_3$ | (4-C(=O)OEt)Ph | Cl |
| Me | Me | H | H | 0 | H | H | CF$_3$ | (4-C(=O)OPr-i)Ph | Cl |
| Me | Me | H | H | 0 | H | H | CF$_3$ | (4-C(=O)NH$_2$)Ph | Cl |
| Me | Me | H | H | 0 | H | H | CF$_3$ | (4-C(=O)NHMe)Ph | Cl |
| Me | Me | H | H | 0 | H | H | CF$_3$ | C4-C(=O)NMe$_2$)Ph | Cl |
| Me | Me | H | H | 0 | H | H | CF$_3$ | Pyrmidin-2-yl | Cl |
| Me | Me | H | H | 0 | H | H | CF$_3$ | 4,6-Dimethoxypyrmidin-2-yl | Cl |
| Me | Me | H | H | 0 | H | H | CF$_3$ | Thiophen-2-yl | Cl |
| Me | Me | H | H | 0 | H | H | CF$_3$ | Furan-2-yl | Cl |
| Me | Me | H | H | 0 | H | H | CF$_3$ | SO$_2$Me | Cl |
| Me | Me | H | H | 0 | H | H | CF$_3$ | SO$_2$Et | Cl |
| Me | Me | H | H | 0 | H | H | CF$_3$ | SO$_2$Pr-i | Cl |
| Me | Me | H | H | 0 | H | H | CF$_3$ | SO$_2$CH$_2$Ph | Cl |
| Me | Me | H | H | 0 | H | H | CF$_3$ | SO$_2$CHF$_2$ | Cl |
| Me | Me | H | H | 0 | H | H | CF$_3$ | SO$_2$CF$_3$ | Cl |
| Me | Me | H | H | 0 | H | H | CF$_3$ | SO$_2$Ph | Cl |
| Me | Me | H | H | 0 | H | H | CF$_3$ | C(=O)Me | Cl |
| Me | Me | H | H | 0 | H | H | CF$_3$ | C(=O)Et | Cl |
| Me | Me | H | H | 0 | H | H | CF$_3$ | C(=O)Pr-i | Cl |
| Me | Me | H | H | 0 | H | H | CF$_3$ | C(=O)Bu-t | Cl |
| Me | Me | H | H | 0 | H | H | CF$_3$ | C(=O)Ph | Cl |
| Me | Me | H | H | 0 | H | H | CF$_3$ | C(=O)CH$_2$Ph | Cl |
| Me | Me | H | H | 0 | H | H | CF$_3$ | C(=O)CH$_2$Cl | Cl |
| Me | Me | H | H | 0 | H | H | CF$_3$ | C(=O)CHCl$_2$ | Cl |
| Me | Me | H | H | 0 | H | H | CF$_3$ | C(=O)CF$_3$ | Cl |
| Me | Me | H | H | 0 | H | H | CF$_3$ | C(=O)OMe | Cl |
| Me | Me | H | H | 0 | H | H | CF$_3$ | C(=O)OPh | Cl |
| Me | Me | H | H | 0 | H | H | CF$_3$ | C(=O)OCH$_2$Ph | Cl |
| Me | Me | H | H | 0 | H | H | CF$_3$ | C(=O)NHMe | Cl |
| Me | Me | H | H | 0 | H | H | CF$_3$ | C(=O)N(Me)$_2$ | Cl |
| Me | Me | H | H | 0 | H | H | CF$_3$ | C(=O)NHPh | Cl |
| Me | Me | H | H | 0 | H | H | CF$_3$ | NH$_2$ | Cl |
| Me | Me | H | H | 0 | H | H | Cl | | —(CH$_2$)$_2$O— |
| Me | Me | H | H | 0 | H | H | Cl | | —(CH$_2$)$_3$O— |
| Me | Me | H | H | 0 | H | H | Cl | | —(CH$_2$)$_3$S— |
| Me | Me | H | H | 0 | H | H | Cl | | —(CH$_2$)$_3$SO$_2$— |
| Me | Me | H | H | 0 | H | H | CF$_3$ | | —(CH$_2$)$_2$O— |
| Me | Me | H | H | 0 | H | H | CF$_3$ | | —(CH$_2$)$_3$O— |
| Me | Me | H | H | 0 | H | H | CF$_3$ | | —(CH$_2$)$_3$S— |
| Me | Me | H | H | 0 | H | H | CF$_3$ | | —(CH$_2$)$_3$SO$_2$— |
| Me | Me | H | H | 0 | H | H | OMe | | —(CH$_2$)$_4$— |
| Me | Me | H | H | 0 | H | H | OCHF$_2$ | | —(CH$_2$)$_4$— |
| H | H | H | H | 0 | H | H | CF$_3$ | Me | Cl |
| Me | H | H | H | 0 | H | H | CF$_3$ | Me | Cl |
| Me | H | Me | H | 0 | H | H | CF$_3$ | Me | Cl |
| Me | Me | Me | H | 0 | H | H | CF$_3$ | Me | Cl |
| Me | Me | H | H | 0 | Me | H | CF$_3$ | Me | Cl |
| Me | Me | H | H | 0 | Et | H | CF$_3$ | Me | Cl |
| Me | Me | H | H | 0 | Pr-i | H | CF$_3$ | Me | Cl |
| Me | Me | H | H | 0 | Me | Me | CF$_3$ | Me | Cl |
| Me | Et | H | H | 0 | H | H | CF$_3$ | Me | Cl |
| Et | Et | H | H | 0 | H | H | CF$_3$ | Me | Cl |
| Me | Pr-i | H | H | 0 | H | H | CF$_3$ | Me | Cl |

TABLE 3-continued

| $R^1$ | $R^2$ | $R^3$ | $R^4$ | n | $R^5$ | $R^6$ | $R^{29}$ | $R^{28}$ | $R^{30}$ |
|---|---|---|---|---|---|---|---|---|---|
| Me | Pr | H | H | 0 | H | H | $CF_3$ | Me | Cl |
| Me | Pr-c | H | H | 0 | H | H | $CF_3$ | Me | Cl |
| Me | $CH_2$Pr-c | H | H | 0 | H | H | $CF_3$ | Me | Cl |
| —$(CH_2)_2$— | | H | H | 0 | H | H | $CF_3$ | Me | Cl |
| —$(CH_2)_3$— | | H | H | 0 | H | H | $CF_3$ | Me | Cl |
| —$(CH_2)_4$— | | H | H | 0 | H | H | $CF_3$ | Me | Cl |
| —$(CH_2)_5$— | | H | H | 0 | H | H | $CF_3$ | Me | Cl |
| H | —$(CH_2)_3$— | | H | 0 | H | H | $CF_3$ | Me | Cl |
| H | —$(CH_2)_4$— | | H | 0 | H | H | $CF_3$ | Me | Cl |
| H | —$(CH_2)_5$— | | H | 0 | H | H | $CF_3$ | Me | Cl |
| H | —$(CH_2)_6$— | | H | 0 | H | H | $CF_3$ | Me | Cl |
| Me | Et | H | H | 2 | H | H | H | | H | H |

TABLE 4

| $R^1$ | $R^2$ | $R^3$ | $R^4$ | n | $R^5$ | $R^6$ | $Z^3$ | $R^{31}$ | $R^{32}$ |
|---|---|---|---|---|---|---|---|---|---|
| Me | Me | H | H | 2 | H | H | O | Me | F |
| Me | Me | H | H | 2 | H | H | O | Me | Cl |
| Me | Me | H | H | 2 | H | H | O | Me | OMe |
| Me | Me | H | H | 2 | H | H | O | Me | OEt |
| Me | Me | H | H | 2 | H | H | O | Me | OPr-i |
| Me | Me | H | H | 2 | H | H | O | Me | OPh |
| Me | Me | H | H | 2 | H | H | O | Me | $OCHF_2$ |
| Me | Me | H | H | 2 | H | H | O | Me | Me |
| Me | Me | H | H | 2 | H | H | O | Me | $CF_3$ |
| Me | Me | H | H | 2 | H | H | O | Me | CN |
| Me | Me | H | H | 2 | H | H | O | $OCHF_2$ | F |
| Me | Me | H | H | 2 | H | H | O | $OCHF_2$ | Cl |
| Me | Me | H | H | 2 | H | H | O | $OCHF_2$ | Me |
| Me | Me | H | H | 2 | H | H | O | $OCHF_2$ | $CF_3$ |
| Me | Me | H | H | 2 | H | H | O | $OCHF_2$ | CN |
| Me | Me | H | H | 2 | H | H | O | $CF_3$ | F |
| Me | Me | H | H | 2 | H | H | O | $CF_3$ | Cl |
| Me | Me | H | H | 2 | H | H | O | $CF_3$ | OMe |
| Me | Me | H | H | 2 | H | H | O | $CF_3$ | OEt |
| Me | Me | H | H | 2 | H | H | O | $CF_3$ | OPr-i |
| Me | Me | H | H | 2 | H | H | O | $CF_3$ | OPh |
| Me | Me | H | H | 2 | H | H | O | $CF_3$ | $OCHF_2$ |
| Me | Me | H | H | 2 | H | H | O | $CF_3$ | SMe |
| Me | Me | H | H | 2 | H | H | O | $CF_3$ | SOMe |
| Me | Me | H | H | 2 | H | H | O | $CF_3$ | $SO_2Me$ |
| Me | Me | H | H | 2 | H | H | O | $CF_3$ | SEt |
| Me | Me | H | H | 2 | H | H | O | $CF_3$ | SOEt |
| Me | Me | H | H | 2 | H | H | O | $CF_3$ | $SO_2Et$ |
| Me | Me | H | H | 2 | H | H | O | $CF_3$ | SPr-i |
| Me | Me | H | H | 2 | H | H | O | $CF_3$ | SOPr-i |
| Me | Me | H | H | 2 | H | H | O | $CF_3$ | $SO_2Pr$-i |
| Me | Me | H | H | 2 | H | H | O | $CF_3$ | SPh |
| Me | Me | H | H | 2 | H | H | O | $CF_3$ | SOPh |
| Me | Me | H | H | 2 | H | H | O | $CF_3$ | $SO_2Ph$ |
| Me | Me | H | H | 2 | H | H | O | $CF_3$ | $SCHF_2$ |
| Me | Me | H | H | 2 | H | H | O | $CF_3$ | $SOCHF_2$ |
| Me | Me | H | H | 2 | H | H | O | $CF_3$ | $SO_2CHF_2$ |

TABLE 4-continued

| R¹ | R² | R³ | R⁴ | n | R⁵ | R⁶ | Z³ | R³¹ | R³² |
|---|---|---|---|---|---|---|---|---|---|
| Me | Me | H | H | 2 | H | H | O | CF₃ | SCF₃ |
| Me | Me | H | H | 2 | H | H | O | CF₃ | SOCF₃ |
| Me | Me | H | H | 2 | H | H | O | CF₃ | SO₂CF₃ |
| Me | Me | H | H | 2 | H | H | O | CF₃ | NH₂ |
| Me | Me | H | H | 2 | H | H | O | CF₃ | NHC(=O)Me |
| Me | Me | H | H | 2 | H | H | O | CF₃ | NHC(=O)Ph |
| Me | Me | H | H | 2 | H | H | O | CF₃ | NHC(=O)CH₂Ph |
| Me | Me | H | H | 2 | H | H | O | CF₃ | NHC(=O)CF₃ |
| Me | Me | H | H | 2 | H | H | O | CF₃ | NHSO₂Me |
| Me | Me | H | H | 2 | H | H | O | CF₃ | NHSO₂Ph |
| Me | Me | H | H | 2 | H | H | O | CF₃ | NHSO₂CHF₂ |
| Me | Me | H | H | 2 | H | H | O | CF₃ | NHSO₂CF₃ |
| Me | Me | H | H | 2 | H | H | O | CF₃ | NHMe |
| Me | Me | H | H | 2 | H | H | O | CF₃ | NHPh |
| Me | Me | H | H | 2 | H | H | O | CF₃ | N(Me)C(=O)Me |
| Me | Me | H | H | 2 | H | H | O | CF₃ | N(Me)C(=O)Ph |
| Me | Me | H | H | 2 | H | H | O | CF₃ | N(Me)C(=O)CH₂Ph |
| Me | Me | H | H | 2 | H | H | O | CF₃ | N(Me)C(=O)CF₃ |
| Me | Me | H | H | 2 | H | H | O | CF₃ | N(Me)SO₂Me |
| Me | Me | H | H | 2 | H | H | O | CF₃ | N(Me)SO₂Ph |
| Me | Me | H | H | 2 | H | H | O | CF₃ | N(Me)SO₂CHF₂ |
| Me | Me | H | H | 2 | H | H | O | CF₃ | N(Me)SO₂CF₃ |
| Me | Me | H | H | 2 | H | H | O | CF₃ | N(Me)₂ |
| Me | Me | H | H | 2 | H | H | O | CF₃ | N(Me)Ph |
| Me | Me | H | H | 2 | H | H | O | CF₃ | Me |
| Me | Me | H | H | 2 | H | H | O | CF₃ | CF₃ |
| Me | Me | H | H | 2 | H | H | O | CF₃ | CN |
| Me | Me | H | H | 2 | H | H | O | Ph | Me |
| H | H | H | H | 2 | H | H | O | CF₃ | Me |
| Me | H | H | H | 2 | H | H | O | CF₃ | Me |
| Me | H | Me | H | 2 | H | H | O | CF₃ | Me |
| Me | Me | Me | H | 2 | H | H | O | CF₃ | Me |
| Me | Me | H | H | 2 | Me | H | O | CF₃ | Me |
| Me | Me | H | H | 2 | Et | H | O | CF₃ | Me |
| Me | Me | H | H | 2 | Pr-i | H | O | CF₃ | Me |
| Me | Me | H | H | 2 | Me | Me | O | CF₃ | Me |
| Me | Et | H | H | 2 | H | H | O | CF₃ | Me |
| Et | Et | H | H | 2 | H | H | O | CF₃ | Me |
| Me | Pr-i | H | H | 2 | H | H | O | CF₃ | Me |
| Me | Pr | H | H | 2 | H | H | O | CF₃ | Me |
| Me | Pr-c | H | H | 2 | H | H | O | CF₃ | Me |
| Me | CH₂Pr-c | H | H | 2 | H | H | O | CF₃ | Me |
| —(CH₂)₂— | | H | H | 2 | H | H | O | CF₃ | Me |
| —(CH₂)₃— | | H | H | 2 | H | H | O | CF₃ | Me |
| —(CH₂)₄— | | H | H | 2 | H | H | O | CF₃ | Me |
| —(CH₂)₅— | | H | H | 2 | H | H | O | CF₃ | Me |
| H | —(CH₂)₃— | H | H | 2 | H | H | O | CF₃ | Me |
| H | —(CH₂)₄— | H | H | 2 | H | H | O | CF₃ | Me |
| H | —(CH₂)₅— | H | H | 2 | H | H | O | CF₃ | Me |
| H | —(CH₂)₆— | H | H | 2 | H | H | O | CF₃ | Me |
| Me | Me | H | H | 2 | H | H | S | Me | F |
| Me | Me | H | H | 2 | H | H | S | Me | Cl |
| Me | Me | H | H | 2 | H | H | S | Me | OMe |
| Me | Me | H | H | 2 | H | H | S | Me | OEt |
| Me | Me | H | H | 2 | H | H | S | Me | OPr-i |
| Me | Me | H | H | 2 | H | H | S | Me | OPh |
| Me | Me | H | H | 2 | H | H | S | Me | OCHF₂ |
| Me | Me | H | H | 2 | H | H | S | OCHF₂ | F |
| Me | Me | H | H | 2 | H | H | S | OCHF₂ | Cl |
| Me | Me | H | H | 2 | H | H | S | OCHF₂ | Me |
| Me | Me | H | H | 2 | H | H | S | OCHF₂ | CF₃ |
| Me | Me | H | H | 2 | H | H | S | OCHF₂ | CN |
| Me | Me | H | H | 2 | H | H | S | CF₃ | F |
| Me | Me | H | H | 2 | H | H | S | CF₃ | Cl |
| Me | Me | H | H | 2 | H | H | S | CF₃ | OMe |
| Me | Me | H | H | 2 | H | H | S | CF₃ | OEt |

TABLE 4-continued

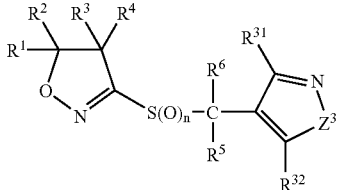

| R$^1$ | R$^2$ | R$^3$ | R$^4$ | n | R$^5$ | R$^6$ | Z$^3$ | R$^{31}$ | R$^{32}$ |
|---|---|---|---|---|---|---|---|---|---|
| Me | Me | H | H | 2 | H | H | S | CF$_3$ | OPh |
| Me | Me | H | H | 2 | H | H | S | CF$_3$ | OCHF$_2$ |
| Me | Me | H | H | 2 | H | H | S | CF$_3$ | SMe |
| Me | Me | H | H | 2 | H | H | S | CF$_3$ | SOMe |
| Me | Me | H | H | 2 | H | H | S | CF$_3$ | SO$_2$Me |
| Me | Me | H | H | 2 | H | H | S | CF$_3$ | SEt |
| Me | Me | H | H | 2 | H | H | S | CF$_3$ | SOEt |
| Me | Me | H | H | 2 | H | H | S | CF$_3$ | SO$_2$Et |
| Me | Me | H | H | 2 | H | H | S | CF$_3$ | SPr-i |
| Me | Me | H | H | 2 | H | H | S | CF$_3$ | SOPr-i |
| Me | Me | H | H | 2 | H | H | S | CF$_3$ | SO$_2$Pr-i |
| Me | Me | H | H | 2 | H | H | S | CF$_3$ | SPh |
| Me | Me | H | H | 2 | H | H | S | CF$_3$ | SOPh |
| Me | Me | H | H | 2 | H | H | S | CF$_3$ | SO$_2$Ph |
| Me | Me | H | H | 2 | H | H | S | CF$_3$ | SCHF$_2$ |
| Me | Me | H | H | 2 | H | H | S | CF$_3$ | SOCHF$_2$ |
| Me | Me | H | H | 2 | H | H | S | CF$_3$ | SO$_2$CHF$_2$ |
| Me | Me | H | H | 2 | H | H | S | CF$_3$ | SCF$_3$ |
| Me | Me | H | H | 2 | H | H | S | CF$_3$ | SOCF$_3$ |
| Me | Me | H | H | 2 | H | H | S | CF$_3$ | SO$_2$CF$_3$ |
| Me | Me | H | H | 2 | H | H | S | CF$_3$ | NH$_2$ |
| Me | Me | H | H | 2 | H | H | S | CF$_3$ | NHC(=O)Me |
| Me | Me | H | H | 2 | H | H | S | CF$_3$ | NHC(=O)Ph |
| Me | Me | H | H | 2 | H | H | S | CF$_3$ | NHC(=O)CH$_2$Ph |
| Me | Me | H | H | 2 | H | H | S | CF$_3$ | NHC(=O)CF$_3$ |
| Me | Me | H | H | 2 | H | H | S | CF$_3$ | NHSO$_2$Me |
| Me | Me | H | H | 2 | H | H | S | CF$_3$ | NHSO$_2$Ph |
| Me | Me | H | H | 2 | H | H | S | CF$_3$ | NHSO$_2$CHF$_2$ |
| Me | Me | H | H | 2 | H | H | S | CF$_3$ | NHSO$_2$CF$_3$ |
| Me | Me | H | H | 2 | H | H | S | CF$_3$ | NHMe |
| Me | Me | H | H | 2 | H | H | S | CF$_3$ | NHPh |
| Me | Me | H | H | 2 | H | H | S | CF$_3$ | N(Me)C(=O)Me |
| Me | Me | H | H | 2 | H | H | S | CF$_3$ | N(Me)C(=O)Ph |
| Me | Me | H | H | 2 | H | H | S | CF$_3$ | N(Me)C(=O)CH$_2$Ph |
| Me | Me | H | H | 2 | H | H | S | CF$_3$ | N(Me)C(=O)CF$_3$ |
| Me | Me | H | H | 2 | H | H | S | CF$_3$ | N(Me)SO$_2$Me |
| Me | Me | H | H | 2 | H | H | S | CF$_3$ | N(Me)SO$_2$Ph |
| Me | Me | H | H | 2 | H | H | S | CF$_3$ | N(Me)SO$_2$CHF$_2$ |
| Me | Me | H | H | 2 | H | H | S | CF$_3$ | N(Me)SO$_2$CF$_3$ |
| Me | Me | H | H | 2 | H | H | S | CF$_3$ | N(Me)$_2$ |
| Me | Me | H | H | 2 | H | H | S | CF$_3$ | N(Me)Ph |
| Me | Me | H | H | 2 | H | H | S | CF$_3$ | Me |
| Me | Me | H | H | 2 | H | H | S | CF$_3$ | CN |
| H | H | H | H | 2 | H | H | S | CF$_3$ | Cl |
| Me | H | H | H | 2 | H | H | S | CF$_3$ | Cl |
| Me | H | Me | H | 2 | H | H | S | CF$_3$ | Cl |
| Me | Me | Me | H | 2 | H | H | S | CF$_3$ | Cl |
| Me | Me | H | H | 2 | Me | H | S | CF$_3$ | Cl |
| Me | Me | H | H | 2 | Et | H | S | CF$_3$ | Cl |
| Me | Me | H | H | 2 | Pr-i | H | S | CF$_3$ | Cl |
| Me | Me | H | H | 2 | Me | Me | S | CF$_3$ | Cl |
| Me | Et | H | H | 2 | H | H | S | CF$_3$ | Cl |
| Et | Et | H | H | 2 | H | H | S | CF$_3$ | Cl |
| Me | Pr-i | H | H | 2 | H | H | S | CF$_3$ | Cl |
| Me | Pr | H | H | 2 | H | H | S | CF$_3$ | Cl |
| Me | Pr-c | H | H | 2 | H | H | S | CF$_3$ | Cl |
| Me | CH$_2$Pr-c | H | H | 2 | H | H | S | CF$_3$ | Cl |
| —(CH$_2$)$_2$— | | H | H | 2 | H | H | S | CF$_3$ | Cl |
| —(CH$_2$)$_3$— | | H | H | 2 | H | H | S | CF$_3$ | Cl |
| —(CH$_2$)$_4$— | | H | H | 2 | H | H | S | CF$_3$ | Cl |
| —(CH$_2$)$_5$— | | H | H | 2 | H | H | S | CF$_3$ | Cl |
| H | —(CH$_2$)$_3$— | | H | 2 | H | H | S | CF$_3$ | Cl |
| H | —(CH$_2$)$_4$— | | H | 2 | H | H | S | CF$_3$ | Cl |
| H | —(CH$_2$)$_5$— | | H | 2 | H | H | S | CF$_3$ | Cl |
| H | —(CH$_2$)$_6$— | | H | 2 | H | H | S | CF$_3$ | Cl |
| Me | Me | H | H | 1 | H | H | O | Me | F |

TABLE 4-continued

| R¹ | R² | R³ | R⁴ | n | R⁵ | R⁶ | Z³ | R³¹ | R³² |
|---|---|---|---|---|---|---|---|---|---|
| Me | Me | H | H | 1 | H | H | O | Me | Cl |
| Me | Me | H | H | 1 | H | H | O | Me | OMe |
| Me | Me | H | H | 1 | H | H | O | Me | OEt |
| Me | Me | H | H | 1 | H | H | O | Me | OPr-i |
| Me | Me | H | H | 1 | H | H | O | Me | OPh |
| Me | Me | H | H | 1 | H | H | O | Me | OCHF$_2$ |
| Me | Me | H | H | 1 | H | H | O | Me | Me |
| Me | Me | H | H | 1 | H | H | O | Me | CF$_3$ |
| Me | Me | H | H | 1 | H | H | O | Me | CN |
| Me | Me | H | H | 1 | H | H | O | OCHF$_2$ | F |
| Me | Me | H | H | 1 | H | H | O | OCHF$_2$ | Cl |
| Me | Me | H | H | 1 | H | H | O | OCHF$_2$ | Me |
| Me | Me | H | H | 1 | H | H | O | OCHF$_2$ | CF$_3$ |
| Me | Me | H | H | 1 | H | H | O | OCHF$_2$ | CN |
| Me | Me | H | H | 1 | H | H | O | CF$_3$ | F |
| Me | Me | H | H | 1 | H | H | O | CF$_3$ | Cl |
| Me | Me | H | H | 1 | H | H | O | CF$_3$ | OMe |
| Me | Me | H | H | 1 | H | H | O | CF$_3$ | OEt |
| Me | Me | H | H | 1 | H | H | O | CF$_3$ | OPr-i |
| Me | Me | H | H | 1 | H | H | O | CF$_3$ | OPh |
| Me | Me | H | H | 1 | H | H | O | CF$_3$ | OCHF$_2$ |
| Me | Me | H | H | 1 | H | H | O | CF$_3$ | SMe |
| Me | Me | H | H | 1 | H | H | O | CF$_3$ | SO$_2$Me |
| Me | Me | H | H | 1 | H | H | O | CF$_3$ | SEt |
| Me | Me | H | H | 1 | H | H | O | CF$_3$ | SO$_2$Et |
| Me | Me | H | H | 1 | H | H | O | CF$_3$ | SPr-i |
| Me | Me | H | H | 1 | H | H | O | CF$_3$ | SO$_2$Pr-i |
| Me | Me | H | H | 1 | H | H | O | CF$_3$ | SPh |
| Me | Me | H | H | 1 | H | H | O | CF$_3$ | SO$_2$Ph |
| Me | Me | H | H | 1 | H | H | O | CF$_3$ | SCHF$_2$ |
| Me | Me | H | H | 1 | H | H | O | CF$_3$ | SO$_2$CHF$_2$ |
| Me | Me | H | H | 1 | H | H | O | CF$_3$ | SCF$_3$ |
| Me | Me | H | H | 1 | H | H | O | CF$_3$ | SO$_2$CF$_3$ |
| Me | Me | H | H | 1 | H | H | O | CF$_3$ | NH$_2$ |
| Me | Me | H | H | 1 | H | H | O | CF$_3$ | NHC(=O)Me |
| Me | Me | H | H | 1 | H | H | O | CF$_3$ | NHC(=O)Ph |
| Me | Me | H | H | 1 | H | H | O | CF$_3$ | NHC(=O)CH$_2$Ph |
| Me | Me | H | H | 1 | H | H | O | CF$_3$ | NHC(=O)CF$_3$ |
| Me | Me | H | H | 1 | H | H | O | CF$_3$ | NHSO$_2$Me |
| Me | Me | H | H | 1 | H | H | O | CF$_3$ | NHSO$_2$Ph |
| Me | Me | H | H | 1 | H | H | O | CF$_3$ | NHSO$_2$CHF$_2$ |
| Me | Me | H | H | 1 | H | H | O | CF$_3$ | NHSO$_2$CF$_3$ |
| Me | Me | H | H | 1 | H | H | O | CF$_3$ | NHMe |
| Me | Me | H | H | 1 | H | H | O | CF$_3$ | NHPh |
| Me | Me | H | H | 1 | H | H | O | CF$_3$ | N(Me)C(=O)Me |
| Me | Me | H | H | 1 | H | H | O | CF$_3$ | N(Me)C(=O)Ph |
| Me | Me | H | H | 1 | H | H | O | CF$_3$ | N(Me)C(=O)CH$_2$Ph |
| Me | Me | H | H | 1 | H | H | O | CF$_3$ | N(Me)C(=O)CF$_3$ |
| Me | Me | H | H | 1 | H | H | O | CF$_3$ | N(Me)SO$_2$Me |
| Me | Me | H | H | 1 | H | H | O | CF$_3$ | N(Me)SO$_2$Ph |
| Me | Me | H | H | 1 | H | H | O | CF$_3$ | N(Me)SO$_2$CHF$_2$ |
| Me | Me | H | H | 1 | H | H | O | CF$_3$ | N(Me)SO$_2$CF$_3$ |
| Me | Me | H | H | 1 | H | H | O | CF$_3$ | N(Me)$_2$ |
| Me | Me | H | H | 1 | H | H | O | CF$_3$ | N(Me)Ph |
| Me | Me | H | H | 1 | H | H | O | CF$_3$ | Me |
| Me | Me | H | H | 1 | H | H | O | CF$_3$ | CF$_3$ |
| Me | Me | H | H | 1 | H | H | O | CF$_3$ | CN |
| Me | Me | H | H | 1 | H | H | O | Ph | Me |
| H | H | H | H | 1 | H | H | O | CF$_3$ | Me |
| Me | H | H | H | 1 | H | H | O | CF$_3$ | Me |
| Me | H | Me | H | 1 | H | H | O | CF$_3$ | Me |
| Me | Me | Me | H | 1 | H | H | O | CF$_3$ | Me |
| Me | Me | H | H | 1 | Me | H | O | CF$_3$ | Me |
| Me | Me | H | H | 1 | Et | H | O | CF$_3$ | Me |
| Me | Me | H | H | 1 | Pr-i | H | O | CF$_3$ | Me |
| Me | Me | H | H | 1 | Me | Me | O | CF$_3$ | Me |

TABLE 4-continued

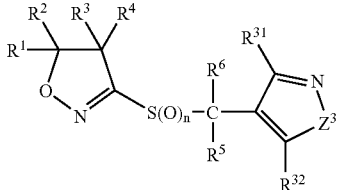

| R¹ | R² | R³ | R⁴ | n | R⁵ | R⁶ | Z³ | R³¹ | R³² |
|---|---|---|---|---|---|---|---|---|---|
| Me | Et | H | H | 1 | H | H | O | CF₃ | Me |
| Et | Et | H | H | 1 | H | H | O | CF₃ | Me |
| Me | Pr-i | H | H | 1 | H | H | O | CF₃ | Me |
| Me | Pr | H | H | 1 | H | H | O | CF₃ | Me |
| Me | Pr-c | H | H | 1 | H | H | O | CF₃ | Me |
| Me | CH₂Pr-c | H | H | 1 | H | H | O | CF₃ | Me |
| —(CH₂)₂— | | H | H | 1 | H | H | O | CF₃ | Me |
| —(CH₂)₃— | | H | H | 1 | H | H | O | CF₃ | Me |
| —(CH₂)₄— | | H | H | 1 | H | H | O | CF₃ | Me |
| —(CH₂)₅— | | H | H | 1 | H | H | O | CF₃ | Me |
| H | —(CH₂)₃— | H | H | 1 | H | H | O | CF₃ | Me |
| H | —(CH₂)₄— | H | H | 1 | H | H | O | CF₃ | Me |
| H | —(CH₂)₅— | H | H | 1 | H | H | O | CF₃ | Me |
| H | —(CH₂)₆— | H | H | 1 | H | H | O | CF₃ | Me |
| Me | Me | H | H | 1 | H | H | S | Me | F |
| Me | Me | H | H | 1 | H | H | S | Me | Cl |
| Me | Me | H | H | 1 | H | H | S | Me | OMe |
| Me | Me | H | H | 1 | H | H | S | Me | OEt |
| Me | Me | H | H | 1 | H | H | S | Me | OPr-i |
| Me | Me | H | H | 1 | H | H | S | Me | OPh |
| Me | Me | H | H | 1 | H | H | S | Me | OCHF₂ |
| Me | Me | H | H | 1 | H | H | S | OCHF₂ | F |
| Me | Me | H | H | 1 | H | H | S | OCHF₂ | Cl |
| Me | Me | H | H | 1 | H | H | S | OCHF₂ | Me |
| Me | Me | H | H | 1 | H | H | S | OCHF₂ | CF₃ |
| Me | Me | H | H | 1 | H | H | S | OCHF₂ | CN |
| Me | Me | H | H | 1 | H | H | S | CF₃ | F |
| Me | Me | H | H | 1 | H | H | S | CF₃ | Cl |
| Me | Me | H | H | 1 | H | H | S | CF₃ | OMe |
| Me | Me | H | H | 1 | H | H | S | CF₃ | OEt |
| Me | Me | H | H | 1 | H | H | S | CF₃ | OPh |
| Me | Me | H | H | 1 | H | H | S | CF₃ | OCHF₂ |
| Me | Me | H | H | 1 | H | H | S | CF₃ | SMe |
| Me | Me | H | H | 1 | H | H | S | CF₃ | SO₂Me |
| Me | Me | H | H | 1 | H | H | S | CF₃ | SEt |
| Me | Me | H | H | 1 | H | H | S | CF₃ | SO₂Et |
| Me | Me | H | H | 1 | H | H | S | CF₃ | SPr-i |
| Me | Me | H | H | 1 | H | H | S | CF₃ | SO₂Pr-i |
| Me | Me | H | H | 1 | H | H | S | CF₃ | SPh |
| Me | Me | H | H | 1 | H | H | S | CF₃ | SO₂Ph |
| Me | Me | H | H | 1 | H | H | S | CF₃ | SCHF₂ |
| Me | Me | H | H | 1 | H | H | S | CF₃ | SO₂CHF₂ |
| Me | Me | H | H | 1 | H | H | S | CF₃ | SCF₃ |
| Me | Me | H | H | 1 | H | H | S | CF₃ | SO₂CF₃ |
| Me | Me | H | H | 1 | H | H | S | CF₃ | NH₂ |
| Me | Me | H | H | 1 | H | H | S | CF₃ | NHC(=O)Me |
| Me | Me | H | H | 1 | H | H | S | CF₃ | NHC(=O)Ph |
| Me | Me | H | H | 1 | H | H | S | CF₃ | NHC(=O)CH₂Ph |
| Me | Me | H | H | 1 | H | H | S | CF₃ | NHC(=O)CF₃ |
| Me | Me | H | H | 1 | H | H | S | CF₃ | NHSO₂Me |
| Me | Me | H | H | 1 | H | H | S | CF₃ | NHSO₂Ph |
| Me | Me | H | H | 1 | H | H | S | CF₃ | NHSO₂CHF₂ |
| Me | Me | H | H | 1 | H | H | S | CF₃ | NHSO₂CF₃ |
| Me | Me | H | H | 1 | H | H | S | CF₃ | NHMe |
| Me | Me | H | H | 1 | H | H | S | CF₃ | NHPh |
| Me | Me | H | H | 1 | H | H | S | CF₃ | N(Me)C(=O)Me |
| Me | Me | H | H | 1 | H | H | S | CF₃ | N(Me)C(=O)Ph |
| Me | Me | H | H | 1 | H | H | S | CF₃ | N(Me)C(=O)CH₂Ph |
| Me | Me | H | H | 1 | H | H | S | CF₃ | N(Me)C(=O)CF₃ |
| Me | Me | H | H | 1 | H | H | S | CF₃ | N(Me)SO₂Me |
| Me | Me | H | H | 1 | H | H | S | CF₃ | N(Me)SO₂Ph |
| Me | Me | H | H | 1 | H | H | S | CF₃ | N(Me)SO₂CHF₂ |
| Me | Me | H | H | 1 | H | H | S | CF₃ | N(Me)SO₂CF₃ |
| Me | Me | H | H | 1 | H | H | S | CF₃ | N(Me)₂ |
| Me | Me | H | H | 1 | H | H | S | CF₃ | N(Me)Ph |
| Me | Me | H | H | 1 | H | H | S | CF₃ | Me |

TABLE 4-continued

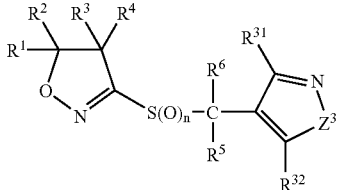

| R¹ | R² | R³ | R⁴ | n | R⁵ | R⁶ | Z³ | R³¹ | R³² |
|---|---|---|---|---|---|---|---|---|---|
| Me | Me | H | H | 1 | H | H | S | CF₃ | CN |
| H | H | H | H | 1 | H | H | S | CF₃ | Cl |
| Me | H | H | H | 1 | H | H | S | CF₃ | Cl |
| Me | H | Me | H | 1 | H | H | S | CF₃ | Cl |
| Me | Me | Me | H | 1 | H | H | S | CF₃ | Cl |
| Me | Me | H | H | 1 | Me | H | S | CF₃ | Cl |
| Me | Me | H | H | 1 | Et | H | S | CF₃ | Cl |
| Me | Me | H | H | 1 | Pr-i | H | S | CF₃ | Cl |
| Me | Me | H | H | 1 | Me | Me | S | CF₃ | Cl |
| Me | Et | H | H | 1 | H | H | S | CF₃ | Cl |
| Et | Et | H | H | 1 | H | H | S | CF₃ | Cl |
| Me | Pr-i | H | H | 1 | H | H | S | CF₃ | Cl |
| Me | Pr | H | H | 1 | H | H | S | CF₃ | Cl |
| Me | Pr-c | H | H | 1 | H | H | S | CF₃ | Cl |
| Me | CH₂Pr-c | H | H | 1 | H | H | S | CF₃ | Cl |
| —(CH₂)₂— | | H | H | 1 | H | H | S | CF₃ | Cl |
| —(CH₂)₃— | | H | H | 1 | H | H | S | CF₃ | Cl |
| —(CH₂)₄— | | H | H | 1 | H | H | S | CF₃ | Cl |
| —(CH₂)₅— | | H | H | 1 | H | H | S | CF₃ | Cl |
| H | —(CH₂)₃— | | H | 1 | H | H | S | CF₃ | Cl |
| H | —(CH₂)₄— | | H | 1 | H | H | S | CF₃ | Cl |
| H | —(CH₂)₅— | | H | 1 | H | H | S | CF₃ | Cl |
| H | —(CH₂)₆— | | H | 1 | H | H | S | CF₃ | Cl |
| Me | Me | H | H | 0 | H | H | O | Me | F |
| Me | Me | H | H | 0 | H | H | O | Me | Cl |
| Me | Me | H | H | 0 | H | H | O | Me | OMe |
| Me | Me | H | H | 0 | H | H | O | Me | OEt |
| Me | Me | H | H | 0 | H | H | O | Me | OPr-i |
| Me | Me | H | H | 0 | H | H | O | Me | OPh |
| Me | Me | H | H | 0 | H | H | O | Me | OCHF₂ |
| Me | Me | H | H | 0 | H | H | O | Me | Me |
| Me | Me | H | H | 0 | H | H | O | Me | CF₃ |
| Me | Me | H | H | 0 | H | H | O | Me | CN |
| Me | Me | H | H | 0 | H | H | O | OCHF₂ | F |
| Me | Me | H | H | 0 | H | H | O | OCHF₂ | Cl |
| Me | Me | H | H | 0 | H | H | O | OCHF₂ | Me |
| Me | Me | H | H | 0 | H | H | O | OCHF₂ | CF₃ |
| Me | Me | H | H | 0 | H | H | O | OCHF₂ | CN |
| Me | Me | H | H | 0 | H | H | O | CF₃ | F |
| Me | Me | H | H | 0 | H | H | O | CF₃ | Cl |
| Me | Me | H | H | 0 | H | H | O | CF₃ | OMe |
| Me | Me | H | H | 0 | H | H | O | CF₃ | OEt |
| Me | Me | H | H | 0 | H | H | O | CF₃ | OPr-i |
| Me | Me | H | H | 0 | H | H | O | CF₃ | OPh |
| Me | Me | H | H | 0 | H | H | O | CF₃ | OCHF₂ |
| Me | Me | H | H | 0 | H | H | O | CF₃ | SMe |
| Me | Me | H | H | 0 | H | H | O | CF₃ | SO₂Me |
| Me | Me | H | H | 0 | H | H | O | CF₃ | SEt |
| Me | Me | H | H | 0 | H | H | O | CF₃ | SO₂Et |
| Me | Me | H | H | 0 | H | H | O | CF₃ | SPr-i |
| Me | Me | H | H | 0 | H | H | O | CF₃ | SO₂Pr-i |
| Me | Me | H | H | 0 | H | H | O | CF₃ | SPh |
| Me | Me | H | H | 0 | H | H | O | CF₃ | SO₂Ph |
| Me | Me | H | H | 0 | H | H | O | CF₃ | SCHF₂ |
| Me | Me | H | H | 0 | H | H | O | CF₃ | SO₂CHF₂ |
| Me | Me | H | H | 0 | H | H | O | CF₃ | SCF₃ |
| Me | Me | H | H | 0 | H | H | O | CF₃ | SO₂CF₃ |
| Me | Me | H | H | 0 | H | H | O | CF₃ | NH₂ |
| Me | Me | H | H | 0 | H | H | O | CF₃ | NHC(=O)Me |
| Me | Me | H | H | 0 | H | H | O | CF₃ | NHC(=O)Ph |
| Me | Me | H | H | 0 | H | H | O | CF₃ | NHC(=O)CH₂Ph |
| Me | Me | H | H | 0 | H | H | O | CF₃ | NHC(=O)CF₃ |
| Me | Me | H | H | 0 | H | H | O | CF₃ | NHSO₂Me |
| Me | Me | H | H | 0 | H | H | O | CF₃ | NHSO₂Ph |
| Me | Me | H | H | 0 | H | H | O | CF₃ | NHSO₂CHF₂ |
| Me | Me | H | H | 0 | H | H | O | CF₃ | NHSO₂CF₃ |

TABLE 4-continued

| R¹ | R² | R³ | R⁴ | n | R⁵ | R⁶ | Z³ | R³¹ | R³² |
|---|---|---|---|---|---|---|---|---|---|
| Me | Me | H | H | 0 | H | H | O | CF₃ | NHMe |
| Me | Me | H | H | 0 | H | H | O | CF₃ | NHPh |
| Me | Me | H | H | 0 | H | H | O | CF₃ | N(Me)C(=O)Me |
| Me | Me | H | H | 0 | H | H | O | CF₃ | N(Me)C(=O)Ph |
| Me | Me | H | H | 0 | H | H | O | CF₃ | N(Me)C(=O)CH₂Ph |
| Me | Me | H | H | 0 | H | H | O | CF₃ | N(Me)C(=O)CF₃ |
| Me | Me | H | H | 0 | H | H | O | CF₃ | N(Me)SO₂Me |
| Me | Me | H | H | 0 | H | H | O | CF₃ | N(Me)SO₂Ph |
| Me | Me | H | H | 0 | H | H | O | CF₃ | N(Me)SO₂CHF₂ |
| Me | Me | H | H | 0 | H | H | O | CF₃ | N(Me)SO₂CF₃ |
| Me | Me | H | H | 0 | H | H | O | CF₃ | N(Me)₂ |
| Me | Me | H | H | 0 | H | H | O | CF₃ | N(Me)Ph |
| Me | Me | H | H | 0 | H | H | O | CF₃ | Me |
| Me | Me | H | H | 0 | H | H | O | CF₃ | CF₃ |
| Me | Me | H | H | 0 | H | H | O | CF₃ | CN |
| Me | Me | H | H | 0 | H | H | O | Ph | Me |
| H | H | H | H | 0 | H | H | O | CF₃ | Me |
| Me | H | H | H | 0 | H | H | O | CF₃ | Me |
| Me | H | Me | H | 0 | H | H | O | CF₃ | Me |
| Me | Me | Me | H | 0 | H | H | O | CF₃ | Me |
| Me | Me | H | H | 0 | Me | H | O | CF₃ | Me |
| Me | Me | H | H | 0 | Et | H | O | CF₃ | Me |
| Me | Me | H | H | 0 | Pr-i | H | O | CF₃ | Me |
| Me | Me | H | H | 0 | Me | Me | O | CF₃ | Me |
| Me | Et | H | H | 0 | H | H | O | CF₃ | Me |
| Et | Et | H | H | 0 | H | H | O | CF₃ | Me |
| Me | Pr-i | H | H | 0 | H | H | O | CF₃ | Me |
| Me | Pr | H | H | 0 | H | H | O | CF₃ | Me |
| Me | Pr-c | H | H | 0 | H | H | O | CF₃ | Me |
| Me | CH₂Pr-c | H | H | 0 | H | H | O | CF₃ | Me |
| —(CH₂)₂— | | H | H | 0 | H | H | O | CF₃ | Me |
| —(CH₂)₃— | | H | H | 0 | H | H | O | CF₃ | Me |
| —(CH₂)₄— | | H | H | 0 | H | H | O | CF₃ | Me |
| —(CH₂)₅— | | H | H | 0 | H | H | O | CF₃ | Me |
| H | —(CH₂)₃— | | H | 0 | H | H | O | CF₃ | Me |
| H | —(CH₂)₄— | | H | 0 | H | H | O | CF₃ | Me |
| H | —(CH₂)₅— | | H | 0 | H | H | O | CF₃ | Me |
| H | —(CH₂)₆— | | H | 0 | H | H | O | CF₃ | Me |
| Me | Me | H | H | 0 | H | H | S | Me | F |
| Me | Me | H | H | 0 | H | H | S | Me | Cl |
| Me | Me | H | H | 0 | H | H | S | Me | OMe |
| Me | Me | H | H | 0 | H | H | S | Me | OEt |
| Me | Me | H | H | 0 | H | H | S | Me | OPr-i |
| Me | Me | H | H | 0 | H | H | S | Me | OPh |
| Me | Me | H | H | 0 | H | H | S | Me | OCHF₂ |
| Me | Me | H | H | 0 | H | H | S | OCHF₂ | F |
| Me | Me | H | H | 0 | H | H | S | OCHF₂ | Cl |
| Me | Me | H | H | 0 | H | H | S | OCHF₂ | Me |
| Me | Me | H | H | 0 | H | H | S | OCHF₂ | CF₃ |
| Me | Me | H | H | 0 | H | H | S | OCHF₂ | CN |
| Me | Me | H | H | 0 | H | H | S | CF₃ | F |
| Me | Me | H | H | 0 | H | H | S | CF₃ | Cl |
| Me | Me | H | H | 0 | H | H | S | CF₃ | OMe |
| Me | Me | H | H | 0 | H | H | S | CF₃ | OEt |
| Me | Me | H | H | 0 | H | H | S | CF₃ | OPh |
| Me | Me | H | H | 0 | H | H | S | CF₃ | OCHF₂ |
| Me | Me | H | H | 0 | H | H | S | CF₃ | SMe |
| Me | Me | H | H | 0 | H | H | S | CF₃ | SO₂Me |
| Me | Me | H | H | 0 | H | H | S | CF₃ | SEt |
| Me | Me | H | H | 0 | H | H | S | CF₃ | SO₂Et |
| Me | Me | H | H | 0 | H | H | S | CF₃ | SPr-i |
| Me | Me | H | H | 0 | H | H | S | CF₃ | SO₂Pr-i |
| Me | Me | H | H | 0 | H | H | S | CF₃ | SPh |
| Me | Me | H | H | 0 | H | H | S | CF₃ | SO₂Ph |
| Me | Me | H | H | 0 | H | H | S | CF₃ | SCHF₂ |
| Me | Me | H | H | 0 | H | H | S | CF₃ | SO₂CHF₂ |

TABLE 4-continued

| $R^1$ | $R^2$ | $R^3$ | $R^4$ | n | $R^5$ | $R^6$ | $Z^3$ | $R^{31}$ | $R^{32}$ |
|---|---|---|---|---|---|---|---|---|---|
| Me | Me | H | H | 0 | H | H | S | $CF_3$ | $SCF_3$ |
| Me | Me | H | H | 0 | H | H | S | $CF_3$ | $SO_2CF_3$ |
| Me | Me | H | H | 0 | H | H | S | $CF_3$ | $NH_2$ |
| Me | Me | H | H | 0 | H | H | S | $CF_3$ | NHC(=O)Me |
| Me | Me | H | H | 0 | H | H | S | $CF_3$ | NHC(=O)Ph |
| Me | Me | H | H | 0 | H | H | S | $CF_3$ | NHC(=O)CH$_2$Ph |
| Me | Me | H | H | 0 | H | H | S | $CF_3$ | NHC(=O)CF$_3$ |
| Me | Me | H | H | 0 | H | H | S | $CF_3$ | NHSO$_2$Me |
| Me | Me | H | H | 0 | H | H | S | $CF_3$ | NHSO$_2$Ph |
| Me | Me | H | H | 0 | H | H | S | $CF_3$ | NHSO$_2$CHF$_2$ |
| Me | Me | H | H | 0 | H | H | S | $CF_3$ | NHSO$_2$CF$_3$ |
| Me | Me | H | H | 0 | H | H | S | $CF_3$ | NHMe |
| Me | Me | H | H | 0 | H | H | S | $CF_3$ | NHPh |
| Me | Me | H | H | 0 | H | H | S | $CF_3$ | N(Me)C(=O)Me |
| Me | Me | H | H | 0 | H | H | S | $CF_3$ | N(Me)C(=O)Ph |
| Me | Me | H | H | 0 | H | H | S | $CF_3$ | N(Me)C(=O)CH$_2$Ph |
| Me | Me | H | H | 0 | H | H | S | $CF_3$ | N(Me)C(=O)CF$_3$ |
| Me | Me | H | H | 0 | H | H | S | $CF_3$ | N(Me)SO$_2$Me |
| Me | Me | H | H | 0 | H | H | S | $CF_3$ | N(Me)SO$_2$Ph |
| Me | Me | H | H | 0 | H | H | S | $CF_3$ | N(Me)SO$_2$CHF$_2$ |
| Me | Me | H | H | 0 | H | H | S | $CF_3$ | N(Me)SO$_2$CF$_3$ |
| Me | Me | H | H | 0 | H | H | S | $CF_3$ | N(Me)$_2$ |
| Me | Me | H | H | 0 | H | H | S | $CF_3$ | N(Me)Ph |
| Me | Me | H | H | 0 | H | H | S | $CF_3$ | Me |
| Me | Me | H | H | 0 | H | H | S | $CF_3$ | CN |
| H | H | H | H | 0 | H | H | S | $CF_3$ | Cl |
| Me | H | H | H | 0 | H | H | S | $CF_3$ | Cl |
| Me | H | Me | H | 0 | H | H | S | $CF_3$ | Cl |
| Me | Me | Me | H | 0 | H | H | S | $CF_3$ | Cl |
| Me | Me | H | H | 0 | Me | H | S | $CF_3$ | Cl |
| Me | Me | H | H | 0 | Et | H | S | $CF_3$ | Cl |
| Me | Me | H | H | 0 | Pr-i | H | S | $CF_3$ | Cl |
| Me | Me | H | H | 0 | Me | Me | S | $CF_3$ | Cl |
| Me | Et | H | H | 0 | H | H | S | $CF_3$ | Cl |
| Et | Et | H | H | 0 | H | H | S | $CF_3$ | Cl |
| Me | Pr-i | H | H | 0 | H | H | S | $CF_3$ | Cl |
| Me | Pr | H | H | 0 | H | H | S | $CF_3$ | Cl |
| Me | Pr-c | H | H | 0 | H | H | S | $CF_3$ | Cl |
| Me | CH$_2$Pr-c | H | H | 0 | H | H | S | $CF_3$ | Cl |
| —(CH$_2$)$_2$— | | H | H | 0 | H | H | S | $CF_3$ | Cl |
| —(CH$_2$)$_3$— | | H | H | 0 | H | H | S | $CF_3$ | Cl |
| —(CH$_2$)$_4$— | | H | H | 0 | H | H | S | $CF_3$ | Cl |
| —(CH$_2$)$_5$— | | H | H | 0 | H | H | S | $CF_3$ | Cl |
| H | —(CH$_2$)$_3$— | | H | 0 | H | H | S | $CF_3$ | Cl |
| H | —(CH$_2$)$_4$— | | H | 0 | H | H | S | $CF_3$ | Cl |
| H | —(CH$_2$)$_5$— | | H | 0 | H | H | S | $CF_3$ | Cl |
| H | —(CH$_2$)$_6$— | | H | 0 | H | H | S | $CF_3$ | Cl |

TABLE 5

| $R^1$ | $R^2$ | $R^3$ | $R^4$ | n | $R^5$ | $R^6$ | $Z^4$ | $R^{33}$ | $R^{34}$ |
|---|---|---|---|---|---|---|---|---|---|
| Me | Me | H | H | 2 | H | H | NMe | Cl | H |
| Me | Me | H | H | 2 | H | H | NMe | Cl | Me |
| Me | Me | H | H | 2 | H | H | NMe | Cl | Et |

TABLE 5-continued

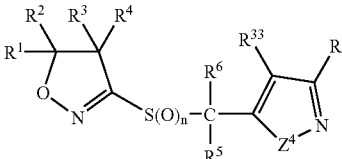

| R¹ | R² | R³ | R⁴ | n | R⁵ | R⁶ | Z⁴ | R³³ | R³⁴ |
|---|---|---|---|---|---|---|---|---|---|
| Me | Me | H | H | 2 | H | H | NMe | Cl | CF₃ |
| Me | Me | H | H | 2 | H | H | NMe | CF₃ | H |
| Me | Me | H | H | 2 | H | H | NMe | CF₃ | Me |
| Me | Me | H | H | 2 | H | H | NMe | OCHF₂ | H |
| Me | Me | H | H | 2 | H | H | NMe | OCHF₂ | Me |
| Me | Me | H | H | 2 | H | H | NMe | C(=O)Me | H |
| Me | Me | H | H | 2 | H | H | NMe | C(=O)Me | Me |
| Me | Me | H | H | 2 | H | H | NMe | —(CH₂)₃— | |
| Me | Me | H | H | 2 | H | H | NMe | —(CH₂)₄— | |
| Me | Me | H | H | 2 | H | H | NEt | Cl | Me |
| Me | Me | H | H | 2 | H | H | NEt | CF₃ | H |
| Me | Me | H | H | 2 | H | H | NEt | CF₃ | Me |
| Me | Me | H | H | 2 | H | H | NEt | OCHF₂ | H |
| Me | Me | H | H | 2 | H | H | NEt | OCHF₂ | Me |
| Me | Me | H | H | 2 | H | H | NEt | —(CH₂)₃— | |
| Me | Me | H | H | 2 | H | H | NEt | —(CH₂)₄— | |
| Me | Me | H | H | 2 | H | H | NPr-i | Cl | Me |
| Me | Me | H | H | 2 | H | H | NPr-i | CF₃ | H |
| Me | Me | H | H | 2 | H | H | NPr-i | CF₃ | Me |
| Me | Me | H | H | 2 | H | H | NPr-i | OCHF₂ | H |
| Me | Me | H | H | 2 | H | H | NPr-i | OCHF₂ | Me |
| Me | Me | H | H | 2 | H | H | NPr-i | —(CH₂)₃— | |
| Me | Me | H | H | 2 | H | H | NPr-i | —(CH₂)₄— | |
| Me | Me | H | H | 2 | H | H | NPr | Cl | Me |
| Me | Me | H | H | 2 | H | H | NPr | CF₃ | H |
| Me | Me | H | H | 2 | H | H | NPr | CF₃ | Me |
| Me | Me | H | H | 2 | H | H | NPr | OCHF₂ | H |
| Me | Me | H | H | 2 | H | H | NPr | OCHF₂ | Me |
| Me | Me | H | H | 2 | H | H | NPr | —(CH₂)₃— | |
| Me | Me | H | H | 2 | H | H | NPr | —(CH₂)₄— | |
| Me | Me | H | H | 2 | H | H | NBu-t | Cl | Me |
| Me | Me | H | H | 2 | H | H | NBu-t | CF₃ | H |
| Me | Me | H | H | 2 | H | H | NBu-t | CF₃ | Me |
| Me | Me | H | H | 2 | H | H | NBu-t | OCHF₂ | H |
| Me | Me | H | H | 2 | H | H | NBu-t | OCHF₂ | Me |
| Me | Me | H | H | 2 | H | H | NBu-t | —(CH₂)₃— | |
| Me | Me | H | H | 2 | H | H | NBu-t | —(CH₂)₄— | |
| Me | Me | H | H | 2 | H | H | NCH₂Ph | Cl | Me |
| Me | Me | H | H | 2 | H | H | NCH₂Ph | CF₃ | H |
| Me | Me | H | H | 2 | H | H | NCH₂Ph | OCHF₂ | H |
| Me | Me | H | H | 2 | H | H | NCH₂OMe | Cl | Me |
| Me | Me | H | H | 2 | H | H | NCH₂OMe | CF₃ | H |
| Me | Me | H | H | 2 | H | H | NCH₂OMe | OCHF₂ | H |
| Me | Me | H | H | 2 | H | H | NCH₂C≡CH | Cl | Me |
| Me | Me | H | H | 2 | H | H | NCH₂C≡CH | CF₃ | H |
| Me | Me | H | H | 2 | H | H | NCH₂C≡CH | OCHF₂ | H |
| Me | Me | H | H | 2 | H | H | NCH₂CH=CH₂ | Cl | Me |
| Me | Me | H | H | 2 | H | H | NCH₂CH=CH₂ | CF₃ | H |
| Me | Me | H | H | 2 | H | H | NCH₂CH=CH₂ | OCHF₂ | H |
| Me | Me | H | H | 2 | H | H | NCHF₂ | Cl | Me |
| Me | Me | H | H | 2 | H | H | NCHF₂ | CF₃ | H |
| Me | Me | H | H | 2 | H | H | NCHF₂ | CF₃ | Me |
| Me | Me | H | H | 2 | H | H | NCHF₂ | OCHF₂ | H |
| Me | Me | H | H | 2 | H | H | NCHF₂ | OCHF₂ | Me |
| Me | Me | H | H | 2 | H | H | NCHF₂ | C(=O)Me | H |
| Me | Me | H | H | 2 | H | H | NCHF₂ | C(=O)Me | Me |
| Me | Me | H | H | 2 | H | H | NCHF₂ | —(CH₂)₃— | |
| Me | Me | H | H | 2 | H | H | NCHF₂ | —(CH₂)₄— | |
| Me | Me | H | H | 2 | H | H | NPh | OMe | Me |
| Me | Me | H | H | 2 | H | H | NPh | OEt | Me |
| Me | Me | H | H | 2 | H | H | NPh | OCHF₂ | Me |
| Me | Me | H | H | 2 | H | H | NPh | OCH₂CF₃ | Me |
| Me | Me | H | H | 2 | H | H | NPh | CF₃ | H |
| Me | Me | H | H | 2 | H | H | NPh | OCH₂CH=CH₂ | Me |
| Me | Me | H | H | 2 | H | H | NPh | OCH₂CH≡CH | Me |
| Me | Me | H | H | 2 | H | H | NPh | Cl | Me |
| Me | Me | H | H | 2 | H | H | N(2-Cl)Ph | Cl | Me |
| Me | Me | H | H | 2 | H | H | N(2-F)Ph | Cl | Me |

TABLE 5-continued

| R¹ | R² | R³ | R⁴ | n | R⁵ | R⁶ | Z⁴ | R³³ | R³⁴ |
|---|---|---|---|---|---|---|---|---|---|
| Me | Me | H | H | 2 | H | H | N(2-OMe)Ph | Cl | Me |
| Me | Me | H | H | 2 | H | H | N(2-Me)Ph | Cl | Me |
| Me | Me | H | H | 2 | H | H | N(3-Cl)Ph | Cl | Me |
| Me | Me | H | H | 2 | H | H | N(3-F)Ph | Cl | Me |
| Me | Me | H | H | 2 | H | H | N(3-OMe)Ph | Cl | Me |
| Me | Me | H | H | 2 | H | H | N(3-Me)Ph | Cl | Me |
| Me | Me | H | H | 2 | H | H | N(4-Cl)Ph | Cl | Me |
| Me | Me | H | H | 2 | H | H | N(4-F)Ph | Cl | Me |
| Me | Me | H | H | 2 | H | H | N(4-OMe)Ph | Cl | Me |
| Me | Me | H | H | 2 | H | H | N(4-Me)Ph | Cl | Me |
| Me | Me | H | H | 2 | H | H | N(Thiophen-2-yl) | Cl | Me |
| Me | Me | H | H | 2 | H | H | N(Thiophen-2-yl) | CF₃ | H |
| Me | Me | H | H | 2 | H | H | N(Thiophen-2-yl) | OCHF₂ | H |
| Me | Me | H | H | 2 | H | H | NC(=O)Me | Cl | Me |
| Me | Me | H | H | 2 | H | H | NC(=O)Me | CF₃ | H |
| Me | Me | H | H | 2 | H | H | NC(=O)Me | OCHF₂ | H |
| Me | Me | H | H | 2 | H | H | NC(=O)CF₃ | Cl | Me |
| Me | Me | H | H | 2 | H | H | NC(=O)CF₃ | CF₃ | H |
| Me | Me | H | H | 2 | H | H | NC(=O)CF₃ | OCHF₂ | H |
| Me | Me | H | H | 2 | H | H | NC(=O)CH₂Ph | Cl | Me |
| Me | Me | H | H | 2 | H | H | NC(=O)CH₂Ph | CF₃ | H |
| Me | Me | H | H | 2 | H | H | NC(=O)CH₂Ph | OCHF₂ | H |
| Me | Me | H | H | 2 | H | H | NC(=O)Ph | Cl | Me |
| Me | Me | H | H | 2 | H | H | NC(=O)Ph | CF₃ | H |
| Me | Me | H | H | 2 | H | H | NC(=O)Ph | OCHF₂ | H |
| Me | Me | H | H | 2 | H | H | NC(=O)OMe | Cl | Me |
| Me | Me | H | H | 2 | H | H | NC(=O)OMe | CF₃ | H |
| Me | Me | H | H | 2 | H | H | NC(=O)OMe | OCHF₂ | H |
| Me | Me | H | H | 2 | H | H | NC(=O)OCH₂Ph | Cl | Me |
| Me | Me | H | H | 2 | H | H | NC(=O)OCH₂Ph | CF₃ | H |
| Me | Me | H | H | 2 | H | H | NC(=O)OCH₂Ph | OCHF₂ | H |
| Me | Me | H | H | 2 | H | H | NC(=O)OPh | Cl | Me |
| Me | Me | H | H | 2 | H | H | NC(=O)OPh | CF₃ | H |
| Me | Me | H | H | 2 | H | H | NC(=O)OPh | OCHF₂ | H |
| Me | Me | H | H | 2 | H | H | NC(=O)NHMe | Cl | Me |
| Me | Me | H | H | 2 | H | H | NC(=O)NHMe | CF₃ | H |
| Me | Me | H | H | 2 | H | H | NC(=O)NHMe | OCHF₂ | H |
| Me | Me | H | H | 2 | H | H | NC(=O)N(Me)₂ | Cl | Me |
| Me | Me | H | H | 2 | H | H | NC(=O)N(Me)₂ | CF₃ | H |
| Me | Me | H | H | 2 | H | H | NC(=O)N(Me)₂ | OCHF₂ | H |
| H | H | H | H | 2 | H | H | NPh | Cl | Me |
| Me | H | H | H | 2 | H | H | NPh | Cl | Me |
| Me | H | Me | H | 2 | H | H | NPh | Cl | Me |
| Me | Me | H | H | 2 | Me | H | NPh | Cl | Me |
| Me | Me | H | H | 2 | Et | H | NPh | Cl | Me |
| Me | Me | H | H | 2 | Pr-i | H | NPh | Cl | Me |
| Me | Me | H | H | 2 | Me | Me | NPh | Cl | Me |
| Me | Et | H | H | 2 | H | H | NPh | Cl | Me |
| Et | Et | H | H | 2 | H | H | NPh | Cl | Me |
| Me | Pr-i | H | H | 2 | H | H | NPh | Cl | Me |
| Me | Pr | H | H | 2 | H | H | NPh | Cl | Me |
| Me | Pr-c | H | H | 2 | H | H | NPh | Cl | Me |
| Me | CH₂Pr-c | H | H | 2 | H | H | NPh | Cl | Me |
| —(CH₂)₂— | | H | H | 2 | H | H | NPh | Cl | Me |
| —(CH₂)₃— | | H | H | 2 | H | H | NPh | Cl | Me |
| —(CH₂)₄— | | H | H | 2 | H | H | NPh | Cl | Me |
| —(CH₂)₅— | | H | H | 2 | H | H | NPh | Cl | Me |
| H | —(CH₂)₃— | | H | 2 | H | H | NPh | Cl | Me |
| H | —(CH₂)₄— | | H | 2 | H | H | NPh | Cl | Me |
| H | —(CH₂)₅— | | H | 2 | H | H | NPh | Cl | Me |
| H | —(CH₂)₆— | | H | 2 | H | H | NPh | Cl | Me |
| Me | Me | H | H | 2 | H | H | O | H | Me |
| Me | Me | H | H | 2 | H | H | O | Cl | Me |
| Me | Me | H | H | 2 | H | H | S | H | Me |
| Me | Me | H | H | 2 | H | H | S | Cl | Me |
| Me | Me | H | H | 1 | H | H | NMe | Cl | H |
| Me | Me | H | H | 1 | H | H | NMe | Cl | Me |
| Me | Me | H | H | 1 | H | H | NMe | Cl | Et |

TABLE 5-continued

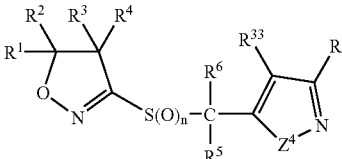

| $R^1$ | $R^2$ | $R^3$ | $R^4$ | n | $R^5$ | $R^6$ | $Z^4$ | $R^{33}$ | $R^{34}$ |
|---|---|---|---|---|---|---|---|---|---|
| Me | Me | H | H | 1 | H | H | NMe | Cl | $CF_3$ |
| Me | Me | H | H | 1 | H | H | MAe | $CF_3$ | H |
| Me | Me | H | H | 1 | H | H | NMe | $CF_3$ | Me |
| Me | Me | H | H | 1 | H | H | NMe | $OCHF_2$ | H |
| Me | Me | H | H | 1 | H | H | NMe | $OCHF_2$ | Me |
| Me | Me | H | H | 1 | H | H | NMe | C(=O)Me | H |
| Me | Me | H | H | 1 | H | H | NMe | C(=O)Me | Me |
| Me | Me | H | H | 1 | H | H | NMe | —$(CH_2)_3$— | |
| Me | Me | H | H | 1 | H | H | NMe | —$(CH_2)_4$— | |
| Me | Me | H | H | 1 | H | H | NEt | Cl | Me |
| Me | Me | H | H | 1 | H | H | NEt | $CF_3$ | H |
| Me | Me | H | H | 1 | H | H | NEt | $CF_3$ | Me |
| Me | Me | H | H | 1 | H | H | NEt | $OCHF_2$ | H |
| Me | Me | H | H | 1 | H | H | NEt | $OCHF_2$ | Me |
| Me | Me | H | H | 1 | H | H | NEt | —$(CH_2)_3$— | |
| Me | Me | H | H | 1 | H | H | NEt | —$(CH_2)_4$— | |
| Me | Me | H | H | 1 | H | H | NPr-i | Cl | Me |
| Me | Me | H | H | 1 | H | H | NPr-i | $CF_3$ | H |
| Me | Me | H | H | 1 | H | H | NPr-i | $CF_3$ | Me |
| Me | Me | H | H | 1 | H | H | NPr-i | $OCHF_2$ | H |
| Me | Me | H | H | 1 | H | H | NPr-i | $OCHF_2$ | Me |
| Me | Me | H | H | 1 | H | H | NPr-i | —$(CH_2)_3$— | |
| Me | Me | H | H | 1 | H | H | NPr-i | —$(CH_2)_4$— | |
| Me | Me | H | H | 1 | H | H | NPr | Cl | Me |
| Me | Me | H | H | 1 | H | H | NPr | $CF_3$ | H |
| Me | Me | H | H | I | H | H | NPr | $CF_3$ | Me |
| Me | Me | H | H | 1 | H | H | NPr | $OCHF_2$ | H |
| Me | Me | H | H | 1 | H | H | NPr | $OCHF_2$ | Me |
| Me | Me | H | H | 1 | H | H | NPr | —$(CH_2)_3$— | |
| Me | Me | H | H | 1 | H | H | NPr | —$(CH_2)_4$— | |
| Me | Me | H | H | 1 | H | H | NBu-t | Cl | Me |
| Me | Me | H | H | 1 | H | H | NBu-t | $CF_3$ | H |
| Me | Me | H | H | 1 | H | H | NBu-t | $CF_3$ | Me |
| Me | Me | H | H | 1 | H | H | NBu-t | $OCHF_2$ | H |
| Me | Me | H | H | 1 | H | H | NBu-t | $OCHF_2$ | Me |
| Me | Me | H | H | 1 | H | H | NBu-t | —$(CH_2)_3$— | |
| Me | Me | H | H | 1 | H | H | NBu-t | —$(CH_2)_4$— | |
| Me | Me | H | H | 1 | H | H | $NCH_2Ph$ | Cl | Me |
| Me | Me | H | H | 1 | H | H | $NCH_2Ph$ | $CF_3$ | H |
| Me | Me | H | H | 1 | H | H | $NCH_2Ph$ | $OCHF_2$ | H |
| Me | Me | H | H | 1 | H | H | $NCH_2OMe$ | Cl | Me |
| Me | Me | H | H | 1 | H | H | $NCH_2OMe$ | $CF_3$ | H |
| Me | Me | H | H | 1 | H | H | $NCH_2OMe$ | $OCHF_2$ | H |
| Me | Me | H | H | 1 | H | H | $NCH_2C≡CH$ | Cl | Me |
| Me | Me | H | H | 1 | H | H | $NCH_2C≡CH$ | $CF_3$ | H |
| Me | Me | H | H | 1 | H | H | $NCH_2C≡CH$ | $OCHF_2$ | H |
| Me | Me | H | H | 1 | H | H | $NCH_2CH=CH_2$ | Cl | Me |
| Me | Me | H | H | 1 | H | H | $NCH_2CH=CH_2$ | $CF_3$ | H |
| Me | Me | H | H | 1 | H | H | $NCH_2CH=CH_2$ | $OCHF_2$ | H |
| Me | Me | H | H | 1 | H | H | $NCHF_2$ | Cl | Me |
| Me | Me | H | H | 1 | H | H | $NCHF_2$ | $CF_3$ | H |
| Me | Me | H | H | 1 | H | H | $NCHF_2$ | $CF_3$ | Me |
| Me | Me | H | H | 1 | H | H | $NCHF_2$ | $OCHF_2$ | H |
| Me | Me | H | H | 1 | H | H | $NCHF_2$ | $OCHF_2$ | Me |
| Me | Me | H | H | 1 | H | H | $NCHF_2$ | C(=O)Me | H |
| Me | Me | H | H | 1 | H | H | $NCHF_2$ | C(=O)Me | Me |
| Me | Me | H | H | 1 | H | H | $NCHF_2$ | —$(CH_2)_3$— | |
| Me | Me | H | H | 1 | H | H | $NCHF_2$ | —$(CH_2)_4$— | |
| Me | Me | H | H | 1 | H | H | NPh | OMe | Me |
| Me | Me | H | H | 1 | H | H | NPh | OEt | Me |
| Me | Me | H | H | 1 | H | H | NPh | $OCHF_2$ | Me |
| Me | Me | H | H | 1 | H | H | NPh | $OCH_2CF_3$ | Me |
| Me | Me | H | H | 1 | H | H | NPh | $CF_3$ | H |
| Me | Me | H | H | 1 | H | H | NPh | $OCH_2CH=CH_2$ | Me |
| Me | Me | H | H | 1 | H | H | NPh | $OCH_2CH≡CH$ | Me |
| Me | Me | H | H | 1 | H | H | NPh | Cl | Me |
| Me | Me | H | H | 1 | H | H | N(2-Cl)Ph | Cl | Me |
| Me | Me | H | H | 1 | H | H | N(2-F)Ph | Cl | Me |

TABLE 5-continued

| R¹ | R² | R³ | R⁴ | n | R⁵ | R⁶ | Z⁴ | R³³ | R³⁴ |
|---|---|---|---|---|---|---|---|---|---|
| Me | Me | H | H | 1 | H | H | N(2-OMe)Ph | Cl | Me |
| Me | Me | H | H | 1 | H | H | N(2-Me)Ph | Cl | Me |
| Me | Me | H | H | 1 | H | H | N(3-Cl)Ph | Cl | Me |
| Me | Me | H | H | 1 | H | H | N(3-F)Ph | Cl | Me |
| Me | Me | H | H | 1 | H | H | N(3-OMe)Ph | Cl | Me |
| Me | Me | H | H | 1 | H | H | N(3-Me)Ph | Cl | Me |
| Me | Me | H | H | 1 | H | H | N(4-Cl)Ph | Cl | Me |
| Me | Me | H | H | 1 | H | H | N(4-F)Ph | Cl | Me |
| Me | Me | H | H | 1 | H | H | N(4-OMe)Ph | Cl | Me |
| Me | Me | H | H | 1 | H | H | N(4-Me)Ph | Cl | Me |
| Me | Me | H | H | 1 | H | H | N(Thiophen-2-yl) | Cl | Me |
| Me | Me | H | H | 1 | H | H | N(Thiophen-2-yl) | CF₃ | H |
| Me | Me | H | H | 1 | H | H | N(Thiophen-2-yl) | OCHF₂ | H |
| Me | Me | H | H | 1 | H | H | NC(=O)Me | Cl | Me |
| Me | Me | H | H | 1 | H | H | NC(=O)Me | CF₃ | H |
| Me | Me | H | H | 1 | H | H | NC(=O)Me | OCHF₂ | H |
| Me | Me | H | H | 1 | H | H | NC(=O)CF₃ | Cl | Me |
| Me | Me | H | H | 1 | H | H | NC(=O)CF₃ | CF₃ | H |
| Me | Me | H | H | 1 | H | H | NC(=O)CF₃ | OCHF₂ | H |
| Me | Me | H | H | 1 | H | H | NC(=O)CH₂Ph | Cl | Me |
| Me | Me | H | H | 1 | H | H | NC(=O)CH₂Ph | CF₃ | H |
| Me | Me | H | H | 1 | H | H | NC(=O)CH₂Ph | OCHF₂ | H |
| Me | Me | H | H | 1 | H | H | NC(=O)Ph | Cl | Me |
| Me | Me | H | H | 1 | H | H | NC(=O)Ph | CF₃ | H |
| Me | Me | H | H | 1 | H | H | NC(=O)Ph | OCHF₂ | H |
| Me | Me | H | H | 1 | H | H | NC(=O)OMe | Cl | Me |
| Me | Me | H | H | 1 | H | H | NC(=O)OMe | CF₃ | H |
| Me | Me | H | H | 1 | H | H | NC(=O)OMe | OCHF₂ | H |
| Me | Me | H | H | 1 | H | H | NC(=O)OCH₂Ph | Cl | Me |
| Me | Me | H | H | 1 | H | H | NC(=O)OCH₂Ph | CF₃ | H |
| Me | Me | H | H | 1 | H | H | NC(=O)OCH₂Ph | OCHF₂ | H |
| Me | Me | H | H | 1 | H | H | NC(=O)OPh | Cl | Me |
| Me | Me | H | H | 1 | H | H | NC(=O)OPh | CF₃ | H |
| Me | Me | H | H | 1 | H | H | NC(=O)OPh | OCHF₂ | H |
| Me | Me | H | H | 1 | H | H | NC(=O)NHMe | Cl | Me |
| Me | Me | H | H | 1 | H | H | NC(=O)NHMe | CF₃ | H |
| Me | Me | H | H | 1 | H | H | NC(=O)NHMe | OCHF₂ | H |
| Me | Me | H | H | 1 | H | H | NC(=O)N(Me)₂ | Cl | Me |
| Me | Me | H | H | 1 | H | H | NC(=O)N(Me)₂ | CF₃ | H |
| Me | Me | H | H | 1 | H | H | NC(=O)N(Me)₂ | OCHF₂ | H |
| H | H | H | H | 1 | H | H | NPh | Cl | Me |
| Me | H | H | H | 1 | H | H | NPh | Cl | Me |
| Me | H | Me | H | 1 | H | H | NPh | Cl | Me |
| Me | Me | H | H | 1 | Me | H | NPh | Cl | Me |
| Me | Me | H | H | 1 | Et | H | NPh | Cl | Me |
| Me | Me | H | H | 1 | Pr-i | H | NPh | Cl | Me |
| Me | Me | H | H | 1 | Me | Me | NPh | Cl | Me |
| Me | Et | H | H | 1 | H | H | NPh | Cl | Me |
| Et | Et | H | H | 1 | H | H | NPh | Cl | Me |
| Me | Pr-i | H | H | 1 | H | H | NPh | Cl | Me |
| Me | Pr | H | H | 1 | H | H | NPh | Cl | Me |
| Me | Pr-c | H | H | 1 | H | H | NPh | Cl | Me |
| Me | CH₂Pr-c | H | H | 1 | H | H | NPh | Cl | Me |
| —(CH₂)₂— | | H | H | 1 | H | H | NPh | Cl | Me |
| —(CH₂)₃— | | H | H | 1 | H | H | NPh | Cl | Me |
| —(CH₂)₄— | | H | H | 1 | H | H | NPh | Cl | Me |
| —(CH₂)₅— | | H | H | 1 | H | H | NPh | Cl | Me |
| H | —(CH₂)₃— | | H | 1 | H | H | NPh | Cl | Me |
| H | —(CH₂)₄— | | H | 1 | H | H | NPh | Cl | Me |
| H | —(CH₂)₅— | | H | 1 | H | H | NPh | Cl | Me |
| H | —(CH₂)₆— | | H | 1 | H | H | NPh | Cl | Me |
| Me | Me | H | H | 1 | H | H | O | H | Me |
| Me | Me | H | H | 1 | H | H | O | Cl | Me |
| Me | Me | H | H | 1 | H | H | S | H | Me |
| Me | Me | H | H | 1 | H | H | S | Cl | Me |
| Me | Me | H | H | 0 | H | H | NMe | Cl | H |
| Me | Me | H | H | 0 | H | H | NMe | Cl | Me |
| Me | Me | H | H | 0 | H | H | NMe | Cl | Et |

TABLE 5-continued

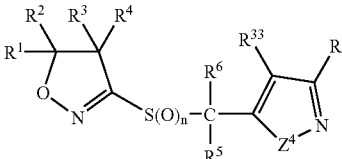

| $R^1$ | $R^2$ | $R^3$ | $R^4$ | n | $R^5$ | $R^6$ | $Z^4$ | $R^{33}$ | $R^{34}$ |
|---|---|---|---|---|---|---|---|---|---|
| Me | Me | H | H | 0 | H | H | NMe | Cl | $CF_3$ |
| Me | Me | H | H | 0 | H | H | NMe | $CF_3$ | H |
| Me | Me | H | H | 0 | H | H | MAe | $CF_3$ | Me |
| Me | Me | H | H | 0 | H | H | NMe | $OCHF_2$ | H |
| Me | Me | H | H | 0 | H | H | NMe | $OCHF_2$ | Me |
| Me | Me | H | H | 0 | H | H | NMe | C(=O)Me | H |
| Me | Me | H | H | 0 | H | H | NMe | C(=O)Me | Me |
| Me | Me | H | H | 0 | H | H | NMe | —$(CH_2)_3$— | |
| Me | Me | H | H | 0 | H | H | NMe | —$(CH_2)_4$— | |
| Me | Me | H | H | 0 | H | H | NEt | Cl | Me |
| Me | Me | H | H | 0 | H | H | NEt | $CF_3$ | H |
| Me | Me | H | H | 0 | H | H | NEt | $CF_3$ | Me |
| Me | Me | H | H | 0 | H | H | NEt | $OCHF_2$ | H |
| Me | Me | H | H | 0 | H | H | NEt | $OCHF_2$ | Me |
| Me | Me | H | H | 0 | H | H | NEt | —$(CH_2)_3$— | |
| Me | Me | H | H | 0 | H | H | NEt | —$(CH_2)_4$— | |
| Me | Me | H | H | 0 | H | H | NPr-i | Cl | Me |
| Me | Me | H | H | 0 | H | H | NPr-i | $CF_3$ | H |
| Me | Me | H | H | 0 | H | H | NPr-i | $CF_3$ | Me |
| Me | Me | H | H | 0 | H | H | NPr-i | $OCHF_2$ | H |
| Me | Me | H | H | 0 | H | H | NPr-i | $OCHF_2$ | Me |
| Me | Me | H | H | 0 | H | H | NPr-i | —$(CH_2)_3$— | |
| Me | Me | H | H | 0 | H | H | NPr-i | —$(CH_2)_4$— | |
| Me | Me | H | H | 0 | H | H | NPr | Cl | Me |
| Me | Me | H | H | 0 | H | H | NPr | $CF_3$ | H |
| Me | Me | H | H | 0 | H | H | NPr | $CF_3$ | Me |
| Me | Me | H | H | 0 | H | H | NPr | $OCHF_2$ | H |
| Me | Me | H | H | 0 | H | H | NPr | $OCHF_2$ | Me |
| Me | Me | H | H | 0 | H | H | NPr | —$(CH_2)_3$— | |
| Me | Me | H | H | 0 | H | H | NPr | —$(CH_2)_4$— | |
| Me | Me | H | H | 0 | H | H | NBu-t | Cl | Me |
| Me | Me | H | H | 0 | H | H | NBu-t | $CF_3$ | H |
| Me | Me | H | H | 0 | H | H | NBu-t | $CF_3$ | Me |
| Me | Me | H | H | 0 | H | H | NBu-t | $OCHF_2$ | H |
| Me | Me | H | H | 0 | H | H | NBu-t | $OCHF_2$ | Me |
| Me | Me | H | H | 0 | H | H | NBu-t | —$(CH_2)_3$— | |
| Me | Me | H | H | 0 | H | H | NBu-t | —$(CH_2)_4$— | |
| Me | Me | H | H | 0 | H | H | $NCH_2Ph$ | Cl | Me |
| Me | Me | H | H | 0 | H | H | $NCH_2Ph$ | $CF_3$ | H |
| Me | Me | H | H | 0 | H | H | $NCH_2Ph$ | $OCHF_2$ | H |
| Me | Me | H | H | 0 | H | H | $NCH_2OMe$ | Cl | Me |
| Me | Me | H | H | 0 | H | H | $NCH_2OMe$ | $CF_3$ | H |
| Me | Me | H | H | 0 | H | H | $NCH_2OMe$ | $OCHF_2$ | H |
| Me | Me | H | H | 0 | H | H | $NCH_2C≡CH$ | Cl | Me |
| Me | Me | H | H | 0 | H | H | $NCH_2C≡CH$ | $CF_3$ | H |
| Me | Me | H | H | 0 | H | H | $NCH_2C≡CH$ | $OCHF_2$ | H |
| Me | Me | H | H | 0 | H | H | $NCH_2CH=CH_2$ | Cl | Me |
| Me | Me | H | H | 0 | H | H | $NCH_2CH=CH_2$ | $CF_3$ | H |
| Me | Me | H | H | 0 | H | H | $NCH_2CH=CH_2$ | $OCHF_2$ | H |
| Me | Me | H | H | 0 | H | H | $NCHF_2$ | Cl | Me |
| Me | Me | H | H | 0 | H | H | $NCHF_2$ | $CF_3$ | H |
| Me | Me | H | H | 0 | H | H | $NCHF_2$ | $CF_3$ | Me |
| Me | Me | H | H | 0 | H | H | $NCHF_2$ | $OCHF_2$ | H |
| Me | Me | H | H | 0 | H | H | $NCHF_2$ | $OCHF_2$ | Me |
| Me | Me | H | H | 0 | H | H | $NCHF_2$ | C(=O)Me | H |
| Me | Me | H | H | 0 | H | H | $NCHF_2$ | C(=O)Me | Me |
| Me | Me | H | H | 0 | H | H | $NCHF_2$ | —$(CH_2)_3$— | |
| Me | Me | H | H | 0 | H | H | $NCHF_2$ | —$(CH_2)_4$— | |
| Me | Me | H | H | 0 | H | H | NPh | OMe | Me |
| Me | Me | H | H | 0 | H | H | NPh | OEt | Me |
| Me | Me | H | H | 0 | H | H | NPh | $OCHF_2$ | Me |
| Me | Me | H | H | 0 | H | H | NPh | $OCH_2CF_3$ | Me |
| Me | Me | H | H | 0 | H | H | NPh | $CF_3$ | H |
| Me | Me | H | H | 0 | H | H | NPh | $OCH_2CH=CH_2$ | Me |
| Me | Me | H | H | 0 | H | H | NPh | $OCH_2CH≡CH$ | Me |
| Me | Me | H | H | 0 | H | H | NPh | Cl | Me |
| Me | Me | H | H | 0 | H | H | N(2-Cl)Ph | Cl | Me |
| Me | Me | H | H | 0 | H | H | N(2-F)Ph | Cl | Me |

TABLE 5-continued

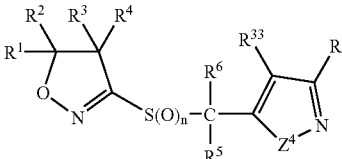

| R¹ | R² | R³ | R⁴ | n | R⁵ | R⁶ | Z⁴ | R³³ | R³⁴ |
|---|---|---|---|---|---|---|---|---|---|
| Me | Me | H | H | 0 | H | H | N(2-OMe)Ph | Cl | Me |
| Me | Me | H | H | 0 | H | H | N(2-Me)Ph | Cl | Me |
| Me | Me | H | H | 0 | H | H | N(3-Cl)Ph | Cl | Me |
| Me | Me | H | H | 0 | H | H | N(3-F)Ph | Cl | Me |
| Me | Me | H | H | 0 | H | H | N(3-OMe)Ph | Cl | Me |
| Me | Me | H | H | 0 | H | H | N(3-Me)Ph | Cl | Me |
| Me | Me | H | H | 0 | H | H | N(4-Cl)Ph | Cl | Me |
| Me | Me | H | H | 0 | H | H | N(4-F)Ph | Cl | Me |
| Me | Me | H | H | 0 | H | H | N(4-OMe)Ph | Cl | Me |
| Me | Me | H | H | 0 | H | H | N(4-Me)Ph | Cl | Me |
| Me | Me | H | H | 0 | H | H | N(Thiophen-2-yl) | Cl | Me |
| Me | Me | H | H | 0 | H | H | N(Thiophen-2-yl) | CF₃ | H |
| Me | Me | H | H | 0 | H | H | N(Thiophen-2-yl) | OCHF₂ | H |
| Me | Me | H | H | 0 | H | H | NC(=O)Me | Cl | Me |
| Me | Me | H | H | 0 | H | H | NC(=O)Me | CF₃ | H |
| Me | Me | H | H | 0 | H | H | NC(=O)Me | OCHF₂ | H |
| Me | Me | H | H | 0 | H | H | NC(=O)CF₃ | Cl | Me |
| Me | Me | H | H | 0 | H | H | NC(=O)CF₃ | CF₃ | H |
| Me | Me | H | H | 0 | H | H | NC(=O)CF₃ | OCHF₂ | H |
| Me | Me | H | H | 0 | H | H | NC(=O)CH₂Ph | Cl | Me |
| Me | Me | H | H | 0 | H | H | NC(=O)CH₂Ph | CF₃ | H |
| Me | Me | H | H | 0 | H | H | NC(=O)CH₂Ph | OCHF₂ | H |
| Me | Me | H | H | 0 | H | H | NC(=O)Ph | Cl | Me |
| Me | Me | H | H | 0 | H | H | NC(=O)Ph | CF₃ | H |
| Me | Me | H | H | 0 | H | H | NC(=O)Ph | OCHF₂ | H |
| Me | Me | H | H | 0 | H | H | NC(=O)OMe | Cl | Me |
| Me | Me | H | H | 0 | H | H | NC(=O)OMe | CF₃ | H |
| Me | Me | H | H | 0 | H | H | NC(=O)OMe | OCHF₂ | H |
| Me | Me | H | H | 0 | H | H | NC(=O)OCH₂Ph | Cl | Me |
| Me | Me | H | H | 0 | H | H | NC(=O)OCH₂Ph | CF₃ | H |
| Me | Me | H | H | 0 | H | H | NC(=O)OCH₂Ph | OCHF₂ | H |
| Me | Me | H | H | 0 | H | H | NC(=O)OPh | Cl | Me |
| Me | Me | H | H | 0 | H | H | NC(=O)OPh | CF₃ | H |
| Me | Me | H | H | 0 | H | H | NC(=O)OPh | OCHF₂ | H |
| Me | Me | H | H | 0 | H | H | NC(=O)NHMe | Cl | Me |
| Me | Me | H | H | 0 | H | H | NC(=O)NHMe | CF₃ | H |
| Me | Me | H | H | 0 | H | H | NC(=O)NHMe | OCHF₂ | H |
| Me | Me | H | H | 0 | H | H | NC(=O)N(Me)₂ | Cl | Me |
| Me | Me | H | H | 0 | H | H | NC(=O)N(Me)₂ | CF₃ | H |
| Me | Me | H | H | 0 | H | H | NC(=O)N(Me)₂ | OCHF₂ | H |
| H | H | H | H | 0 | H | H | NPh | Cl | Me |
| Me | H | H | H | 0 | H | H | NPh | Cl | Me |
| Me | H | Me | H | 0 | H | H | NPh | Cl | Me |
| Me | Me | H | H | 0 | Me | H | NPh | Cl | Me |
| Me | Me | H | H | 0 | Et | H | NPh | Cl | Me |
| Me | Me | H | H | 0 | Pr-i | H | NPh | Cl | Me |
| Me | Me | H | H | 0 | Me | Me | NPh | Cl | Me |
| Me | Et | H | H | 0 | H | H | NPh | Cl | Me |
| Et | Et | H | H | 0 | H | H | NPh | Cl | Me |
| Me | Pr-i | H | H | 0 | H | H | NPh | Cl | Me |
| Me | Pr | H | H | 0 | H | H | NPh | Cl | Me |
| Me | Pr-c | H | H | 0 | H | H | NPh | Cl | Me |
| Me | CH₂Pr-c | H | H | 0 | H | H | NPh | Cl | Me |
| —(CH₂)₂— | | H | H | 0 | H | H | NPh | Cl | Me |
| —(CH₂)₃— | | H | H | 0 | H | H | NPh | Cl | Me |
| —(CH₂)₄— | | H | H | 0 | H | H | NPh | Cl | Me |
| —(CH₂)₅— | | H | H | 0 | H | H | NPh | Cl | Me |
| H | —(CH₂)₃— | | H | 0 | H | H | NPh | Cl | Me |
| H | —(CH₂)₄— | | H | 0 | H | H | NPh | Cl | Me |
| H | —(CH₂)₅— | | H | 0 | H | H | NPh | Cl | Me |
| H | —(CH₂)₆— | | H | 0 | H | H | NPh | Cl | Me |
| Me | Me | H | H | 0 | H | H | O | H | Me |
| Me | Me | H | H | 0 | H | H | O | Cl | Me |
| Me | Me | H | H | 0 | H | H | S | H | Me |
| Me | Me | H | H | 0 | H | H | S | Cl | Me |
| Me | Et | H | H | 2 | H | H | NH | H | H |

TABLE 6

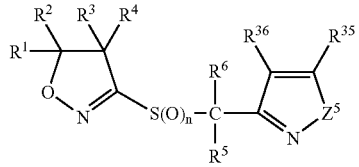

| R¹ | R² | R³ | R⁴ | n | R⁵ | R⁶ | Z⁵ | R³⁵ | R³⁶ |
|---|---|---|---|---|---|---|---|---|---|
| Me | Me | H | H | 2 | H | H | NMe | H | OMe |
| Me | Me | H | H | 2 | H | H | NMe | H | OEt |
| Me | Me | H | H | 2 | H | H | NMe | H | OCHF₂ |
| Me | Me | H | H | 2 | H | H | NMe | H | OCH₂CF₃ |
| Me | Me | H | H | 2 | H | H | NMe | —(CH₂)₃— | |
| Me | Me | H | H | 2 | H | H | NMe | —(CH₂)₄— | |
| Me | Me | H | H | 2 | H | H | NEt | —(CH₂)₃— | |
| Me | Me | H | H | 2 | H | H | NEt | —(CH₂)₄— | |
| Me | Me | H | H | 2 | H | H | NPr-i | —(CH₂)₃— | |
| Me | Me | H | H | 2 | H | H | NPr-i | —(CH₂)₄— | |
| Me | Me | H | H | 2 | H | H | NCHF₂ | —(CH₂)₃— | |
| Me | Me | H | H | 2 | H | H | NCHF₂ | —(CH₂)₄— | |
| Me | Me | H | H | 2 | H | H | N(CH₂)₃O— | H | |
| Me | Me | H | H | 2 | H | H | N(CH₂)₄O— | H | |
| Me | Me | H | H | 2 | H | H | N(CH₂)₄— | H | |
| Me | Me | H | H | 2 | H | H | N(CH₂)₅— | H | |
| Me | Me | H | H | 2 | H | H | NPh | H | OMe |
| Me | Me | H | H | 2 | H | H | NPh | H | OEt |
| Me | Me | H | H | 2 | H | H | NPh | H | OCHF₂ |
| Me | Me | H | H | 2 | H | H | NPh | H | OCH₂CF₃ |
| Me | Me | H | H | 2 | H | H | O | H | H |
| Me | Me | H | H | 2 | H | H | S | Me | H |
| H | H | H | H | 2 | H | H | NPh | H | OMe |
| Me | H | H | H | 2 | H | H | NPh | H | OEt |
| Me | H | Me | H | 2 | H | H | NPh | H | OMe |
| Me | Me | H | H | 2 | Me | H | NPh | H | OEt |
| Me | Me | H | H | 2 | Et | H | NPh | H | OMe |
| Me | Me | H | H | 2 | Pr-i | H | NPh | H | OEt |
| Me | Me | H | H | 2 | Me | Me | NPh | H | OMe |
| Me | Et | H | H | 2 | H | H | NPh | H | OEt |
| Et | Et | H | H | 2 | H | H | NPh | H | OMe |
| Me | Pr-i | H | H | 2 | H | H | NPh | H | OEt |
| Me | Pr | H | H | 2 | H | H | NPh | H | OMe |
| Me | Pr-c | H | H | 2 | H | H | NPh | H | OEt |
| Me | CH₂Pr-c | H | H | 2 | H | H | NPh | H | OMe |
| —(CH₂)₂— | | H | H | 2 | H | H | NPh | H | OEt |
| —(CH₂)₃— | | H | H | 2 | H | H | NPh | H | OMe |
| —(CH₂)₄— | | H | H | 2 | H | H | NPh | H | OEt |
| —(CH₂)₅— | | H | H | 2 | H | H | NPh | H | OMe |
| H | —(CH₂)₃— | | H | 2 | H | H | NPh | H | OEt |
| H | —(CH₂)₄— | | H | 2 | H | H | NPh | H | OMe |
| H | —(CH₂)₅— | | H | 2 | H | H | NPh | H | OEt |
| H | —(CH₂)₆— | | H | 2 | H | H | NPh | H | OMe |
| Me | Me | H | H | 1 | H | H | NMe | H | OMe |
| Me | Me | H | H | 1 | H | H | NMe | H | OEt |
| Me | Me | H | H | 1 | H | H | NMe | H | OCHF₂ |
| Me | Me | H | H | 1 | H | H | NMe | H | OCH₂CF₃ |
| Me | Me | H | H | 1 | H | H | NMe | —(CH₂)₃— | |
| Me | Me | H | H | 1 | H | H | NMe | —(CH₂)₄— | |
| Me | Me | H | H | 1 | H | H | NEt | —(CH₂)₃— | |
| Me | Me | H | H | 1 | H | H | NEt | —(CH₂)₄— | |
| Me | Me | H | H | 1 | H | H | NPr-i | —(CH₂)₃— | |
| Me | Me | H | H | 1 | H | H | NPr-i | —(CH₂)₄— | |
| Me | Me | H | H | 1 | H | H | NCHF₂ | —(CH₂)₃— | |
| Me | Me | H | H | 1 | H | H | NCHF₂ | —(CH₂)₄— | |
| Me | Me | H | H | 1 | H | H | N(CH₂)₃O— | H | |
| Me | Me | H | H | 1 | H | H | N(CH₂)₄O— | H | |
| Me | Me | H | H | 1 | H | H | N(CH₂)₄— | H | |
| Me | Me | H | H | 1 | H | H | N(CH₂)₅— | H | |
| Me | Me | H | H | 1 | H | H | NPh | H | OMe |
| Me | Me | H | H | 1 | H | H | NPh | H | OEt |
| Me | Me | H | H | 1 | H | H | NPh | H | OCHF₂ |
| Me | Me | H | H | 1 | H | H | NPh | H | OCH₂CF₃ |
| Me | Me | H | H | 1 | H | H | O | Me | H |
| Me | Me | H | H | 1 | H | H | S | Me | H |
| H | H | H | H | 1 | H | H | NPh | H | OMe |
| Me | H | H | H | 1 | H | H | NPh | H | OEt |
| Me | H | Me | H | 1 | H | H | NPh | H | OMe |

TABLE 6-continued

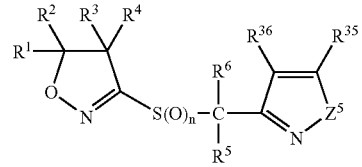

| R¹ | R² | R³ | R⁴ | n | R⁵ | R⁶ | Z⁵ | R³⁵ | R³⁶ |
|---|---|---|---|---|---|---|---|---|---|
| Me | Me | H | H | 1 | Me | H | NPh | H | OEt |
| Me | Me | H | H | 1 | Et | H | NPh | H | OMe |
| Me | Me | H | H | 1 | Pr-i | H | NPh | H | OEt |
| Me | Me | H | H | 1 | Me | Me | NPh | H | OMe |
| Me | Et | H | H | 1 | H | H | NPh | H | OEt |
| Et | Et | H | H | 1 | H | H | NPh | H | OMe |
| Me | Pr-i | H | H | 1 | H | H | NPh | H | OEt |
| Me | Pr | H | H | 1 | H | H | NPh | H | OMe |
| Me | Pr-c | H | H | 1 | H | H | NPh | H | OEt |
| Me | CH₂Pr-c | H | H | 1 | H | H | NPh | H | OMe |
| —(CH₂)₂— | | H | H | 1 | H | H | NPh | H | OEt |
| —(CH₂)₃— | | H | H | 1 | H | H | NPh | H | OMe |
| —(CH₂)₄— | | H | H | 1 | H | H | NPh | H | OEt |
| —(CH₂)₅— | | H | H | 1 | H | H | NPh | H | OMe |
| H | —(CH₂)₃— | | H | 1 | H | H | NPh | H | OEt |
| H | —(CH₂)₄— | | H | 1 | H | H | NPh | H | OMe |
| H | —(CH₂)₅— | | H | 1 | H | H | NPh | H | OEt |
| H | —(CH₂)₆— | | H | 1 | H | H | NPh | H | OMe |
| Me | Me | H | H | 0 | H | H | NMe | H | OMe |
| Me | Me | H | H | 0 | H | H | NMe | H | OEt |
| Me | Me | H | H | 0 | H | H | NMe | H | OCHF₂ |
| Me | Me | H | H | 0 | H | H | NMe | H | OCH₂CF₃ |
| Me | Me | H | H | 0 | H | H | NMe | —(CH₂)₃— | |
| Me | Me | H | H | 0 | H | H | NMe | —(CH₂)₄— | |
| Me | Me | H | H | 0 | H | H | NEt | —(CH₂)₃— | |
| Me | Me | H | H | 0 | H | H | NEt | —(CH₂)₄— | |
| Me | Me | H | H | 0 | H | H | NPr-i | —(CH₂)₃— | |
| Me | Me | H | H | 0 | H | H | NPr-i | —(CH₂)₄— | |
| Me | Me | H | H | 0 | H | H | NCHF₂ | —(CH₂)₃— | |
| Me | Me | H | H | 0 | H | H | NCHF₂ | —(CH₂)₄— | |
| Me | Me | H | H | 0 | H | H | N(CH₂)₃O— | H | |
| Me | Me | H | H | 0 | H | H | N(CH₂)₄O— | H | |
| Me | Me | H | H | 0 | H | H | N(CH₂)₄— | H | |
| Me | Me | H | H | 0 | H | H | N(CH₂)₅— | H | |
| Me | Me | H | H | 0 | H | H | NPh | H | OMe |
| Me | Me | H | H | 0 | H | H | NPh | H | OEt |
| Me | Me | H | H | 0 | H | H | NPh | H | OCHF₂ |
| Me | Me | H | H | 0 | H | H | NPh | H | OCH₂CF₃ |
| Me | Me | H | H | 0 | H | H | O | Me | H |
| Me | Me | H | H | 0 | H | H | S | Me | H |
| H | H | H | H | 0 | H | H | NPh | H | OMe |
| Me | H | H | H | 0 | H | H | NPh | H | OEt |
| Me | H | Me | H | 0 | H | H | NPh | H | OMe |
| Me | Me | H | H | 0 | Me | H | NPh | H | OEt |
| Me | Me | H | H | 0 | Et | H | NPh | H | OMe |
| Me | Me | H | H | 0 | Pr-i | H | NPh | H | OEt |
| Me | Me | H | H | 0 | Me | Me | NPh | H | OMe |
| Me | Et | H | H | 0 | H | H | NPh | H | OEt |
| Et | Et | H | H | 0 | H | H | NPh | H | OMe |
| Me | Pr-i | H | H | 0 | H | H | NPh | H | OEt |
| Me | Pr | H | H | 0 | H | H | NPh | H | OMe |
| Me | Pr-c | H | H | 0 | H | H | NPh | H | OEt |
| Me | CH₂Pr-c | H | H | 0 | H | H | NPh | H | OMe |
| —(CH₂)₂— | | H | H | 0 | H | H | NPh | H | OEt |
| —(CH₂)₃— | | H | H | 0 | H | H | NPh | H | OMe |
| —(CH₂)₄— | | H | H | 0 | H | H | NPh | H | OEt |
| —(CH₂)₅— | | H | H | 0 | H | H | NPh | H | OMe |
| H | —(CH₂)₃— | | H | 0 | H | H | NPh | H | OEt |
| H | —(CH₂)₄— | | H | 0 | H | H | NPh | H | OMe |
| H | —(CH₂)₅— | | H | 0 | H | H | NPh | H | OMe |
| H | —(CH₂)₆— | | H | 0 | H | H | NPh | H | OEt |
| Me | Et | H | H | 2 | H | H | O | H | H |
| Me | Et | H | H | 2 | H | H | S | H | H |
| Me | Et | H | H | 2 | H | H | NH | H | H |

TABLE 7

| R¹ | R² | R³ | R⁴ | n | R⁵ | R⁶ | R³⁷ | R³⁸ | R³⁹ | R⁴⁰ | |
|---|---|---|---|---|---|---|---|---|---|---|---|
| Me | Me | H | H | 2 | H | H | H | H | H | H | — |
| Me | Me | H | H | 2 | H | H | H | H | H | H | N-oxide |
| Me | Me | H | H | 2 | H | H | Cl | Ph | H | H | — |
| Me | Me | H | H | 2 | H | H | OMe | Ph | H | H | — |
| Me | Me | H | H | 2 | H | H | Cl | Me | H | H | — |
| Me | Me | H | H | 2 | H | H | OMe | Me | H | H | — |
| Me | Me | H | H | 2 | H | H | H | CF₃ | H | H | — |
| Me | Me | H | H | 2 | H | H | H | CF₃ | H | H | N-oxide |
| Me | Me | H | H | 2 | H | H | Cl | CF₃ | H | H | — |
| Me | Me | H | H | 2 | H | H | CN | CF₃ | H | H | — |
| Me | Me | H | H | 2 | H | H | OMe | CF₃ | H | H | — |
| Me | Me | H | H | 2 | H | H | OEt | CF₃ | H | H | — |
| Me | Me | H | H | 2 | H | H | Me | Me | H | H | N-oxide |
| Me | Me | H | H | 2 | H | H | Ph | Ph | H | H | — |
| Me | Me | H | H | 2 | H | H | Cl | (4-Cl)Ph | H | Me | — |
| Me | Me | H | H | 2 | H | H | Cl | (4-Cl)Ph | H | H | — |
| Me | Me | H | H | 2 | H | H | OMe | Cl | H | H | — |
| Me | Me | H | H | 2 | H | H | Cl | (CH₂)₃ | H | — | |
| Me | Me | H | H | 2 | H | H | Me | (CH₂)₃ | H | — | |
| Me | Me | H | H | 2 | H | H | Cl | (CH₂)₄ | H | — | |
| Me | Me | H | H | 2 | H | H | Me | (CH₂)₄ | H | — | |
| Me | Me | H | H | 2 | H | H | Cl | H | (CH₂)₃ | — | |
| Me | Me | H | H | 2 | H | H | Me | H | (CH₂)₃ | — | |
| Me | Me | H | H | 2 | H | H | Cl | H | (CH₂)₄ | — | |
| Me | Me | H | H | 2 | H | H | Me | H | (CH₂)₄ | — | |
| H | H | H | H | 2 | H | H | H | CF₃ | H | H | — |
| Me | H | H | H | 2 | H | H | H | CF₃ | H | H | — |
| Me | H | Me | H | 2 | H | H | H | CF₃ | H | H | — |
| Me | Me | Me | H | 2 | H | H | H | CF₃ | H | H | — |
| Me | Me | H | H | 2 | Me | H | H | CF₃ | H | H | — |
| Me | Me | H | H | 2 | Et | H | H | CF₃ | H | H | — |
| Me | Me | H | H | 2 | Pr-i | H | H | CF₃ | H | H | — |
| Me | Me | H | H | 2 | Me | Me | H | CF₃ | H | H | — |
| Me | Et | H | H | 2 | H | H | H | CF₃ | H | H | — |
| Et | Et | H | H | 2 | H | H | H | CF₃ | H | H | — |
| Me | Pr-i | H | H | 2 | H | H | H | CF₃ | H | H | — |
| Me | Pr | H | H | 2 | H | H | H | CF₃ | H | H | — |
| Me | Pr-c | H | H | 2 | H | H | H | CF₃ | H | H | — |
| Me | CH₂Pr-c | H | H | 2 | H | H | H | CF₃ | H | H | — |
| —(CH₂)₂— | | H | H | 2 | H | H | H | CF₃ | H | H | — |
| —(CH₂)₃— | | H | H | 2 | H | H | H | CF₃ | H | H | — |
| —(CH₂)₄— | | H | H | 2 | H | H | H | CF₃ | H | H | — |
| —(CH₂)₅— | | H | H | 2 | H | H | H | CF₃ | H | H | — |
| H | —(CH₂)₃— | | H | 2 | H | H | H | CF₃ | H | H | — |
| H | —(CH₂)₄— | | H | 2 | H | H | H | CF₃ | H | H | — |
| H | —(CH₂)₅— | | H | 2 | H | H | H | CF₃ | H | H | — |
| H | —(CH₂)₆— | | H | 2 | H | H | H | CF₃ | H | H | — |
| Me | Me | H | H | 1 | H | H | H | H | H | H | — |
| Me | Me | H | H | 1 | H | H | H | H | H | H | N-oxide |
| Me | Me | H | H | 1 | H | H | Cl | Ph | H | H | — |
| Me | Me | H | H | 1 | H | H | OMe | Ph | H | H | — |
| Me | Me | H | H | 1 | H | H | Cl | Me | H | H | — |
| Me | Me | H | H | 1 | H | H | OMe | Me | H | H | — |
| Me | Me | H | H | 1 | H | H | H | CF₃ | H | H | — |
| Me | Me | H | H | 1 | H | H | Cl | CF₃ | H | H | — |
| Me | Me | H | H | 1 | H | H | CN | CF₃ | H | H | — |
| Me | Me | H | H | 1 | H | H | OMe | CF₃ | H | H | — |
| Me | Me | H | H | 1 | H | H | OEt | CF₃ | H | H | — |
| Me | Me | H | H | 1 | H | H | Me | Me | H | H | N-oxide |
| Me | Me | H | H | 1 | H | H | Ph | Ph | H | H | — |
| Me | Me | H | H | 1 | H | H | Cl | (4-Cl)Ph | H | Me | — |
| Me | Me | H | H | 1 | H | H | Cl | (4-Cl)Ph | H | H | — |
| Me | Me | H | H | 1 | H | H | OMe | Cl | H | H | — |
| Me | Me | H | H | 1 | H | H | Cl | (CH₂)₃ | H | — | |
| Me | Me | H | H | 1 | H | H | Me | (CH₂)₃ | H | — | |

TABLE 7-continued

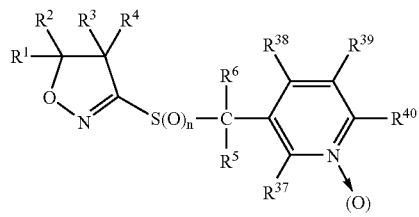

| R¹ | R² | R³ | R⁴ | n | R⁵ | R⁶ | R³⁷ | R³⁸ | R³⁹ | R⁴⁰ | |
|---|---|---|---|---|---|---|---|---|---|---|---|
| Me | Me | H | H | 1 | H | H | Cl | $(CH_2)_4$ | | H | — |
| Me | Me | H | H | 1 | H | H | Me | $(CH_2)_4$ | | H | — |
| Me | Me | H | H | 1 | H | H | Cl | H | $(CH_2)_3$ | | — |
| Me | Me | H | H | 1 | H | H | Me | H | $(CH_2)_3$ | | — |
| Me | Me | H | H | 1 | H | H | Cl | H | $(CH_2)_4$ | | — |
| Me | Me | H | H | 1 | H | H | Me | H | $(CH_2)_4$ | | — |
| H | H | H | H | 1 | H | H | H | $CF_3$ | H | H | — |
| Me | H | H | H | 1 | H | H | H | $CF_3$ | H | H | — |
| Me | H | Me | H | 1 | H | H | H | $CF_3$ | H | H | — |
| Me | Me | Me | H | 1 | H | H | H | $CF_3$ | H | H | — |
| Me | Me | H | H | 1 | Me | H | H | $CF_3$ | H | H | — |
| Me | Me | H | H | 1 | Et | H | H | $CF_3$ | H | H | — |
| Me | Me | H | H | 1 | Pr-i | H | H | $CF_3$ | H | H | — |
| Me | Me | H | H | 1 | Me | Me | H | $CF_3$ | H | H | — |
| Me | Et | H | H | 1 | H | H | H | $CF_3$ | H | H | — |
| Et | Et | H | H | 1 | H | H | H | $CF_3$ | H | H | — |
| Me | Pr-i | H | H | 1 | H | H | H | $CF_3$ | H | H | — |
| Me | Pr | H | H | 1 | H | H | H | $CF_3$ | H | H | — |
| Me | Pr-c | H | H | 1 | H | H | H | $CF_3$ | H | H | — |
| Me | $CH_2Pr$-c | H | H | 1 | H | H | H | $CF_3$ | H | H | — |
| —$(CH_2)_2$— | | H | H | 1 | H | H | H | $CF_3$ | H | H | — |
| —$(CH_2)_3$— | | H | H | 1 | H | H | H | $CF_3$ | H | H | — |
| —$(CH_2)_4$— | | H | H | 1 | H | H | H | $CF_3$ | H | H | — |
| —$(CH_2)_5$— | | H | H | 1 | H | H | H | $CF_3$ | H | H | — |
| H | —$(CH_2)_3$— | | H | 1 | H | H | H | $CF_3$ | H | H | — |
| H | —$(CH_2)_4$— | | H | 1 | H | H | H | $CF_3$ | H | H | — |
| H | —$(CH_2)_5$— | | H | 1 | H | H | H | $CF_3$ | H | H | — |
| H | —$(CH_2)_6$— | | H | 1 | H | H | H | $CF_3$ | H | H | — |
| Me | Me | H | H | 0 | H | H | H | H | H | H | — |
| Me | Me | H | H | 0 | H | H | H | H | H | H | N-oxide |
| Me | Me | H | H | 0 | H | H | Cl | Ph | H | H | — |
| Me | Me | H | H | 0 | H | H | OMe | Ph | H | H | — |
| Me | Me | H | H | 0 | H | H | Cl | Me | H | H | — |
| Me | Me | H | H | 0 | H | H | OMe | Me | H | H | — |
| Me | Me | H | H | 0 | H | H | H | $CF_3$ | H | H | — |
| Me | Me | H | H | 0 | H | H | Cl | $CF_3$ | H | H | — |
| Me | Me | H | H | 0 | H | H | CN | $CF_3$ | H | H | — |
| Me | Me | H | H | 0 | H | H | OMe | $CF_3$ | H | H | — |
| Me | Me | H | H | 0 | H | H | OEt | $CF_3$ | H | H | — |
| Me | Me | H | H | 0 | H | H | Me | Me | H | H | N-oxide |
| Me | Me | H | H | 0 | H | H | Ph | Ph | H | H | — |
| Me | Me | H | H | 0 | H | H | Cl | (4-Cl)Ph | H | Me | — |
| Me | Me | H | H | 0 | H | H | Cl | (4-Cl)Ph | H | H | — |
| Me | Me | H | H | 0 | H | H | OMe | Cl | H | H | — |
| Me | Me | H | H | 0 | H | H | Cl | $(CH_2)_3$ | | H | — |
| Me | Me | H | H | 0 | H | H | Me | $(CH_2)_3$ | | H | — |
| Me | Me | H | H | 0 | H | H | Cl | $(CH_2)_4$ | | H | — |
| Me | Me | H | H | 0 | H | H | Me | $(CH_2)_4$ | | H | — |
| Me | Me | H | H | 0 | H | H | Cl | H | $(CH_2)_3$ | | — |
| Me | Me | H | H | 0 | H | H | Me | H | $(CH_2)_3$ | | — |
| Me | Me | H | H | 0 | H | H | Cl | H | $(CH_2)_4$ | | — |
| Me | Me | H | H | 0 | H | H | Me | H | $(CH_2)_4$ | | — |
| Me | Me | H | H | 0 | H | H | (2-Chloropyridin-3-yl)methylthio | H | H | H | — |
| H | H | H | H | 0 | H | H | H | $CF_3$ | H | H | — |
| Me | H | H | H | 0 | H | H | H | $CF_3$ | H | H | — |
| Me | Me | Me | H | 0 | H | H | H | $CF_3$ | H | H | — |
| Me | H | Me | H | 0 | H | H | H | $CF_3$ | H | H | — |
| Me | Me | H | H | 0 | Me | H | H | $CF_3$ | H | H | — |
| Me | Me | H | H | 0 | Et | H | H | $CF_3$ | H | H | — |
| Me | Me | H | H | 0 | Pr-i | H | H | $CF_3$ | H | H | — |
| Me | Me | H | H | 0 | Me | Me | H | $CF_3$ | H | H | — |
| Me | Et | H | H | 0 | H | H | H | $CF_3$ | H | H | — |
| Et | Et | H | H | 0 | H | H | H | $CF_3$ | H | H | — |
| Me | Pr-i | H | H | 0 | H | H | H | $CF_3$ | H | H | — |

TABLE 7-continued

| R¹ | R² | R³ | R⁴ | n | R⁵ | R⁶ | R³⁷ | R³⁸ | R³⁹ | R⁴⁰ | |
|---|---|---|---|---|---|---|---|---|---|---|---|
| Me | Pr | H | H | 0 | H | H | H | CF₃ | H | H | — |
| Me | Pr-c | H | H | 0 | H | H | H | CF₃ | H | H | — |
| Me | CH₂Pr-c | H | H | 0 | H | H | H | CF₃ | H | H | — |
| —(CH₂)₂— | | H | H | 0 | H | H | H | CF₃ | H | H | — |
| —(CH₂)₃— | | H | H | 0 | H | H | H | CF₃ | H | H | — |
| —(CH₂)₄— | | H | H | 0 | H | H | H | CF₃ | H | H | — |
| —(CH₂)₅— | | H | H | 0 | H | H | H | CF₃ | H | H | — |
| H | —(CH₂)₃— | H | H | 0 | H | H | H | CF₃ | H | H | — |
| H | —(CH₂)₄— | H | H | 0 | H | H | H | CF₃ | H | H | — |
| H | —(CH₂)₅— | H | H | 0 | H | H | H | CF₃ | H | H | — |
| H | —(CH₂)₆— | H | H | 0 | H | H | H | CF₃ | H | H | — |
| Me | Et | H | H | 2 | H | H | H | H | H | H | — |

TABLE 8

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 2 | H | H | H | Cl | Cl |
| Me | Me | H | H | 2 | H | H | H | OH | Cl |
| Me | Me | H | H | 2 | H | H | H | OMe | Cl |
| Me | Me | H | H | 2 | H | H | H | OEt | Cl |
| Me | Me | H | H | 2 | H | H | H | OPr-i | Cl |
| Me | Me | H | H | 2 | H | H | H | OPr | Cl |
| Me | Me | H | H | 2 | H | H | H | OBu-t | Cl |
| Me | Me | H | H | 2 | H | H | H | OCH₂Pr-c | Cl |
| Me | Me | H | H | 2 | H | H | H | OCH₂Bu-c | Cl |
| Me | Me | H | H | 2 | H | H | H | OCH₂Pen-c | Cl |
| Me | Me | H | H | 2 | H | H | H | OCH₂Hex-c | Cl |
| Me | Me | H | H | 2 | H | H | H | OPen-c | Cl |
| Me | Me | H | H | 2 | H | H | H | OHex-c | Cl |
| Me | Me | H | H | 2 | H | H | H | OCH₂Ph | Cl |
| Me | Me | H | H | 2 | H | H | H | OPh | Cl |
| Me | Me | H | H | 2 | H | H | H | OCHF₂ | Cl |
| Me | Me | H | H | 2 | H | H | H | SH | Cl |
| Me | Me | H | H | 2 | H | H | H | SMe | Cl |
| Me | Me | H | H | 2 | H | H | H | SO₂Me | Cl |
| Me | Me | H | H | 2 | H | H | H | SEt | Cl |
| Me | Me | H | H | 2 | H | H | H | SO₂Et | Cl |
| Me | Me | H | H | 2 | H | H | H | SPr-i | Cl |
| Me | Me | H | H | 2 | H | H | H | SO₂Pr-i | Cl |
| Me | Me | H | H | 2 | H | H | H | SPh | Cl |
| Me | Me | H | H | 2 | H | H | H | SO₂Ph | Cl |
| Me | Me | H | H | 2 | H | H | H | SCHF₂ | Cl |
| Me | Me | H | H | 2 | H | H | H | SO₂CHF₂ | Cl |
| Me | Me | H | H | 2 | H | H | H | NH₂ | Cl |
| Me | Me | H | H | 2 | H | H | H | NHMe | Cl |
| Me | Me | H | H | 2 | H | H | H | NMe2 | Cl |
| Me | Me | H | H | 2 | H | H | H | NHEt | Cl |
| Me | Me | H | H | 2 | H | H | H | NEt₂ | Cl |
| Me | Me | H | H | 2 | H | H | H | NHPh | Cl |
| Me | Me | H | H | 2 | H | H | H | N(Me)Ph | Cl |
| Me | Me | H | H | 2 | H | H | H | CN | Cl |
| Me | Me | H | H | 2 | H | H | H | F | Me |

TABLE 8-continued

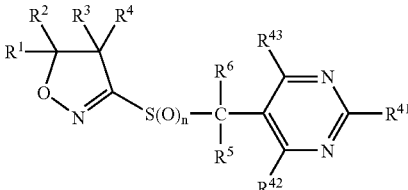

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 2 | H | H | H | Cl | Me |
| Me | Me | H | H | 2 | H | H | H | OH | Me |
| Me | Me | H | H | 2 | H | H | H | OMe | Me |
| Me | Me | H | H | 2 | H | H | H | OEt | Me |
| Me | Me | H | H | 2 | H | H | H | OPr-i | Me |
| Me | Me | H | H | 2 | H | H | H | OPr | Me |
| Me | Me | H | H | 2 | H | H | H | OBu-t | Me |
| Me | Me | H | H | 2 | H | H | H | OCH₂Pr-c | Me |
| Me | Me | H | H | 2 | H | H | H | OCH₂Bu-c | Me |
| Me | Me | H | H | 2 | H | H | H | OCH₂Pen-c | Me |
| Me | Me | H | H | 2 | H | H | H | OCH₂Hex-c | Me |
| Me | Me | H | H | 2 | H | H | H | OPen-c | Me |
| Me | Me | H | H | 2 | H | H | H | OHex-c | Me |
| Me | Me | H | H | 2 | H | H | H | OCH₂Ph | Me |
| Me | Me | H | H | 2 | H | H | H | OPh | Me |
| Me | Me | H | H | 2 | H | H | H | OCHF₂ | Me |
| Me | Me | H | H | 2 | H | H | H | SH | Me |
| Me | Me | H | H | 2 | H | H | H | SMe | Me |
| Me | Me | H | H | 2 | H | H | H | SO₂Me | Me |
| Me | Me | H | H | 2 | H | H | H | SEt | Me |
| Me | Me | H | H | 2 | H | H | H | SO₂Et | Me |
| Me | Me | H | H | 2 | H | H | H | SPr-i | Me |
| Me | Me | H | H | 2 | H | H | H | SO₂Pr-i | Me |
| Me | Me | H | H | 2 | H | H | H | SPh | Me |
| Me | Me | H | H | 2 | H | H | H | SO₂Ph | Me |
| Me | Me | H | H | 2 | H | H | H | SCHF₂ | Me |
| Me | Me | H | H | 2 | H | H | H | SO₂CHF₂ | Me |
| Me | Me | H | H | 2 | H | H | H | NH₂ | Me |
| Me | Me | H | H | 2 | H | H | H | NHMe | Me |
| Me | Me | H | H | 2 | H | H | H | NMe₂ | Me |
| Me | Me | H | H | 2 | H | H | H | NHEt | Me |
| Me | Me | H | H | 2 | H | H | H | NEt₂ | Me |
| Me | Me | H | H | 2 | H | H | H | NHPh | Me |
| Me | Me | H | H | 2 | H | H | H | N(Me)Ph | Me |
| Me | Me | H | H | 2 | H | H | H | CN | Me |
| Me | Me | H | H | 2 | H | H | H | F | Pr-i |
| Me | Me | H | H | 2 | H | H | H | Cl | Pr-i |
| Me | Me | H | H | 2 | H | H | H | OH | Pr-i |
| Me | Me | H | H | 2 | H | H | H | OMe | Pr-i |
| Me | Me | H | H | 2 | H | H | H | OEt | Pr-i |
| Me | Me | H | H | 2 | H | H | H | OPr-i | Pr-i |
| Me | Me | H | H | 2 | H | H | H | OPr | Pr-i |
| Me | Me | H | H | 2 | H | H | H | OBu-t | Pr-i |
| Me | Me | H | H | 2 | H | H | H | OCH₂Pr-c | Pr-i |
| Me | Me | H | H | 2 | H | H | H | OCH₂Bu-c | Pr-i |
| Me | Me | H | H | 2 | H | H | H | OCH₂Pen-c | Pr-i |
| Me | Me | H | H | 2 | H | H | H | OCH₂Hex-c | Pr-i |
| Me | Me | H | H | 2 | H | H | H | OPen-c | Pr-i |
| Me | Me | H | H | 2 | H | H | H | OHex-c | Pr-i |
| Me | Me | H | H | 2 | H | H | H | OCH₂Ph | Pr-i |
| Me | Me | H | H | 2 | H | H | H | OPh | Pr-i |
| Me | Me | H | H | 2 | H | H | H | OCHF₂ | Pr-i |
| Me | Me | H | H | 2 | H | H | H | SH | Pr-i |
| Me | Me | H | H | 2 | H | H | H | SMe | Pr-i |
| Me | Me | H | H | 2 | H | H | H | SO₂Me | Pr-i |
| Me | Me | H | H | 2 | H | H | H | SEt | Pr-i |
| Me | Me | H | H | 2 | H | H | H | SO₂Et | Pr-i |
| Me | Me | H | H | 2 | H | H | H | SPr-i | Pr-i |
| Me | Me | H | H | 2 | H | H | H | SO₂Pr-i | Pr-i |
| Me | Me | H | H | 2 | H | H | H | SPh | Pr-i |
| Me | Me | H | H | 2 | H | H | H | SO₂Ph | Pr-i |
| Me | Me | H | H | 2 | H | H | H | SCHF₂ | Pr-i |
| Me | Me | H | H | 2 | H | H | H | SO₂CHF₂ | Pr-i |
| Me | Me | H | H | 2 | H | H | H | NH₂ | Pr-i |
| Me | Me | H | H | 2 | H | H | H | NHMe | Pr-i |
| Me | Me | H | H | 2 | H | H | H | NMe₂ | Pr-i |

TABLE 8-continued

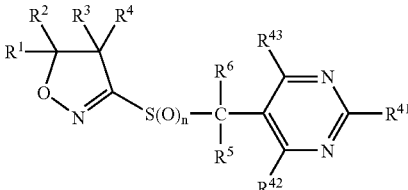

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 2 | H | H | H | NHEt | Pr-i |
| Me | Me | H | H | 2 | H | H | H | NEt₂ | Pr-i |
| Me | Me | H | H | 2 | H | H | H | NHPh | Pr-i |
| Me | Me | H | H | 2 | H | H | H | N(Me)Ph | Pr-i |
| Me | Me | H | H | 2 | H | H | H | CN | Pr-i |
| Me | Me | H | H | 2 | H | H | H | F | Pr-c |
| Me | Me | H | H | 2 | H | H | H | Cl | Pr-c |
| Me | Me | H | H | 2 | H | H | H | OH | Pr-c |
| Me | Me | H | H | 2 | H | H | H | OMe | Pr-c |
| Me | Me | H | H | 2 | H | H | H | OEt | Pr-c |
| Me | Me | H | H | 2 | H | H | H | OPr-i | Pr-c |
| Me | Me | H | H | 2 | H | H | H | OPr | Pr-c |
| Me | Me | H | H | 2 | H | H | H | OBu-t | Pr-c |
| Me | Me | H | H | 2 | H | H | H | OCH₂Pr-c | Pr-c |
| Me | Me | H | H | 2 | H | H | H | OCH₂Bu-c | Pr-c |
| Me | Me | H | H | 2 | H | H | H | OCH₂Pen-c | Pr-c |
| Me | Me | H | H | 2 | H | H | H | OCH₂Hex-c | Pr-c |
| Me | Me | H | H | 2 | H | H | H | OPen-c | Pr-c |
| Me | Me | H | H | 2 | H | H | H | OHex-c | Pr-c |
| Me | Me | H | H | 2 | H | H | H | OCH₂Ph | Pr-c |
| Me | Me | H | H | 2 | H | H | H | OPh | Pr-c |
| Me | Me | H | H | 2 | H | H | H | OCHF₂ | Pr-c |
| Me | Me | H | H | 2 | H | H | H | SH | Pr-c |
| Me | Me | H | H | 2 | H | H | H | SMe | Pr-c |
| Me | Me | H | H | 2 | H | H | H | SO₂Me | Pr-c |
| Me | Me | H | H | 2 | H | H | H | SEt | Pr-c |
| Me | Me | H | H | 2 | H | H | H | SO₂Et | Pr-c |
| Me | Me | H | H | 2 | H | H | H | SPr-i | Pr-c |
| Me | Me | H | H | 2 | H | H | H | SO₂Pr-i | Pr-c |
| Me | Me | H | H | 2 | H | H | H | SPh | Pr-c |
| Me | Me | H | H | 2 | H | H | H | SO₂Ph | Pr-c |
| Me | Me | H | H | 2 | H | H | H | SCHF₂ | Pr-c |
| Me | Me | H | H | 2 | H | H | H | SO₂CHF₂ | Pr-c |
| Me | Me | H | H | 2 | H | H | H | NH₂ | Pr-c |
| Me | Me | H | H | 2 | H | H | H | NHMe | Pr-c |
| Me | Me | H | H | 2 | H | H | H | NMe₂ | Pr-c |
| Me | Me | H | H | 2 | H | H | H | NHEt | Pr-c |
| Me | Me | H | H | 2 | H | H | H | NEt₂ | Pr-c |
| Me | Me | H | H | 2 | H | H | H | NHPh | Pr-c |
| Me | Me | H | H | 2 | H | H | H | N(Me)Ph | Pr-c |
| Me | Me | H | H | 2 | H | H | H | CN | Pr-c |
| Me | Me | H | H | 2 | H | H | H | F | CHF₂ |
| Me | Me | H | H | 2 | H | H | H | Cl | CHF₂ |
| Me | Me | H | H | 2 | H | H | H | OH | CHF₂ |
| Me | Me | H | H | 2 | H | H | H | OMe | CHF₂ |
| Me | Me | H | H | 2 | H | H | H | OEt | CHF₂ |
| Me | Me | H | H | 2 | H | H | H | OPr-i | CHF₂ |
| Me | Me | H | H | 2 | H | H | H | OPr | CHF₂ |
| Me | Me | H | H | 2 | H | H | H | OBu-t | CHF₂ |
| Me | Me | H | H | 2 | H | H | H | OCH₂Pr-c | CHF₂ |
| Me | Me | H | H | 2 | H | H | H | OCH₂Bu-c | CHF₂ |
| Me | Me | H | H | 2 | H | H | H | OCH₂Pen-c | CHF₂ |
| Me | Me | H | H | 2 | H | H | H | OCH₂Hex-c | CHF₂ |
| Me | Me | H | H | 2 | H | H | H | OPen-c | CHF₂ |
| Me | Me | H | H | 2 | H | H | H | OHex-c | CHF₂ |
| Me | Me | H | H | 2 | H | H | H | OCH₂Ph | CHF₂ |
| Me | Me | H | H | 2 | H | H | H | OPh | CHF₂ |
| Me | Me | H | H | 2 | H | H | H | OCHF₂ | CHF₂ |
| Me | Me | H | H | 2 | H | H | H | SH | CHF₂ |
| Me | Me | H | H | 2 | H | H | H | SMe | CHF₂ |
| Me | Me | H | H | 2 | H | H | H | SO₂Me | CHF₂ |
| Me | Me | H | H | 2 | H | H | H | SEt | CHF₂ |
| Me | Me | H | H | 2 | H | H | H | SO₂Et | CHF₂ |
| Me | Me | H | H | 2 | H | H | H | SPr-i | CHF₂ |
| Me | Me | H | H | 2 | H | H | H | SO₂Pr-i | CHF₂ |
| Me | Me | H | H | 2 | H | H | H | SPh | CHF₂ |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 2 | H | H | H | SO₂Ph | CHF₂ |
| Me | Me | H | H | 2 | H | H | H | SCHF₂ | CHF₂ |
| Me | Me | H | H | 2 | H | H | H | SO₂CHF₂ | CHF₂ |
| Me | Me | H | H | 2 | H | H | H | NH₂ | CHF₂ |
| Me | Me | H | H | 2 | H | H | H | NHMe | CHF₂ |
| Me | Me | H | H | 2 | H | H | H | NMe₂ | CHF₂ |
| Me | Me | H | H | 2 | H | H | H | NHEt | CHF₂ |
| Me | Me | H | H | 2 | H | H | H | NEt₂ | CHF₂ |
| Me | Me | H | H | 2 | H | H | H | NHPh | CHF₂ |
| Me | Me | H | H | 2 | H | H | H | N(Me)Ph | CHF₂ |
| Me | Me | H | H | 2 | H | H | H | CN | CHF₂ |
| Me | Me | H | H | 2 | H | H | H | F | CF₃ |
| Me | Me | H | H | 2 | H | H | H | Cl | CF₃ |
| Me | Me | H | H | 2 | H | H | H | OH | CF₃ |
| Me | Me | H | H | 2 | H | H | H | OMe | CF₃ |
| Me | Me | H | H | 2 | H | H | H | OEt | CF₃ |
| Me | Me | H | H | 2 | H | H | H | OPr-i | CF₃ |
| Me | Me | H | H | 2 | H | H | H | OPr | CF₃ |
| Me | Me | H | H | 2 | H | H | H | OBu-t | CF₃ |
| Me | Me | H | H | 2 | H | H | H | OCH₂Pr-c | CF₃ |
| Me | Me | H | H | 2 | H | H | H | OCH₂Bu-c | CF₃ |
| Me | Me | H | H | 2 | H | H | H | OCH₂Pen-c | CF₃ |
| Me | Me | H | H | 2 | H | H | H | OCH₂Hex-c | CF₃ |
| Me | Me | H | H | 2 | H | H | H | OPen-c | CF₃ |
| Me | Me | H | H | 2 | H | H | H | OHex-c | CF₃ |
| Me | Me | H | H | 2 | H | H | H | OCH₂Ph | CF₃ |
| Me | Me | H | H | 2 | H | H | H | OPh | CF₃ |
| Me | Me | H | H | 2 | H | H | H | OCHF₂ | CF₃ |
| Me | Me | H | H | 2 | H | H | H | SH | CF₃ |
| Me | Me | H | H | 2 | H | H | H | SMe | CF₃ |
| Me | Me | H | H | 2 | H | H | H | SO₂Me | CF₃ |
| Me | Me | H | H | 2 | H | H | H | SEt | CF₃ |
| Me | Me | H | H | 2 | H | H | H | SO₂Et | CF₃ |
| Me | Me | H | H | 2 | H | H | H | SPr-i | CF₃ |
| Me | Me | H | H | 2 | H | H | H | SO₂Pr-i | CF₃ |
| Me | Me | H | H | 2 | H | H | H | SPh | CF₃ |
| Me | Me | H | H | 2 | H | H | H | SO₂Ph | CF₃ |
| Me | Me | H | H | 2 | H | H | H | SCHF₂ | CF₃ |
| Me | Me | H | H | 2 | H | H | H | SO₂CHF₂ | CF₃ |
| Me | Me | H | H | 2 | H | H | H | NH₂ | CF₃ |
| Me | Me | H | H | 2 | H | H | H | NHMe | CF₃ |
| Me | Me | H | H | 2 | H | H | H | NMe₂ | CF₃ |
| Me | Me | H | H | 2 | H | H | H | NHEt | CF₃ |
| Me | Me | H | H | 2 | H | H | H | NEt₂ | CF₃ |
| Me | Me | H | H | 2 | H | H | H | NHPh | CF₃ |
| Me | Me | H | H | 2 | H | H | H | N(Me)Ph | CF₃ |
| Me | Me | H | H | 2 | H | H | H | CN | CF₃ |
| Me | Me | H | H | 2 | H | H | H | F | OMe |
| Me | Me | H | H | 2 | H | H | H | OH | OMe |
| Me | Me | H | H | 2 | H | H | H | OMe | OMe |
| Me | Me | H | H | 2 | H | H | H | OEt | OMe |
| Me | Me | H | H | 2 | H | H | H | OPr-i | OMe |
| Me | Me | H | H | 2 | H | H | H | OPr | OMe |
| Me | Me | H | H | 2 | H | H | H | OBu-t | OMe |
| Me | Me | H | H | 2 | H | H | H | OCH₂Pr-c | OMe |
| Me | Me | H | H | 2 | H | H | H | OCH₂Bu-c | OMe |
| Me | Me | H | H | 2 | H | H | H | OCH₂Pen-c | OMe |
| Me | Me | H | H | 2 | H | H | H | OCH₂Hex-c | OMe |
| Me | Me | H | H | 2 | H | H | H | OPen-c | OMe |
| Me | Me | H | H | 2 | H | H | H | OHex-c | OMe |
| Me | Me | H | H | 2 | H | H | H | OCH₂Ph | OMe |
| Me | Me | H | H | 2 | H | H | H | OPh | OMe |
| Me | Me | H | H | 2 | H | H | H | OCHF₂ | OMe |
| Me | Me | H | H | 2 | H | H | H | SH | OMe |
| Me | Me | H | H | 2 | H | H | H | SMe | OMe |
| Me | Me | H | H | 2 | H | H | H | SO₂Me | OMe |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 2 | H | H | H | SEt | OMe |
| Me | Me | H | H | 2 | H | H | H | SO₂Et | OMe |
| Me | Me | H | H | 2 | H | H | H | SPr-i | OMe |
| Me | Me | H | H | 2 | H | H | H | SO₂Pr-i | OMe |
| Me | Me | H | H | 2 | H | H | H | SPh | OMe |
| Me | Me | H | H | 2 | H | H | H | SO₂Ph | OMe |
| Me | Me | H | H | 2 | H | H | H | SCHF₂ | OMe |
| Me | Me | H | H | 2 | H | H | H | SO₂CHF₂ | OMe |
| Me | Me | H | H | 2 | H | H | H | NH₂ | OMe |
| Me | Me | H | H | 2 | H | H | H | NHMe | OMe |
| Me | Me | H | H | 2 | H | H | H | NMe₂ | OMe |
| Me | Me | H | H | 2 | H | H | H | NHEt | OMe |
| Me | Me | H | H | 2 | H | H | H | NEt₂ | OMe |
| Me | Me | H | H | 2 | H | H | H | NHPh | OMe |
| Me | Me | H | H | 2 | H | H | H | N(Me)Ph | OMe |
| Me | Me | H | H | 2 | H | H | H | CN | OMe |
| Me | Me | H | H | 2 | H | H | H | F | OPh |
| Me | Me | H | H | 2 | H | H | H | OH | OPh |
| Me | Me | H | H | 2 | H | H | H | OMe | OPh |
| Me | Me | H | H | 2 | H | H | H | OEt | OPh |
| Me | Me | H | H | 2 | H | H | H | OPr-i | OPh |
| Me | Me | H | H | 2 | H | H | H | OPr | OPh |
| Me | Me | H | H | 2 | H | H | H | OBu-t | OPh |
| Me | Me | H | H | 2 | H | H | H | OCH₂Pr-c | OPh |
| Me | Me | H | H | 2 | H | H | H | OCH₂Bu-c | OPh |
| Me | Me | H | H | 2 | H | H | H | OCH₂Pen-c | OPh |
| Me | Me | H | H | 2 | H | H | H | OCH₂Hex-c | OPh |
| Me | Me | H | H | 2 | H | H | H | OPen-c | OPh |
| Me | Me | H | H | 2 | H | H | H | OHex-c | OPh |
| Me | Me | H | H | 2 | H | H | H | OCH₂Ph | OPh |
| Me | Me | H | H | 2 | H | H | H | OPh | OPh |
| Me | Me | H | H | 2 | H | H | H | OCHF₂ | OPh |
| Me | Me | H | H | 2 | H | H | H | SH | OPh |
| Me | Me | H | H | 2 | H | H | H | SMe | OPh |
| Me | Me | H | H | 2 | H | H | H | SO₂Me | OPh |
| Me | Me | H | H | 2 | H | H | H | SEt | OPh |
| Me | Me | H | H | 2 | H | H | H | SO₂Et | OPh |
| Me | Me | H | H | 2 | H | H | H | SPr-i | OPh |
| Me | Me | H | H | 2 | H | H | H | SO₂Pr-i | OPh |
| Me | Me | H | H | 2 | H | H | H | SPh | OPh |
| Me | Me | H | H | 2 | H | H | H | SO₂Ph | OPh |
| Me | Me | H | H | 2 | H | H | H | SCHF₂ | OPh |
| Me | Me | H | H | 2 | H | H | H | SO₂CHF₂ | OPh |
| Me | Me | H | H | 2 | H | H | H | NH₂ | OPh |
| Me | Me | H | H | 2 | H | H | H | NHMe | OPh |
| Me | Me | H | H | 2 | H | H | H | NMe₂ | OPh |
| Me | Me | H | H | 2 | H | H | H | NHEt | OPh |
| Me | Me | H | H | 2 | H | H | H | NEt₂ | OPh |
| Me | Me | H | H | 2 | H | H | H | NHPh | OPh |
| Me | Me | H | H | 2 | H | H | H | N(Me)Ph | OPh |
| Me | Me | H | H | 2 | H | H | H | CN | OPh |
| Me | Me | H | H | 2 | H | H | H | F | OCHF₂ |
| Me | Me | H | H | 2 | H | H | H | OH | OCHF₂ |
| Me | Me | H | H | 2 | H | H | H | OMe | OCHF₂ |
| Me | Me | H | H | 2 | H | H | H | OEt | OCHF₂ |
| Me | Me | H | H | 2 | H | H | H | OPr-i | OCHF₂ |
| Me | Me | H | H | 2 | H | H | H | OPr | OCHF₂ |
| Me | Me | H | H | 2 | H | H | H | OBu-t | OCHF₂ |
| Me | Me | H | H | 2 | H | H | H | OCH₂Pr-c | OCHF₂ |
| Me | Me | H | H | 2 | H | H | H | OCH₂Bu-c | OCHF₂ |
| Me | Me | H | H | 2 | H | H | H | OCH₂Pen-c | OCHF₂ |
| Me | Me | H | H | 2 | H | H | H | OCH₂Hex-c | OCHF₂ |
| Me | Me | H | H | 2 | H | H | H | OPen-c | OCHF₂ |
| Me | Me | H | H | 2 | H | H | H | OHex-c | OCHF₂ |
| Me | Me | H | H | 2 | H | H | H | OCH₂Ph | OCHF₂ |
| Me | Me | H | H | 2 | H | H | H | OPh | OCHF₂ |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 2 | H | H | H | $OCHF_2$ | $OCHF_2$ |
| Me | Me | H | H | 2 | H | H | H | SH | $OCHF_2$ |
| Me | Me | H | H | 2 | H | H | H | SMe | $OCHF_2$ |
| Me | Me | H | H | 2 | H | H | H | $SO_2Me$ | $OCHF_2$ |
| Me | Me | H | H | 2 | H | H | H | SEt | $OCHF_2$ |
| Me | Me | H | H | 2 | H | H | H | $SO_2Et$ | $OCHF_2$ |
| Me | Me | H | H | 2 | H | H | H | SPr-i | $OCHF_2$ |
| Me | Me | H | H | 2 | H | H | H | $SO_2$Pr-i | $OCHF_2$ |
| Me | Me | H | H | 2 | H | H | H | SPh | $OCHF_2$ |
| Me | Me | H | H | 2 | H | H | H | $SO_2Ph$ | $OCHF_2$ |
| Me | Me | H | H | 2 | H | H | H | $SCHF_2$ | $OCHF_2$ |
| Me | Me | H | H | 2 | H | H | H | $SO_2CHF_2$ | $OCHF_2$ |
| Me | Me | H | H | 2 | H | H | H | $NH_2$ | $OCHF_2$ |
| Me | Me | H | H | 2 | H | H | H | NHMe | $OCHF_2$ |
| Me | Me | H | H | 2 | H | H | H | $NMe_2$ | $OCHF_2$ |
| Me | Me | H | H | 2 | H | H | H | NHEt | $OCHF_2$ |
| Me | Me | H | H | 2 | H | H | H | $NEt_2$ | $OCHF_2$ |
| Me | Me | H | H | 2 | H | H | H | NHPh | $OCHF_2$ |
| Me | Me | H | H | 2 | H | H | H | N(Me)Ph | $OCHF_2$ |
| Me | Me | H | H | 2 | H | H | H | CN | $OCHF_2$ |
| Me | Me | H | H | 2 | H | H | Me | F | $CF_3$ |
| Me | Me | H | H | 2 | H | H | Me | Cl | $CF_3$ |
| Me | Me | H | H | 2 | H | H | Me | OH | $CF_3$ |
| Me | Me | H | H | 2 | H | H | Me | OMe | $CF_3$ |
| Me | Me | H | H | 2 | H | H | Me | OEt | $CF_3$ |
| Me | Me | H | H | 2 | H | H | Me | OPr-i | $CF_3$ |
| Me | Me | H | H | 2 | H | H | Me | OPr | $CF_3$ |
| Me | Me | H | H | 2 | H | H | Me | OBu-t | $CF_3$ |
| Me | Me | H | H | 2 | H | H | Me | $OCH_2$Pr-c | $CF_3$ |
| Me | Me | H | H | 2 | H | H | Me | $OCH_2$Bu-c | $CF_3$ |
| Me | Me | H | H | 2 | H | H | Me | $OCH_2$Pen-c | $CF_3$ |
| Me | Me | H | H | 2 | H | H | Me | $OCH_2$Hex-c | $CF_3$ |
| Me | Me | H | H | 2 | H | H | Me | OPen-c | $CF_3$ |
| Me | Me | H | H | 2 | H | H | Me | OHex-c | $CF_3$ |
| Me | Me | H | H | 2 | H | H | Me | $OCH_2Ph$ | $CF_3$ |
| Me | Me | H | H | 2 | H | H | Me | OPh | $CF_3$ |
| Me | Me | H | H | 2 | H | H | Me | $OCHF_2$ | $CF_3$ |
| Me | Me | H | H | 2 | H | H | Me | SH | $CF_3$ |
| Me | Me | H | H | 2 | H | H | Me | SMe | $CF_3$ |
| Me | Me | H | H | 2 | H | H | Me | $SO_2Me$ | $CF_3$ |
| Me | Me | H | H | 2 | H | H | Me | SEt | $CF_3$ |
| Me | Me | H | H | 2 | H | H | Me | $SO_2Et$ | $CF_3$ |
| Me | Me | H | H | 2 | H | H | Me | SPr-i | $CF_3$ |
| Me | Me | H | H | 2 | H | H | Me | $SO_2$Pr-i | $CF_3$ |
| Me | Me | H | H | 2 | H | H | Me | SPh | $CF_3$ |
| Me | Me | H | H | 2 | H | H | Me | $SO_2Ph$ | $CF_3$ |
| Me | Me | H | H | 2 | H | H | Me | $SCHF_2$ | $CF_3$ |
| Me | Me | H | H | 2 | H | H | Me | $SO_2CHF_2$ | $CF_3$ |
| Me | Me | H | H | 2 | H | H | Me | $NH_2$ | $CF_3$ |
| Me | Me | H | H | 2 | H | H | Me | NHMe | $CF_3$ |
| Me | Me | H | H | 2 | H | H | Me | $NMe_2$ | $CF_3$ |
| Me | Me | H | H | 2 | H | H | Me | NHEt | $CF_3$ |
| Me | Me | H | H | 2 | H | H | Me | $NEt_2$ | $CF_3$ |
| Me | Me | H | H | 2 | H | H | Me | NHPh | $CF_3$ |
| Me | Me | H | H | 2 | H | H | Me | N(Me)Ph | $CF_3$ |
| Me | Me | H | H | 2 | H | H | Me | CN | $CF_3$ |
| Me | Me | H | H | 2 | H | H | OMe | F | $CF_3$ |
| Me | Me | H | H | 2 | H | H | OMe | Cl | $CF_3$ |
| Me | Me | H | H | 2 | H | H | OMe | OH | $CF_3$ |
| Me | Me | H | H | 2 | H | H | OMe | OMe | $CF_3$ |
| Me | Me | H | H | 2 | H | H | OMe | OEt | $CF_3$ |
| Me | Me | H | H | 2 | H | H | OMe | OPr-i | $CF_3$ |
| Me | Me | H | H | 2 | H | H | OMe | OPr | $CF_3$ |
| Me | Me | H | H | 2 | H | H | OMe | OBu-t | $CF_3$ |
| Me | Me | H | H | 2 | H | H | OMe | $OCH_2$Pr-c | $CF_3$ |
| Me | Me | H | H | 2 | H | H | OMe | $OCH_2$Bu-c | $CF_3$ |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 2 | H | H | OMe | OCH₂Pen-c | CF₃ |
| Me | Me | H | H | 2 | H | H | OMe | OCH₂Hex-c | CF₃ |
| Me | Me | H | H | 2 | H | H | OMe | OPen-c | CF₃ |
| Me | Me | H | H | 2 | H | H | OMe | OHex-c | CF₃ |
| Me | Me | H | H | 2 | H | H | OMe | OCH₂Ph | CF₃ |
| Me | Me | H | H | 2 | H | H | OMe | OPh | CF₃ |
| Me | Me | H | H | 2 | H | H | OMe | OCHF₂ | CF₃ |
| Me | Me | H | H | 2 | H | H | OMe | SH | CF₃ |
| Me | Me | H | H | 2 | H | H | OMe | SMe | CF₃ |
| Me | Me | H | H | 2 | H | H | OMe | SO₂Me | CF₃ |
| Me | Me | H | H | 2 | H | H | OMe | SEt | CF₃ |
| Me | Me | H | H | 2 | H | H | OMe | SO₂Et | CF₃ |
| Me | Me | H | H | 2 | H | H | OMe | SPr-i | CF₃ |
| Me | Me | H | H | 2 | H | H | OMe | SO₂Pr-i | CF₃ |
| Me | Me | H | H | 2 | H | H | OMe | SPh | CF₃ |
| Me | Me | H | H | 2 | H | H | OMe | SO₂Ph | CF₃ |
| Me | Me | H | H | 2 | H | H | OMe | SCHF₂ | CF₃ |
| Me | Me | H | H | 2 | H | H | OMe | SO₂CHF₂ | CF₃ |
| Me | Me | H | H | 2 | H | H | OMe | NH₂ | CF₃ |
| Me | Me | H | H | 2 | H | H | OMe | NHMe | CF₃ |
| Me | Me | H | H | 2 | H | H | OMe | NMe₂ | CF₃ |
| Me | Me | H | H | 2 | H | H | OMe | NHEt | CF₃ |
| Me | Me | H | H | 2 | H | H | OMe | NEt₂ | CF₃ |
| Me | Me | H | H | 2 | H | H | OMe | NHPh | CF₃ |
| Me | Me | H | H | 2 | H | H | OMe | N(Me)Ph | CF₃ |
| Me | Me | H | H | 2 | H | H | OMe | CN | CF₃ |
| Me | Me | H | H | 2 | H | H | SMe | F | CF₃ |
| Me | Me | H | H | 2 | H | H | SMe | Cl | CF₃ |
| Me | Me | H | H | 2 | H | H | SMe | OH | CF₃ |
| Me | Me | H | H | 2 | H | H | SMe | OMe | CF₃ |
| Me | Me | H | H | 2 | H | H | SMe | OEt | CF₃ |
| Me | Me | H | H | 2 | H | H | SMe | OPr-i | CF₃ |
| Me | Me | H | H | 2 | H | H | SMe | OPr | CF₃ |
| Me | Me | H | H | 2 | H | H | SMe | OBu-t | CF₃ |
| Me | Me | H | H | 2 | H | H | SMe | OCH₂Pr-c | CF₃ |
| Me | Me | H | H | 2 | H | H | SMe | OCH₂Bu-c | CF₃ |
| Me | Me | H | H | 2 | H | H | SMe | OCH₂Pen-c | CF₃ |
| Me | Me | H | H | 2 | H | H | SMe | OCH₂Hex-c | CF₃ |
| Me | Me | H | H | 2 | H | H | SMe | OPen-c | CF₃ |
| Me | Me | H | H | 2 | H | H | SMe | OHex-c | CF₃ |
| Me | Me | H | H | 2 | H | H | SMe | OCH₂Ph | CF₃ |
| Me | Me | H | H | 2 | H | H | SMe | OPh | CF₃ |
| Me | Me | H | H | 2 | H | H | SMe | OCHF₂ | CF₃ |
| Me | Me | H | H | 2 | H | H | SMe | SH | CF₃ |
| Me | Me | H | H | 2 | H | H | SMe | SMe | CF₃ |
| Me | Me | H | H | 2 | H | H | SMe | SO₂Me | CF₃ |
| Me | Me | H | H | 2 | H | H | SMe | SEt | CF₃ |
| Me | Me | H | H | 2 | H | H | SMe | SO₂Et | CF₃ |
| Me | Me | H | H | 2 | H | H | SMe | SPr-i | CF₃ |
| Me | Me | H | H | 2 | H | H | SMe | SO₂Pr-i | CF₃ |
| Me | Me | H | H | 2 | H | H | SMe | SPh | CF₃ |
| Me | Me | H | H | 2 | H | H | SMe | SO₂Ph | CF₃ |
| Me | Me | H | H | 2 | H | H | SMe | SCHF₂ | CF₃ |
| Me | Me | H | H | 2 | H | H | SMe | SO₂CHF₂ | CF₃ |
| Me | Me | H | H | 2 | H | H | SMe | NH₂ | CF₃ |
| Me | Me | H | H | 2 | H | H | SMe | NHMe | CF₃ |
| Me | Me | H | H | 2 | H | H | SMe | NMe₂ | CF₃ |
| Me | Me | H | H | 2 | H | H | SMe | NHEt | CF₃ |
| Me | Me | H | H | 2 | H | H | SMe | NEt₂ | CF₃ |
| Me | Me | H | H | 2 | H | H | SMe | NHPh | CF₃ |
| Me | Me | H | H | 2 | H | H | SMe | N(Me)Ph | CF₃ |
| Me | Me | H | H | 2 | H | H | SMe | CN | CF₃ |
| Me | Me | H | H | 2 | H | H | SO₂Me | F | CF₃ |
| Me | Me | H | H | 2 | H | H | SO₂Me | Cl | CF₃ |
| Me | Me | H | H | 2 | H | H | SO₂Me | OH | CF₃ |
| Me | Me | H | H | 2 | H | H | SO₂Me | OMe | CF₃ |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 2 | H | H | SO₂Me | OEt | CF₃ |
| Me | Me | H | H | 2 | H | H | SO₂Me | OPr-i | CF₃ |
| Me | Me | H | H | 2 | H | H | SO₂Me | OPr | CF₃ |
| Me | Me | H | H | 2 | H | H | SO₂Me | OBu-t | CF₃ |
| Me | Me | H | H | 2 | H | H | SO₂Me | OCH2Pr-c | CF₃ |
| Me | Me | H | H | 2 | H | H | SO₂Me | OCH₂Bu-c | CF₃ |
| Me | Me | H | H | 2 | H | H | SO₂Me | OCH₂Pen-c | CF₃ |
| Me | Me | H | H | 2 | H | H | SO₂Me | OCH₂Hex-c | CF₃ |
| Me | Me | H | H | 2 | H | H | SO₂Me | OPen-c | CF₃ |
| Me | Me | H | H | 2 | H | H | SO₂Me | OHex-c | CF₃ |
| Me | Me | H | H | 2 | H | H | SO₂Me | OCH₂Ph | CF₃ |
| Me | Me | H | H | 2 | H | H | SO₂Me | OPh | CF₃ |
| Me | Me | H | H | 2 | H | H | SO₂Me | OCHF₂ | CF₃ |
| Me | Me | H | H | 2 | H | H | SO₂Me | SH | CF₃ |
| Me | Me | H | H | 2 | H | H | SO₂Me | SMe | CF₃ |
| Me | Me | H | H | 2 | H | H | SO₂Me | SO₂Me | CF₃ |
| Me | Me | H | H | 2 | H | H | SO₂Me | SEt | CF₃ |
| Me | Me | H | H | 2 | H | H | SO₂Me | SO₂Et | CF₃ |
| Me | Me | H | H | 2 | H | H | SO₂Me | SPr-i | CF₃ |
| Me | Me | H | H | 2 | H | H | SO₂Me | SO₂Pr-i | CF₃ |
| Me | Me | H | H | 2 | H | H | SO₂Me | SPh | CF₃ |
| Me | Me | H | H | 2 | H | H | SO₂Me | SO₂Ph | CF₃ |
| Me | Me | H | H | 2 | H | H | SO₂Me | SCHF₂ | CF₃ |
| Me | Me | H | H | 2 | H | H | SO₂Me | SO₂CHF₂ | CF₃ |
| Me | Me | H | H | 2 | H | H | SO₂Me | NH₂ | CF₃ |
| Me | Me | H | H | 2 | H | H | SO₂Me | NHMe | CF₃ |
| Me | Me | H | H | 2 | H | H | SO₂Me | NMe₂ | CF₃ |
| Me | Me | H | H | 2 | H | H | SO₂Me | NHEt | CF₃ |
| Me | Me | H | H | 2 | H | H | SO₂Me | NEt₂ | CF₃ |
| Me | Me | H | H | 2 | H | H | SO₂Me | NHPh | CF₃ |
| Me | Me | H | H | 2 | H | H | SO₂Me | N(Me)Ph | CF₃ |
| Me | Me | H | H | 2 | H | H | SO₂Me | CN | CF₃ |
| Me | Me | H | H | 2 | H | H | NH₂ | F | CF₃ |
| Me | Me | H | H | 2 | H | H | NH₂ | Cl | CF₃ |
| Me | Me | H | H | 2 | H | H | NH₂ | OH | CF₃ |
| Me | Me | H | H | 2 | H | H | NH₂ | OMe | CF₃ |
| Me | Me | H | H | 2 | H | H | NH₂ | OEt | CF₃ |
| Me | Me | H | H | 2 | H | H | NH₂ | OPr-i | CF₃ |
| Me | Me | H | H | 2 | H | H | NH₂ | OPr | CF₃ |
| Me | Me | H | H | 2 | H | H | NH₂ | OBu-t | CF₃ |
| Me | Me | H | H | 2 | H | H | NH₂ | OCH₂Pr-c | CF₃ |
| Me | Me | H | H | 2 | H | H | NH₂ | OCH₂Bu-c | CF₃ |
| Me | Me | H | H | 2 | H | H | NH₂ | OCH₂Pen-c | CF₃ |
| Me | Me | H | H | 2 | H | H | NH₂ | OCH₂Hex-c | CF₃ |
| Me | Me | H | H | 2 | H | H | NH₂ | OPen-c | CF₃ |
| Me | Me | H | H | 2 | H | H | NH₂ | OHex-c | CF₃ |
| Me | Me | H | H | 2 | H | H | NH₂ | OCH₂Ph | CF₃ |
| Me | Me | H | H | 2 | H | H | NH₂ | OPh | CF₃ |
| Me | Me | H | H | 2 | H | H | NH₂ | OCHF₂ | CF₃ |
| Me | Me | H | H | 2 | H | H | NH₂ | SH | CF₃ |
| Me | Me | H | H | 2 | H | H | NH₂ | SMe | CF₃ |
| Me | Me | H | H | 2 | H | H | NH₂ | SO₂Me | CF₃ |
| Me | Me | H | H | 2 | H | H | NH₂ | SEt | CF₃ |
| Me | Me | H | H | 2 | H | H | NH₂ | SO₂Et | CF₃ |
| Me | Me | H | H | 2 | H | H | NH₂ | SPr-i | CF₃ |
| Me | Me | H | H | 2 | H | H | NH₂ | SO₂Pr-i | CF₃ |
| Me | Me | H | H | 2 | H | H | NH₂ | SPh | CF₃ |
| Me | Me | H | H | 2 | H | H | NH₂ | SO₂Ph | CF₃ |
| Me | Me | H | H | 2 | H | H | NH₂ | SCHF₂ | CF₃ |
| Me | Me | H | H | 2 | H | H | NH₂ | SO₂CHF₂ | CF₃ |
| Me | Me | H | H | 2 | H | H | NH₂ | NH₂ | CF₃ |
| Me | Me | H | H | 2 | H | H | NH₂ | NHMe | CF₃ |
| Me | Me | H | H | 2 | H | H | NH₂ | NMe₂ | CF₃ |
| Me | Me | H | H | 2 | H | H | NH₂ | NHEt | CF₃ |
| Me | Me | H | H | 2 | H | H | NH₂ | NEt₂ | CF₃ |
| Me | Me | H | H | 2 | H | H | NH₂ | NHPh | CF₃ |

TABLE 8-continued

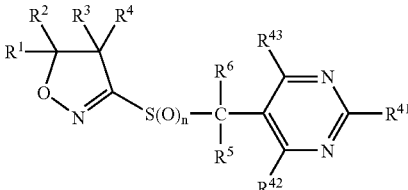

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 2 | H | H | NH₂ | N(Me)Ph | CF₃ |
| Me | Me | H | H | 2 | H | H | NH₂ | CN | CF₃ |
| H | H | H | H | 2 | H | H | H | OMe | CF₃ |
| H | H | H | H | 2 | H | H | H | OEt | CF₃ |
| Me | H | H | H | 2 | H | H | H | OMe | CF₃ |
| Me | H | H | H | 2 | H | H | H | OEt | CF₃ |
| Me | H | Me | H | 2 | H | H | H | OMe | CF₃ |
| Me | H | Me | H | 2 | H | H | H | OEt | CF₃ |
| Me | Me | H | H | 2 | Me | H | H | OMe | CF₃ |
| Me | Me | H | H | 2 | Me | H | H | OEt | CF₃ |
| Me | Me | H | H | 2 | Et | H | H | OMe | CF₃ |
| Me | Me | H | H | 2 | Et | H | H | OEt | CF₃ |
| Me | Me | H | H | 2 | Pr-i | H | H | H | CF₃ |
| Me | Me | H | H | 2 | Pr-i | H | H | OMe | CF₃ |
| Me | Me | H | H | 2 | Pr-i | H | H | OEt | CF₃ |
| Me | Me | H | H | 2 | Me | Me | H | OMe | CF₃ |
| Me | Me | H | H | 2 | Me | Me | H | OEt | CF₃ |
| Me | Et | H | H | 2 | H | H | H | OMe | CF₃ |
| Me | Et | H | H | 2 | H | H | H | OEt | CF₃ |
| Et | Et | H | H | 2 | H | H | H | OMe | CF₃ |
| Et | Et | H | H | 2 | H | H | H | OEt | CF₃ |
| Me | Pr-i | H | H | 2 | H | H | H | OMe | CF₃ |
| Me | Pr-i | H | H | 2 | H | H | H | OEt | CF₃ |
| Me | Pr | H | H | 2 | H | H | H | OMe | CF₃ |
| Me | Pr | H | H | 2 | H | H | H | OEt | CF₃ |
| Me | Pr-c | H | H | 2 | H | H | H | OMe | CF₃ |
| Me | Pr-c | H | H | 2 | H | H | H | OEt | CF₃ |
| Me | CH₂Pr-c | H | H | 2 | H | H | H | OMe | CF₃ |
| Me | CH₂Pr-c | H | H | 2 | H | H | H | OEt | CF₃ |
| —(CH₂)₂— | | H | H | 2 | H | H | H | OMe | CF₃ |
| —(CH₂)₂— | | H | H | 2 | H | H | H | OEt | CF₃ |
| —(CH₂)₃— | | H | H | 2 | H | H | H | OMe | CF₃ |
| —(CH₂)₃— | | H | H | 2 | H | H | H | OEt | CF₃ |
| —(CH₂)₄— | | H | H | 2 | H | H | H | OMe | CF₃ |
| —(CH₂)₄— | | H | H | 2 | H | H | H | OEt | CF₃ |
| —(CH₂)₅— | | H | H | 2 | H | H | H | OMe | CF₃ |
| —(CH₂)₅— | | H | H | 2 | H | H | H | OEt | CF₃ |
| H | —(CH₂)₃— | | H | 2 | H | H | H | OMe | CF₃ |
| H | —(CH₂)₃— | | H | 2 | H | H | H | OEt | CF₃ |
| H | —(CH₂)₄— | | H | 2 | H | H | H | OMe | CF₃ |
| H | —(CH₂)₄— | | H | 2 | H | H | H | OEt | CF₃ |
| H | —(CH₂)₅— | | H | 2 | H | H | H | OMe | CF₃ |
| H | —(CH₂)₅— | | H | 2 | H | H | H | OEt | CF₃ |
| H | —(CH₂)₆— | | H | 2 | H | H | H | OMe | CF₃ |
| H | —(CH₂)₆— | | H | 2 | H | H | H | OEt | CF₃ |
| Me | Me | H | H | 1 | H | H | H | Cl | Cl |
| Me | Me | H | H | 1 | H | H | H | OH | Cl |
| Me | Me | H | H | 1 | H | H | H | OMe | Cl |
| Me | Me | H | H | 1 | H | H | H | OEt | Cl |
| Me | Me | H | H | 1 | H | H | H | OPr-i | Cl |
| Me | Me | H | H | 1 | H | H | H | OPr | Cl |
| Me | Me | H | H | 1 | H | H | H | OBu-t | Cl |
| Me | Me | H | H | 1 | H | H | H | OCH₂Pr-c | Cl |
| Me | Me | H | H | 1 | H | H | H | OCH₂Bu-c | Cl |
| Me | Me | H | H | 1 | H | H | H | OCH₂Pen-c | Cl |
| Me | Me | H | H | 1 | H | H | H | OCH₂Hex-c | Cl |
| Me | Me | H | H | 1 | H | H | H | OPen-c | Cl |
| Me | Me | H | H | 1 | H | H | H | OHex-c | Cl |
| Me | Me | H | H | 1 | H | H | H | OCH₂Ph | Cl |
| Me | Me | H | H | 1 | H | H | H | OPh | Cl |
| Me | Me | H | H | 1 | H | H | H | OCHF₂ | Cl |
| Me | Me | H | H | 1 | H | H | H | SH | Cl |
| Me | Me | H | H | 1 | H | H | H | SMe | Cl |
| Me | Me | H | H | 1 | H | H | H | SO₂Me | Cl |
| Me | Me | H | H | 1 | H | H | H | SEt | Cl |
| Me | Me | H | H | 1 | H | H | H | SO₂Et | Cl |

TABLE 8-continued

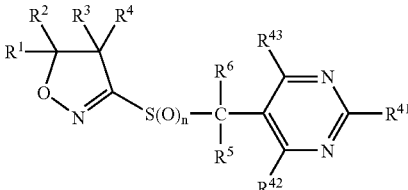

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 1 | H | H | H | SPr-i | Cl |
| Me | Me | H | H | 1 | H | H | H | SO₂Pr-i | Cl |
| Me | Me | H | H | 1 | H | H | H | SPh | Cl |
| Me | Me | H | H | 1 | H | H | H | SO₂Ph | Cl |
| Me | Me | H | H | 1 | H | H | H | SCHF₂ | Cl |
| Me | Me | H | H | 1 | H | H | H | SO₂CHF₂ | Cl |
| Me | Me | H | H | 1 | H | H | H | NH₂ | Cl |
| Me | Me | H | H | 1 | H | H | H | NHMe | Cl |
| Me | Me | H | H | 1 | H | H | H | NMe₂ | Cl |
| Me | Me | H | H | 1 | H | H | H | NHEt | Cl |
| Me | Me | H | H | 1 | H | H | H | NEt₂ | Cl |
| Me | Me | H | H | 1 | H | H | H | NHPh | Cl |
| Me | Me | H | H | 1 | H | H | H | N(Me)Ph | Cl |
| Me | Me | H | H | 1 | H | H | H | CN | Cl |
| Me | Me | H | H | 1 | H | H | H | F | Me |
| Me | Me | H | H | 1 | H | H | H | Cl | Me |
| Me | Me | H | H | 1 | H | H | H | OH | Me |
| Me | Me | H | H | 1 | H | H | H | OMe | Me |
| Me | Me | H | H | 1 | H | H | H | OEt | Me |
| Me | Me | H | H | 1 | H | H | H | OPr-i | Me |
| Me | Me | H | H | 1 | H | H | H | OPr | Me |
| Me | Me | H | H | 1 | H | H | H | OBu-t | Me |
| Me | Me | H | H | 1 | H | H | H | OCH₂Pr-c | Me |
| Me | Me | H | H | 1 | H | H | H | OCH₂Bu-c | Me |
| Me | Me | H | H | 1 | H | H | H | OCH₂Pen-c | Me |
| Me | Me | H | H | 1 | H | H | H | OCH₂Hex-c | Me |
| Me | Me | H | H | 1 | H | H | H | OPen-c | Me |
| Me | Me | H | H | 1 | H | H | H | OHex-c | Me |
| Me | Me | H | H | 1 | H | H | H | OCH₂Ph | Me |
| Me | Me | H | H | 1 | H | H | H | OPh | Me |
| Me | Me | H | H | 1 | H | H | H | OCHF₂ | Me |
| Me | Me | H | H | 1 | H | H | H | SH | Me |
| Me | Me | H | H | 1 | H | H | H | SMe | Me |
| Me | Me | H | H | 1 | H | H | H | SO₂Me | Me |
| Me | Me | H | H | 1 | H | H | H | SEt | Me |
| Me | Me | H | H | 1 | H | H | H | SO₂Et | Me |
| Me | Me | H | H | 1 | H | H | H | SPr-i | Me |
| Me | Me | H | H | 1 | H | H | H | SO₂Pr-i | Me |
| Me | Me | H | H | 1 | H | H | H | SPh | Me |
| Me | Me | H | H | 1 | H | H | H | SO₂Ph | Me |
| Me | Me | H | H | 1 | H | H | H | SCHF₂ | Me |
| Me | Me | H | H | 1 | H | H | H | SO₂CHF₂ | Me |
| Me | Me | H | H | 1 | H | H | H | NH₂ | Me |
| Me | Me | H | H | 1 | H | H | H | NHMe | Me |
| Me | Me | H | H | 1 | H | H | H | NMe₂ | Me |
| Me | Me | H | H | 1 | H | H | H | NHEt | Me |
| Me | Me | H | H | 1 | H | H | H | NEt₂ | Me |
| Me | Me | H | H | 1 | H | H | H | NHPh | Me |
| Me | Me | H | H | 1 | H | H | H | N(Me)Ph | Me |
| Me | Me | H | H | 1 | H | H | H | CN | Me |
| Me | Me | H | H | 1 | H | H | H | F | Pr-i |
| Me | Me | H | H | 1 | H | H | H | Cl | Pr-i |
| Me | Me | H | H | 1 | H | H | H | OH | Pr-i |
| Me | Me | H | H | 1 | H | H | H | OMe | Pr-i |
| Me | Me | H | H | 1 | H | H | H | OEt | Pr-i |
| Me | Me | H | H | 1 | H | H | H | OPr-i | Pr-i |
| Me | Me | H | H | 1 | H | H | H | OPr | Pr-i |
| Me | Me | H | H | 1 | H | H | H | OBu-t | Pr-i |
| Me | Me | H | H | 1 | H | H | H | OCH₂Pr-c | Pr-i |
| Me | Me | H | H | 1 | H | H | H | OCH₂Bu-c | Pr-i |
| Me | Me | H | H | 1 | H | H | H | OCH₂Pen-c | Pr-i |
| Me | Me | H | H | 1 | H | H | H | OCH₂Hex-c | Pr-i |
| Me | Me | H | H | 1 | H | H | H | OPen-c | Pr-i |
| Me | Me | H | H | 1 | H | H | H | OHex-c | Pr-i |
| Me | Me | H | H | 1 | H | H | H | OCH₂Ph | Pr-i |
| Me | Me | H | H | 1 | H | H | H | OPh | Pr-i |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 1 | H | H | H | OCHF₂ | Pr-i |
| Me | Me | H | H | 1 | H | H | H | SH | Pr-i |
| Me | Me | H | H | 1 | H | H | H | SMe | Pr-i |
| Me | Me | H | H | 1 | H | H | H | SO₂Me | Pr-i |
| Me | Me | H | H | 1 | H | H | H | SEt | Pr-i |
| Me | Me | H | H | 1 | H | H | H | SO₂Et | Pr-i |
| Me | Me | H | H | 1 | H | H | H | SPr-i | Pr-i |
| Me | Me | H | H | 1 | H | H | H | SO₂Pr-i | Pr-i |
| Me | Me | H | H | 1 | H | H | H | SPh | Pr-i |
| Me | Me | H | H | 1 | H | H | H | SO₂Ph | Pr-i |
| Me | Me | H | H | 1 | H | H | H | SCHF₂ | Pr-i |
| Me | Me | H | H | 1 | H | H | H | SO₂CHF₂ | Pr-i |
| Me | Me | H | H | 1 | H | H | H | NH₂ | Pr-i |
| Me | Me | H | H | 1 | H | H | H | NHMe | Pr-i |
| Me | Me | H | H | 1 | H | H | H | NMe₂ | Pr-i |
| Me | Me | H | H | 1 | H | H | H | NHEt | Pr-i |
| Me | Me | H | H | 1 | H | H | H | NEt₂ | Pr-i |
| Me | Me | H | H | 1 | H | H | H | NHPh | Pr-i |
| Me | Me | H | H | 1 | H | H | H | N(Me)Ph | Pr-i |
| Me | Me | H | H | 1 | H | H | H | CN | Pr-i |
| Me | Me | H | H | 1 | H | H | H | F | Pr-c |
| Me | Me | H | H | 1 | H | H | H | Cl | Pr-c |
| Me | Me | H | H | 1 | H | H | H | OH | Pr-c |
| Me | Me | H | H | 1 | H | H | H | OMe | Pr-c |
| Me | Me | H | H | 1 | H | H | H | OEt | Pr-c |
| Me | Me | H | H | 1 | H | H | H | OPr-i | Pr-c |
| Me | Me | H | H | 1 | H | H | H | OPr | Pr-c |
| Me | Me | H | H | 1 | H | H | H | OBu-t | Pr-c |
| Me | Me | H | H | 1 | H | H | H | OCH₂Pr-c | Pr-c |
| Me | Me | H | H | 1 | H | H | H | OCH₂Bu-c | Pr-c |
| Me | Me | H | H | 1 | H | H | H | OCH₂Pen-c | Pr-c |
| Me | Me | H | H | 1 | H | H | H | OCH₂Hex-c | Pr-c |
| Me | Me | H | H | 1 | H | H | H | OPen-c | Pr-c |
| Me | Me | H | H | 1 | H | H | H | OHex-c | Pr-c |
| Me | Me | H | H | 1 | H | H | H | OCH₂Ph | Pr-c |
| Me | Me | H | H | 1 | H | H | H | OPh | Pr-c |
| Me | Me | H | H | 1 | H | H | H | OCHF₂ | Pr-c |
| Me | Me | H | H | 1 | H | H | H | SH | Pr-c |
| Me | Me | H | H | 1 | H | H | H | SMe | Pr-c |
| Me | Me | H | H | 1 | H | H | H | SO₂Me | Pr-c |
| Me | Me | H | H | 1 | H | H | H | SEt | Pr-c |
| Me | Me | H | H | 1 | H | H | H | SO₂Et | Pr-c |
| Me | Me | H | H | 1 | H | H | H | SPr-i | Pr-c |
| Me | Me | H | H | 1 | H | H | H | SO₂Pr-i | Pr-c |
| Me | Me | H | H | 1 | H | H | H | SPh | Pr-c |
| Me | Me | H | H | 1 | H | H | H | SO₂Ph | Pr-c |
| Me | Me | H | H | 1 | H | H | H | SCHF₂ | Pr-c |
| Me | Me | H | H | 1 | H | H | H | SO₂CHF₂ | Pr-c |
| Me | Me | H | H | 1 | H | H | H | NH₂ | Pr-c |
| Me | Me | H | H | 1 | H | H | H | NHMe | Pr-c |
| Me | Me | H | H | 1 | H | H | H | NMe₂ | Pr-c |
| Me | Me | H | H | 1 | H | H | H | NHEt | Pr-c |
| Me | Me | H | H | 1 | H | H | H | NEt₂ | Pr-c |
| Me | Me | H | H | 1 | H | H | H | NHPh | Pr-c |
| Me | Me | H | H | 1 | H | H | H | N(Me)Ph | Pr-c |
| Me | Me | H | H | 1 | H | H | H | CN | Pr-c |
| Me | Me | H | H | 1 | H | H | H | F | CHF₂ |
| Me | Me | H | H | 1 | H | H | H | Cl | CHF₂ |
| Me | Me | H | H | 1 | H | H | H | OH | CHF₂ |
| Me | Me | H | H | 1 | H | H | H | OMe | CHF₂ |
| Me | Me | H | H | 1 | H | H | H | OEt | CHF₂ |
| Me | Me | H | H | 1 | H | H | H | OPr-i | CHF₂ |
| Me | Me | H | H | 1 | H | H | H | OPr | CHF₂ |
| Me | Me | H | H | 1 | H | H | H | OBu-t | CHF₂ |
| Me | Me | H | H | 1 | H | H | H | OCH₂Pr-c | CHF₂ |
| Me | Me | H | H | 1 | H | H | H | OCH₂Bu-c | CHF₂ |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 1 | H | H | H | OCH₂Pen-c | CHF₂ |
| Me | Me | H | H | 1 | H | H | H | OCH₂Hex-c | CHF₂ |
| Me | Me | H | H | 1 | H | H | H | OPen-c | CHF₂ |
| Me | Me | H | H | 1 | H | H | H | OHex-c | CHF₂ |
| Me | Me | H | H | 1 | H | H | H | OCH₂Ph | CHF₂ |
| Me | Me | H | H | 1 | H | H | H | OPh | CHF₂ |
| Me | Me | H | H | 1 | H | H | H | OCHF₂ | CHF₂ |
| Me | Me | H | H | 1 | H | H | H | SH | CHF₂ |
| Me | Me | H | H | 1 | H | H | H | SMe | CHF₂ |
| Me | Me | H | H | 1 | H | H | H | SO₂Me | CHF₂ |
| Me | Me | H | H | 1 | H | H | H | SEt | CHF₂ |
| Me | Me | H | H | 1 | H | H | H | SO₂Et | CHF₂ |
| Me | Me | H | H | 1 | H | H | H | SPr-i | CHF₂ |
| Me | Me | H | H | 1 | H | H | H | SO₂Pr-i | CHF₂ |
| Me | Me | H | H | 1 | H | H | H | SPh | CHF₂ |
| Me | Me | H | H | 1 | H | H | H | SO₂Ph | CHF₂ |
| Me | Me | H | H | 1 | H | H | H | SCHF₂ | CHF₂ |
| Me | Me | H | H | 1 | H | H | H | SO₂CHF₂ | CHF₂ |
| Me | Me | H | H | 1 | H | H | H | NH₂ | CHF₂ |
| Me | Me | H | H | 1 | H | H | H | NHMe | CHF₂ |
| Me | Me | H | H | 1 | H | H | H | NMe₂ | CHF₂ |
| Me | Me | H | H | 1 | H | H | H | NHEt | CHF₂ |
| Me | Me | H | H | 1 | H | H | H | NEt₂ | CHF₂ |
| Me | Me | H | H | 1 | H | H | H | NHPh | CHF₂ |
| Me | Me | H | H | 1 | H | H | H | N(Me)Ph | CHF₂ |
| Me | Me | H | H | 1 | H | H | H | CN | CHF₂ |
| Me | Me | H | H | 1 | H | H | H | F | CF₃ |
| Me | Me | H | H | 1 | H | H | H | Cl | CF₃ |
| Me | Me | H | H | 1 | H | H | H | OH | CF₃ |
| Me | Me | H | H | 1 | H | H | H | OMe | CF₃ |
| Me | Me | H | H | 1 | H | H | H | OEt | CF₃ |
| Me | Me | H | H | 1 | H | H | H | OPr-i | CF₃ |
| Me | Me | H | H | 1 | H | H | H | OPr | CF₃ |
| Me | Me | H | H | 1 | H | H | H | OBu-t | CF₃ |
| Me | Me | H | H | 1 | H | H | H | OCH₂Pr-c | CF₃ |
| Me | Me | H | H | 1 | H | H | H | OCH₂Bu-c | CF₃ |
| Me | Me | H | H | 1 | H | H | H | OCH₂Pen-c | CF₃ |
| Me | Me | H | H | 1 | H | H | H | OCH₂Hex-c | CF₃ |
| Me | Me | H | H | 1 | H | H | H | OPen-c | CF₃ |
| Me | Me | H | H | 1 | H | H | H | OHex-c | CF₃ |
| Me | Me | H | H | 1 | H | H | H | OCH₂Ph | CF₃ |
| Me | Me | H | H | 1 | H | H | H | OPh | CF₃ |
| Me | Me | H | H | 1 | H | H | H | OCHF₂ | CF₃ |
| Me | Me | H | H | 1 | H | H | H | SH | CF₃ |
| Me | Me | H | H | 1 | H | H | H | SMe | CF₃ |
| Me | Me | H | H | 1 | H | H | H | SO₂Me | CF₃ |
| Me | Me | H | H | 1 | H | H | H | SEt | CF₃ |
| Me | Me | H | H | 1 | H | H | H | SO₂Et | CF₃ |
| Me | Me | H | H | 1 | H | H | H | SPr-i | CF₃ |
| Me | Me | H | H | 1 | H | H | H | SO₂Pr-i | CF₃ |
| Me | Me | H | H | 1 | H | H | H | SPh | CF₃ |
| Me | Me | H | H | 1 | H | H | H | SO₂Ph | CF₃ |
| Me | Me | H | H | 1 | H | H | H | SCHF₂ | CF₃ |
| Me | Me | H | H | 1 | H | H | H | SO₂CHF₂ | CF₃ |
| Me | Me | H | H | 1 | H | H | H | NH₂ | CF₃ |
| Me | Me | H | H | 1 | H | H | H | NHMe | CF₃ |
| Me | Me | H | H | 1 | H | H | H | NMe₂ | CF₃ |
| Me | Me | H | H | 1 | H | H | H | NHEt | CF₃ |
| Me | Me | H | H | 1 | H | H | H | NEt₂ | CF₃ |
| Me | Me | H | H | 1 | H | H | H | NHPh | CF₃ |
| Me | Me | H | H | 1 | H | H | H | N(Me)Ph | CF₃ |
| Me | Me | H | H | 1 | H | H | H | CN | CF₃ |
| Me | Me | H | H | 1 | H | H | H | F | OMe |
| Me | Me | H | H | 1 | H | H | H | OH | OMe |
| Me | Me | H | H | 1 | H | H | H | OMe | OMe |
| Me | Me | H | H | 1 | H | H | H | OEt | OMe |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 1 | H | H | H | OPr-i | OMe |
| Me | Me | H | H | 1 | H | H | H | OPr | OMe |
| Me | Me | H | H | 1 | H | H | H | OBu-t | OMe |
| Me | Me | H | H | 1 | H | H | H | OCH₂Pr-c | OMe |
| Me | Me | H | H | 1 | H | H | H | OCH₂Bu-c | OMe |
| Me | Me | H | H | 1 | H | H | H | OCH₂Pen-c | OMe |
| Me | Me | H | H | 1 | H | H | H | OCH₂Hex-c | OMe |
| Me | Me | H | H | 1 | H | H | H | OPen-c | OMe |
| Me | Me | H | H | 1 | H | H | H | OHex-c | OMe |
| Me | Me | H | H | 1 | H | H | H | OCH₂Ph | OMe |
| Me | Me | H | H | 1 | H | H | H | OPh | OMe |
| Me | Me | H | H | 1 | H | H | H | OCHF₂ | OMe |
| Me | Me | H | H | 1 | H | H | H | SH | OMe |
| Me | Me | H | H | 1 | H | H | H | SMe | OMe |
| Me | Me | H | H | 1 | H | H | H | SO₂Me | OMe |
| Me | Me | H | H | 1 | H | H | H | SEt | OMe |
| Me | Me | H | H | 1 | H | H | H | SO₂Et | OMe |
| Me | Me | H | H | 1 | H | H | H | SPr-i | OMe |
| Me | Me | H | H | 1 | H | H | H | SO₂Pr-i | OMe |
| Me | Me | H | H | 1 | H | H | H | SPh | OMe |
| Me | Me | H | H | 1 | H | H | H | SO₂Ph | OMe |
| Me | Me | H | H | 1 | H | H | H | SCHF₂ | OMe |
| Me | Me | H | H | 1 | H | H | H | SO₂CHF₂ | OMe |
| Me | Me | H | H | 1 | H | H | H | NH₂ | OMe |
| Me | Me | H | H | 1 | H | H | H | NHMe | OMe |
| Me | Me | H | H | 1 | H | H | H | NMe₂ | OMe |
| Me | Me | H | H | 1 | H | H | H | NHEt | OMe |
| Me | Me | H | H | 1 | H | H | H | NEt₂ | OMe |
| Me | Me | H | H | 1 | H | H | H | NHPh | OMe |
| Me | Me | H | H | 1 | H | H | H | N(Me)Ph | OMe |
| Me | Me | H | H | 1 | H | H | H | CN | OMe |
| Me | Me | H | H | 1 | H | H | H | F | OPh |
| Me | Me | H | H | 1 | H | H | H | OH | OPh |
| Me | Me | H | H | 1 | H | H | H | OMe | OPh |
| Me | Me | H | H | 1 | H | H | H | OEt | OPh |
| Me | Me | H | H | 1 | H | H | H | OPr-i | OPh |
| Me | Me | H | H | 1 | H | H | H | OPr | OPh |
| Me | Me | H | H | 1 | H | H | H | OBu-t | OPh |
| Me | Me | H | H | 1 | H | H | H | OCH₂Pr-c | OPh |
| Me | Me | H | H | 1 | H | H | H | OCH₂Bu-c | OPh |
| Me | Me | H | H | 1 | H | H | H | OCH₂Pen-c | OPh |
| Me | Me | H | H | 1 | H | H | H | OCH₂Hex-c | OPh |
| Me | Me | H | H | 1 | H | H | H | OPen-c | OPh |
| Me | Me | H | H | 1 | H | H | H | OHex-c | OPh |
| Me | Me | H | H | 1 | H | H | H | OCH₂Ph | OPh |
| Me | Me | H | H | 1 | H | H | H | OPh | OPh |
| Me | Me | H | H | 1 | H | H | H | OCHF₂ | OPh |
| Me | Me | H | H | 1 | H | H | H | SH | OPh |
| Me | Me | H | H | 1 | H | H | H | SMe | OPh |
| Me | Me | H | H | 1 | H | H | H | SO₂Me | OPh |
| Me | Me | H | H | 1 | H | H | H | SEt | OPh |
| Me | Me | H | H | 1 | H | H | H | SO₂Et | OPh |
| Me | Me | H | H | 1 | H | H | H | SPr-i | OPh |
| Me | Me | H | H | 1 | H | H | H | SO₂Pr-i | OPh |
| Me | Me | H | H | 1 | H | H | H | SPh | OPh |
| Me | Me | H | H | 1 | H | H | H | SO₂Ph | OPh |
| Me | Me | H | H | 1 | H | H | H | SCHF₂ | OPh |
| Me | Me | H | H | 1 | H | H | H | SO₂CHF₂ | OPh |
| Me | Me | H | H | 1 | H | H | H | NH₂ | OPh |
| Me | Me | H | H | 1 | H | H | H | NHMe | OPh |
| Me | Me | H | H | 1 | H | H | H | NMe₂ | OPh |
| Me | Me | H | H | 1 | H | H | H | NHEt | OPh |
| Me | Me | H | H | 1 | H | H | H | NEt₂ | OPh |
| Me | Me | H | H | 1 | H | H | H | NHPh | OPh |
| Me | Me | H | H | 1 | H | H | H | N(Me)Ph | OPh |
| Me | Me | H | H | 1 | H | H | H | CN | OPh |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 1 | H | H | H | F | OCHF₂ |
| Me | Me | H | H | 1 | H | H | H | OH | OCHF₂ |
| Me | Me | H | H | 1 | H | H | H | OMe | OCHF₂ |
| Me | Me | H | H | 1 | H | H | H | OEt | OCHF₂ |
| Me | Me | H | H | 1 | H | H | H | OPr-i | OCHF₂ |
| Me | Me | H | H | 1 | H | H | H | OPr | OCHF₂ |
| Me | Me | H | H | 1 | H | H | H | OBu-t | OCHF₂ |
| Me | Me | H | H | 1 | H | H | H | OCH₂Pr-c | OCHF₂ |
| Me | Me | H | H | 1 | H | H | H | OCH₂Bu-c | OCHF₂ |
| Me | Me | H | H | 1 | H | H | H | OCH₂Pen-c | OCHF₂ |
| Me | Me | H | H | 1 | H | H | H | OCH₂Hex-c | OCHF₂ |
| Me | Me | H | H | 1 | H | H | H | OPen-c | OCHF₂ |
| Me | Me | H | H | 1 | H | H | H | OHex-c | OCHF₂ |
| Me | Me | H | H | 1 | H | H | H | OCH₂Ph | OCHF₂ |
| Me | Me | H | H | 1 | H | H | H | OPh | OCHF₂ |
| Me | Me | H | H | 1 | H | H | H | OCHF₂ | OCHF₂ |
| Me | Me | H | H | 1 | H | H | H | SH | OCHF2 |
| Me | Me | H | H | 1 | H | H | H | SMe | OCHF₂ |
| Me | Me | H | H | 1 | H | H | H | SO₂Me | OCHF2 |
| Me | Me | H | H | 1 | H | H | H | SEt | OCHF₂ |
| Me | Me | H | H | 1 | H | H | H | SO₂Et | OCHF₂ |
| Me | Me | H | H | 1 | H | H | H | SPr-i | OCHF₂ |
| Me | Me | H | H | 1 | H | H | H | SO₂Pr-i | OCHF₂ |
| Me | Me | H | H | 1 | H | H | H | SPh | OCHF₂ |
| Me | Me | H | H | 1 | H | H | H | SO₂Ph | OCHF₂ |
| Me | Me | H | H | 1 | H | H | H | SCHF₂ | OCHF₂ |
| Me | Me | H | H | 1 | H | H | H | SO₂CHF₂ | OCHF₂ |
| Me | Me | H | H | 1 | H | H | H | NH₂ | OCHF₂ |
| Me | Me | H | H | 1 | H | H | H | NHMe | OCHF₂ |
| Me | Me | H | H | 1 | H | H | H | NMe₂ | OCHF₂ |
| Me | Me | H | H | 1 | H | H | H | NHEt | OCHF₂ |
| Me | Me | H | H | 1 | H | H | H | NEt₂ | OCHF₂ |
| Me | Me | H | H | 1 | H | H | H | NHPh | OCHF₂ |
| Me | Me | H | H | 1 | H | H | H | N(Me)Ph | OCHF₂ |
| Me | Me | H | H | 1 | H | H | H | CN | OCHF₂ |
| Me | Me | H | H | 1 | H | H | Me | F | CF₃ |
| Me | Me | H | H | 1 | H | H | Me | Cl | CF₃ |
| Me | Me | H | H | 1 | H | H | Me | OH | CF₃ |
| Me | Me | H | H | 1 | H | H | Me | OMe | CF₃ |
| Me | Me | H | H | 1 | H | H | Me | OEt | CF₃ |
| Me | Me | H | H | 1 | H | H | Me | OPr-i | CF₃ |
| Me | Me | H | H | 1 | H | H | Me | OPr | CF₃ |
| Me | Me | H | H | 1 | H | H | Me | OBu-t | CF₃ |
| Me | Me | H | H | 1 | H | H | Me | OCH₂Pr-c | CF₃ |
| Me | Me | H | H | 1 | H | H | Me | OCH₂Bu-c | CF₃ |
| Me | Me | H | H | 1 | H | H | Me | OCH₂Pen-c | CF₃ |
| Me | Me | H | H | 1 | H | H | Me | OCH₂Hex-c | CF₃ |
| Me | Me | H | H | 1 | H | H | Me | OPen-c | CF₃ |
| Me | Me | H | H | 1 | H | H | Me | OHex-c | CF₃ |
| Me | Me | H | H | 1 | H | H | Me | OCH₂Ph | CF₃ |
| Me | Me | H | H | 1 | H | H | Me | OPh | CF₃ |
| Me | Me | H | H | 1 | H | H | Me | OCHF₂ | CF₃ |
| Me | Me | H | H | 1 | H | H | Me | SH | CF₃ |
| Me | Me | H | H | 1 | H | H | Me | SMe | CF₃ |
| Me | Me | H | H | 1 | H | H | Me | SO₂Me | CF₃ |
| Me | Me | H | H | 1 | H | H | Me | SEt | CF₃ |
| Me | Me | H | H | 1 | H | H | Me | SO₂Et | CF₃ |
| Me | Me | H | H | 1 | H | H | Me | SPr-i | CF₃ |
| Me | Me | H | H | 1 | H | H | Me | SO₂Pr-i | CF₃ |
| Me | Me | H | H | 1 | H | H | Me | SPh | CF₃ |
| Me | Me | H | H | 1 | H | H | Me | SO₂Ph | CF₃ |
| Me | Me | H | H | 1 | H | H | Me | SCHF₂ | CF₃ |
| Me | Me | H | H | 1 | H | H | Me | SO₂CHF₂ | CF₃ |
| Me | Me | H | H | 1 | H | H | Me | NH₂ | CF₃ |
| Me | Me | H | H | 1 | H | H | Me | NHMe | CF₃ |
| Me | Me | H | H | 1 | H | H | Me | NMe₂ | CF₃ |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 1 | H | H | Me | NHEt | CF₃ |
| Me | Me | H | H | 1 | H | H | Me | NEt₂ | CF₃ |
| Me | Me | H | H | 1 | H | H | Me | NHPh | CF₃ |
| Me | Me | H | H | 1 | H | H | Me | N(Me)Ph | CF₃ |
| Me | Me | H | H | 1 | H | H | Me | CN | CF₃ |
| Me | Me | H | H | 1 | H | H | OMe | F | CF₃ |
| Me | Me | H | H | 1 | H | H | OMe | Cl | CF₃ |
| Me | Me | H | H | 1 | H | H | OMe | OH | CF₃ |
| Me | Me | H | H | 1 | H | H | OMe | OMe | CF₃ |
| Me | Me | H | H | 1 | H | H | OMe | OEt | CF₃ |
| Me | Me | H | H | 1 | H | H | OMe | OPr-i | CF₃ |
| Me | Me | H | H | 1 | H | H | OMe | OPr | CF₃ |
| Me | Me | H | H | 1 | H | H | OMe | OBu-t | CF₃ |
| Me | Me | H | H | 1 | H | H | OMe | OCH₂Pr-c | CF₃ |
| Me | Me | H | H | 1 | H | H | OMe | OCH₂Bu-c | CF₃ |
| Me | Me | H | H | 1 | H | H | OMe | OCH₂Pen-c | CF₃ |
| Me | Me | H | H | 1 | H | H | OMe | OCH₂Hex-c | CF₃ |
| Me | Me | H | H | 1 | H | H | OMe | OPen-c | CF₃ |
| Me | Me | H | H | 1 | H | H | OMe | OHex-c | CF₃ |
| Me | Me | H | H | 1 | H | H | OMe | OCH₂Ph | CF₃ |
| Me | Me | H | H | 1 | H | H | OMe | OPh | CF₃ |
| Me | Me | H | H | 1 | H | H | OMe | OCHF₂ | CF₃ |
| Me | Me | H | H | 1 | H | H | OMe | SH | CF₃ |
| Me | Me | H | H | 1 | H | H | OMe | SMe | CF₃ |
| Me | Me | H | H | 1 | H | H | OMe | SO₂Me | CF₃ |
| Me | Me | H | H | 1 | H | H | OMe | SEt | CF₃ |
| Me | Me | H | H | 1 | H | H | OMe | SO₂Et | CF₃ |
| Me | Me | H | H | 1 | H | H | OMe | SPr-i | CF₃ |
| Me | Me | H | H | 1 | H | H | OMe | SO₂Pr-i | CF₃ |
| Me | Me | H | H | 1 | H | H | OMe | SPh | CF₃ |
| Me | Me | H | H | 1 | H | H | OMe | SO₂Ph | CF₃ |
| Me | Me | H | H | 1 | H | H | OMe | SCHF₂ | CF₃ |
| Me | Me | H | H | 1 | H | H | OMe | SO₂CHF₂ | CF₃ |
| Me | Me | H | H | 1 | H | H | OMe | NH₂ | CF₃ |
| Me | Me | H | H | 1 | H | H | OMe | NHMe | CF₃ |
| Me | Me | H | H | 1 | H | H | OMe | NMe₂ | CF₃ |
| Me | Me | H | H | 1 | H | H | OMe | NHEt | CF₃ |
| Me | Me | H | H | 1 | H | H | OMe | NEt₂ | CF₃ |
| Me | Me | H | H | 1 | H | H | OMe | NHPh | CF₃ |
| Me | Me | H | H | 1 | H | H | OMe | N(Me)Ph | CF₃ |
| Me | Me | H | H | 1 | H | H | OMe | CN | CF₃ |
| Me | Me | H | H | 1 | H | H | SMe | F | CF₃ |
| Me | Me | H | H | 1 | H | H | SMe | Cl | CF₃ |
| Me | Me | H | H | 1 | H | H | SMe | OH | CF₃ |
| Me | Me | H | H | 1 | H | H | SMe | OMe | CF₃ |
| Me | Me | H | H | 1 | H | H | SMe | OEt | CF₃ |
| Me | Me | H | H | 1 | H | H | SMe | OPr-i | CF₃ |
| Me | Me | H | H | 1 | H | H | SMe | OPr | CF₃ |
| Me | Me | H | H | 1 | H | H | SMe | OBu-t | CF₃ |
| Me | Me | H | H | 1 | H | H | SMe | OCH₂Pr-c | CF₃ |
| Me | Me | H | H | 1 | H | H | SMe | OCH₂Bu-c | CF₃ |
| Me | Me | H | H | 1 | H | H | SMe | OCH₂Pen-c | CF₃ |
| Me | Me | H | H | 1 | H | H | SMe | OCH₂Hex-c | CF₃ |
| Me | Me | H | H | 1 | H | H | SMe | OPen-c | CF₃ |
| Me | Me | H | H | 1 | H | H | SMe | OHex-c | CF₃ |
| Me | Me | H | H | 1 | H | H | SMe | OCH₂Ph | CF₃ |
| Me | Me | H | H | 1 | H | H | SMe | OPh | CF₃ |
| Me | Me | H | H | 1 | H | H | SMe | OCHF₂ | CF₃ |
| Me | Me | H | H | 1 | H | H | SMe | SH | CF₃ |
| Me | Me | H | H | 1 | H | H | SMe | SMe | CF₃ |
| Me | Me | H | H | 1 | H | H | SMe | SO₂Me | CF₃ |
| Me | Me | H | H | 1 | H | H | SMe | SEt | CF₃ |
| Me | Me | H | H | 1 | H | H | SMe | SO₂Et | CF₃ |
| Me | Me | H | H | 1 | H | H | SMe | SPr-i | CF₃ |
| Me | Me | H | H | 1 | H | H | SMe | SO₂Pr-i | CF₃ |
| Me | Me | H | H | 1 | H | H | SMe | SPh | CF₃ |

TABLE 8-continued

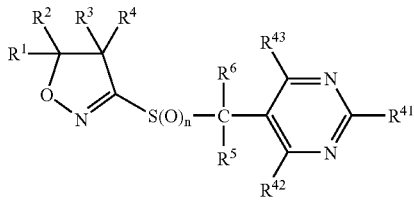

| $R^1$ | $R^2$ | $R^3$ | $R^4$ | n | $R^5$ | $R^6$ | $R^{41}$ | $R^{42}$ | $R^{43}$ |
|---|---|---|---|---|---|---|---|---|---|
| Me | Me | H | H | 1 | H | H | SMe | $SO_2Ph$ | $CF_3$ |
| Me | Me | H | H | 1 | H | H | SMe | $SCHF_2$ | $CF_3$ |
| Me | Me | H | H | 1 | H | H | SMe | $SO_2CHF_2$ | $CF_3$ |
| Me | Me | H | H | 1 | H | H | SMe | $NH_2$ | $CF_3$ |
| Me | Me | H | H | 1 | H | H | SMe | NHMe | $CF_3$ |
| Me | Me | H | H | 1 | H | H | SMe | $NMe_2$ | $CF_3$ |
| Me | Me | H | H | 1 | H | H | SMe | NHEt | $CF_3$ |
| Me | Me | H | H | 1 | H | H | SMe | $NEt_2$ | $CF_3$ |
| Me | Me | H | H | 1 | H | H | SMe | NHPh | $CF_3$ |
| Me | Me | H | H | 1 | H | H | SMe | N(Me)Ph | $CF_3$ |
| Me | Me | H | H | 1 | H | H | SMe | CN | $CF_3$ |
| Me | Me | H | H | 1 | H | H | $SO_2Me$ | F | $CF_3$ |
| Me | Me | H | H | 1 | H | H | $SO_2Me$ | Cl | $CF_3$ |
| Me | Me | H | H | 1 | H | H | $SO_2Me$ | OH | $CF_3$ |
| Me | Me | H | H | 1 | H | H | $SO_2Me$ | OMe | $CF_3$ |
| Me | Me | H | H | 1 | H | H | $SO_2Me$ | OEt | $CF_3$ |
| Me | Me | H | H | 1 | H | H | $SO_2Me$ | OPr-i | $CF_3$ |
| Me | Me | H | H | 1 | H | H | $SO_2Me$ | OPr | $CF_3$ |
| Me | Me | H | H | 1 | H | H | $SO_2Me$ | OBu-t | $CF_3$ |
| Me | Me | H | H | 1 | H | H | $SO_2Me$ | $OCH_2Pr$-c | $CF_3$ |
| Me | Me | H | H | 1 | H | H | $SO_2Me$ | $OCH_2Bu$-c | $CF_3$ |
| Me | Me | H | H | 1 | H | H | $SO_2Me$ | $OCH_2Pen$-c | $CF_3$ |
| Me | Me | H | H | 1 | H | H | $SO_2Me$ | $OCH_2Hex$-c | $CF_3$ |
| Me | Me | H | H | 1 | H | H | $SO_2Me$ | OPen-c | $CF_3$ |
| Me | Me | H | H | 1 | H | H | $SO_2Me$ | OHex-c | $CF_3$ |
| Me | Me | H | H | 1 | H | H | $SO_2Me$ | $OCH_2Ph$ | $CF_3$ |
| Me | Me | H | H | 1 | H | H | $SO_2Me$ | OPh | $CF_3$ |
| Me | Me | H | H | 1 | H | H | $SO_2Me$ | $OCHF_2$ | $CF_3$ |
| Me | Me | H | H | 1 | H | H | $SO_2Me$ | SH | $CF_3$ |
| Me | Me | H | H | 1 | H | H | $SO_2Me$ | SMe | $CF_3$ |
| Me | Me | H | H | 1 | H | H | $SO_2Me$ | $SO_2Me$ | $CF_3$ |
| Me | Me | H | H | 1 | H | H | $SO_2Me$ | SEt | $CF_3$ |
| Me | Me | H | H | 1 | H | H | $SO_2Me$ | $SO_2Et$ | $CF_3$ |
| Me | Me | H | H | 1 | H | H | $SO_2Me$ | SPr-i | $CF_3$ |
| Me | Me | H | H | 1 | H | H | $SO_2Me$ | $SO_2Pr$-i | $CF_3$ |
| Me | Me | H | H | 1 | H | H | $SO_2Me$ | SPh | $CF_3$ |
| Me | Me | H | H | 1 | H | H | $SO_2Me$ | $SO_2Ph$ | $CF_3$ |
| Me | Me | H | H | 1 | H | H | $SO_2Me$ | $SCHF_2$ | $CF_3$ |
| Me | Me | H | H | 1 | H | H | $SO_2Me$ | $SO_2CHF_2$ | $CF_3$ |
| Me | Me | H | H | 1 | H | H | $SO_2Me$ | $NH_2$ | $CF_3$ |
| Me | Me | H | H | 1 | H | H | $SO_2Me$ | NHMe | $CF_3$ |
| Me | Me | H | H | 1 | H | H | $SO_2Me$ | $NMe_2$ | $CF_3$ |
| Me | Me | H | H | 1 | H | H | $SO_2Me$ | NHEt | $CF_3$ |
| Me | Me | H | H | 1 | H | H | $SO_2Me$ | $NEt_2$ | $CF_3$ |
| Me | Me | H | H | 1 | H | H | $SO_2Me$ | NHPh | $CF_3$ |
| Me | Me | H | H | 1 | H | H | $SO_2Me$ | N(Me)Ph | $CF_3$ |
| Me | Me | H | H | 1 | H | H | $SO_2Me$ | CN | $CF_3$ |
| Me | Me | H | H | 1 | H | H | $NH_2$ | F | $CF_3$ |
| Me | Me | H | H | 1 | H | H | $NH_2$ | Cl | $CF_3$ |
| Me | Me | H | H | 1 | H | H | $NH_2$ | OH | $CF_3$ |
| Me | Me | H | H | 1 | H | H | $NH_2$ | OMe | $CF_3$ |
| Me | Me | H | H | 1 | H | H | $NH_2$ | OEt | $CF_3$ |
| Me | Me | H | H | 1 | H | H | $NH_2$ | OPr-i | $CF_3$ |
| Me | Me | H | H | 1 | H | H | $NH_2$ | OPr | $CF_3$ |
| Me | Me | H | H | 1 | H | H | $NH_2$ | OBu-t | $CF_3$ |
| Me | Me | H | H | 1 | H | H | $NH_2$ | $OCH_2Pr$-c | $CF_3$ |
| Me | Me | H | H | 1 | H | H | $NH_2$ | $OCH_2Bu$-c | $CF_3$ |
| Me | Me | H | H | 1 | H | H | $NH_2$ | $OCH_2Pen$-c | $CF_3$ |
| Me | Me | H | H | 1 | H | H | $NH_2$ | $OCH_2Hex$-c | $CF_3$ |
| Me | Me | H | H | 1 | H | H | $NH_2$ | OPen-c | $CF_3$ |
| Me | Me | H | H | 1 | H | H | $NH_2$ | OHex-c | $CF_3$ |
| Me | Me | H | H | 1 | H | H | $NH_2$ | $OCH_2Ph$ | $CF_3$ |
| Me | Me | H | H | 1 | H | H | $NH_2$ | OPh | $CF_3$ |
| Me | Me | H | H | 1 | H | H | $NH_2$ | $OCHF_2$ | $CF_3$ |
| Me | Me | H | H | 1 | H | H | $NH_2$ | SH | $CF_3$ |
| Me | Me | H | H | 1 | H | H | $NH_2$ | SMe | $CF_3$ |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 1 | H | H | NH₂ | SO₂Me | CF₃ |
| Me | Me | H | H | 1 | H | H | NH₂ | SEt | CF₃ |
| Me | Me | H | H | 1 | H | H | NH₂ | SO₂Et | CF₃ |
| Me | Me | H | H | 1 | H | H | NH₂ | SPr-i | CF₃ |
| Me | Me | H | H | 1 | H | H | NH₂ | SO₂Pr-i | CF₃ |
| Me | Me | H | H | 1 | H | H | NH₂ | SPh | CF₃ |
| Me | Me | H | H | 1 | H | H | NH₂ | SO₂Ph | CF₃ |
| Me | Me | H | H | 1 | H | H | NH₂ | SCHF₂ | CF₃ |
| Me | Me | H | H | 1 | H | H | NH₂ | SO₂CHF₂ | CF₃ |
| Me | Me | H | H | 1 | H | H | NH₂ | NH₂ | CF₃ |
| Me | Me | H | H | 1 | H | H | NH₂ | NHMe | CF₃ |
| Me | Me | H | H | 1 | H | H | NH₂ | NMe₂ | CF₃ |
| Me | Me | H | H | 1 | H | H | NH₂ | NHEt | CF₃ |
| Me | Me | H | H | 1 | H | H | NH₂ | NEt₂ | CF₃ |
| Me | Me | H | H | 1 | H | H | NH₂ | NHPh | CF₃ |
| Me | Me | H | H | 1 | H | H | NH₂ | N(Me)Ph | CF₃ |
| Me | Me | H | H | 1 | H | H | NH₂ | CN | CF₃ |
| H | H | H | H | 1 | H | H | H | OMe | CF₃ |
| H | H | H | H | 1 | H | H | H | OEt | CF₃ |
| Me | H | H | H | 1 | H | H | H | OMe | CF₃ |
| Me | H | H | H | 1 | H | H | H | OEt | CF₃ |
| Me | H | Me | H | 1 | H | H | H | OMe | CF₃ |
| Me | H | Me | H | 1 | H | H | H | OEt | CF₃ |
| Me | Me | H | H | 1 | Me | H | H | OMe | CF₃ |
| Me | Me | H | H | 1 | Me | H | H | OEt | CF₃ |
| Me | Me | H | H | 1 | Et | H | H | OMe | CF₃ |
| Me | Me | H | H | 1 | Et | H | H | OEt | CF₃ |
| Me | Me | H | H | 1 | Pr-i | H | H | H | CF₃ |
| Me | Me | H | H | 1 | Pr-i | H | H | OMe | CF₃ |
| Me | Me | H | H | 1 | Pr-i | H | H | OEt | CF₃ |
| Me | Me | H | H | 1 | Me | Me | H | OMe | CF₃ |
| Me | Me | H | H | 1 | Me | Me | H | OEt | CF₃ |
| Me | Et | H | H | 1 | H | H | H | OMe | CF₃ |
| Me | Et | H | H | 1 | H | H | H | OEt | CF₃ |
| Et | Et | H | H | 1 | H | H | H | OMe | CF₃ |
| Et | Et | H | H | 1 | H | H | H | OEt | CF₃ |
| Me | Pr-i | H | H | 1 | H | H | H | OMe | CF₃ |
| Me | Pr-i | H | H | 1 | H | H | H | OEt | CF₃ |
| Me | Pr | H | H | 1 | H | H | H | OMe | CF₃ |
| Me | Pr | H | H | 1 | H | H | H | OEt | CF₃ |
| Me | Pr-c | H | H | 1 | H | H | H | OMe | CF₃ |
| Me | Pr-c | H | H | 1 | H | H | H | OEt | CF₃ |
| Me | CH₂Pr-c | H | H | 1 | H | H | H | OMe | CF₃ |
| Me | CH₂Pr-c | H | H | 1 | H | H | H | OEt | CF₃ |
| —(CH₂)₂— | | H | H | 1 | H | H | H | OMe | CF₃ |
| —(CH₂)₂— | | H | H | 1 | H | H | H | OEt | CF₃ |
| —(CH₂)₃— | | H | H | 1 | H | H | H | OMe | CF₃ |
| —(CH₂)₃— | | H | H | 1 | H | H | H | OEt | CF₃ |
| —(CH₂)₄— | | H | H | 1 | H | H | H | OMe | CF₃ |
| —(CH₂)₄— | | H | H | 1 | H | H | H | OEt | CF₃ |
| —(CH₂)₅— | | H | H | 1 | H | H | H | OMe | CF₃ |
| —(CH₂)₅— | | H | H | 1 | H | H | H | OEt | CF₃ |
| H | —(CH₂)₃— | | H | 1 | H | H | H | OMe | CF₃ |
| H | —(CH₂)₃— | | H | 1 | H | H | H | OEt | CF₃ |
| H | —(CH₂)₄— | | H | 1 | H | H | H | OMe | CF₃ |
| H | —(CH₂)₄— | | H | 1 | H | H | H | OEt | CF₃ |
| H | —(CH₂)₅— | | H | 1 | H | H | H | OMe | CF₃ |
| H | —(CH₂)₅— | | H | 1 | H | H | H | OEt | CF₃ |
| H | —(CH₂)₆— | | H | 1 | H | H | H | OMe | CF₃ |
| H | —(CH₂)₆— | | H | 1 | H | H | H | OEt | CF₃ |
| Me | Me | H | H | 0 | H | H | H | Cl | Cl |
| Me | Me | H | H | 0 | H | H | H | OH | Cl |
| Me | Me | H | H | 0 | H | H | H | OMe | Cl |
| Me | Me | H | H | 0 | H | H | H | OEt | Cl |
| Me | Me | H | H | 0 | H | H | H | OPr-i | Cl |
| Me | Me | H | H | 0 | H | H | H | OPr | Cl |

TABLE 8-continued

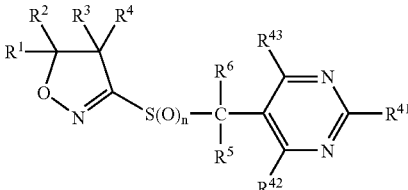

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 0 | H | H | H | OBu-t | Cl |
| Me | Me | H | H | 0 | H | H | H | OCH₂Pr-c | Cl |
| Me | Me | H | H | 0 | H | H | H | OCH₂Bu-c | Cl |
| Me | Me | H | H | 0 | H | H | H | OCH₂Pen-c | Cl |
| Me | Me | H | H | 0 | H | H | H | OCH₂Hex-c | Cl |
| Me | Me | H | H | 0 | H | H | H | OPen-c | Cl |
| Me | Me | H | H | 0 | H | H | H | OHex-c | Cl |
| Me | Me | H | H | 0 | H | H | H | OCH₂Ph | Cl |
| Me | Me | H | H | 0 | H | H | H | OPh | Cl |
| Me | Me | H | H | 0 | H | H | H | OCHF₂ | Cl |
| Me | Me | H | H | 0 | H | H | H | SH | Cl |
| Me | Me | H | H | 0 | H | H | H | SMe | Cl |
| Me | Me | H | H | 0 | H | H | H | SO₂Me | Cl |
| Me | Me | H | H | 0 | H | H | H | SEt | Cl |
| Me | Me | H | H | 0 | H | H | H | SO₂Et | Cl |
| Me | Me | H | H | 0 | H | H | H | SPr-i | Cl |
| Me | Me | H | H | 0 | H | H | H | SO₂Pr-i | Cl |
| Me | Me | H | H | 0 | H | H | H | SPh | Cl |
| Me | Me | H | H | 0 | H | H | H | SO₂Ph | Cl |
| Me | Me | H | H | 0 | H | H | H | SCHF₂ | Cl |
| Me | Me | H | H | 0 | H | H | H | SO₂CHF₂ | Cl |
| Me | Me | H | H | 0 | H | H | H | NH₂ | Cl |
| Me | Me | H | H | 0 | H | H | H | NHMe | Cl |
| Me | Me | H | H | 0 | H | H | H | NMe₂ | Cl |
| Me | Me | H | H | 0 | H | H | H | NHEt | Cl |
| Me | Me | H | H | 0 | H | H | H | NEt₂ | Cl |
| Me | Me | H | H | 0 | H | H | H | NHPh | Cl |
| Me | Me | H | H | 0 | H | H | H | N(Me)Ph | Cl |
| Me | Me | H | H | 0 | H | H | H | CN | Cl |
| Me | Me | H | H | 0 | H | H | H | F | Me |
| Me | Me | H | H | 0 | H | H | H | Cl | Me |
| Me | Me | H | H | 0 | H | H | H | OH | Me |
| Me | Me | H | H | 0 | H | H | H | OMe | Me |
| Me | Me | H | H | 0 | H | H | H | OEt | Me |
| Me | Me | H | H | 0 | H | H | H | OPr-i | Me |
| Me | Me | H | H | 0 | H | H | H | OPr | Me |
| Me | Me | H | H | 0 | H | H | H | OBu-t | Me |
| Me | Me | H | H | 0 | H | H | H | OCH₂Pr-c | Me |
| Me | Me | H | H | 0 | H | H | H | OCH₂Bu-c | Me |
| Me | Me | H | H | 0 | H | H | H | OCH₂Pen-c | Me |
| Me | Me | H | H | 0 | H | H | H | OCH₂Hex-c | Me |
| Me | Me | H | H | 0 | H | H | H | OPen-c | Me |
| Me | Me | H | H | 0 | H | H | H | OHex-c | Me |
| Me | Me | H | H | 0 | H | H | H | OCH₂Ph | Me |
| Me | Me | H | H | 0 | H | H | H | OPh | Me |
| Me | Me | H | H | 0 | H | H | H | OCHF₂ | Me |
| Me | Me | H | H | 0 | H | H | H | SH | Me |
| Me | Me | H | H | 0 | H | H | H | SMe | Me |
| Me | Me | H | H | 0 | H | H | H | SO₂Me | Me |
| Me | Me | H | H | 0 | H | H | H | SEt | Me |
| Me | Me | H | H | 0 | H | H | H | SO₂Et | Me |
| Me | Me | H | H | 0 | H | H | H | SPr-i | Me |
| Me | Me | H | H | 0 | H | H | H | SO₂Pr-i | Me |
| Me | Me | H | H | 0 | H | H | H | SPh | Me |
| Me | Me | H | H | 0 | H | H | H | SO₂Ph | Me |
| Me | Me | H | H | 0 | H | H | H | SCHF₂ | Me |
| Me | Me | H | H | 0 | H | H | H | SO₂CHF₂ | Me |
| Me | Me | H | H | 0 | H | H | H | NH₂ | Me |
| Me | Me | H | H | 0 | H | H | H | NHMe | Me |
| Me | Me | H | H | 0 | H | H | H | NMe₂ | Me |
| Me | Me | H | H | 0 | H | H | H | NHEt | Me |
| Me | Me | H | H | 0 | H | H | H | NEt₂ | Me |
| Me | Me | H | H | 0 | H | H | H | NHPh | Me |
| Me | Me | H | H | 0 | H | H | H | N(Me)Ph | Me |
| Me | Me | H | H | 0 | H | H | H | CN | Me |
| Me | Me | H | H | 0 | H | H | H | F | Pr-i |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 0 | H | H | H | Cl | Pr-i |
| Me | Me | H | H | 0 | H | H | H | OH | Pr-i |
| Me | Me | H | H | 0 | H | H | H | OMe | Pr-i |
| Me | Me | H | H | 0 | H | H | H | OEt | Pr-i |
| Me | Me | H | H | 0 | H | H | H | OPr-i | Pr-i |
| Me | Me | H | H | 0 | H | H | H | OPr | Pr-i |
| Me | Me | H | H | 0 | H | H | H | OBu-t | Pr-i |
| Me | Me | H | H | 0 | H | H | H | OCH₂Pr-c | Pr-i |
| Me | Me | H | H | 0 | H | H | H | OCH₂Bu-c | Pr-i |
| Me | Me | H | H | 0 | H | H | H | OCH₂Pen-c | Pr-i |
| Me | Me | H | H | 0 | H | H | H | OCH₂Hex-c | Pr-i |
| Me | Me | H | H | 0 | H | H | H | OPen-c | Pr-i |
| Me | Me | H | H | 0 | H | H | H | OHex-c | Pr-i |
| Me | Me | H | H | 0 | H | H | H | OCH₂Ph | Pr-i |
| Me | Me | H | H | 0 | H | H | H | OPh | Pr-i |
| Me | Me | H | H | 0 | H | H | H | OCHF₂ | Pr-i |
| Me | Me | H | H | 0 | H | H | H | SH | Pr-i |
| Me | Me | H | H | 0 | H | H | H | SMe | Pr-i |
| Me | Me | H | H | 0 | H | H | H | SO₂Me | Pr-i |
| Me | Me | H | H | 0 | H | H | H | SEt | Pr-i |
| Me | Me | H | H | 0 | H | H | H | SO₂Et | Pr-i |
| Me | Me | H | H | 0 | H | H | H | SPr-i | Pr-i |
| Me | Me | H | H | 0 | H | H | H | SO₂Pr-i | Pr-i |
| Me | Me | H | H | 0 | H | H | H | SPh | Pr-i |
| Me | Me | H | H | 0 | H | H | H | SO₂Ph | Pr-i |
| Me | Me | H | H | 0 | H | H | H | SCHF₂ | Pr-i |
| Me | Me | H | H | 0 | H | H | H | SO₂CHF₂ | Pr-i |
| Me | Me | H | H | 0 | H | H | H | NH₂ | Pr-i |
| Me | Me | H | H | 0 | H | H | H | NHMe | Pr-i |
| Me | Me | H | H | 0 | H | H | H | NMe₂ | Pr-i |
| Me | Me | H | H | 0 | H | H | H | NHEt | Pr-i |
| Me | Me | H | H | 0 | H | H | H | NEt₂ | Pr-i |
| Me | Me | H | H | 0 | H | H | H | NHPh | Pr-i |
| Me | Me | H | H | 0 | H | H | H | N(Me)Ph | Pr-i |
| Me | Me | H | H | 0 | H | H | H | CN | Pr-i |
| Me | Me | H | H | 0 | H | H | H | F | Pr-c |
| Me | Me | H | H | 0 | H | H | H | Cl | Pr-c |
| Me | Me | H | H | 0 | H | H | H | OH | Pr-c |
| Me | Me | H | H | 0 | H | H | H | OMe | Pr-c |
| Me | Me | H | H | 0 | H | H | H | OEt | Pr-c |
| Me | Me | H | H | 0 | H | H | H | OPr-i | Pr-c |
| Me | Me | H | H | 0 | H | H | H | OPr | Pr-c |
| Me | Me | H | H | 0 | H | H | H | OBu-t | Pr-c |
| Me | Me | H | H | 0 | H | H | H | OCH₂Pr-c | Pr-c |
| Me | Me | H | H | 0 | H | H | H | OCH₂Bu-c | Pr-c |
| Me | Me | H | H | 0 | H | H | H | OCH₂Pen-c | Pr-c |
| Me | Me | H | H | 0 | H | H | H | OCH₂Hex-c | Pr-c |
| Me | Me | H | H | 0 | H | H | H | OPen-c | Pr-c |
| Me | Me | H | H | 0 | H | H | H | OHex-c | Pr-c |
| Me | Me | H | H | 0 | H | H | H | OCH₂Ph | Pr-c |
| Me | Me | H | H | 0 | H | H | H | OPh | Pr-c |
| Me | Me | H | H | 0 | H | H | H | OCHF₂ | Pr-c |
| Me | Me | H | H | 0 | H | H | H | SH | Pr-c |
| Me | Me | H | H | 0 | H | H | H | SMe | Pr-c |
| Me | Me | H | H | 0 | H | H | H | SO₂Me | Pr-c |
| Me | Me | H | H | 0 | H | H | H | SEt | Pr-c |
| Me | Me | H | H | 0 | H | H | H | SO₂Et | Pr-c |
| Me | Me | H | H | 0 | H | H | H | SPr-i | Pr-c |
| Me | Me | H | H | 0 | H | H | H | SO₂Pr-i | Pr-c |
| Me | Me | H | H | 0 | H | H | H | SPh | Pr-c |
| Me | Me | H | H | 0 | H | H | H | SO₂Ph | Pr-c |
| Me | Me | H | H | 0 | H | H | H | SCHF₂ | Pr-c |
| Me | Me | H | H | 0 | H | H | H | SO₂CHF₂ | Pr-c |
| Me | Me | H | H | 0 | H | H | H | NH₂ | Pr-c |
| Me | Me | H | H | 0 | H | H | H | NHMe | Pr-c |
| Me | Me | H | H | 0 | H | H | H | NMe₂ | Pr-c |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 0 | H | H | H | NHEt | Pr-c |
| Me | Me | H | H | 0 | H | H | H | NEt₂ | Pr-c |
| Me | Me | H | H | 0 | H | H | H | NHPh | Pr-c |
| Me | Me | H | H | 0 | H | H | H | N(Me)Ph | Pr-c |
| Me | Me | H | H | 0 | H | H | H | CN | Pr-c |
| Me | Me | H | H | 0 | H | H | H | F | CHF₂ |
| Me | Me | H | H | 0 | H | H | H | Cl | CHF₂ |
| Me | Me | H | H | 0 | H | H | H | OH | CHF₂ |
| Me | Me | H | H | 0 | H | H | H | OMe | CHF₂ |
| Me | Me | H | H | 0 | H | H | H | OEt | CHF₂ |
| Me | Me | H | H | 0 | H | H | H | OPr-i | CHF₂ |
| Me | Me | H | H | 0 | H | H | H | OPr | CHF₂ |
| Me | Me | H | H | 0 | H | H | H | OBu-t | CHF₂ |
| Me | Me | H | H | 0 | H | H | H | OCH₂Pr-c | CHF₂ |
| Me | Me | H | H | 0 | H | H | H | OCH₂Bu-c | CHF₂ |
| Me | Me | H | H | 0 | H | H | H | OCH₂Pen-c | CHF₂ |
| Me | Me | H | H | 0 | H | H | H | OCH₂Hex-c | CHF₂ |
| Me | Me | H | H | 0 | H | H | H | OPen-c | CHF₂ |
| Me | Me | H | H | 0 | H | H | H | OHex-c | CHF₂ |
| Me | Me | H | H | 0 | H | H | H | OCH₂Ph | CHF₂ |
| Me | Me | H | H | 0 | H | H | H | OPh | CHF₂ |
| Me | Me | H | H | 0 | H | H | H | OCHF₂ | CHF₂ |
| Me | Me | H | H | 0 | H | H | H | SH | CHF₂ |
| Me | Me | H | H | 0 | H | H | H | SMe | CHF₂ |
| Me | Me | H | H | 0 | H | H | H | SO₂Me | CHF₂ |
| Me | Me | H | H | 0 | H | H | H | SEt | CHF₂ |
| Me | Me | H | H | 0 | H | H | H | SO₂Et | CHF₂ |
| Me | Me | H | H | 0 | H | H | H | SPr-i | CHF₂ |
| Me | Me | H | H | 0 | H | H | H | SO₂Pr-i | CHF₂ |
| Me | Me | H | H | 0 | H | H | H | SPh | CHF₂ |
| Me | Me | H | H | 0 | H | H | H | SO₂Ph | CHF₂ |
| Me | Me | H | H | 0 | H | H | H | SCHF₂ | CHF₂ |
| Me | Me | H | H | 0 | H | H | H | SO₂CHF₂ | CHF₂ |
| Me | Me | H | H | 0 | H | H | H | NH₂ | CHF₂ |
| Me | Me | H | H | 0 | H | H | H | NHMe | CHF₂ |
| Me | Me | H | H | 0 | H | H | H | NMe₂ | CHF₂ |
| Me | Me | H | H | 0 | H | H | H | NHEt | CHF₂ |
| Me | Me | H | H | 0 | H | H | H | NEt₂ | CHF₂ |
| Me | Me | H | H | 0 | H | H | H | NHPh | CHF₂ |
| Me | Me | H | H | 0 | H | H | H | N(Me)Ph | CHF₂ |
| Me | Me | H | H | 0 | H | H | H | CN | CHF₂ |
| Me | Me | H | H | 0 | H | H | H | F | CF₃ |
| Me | Me | H | H | 0 | H | H | H | Cl | CF₃ |
| Me | Me | H | H | 0 | H | H | H | OH | CF₃ |
| Me | Me | H | H | 0 | H | H | H | OMe | CF₃ |
| Me | Me | H | H | 0 | H | H | H | OEt | CF₃ |
| Me | Me | H | H | 0 | H | H | H | OPr-i | CF₃ |
| Me | Me | H | H | 0 | H | H | H | OPr | CF₃ |
| Me | Me | H | H | 0 | H | H | H | OBu-t | CF₃ |
| Me | Me | H | H | 0 | H | H | H | OCH₂Pr-c | CF₃ |
| Me | Me | H | H | 0 | H | H | H | OCH₂Bu-c | CF₃ |
| Me | Me | H | H | 0 | H | H | H | OCH₂Pen-c | CF₃ |
| Me | Me | H | H | 0 | H | H | H | OCH₂Hex-c | CF₃ |
| Me | Me | H | H | 0 | H | H | H | OPen-c | CF₃ |
| Me | Me | H | H | 0 | H | H | H | OHex-c | CF₃ |
| Me | Me | H | H | 0 | H | H | H | OCH₂Ph | CF₃ |
| Me | Me | H | H | 0 | H | H | H | OPh | CF₃ |
| Me | Me | H | H | 0 | H | H | H | OCHF₂ | CF₃ |
| Me | Me | H | H | 0 | H | H | H | SH | CF₃ |
| Me | Me | H | H | 0 | H | H | H | SMe | CF₃ |
| Me | Me | H | H | 0 | H | H | H | SO₂Me | CF₃ |
| Me | Me | H | H | 0 | H | H | H | SEt | CF₃ |
| Me | Me | H | H | 0 | H | H | H | SO₂Et | CF₃ |
| Me | Me | H | H | 0 | H | H | H | SPr-i | CF₃ |
| Me | Me | H | H | 0 | H | H | H | SO₂Pr-i | CF₃ |
| Me | Me | H | H | 0 | H | H | H | SPh | CF₃ |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 0 | H | H | H | SO₂Ph | CF₃ |
| Me | Me | H | H | 0 | H | H | H | SCHF₂ | CF₃ |
| Me | Me | H | H | 0 | H | H | H | SO₂CHF₂ | CF₃ |
| Me | Me | H | H | 0 | H | H | H | NH₂ | CF₃ |
| Me | Me | H | H | 0 | H | H | H | NHMe | CF₃ |
| Me | Me | H | H | 0 | H | H | H | NMe₂ | CF₃ |
| Me | Me | H | H | 0 | H | H | H | NHEt | CF₃ |
| Me | Me | H | H | 0 | H | H | H | NEt₂ | CF₃ |
| Me | Me | H | H | 0 | H | H | H | NHPh | CF₃ |
| Me | Me | H | H | 0 | H | H | H | N(Me)Ph | CF₃ |
| Me | Me | H | H | 0 | H | H | H | CN | CF₃ |
| Me | Me | H | H | 0 | H | H | H | F | OMe |
| Me | Me | H | H | 0 | H | H | H | OH | OMe |
| Me | Me | H | H | 0 | H | H | H | OMe | OMe |
| Me | Me | H | H | 0 | H | H | H | OEt | OMe |
| Me | Me | H | H | 0 | H | H | H | OPr-i | OMe |
| Me | Me | H | H | 0 | H | H | H | OPr | OMe |
| Me | Me | H | H | 0 | H | H | H | OBu-t | OMe |
| Me | Me | H | H | 0 | H | H | H | OCH₂Pr-c | OMe |
| Me | Me | H | H | 0 | H | H | H | OCH₂Bu-c | OMe |
| Me | Me | H | H | 0 | H | H | H | OCH₂Pen-c | OMe |
| Me | Me | H | H | 0 | H | H | H | OCH₂Hex-c | OMe |
| Me | Me | H | H | 0 | H | H | H | OPen-c | OMe |
| Me | Me | H | H | 0 | H | H | H | OHex-c | OMe |
| Me | Me | H | H | 0 | H | H | H | OCH₂Ph | OMe |
| Me | Me | H | H | 0 | H | H | H | OPh | OMe |
| Me | Me | H | H | 0 | H | H | H | OCHF₂ | OMe |
| Me | Me | H | H | 0 | H | H | H | SH | OMe |
| Me | Me | H | H | 0 | H | H | H | SMe | OMe |
| Me | Me | H | H | 0 | H | H | H | SO₂Me | OMe |
| Me | Me | H | H | 0 | H | H | H | SEt | OMe |
| Me | Me | H | H | 0 | H | H | H | SO₂Et | OMe |
| Me | Me | H | H | 0 | H | H | H | SPr-i | OMe |
| Me | Me | H | H | 0 | H | H | H | SO₂Pr-i | OMe |
| Me | Me | H | H | 0 | H | H | H | SPh | OMe |
| Me | Me | H | H | 0 | H | H | H | SO₂Ph | OMe |
| Me | Me | H | H | 0 | H | H | H | SCHF₂ | OMe |
| Me | Me | H | H | 0 | H | H | H | SO₂CHF₂ | OMe |
| Me | Me | H | H | 0 | H | H | H | NH₂ | OMe |
| Me | Me | H | H | 0 | H | H | H | NHMe | OMe |
| Me | Me | H | H | 0 | H | H | H | NMe₂ | OMe |
| Me | Me | H | H | 0 | H | H | H | NHEt | OMe |
| Me | Me | H | H | 0 | H | H | H | NEt₂ | OMe |
| Me | Me | H | H | 0 | H | H | H | NHPh | OMe |
| Me | Me | H | H | 0 | H | H | H | N(Me)Ph | OMe |
| Me | Me | H | H | 0 | H | H | H | CN | OMe |
| Me | Me | H | H | 0 | H | H | H | F | OPh |
| Me | Me | H | H | 0 | H | H | H | OH | OPh |
| Me | Me | H | H | 0 | H | H | H | OMe | OPh |
| Me | Me | H | H | 0 | H | H | H | OEt | OPh |
| Me | Me | H | H | 0 | H | H | H | OPr-i | OPh |
| Me | Me | H | H | 0 | H | H | H | OPr | OPh |
| Me | Me | H | H | 0 | H | H | H | OBu-t | OPh |
| Me | Me | H | H | 0 | H | H | H | OCH₂Pr-c | OPh |
| Me | Me | H | H | 0 | H | H | H | OCH₂Bu-c | OPh |
| Me | Me | H | H | 0 | H | H | H | OCH₂Pen-c | OPh |
| Me | Me | H | H | 0 | H | H | H | OCH₂Hex-c | OPh |
| Me | Me | H | H | 0 | H | H | H | OPen-c | OPh |
| Me | Me | H | H | 0 | H | H | H | OHex-c | OPh |
| Me | Me | H | H | 0 | H | H | H | OCH₂Ph | OPh |
| Me | Me | H | H | 0 | H | H | H | OPh | OPh |
| Me | Me | H | H | 0 | H | H | H | OCHF₂ | OPh |
| Me | Me | H | H | 0 | H | H | H | SH | OPh |
| Me | Me | H | H | 0 | H | H | H | SMe | OPh |
| Me | Me | H | H | 0 | H | H | H | SO₂Me | OPh |
| Me | Me | H | H | 0 | H | H | H | SEt | OPh |

TABLE 8-continued

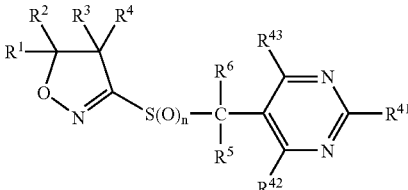

| $R^1$ | $R^2$ | $R^3$ | $R^4$ | n | $R^5$ | $R^6$ | $R^{41}$ | $R^{42}$ | $R^{43}$ |
|---|---|---|---|---|---|---|---|---|---|
| Me | Me | H | H | 0 | H | H | H | SO$_2$Et | OPh |
| Me | Me | H | H | 0 | H | H | H | SPr-i | OPh |
| Me | Me | H | H | 0 | H | H | H | SO$_2$Pr-i | OPh |
| Me | Me | H | H | 0 | H | H | H | SPh | OPh |
| Me | Me | H | H | 0 | H | H | H | SO$_2$Ph | OPh |
| Me | Me | H | H | 0 | H | H | H | SCHF$_2$ | OPh |
| Me | Me | H | H | 0 | H | H | H | SO$_2$CHF$_2$ | OPh |
| Me | Me | H | H | 0 | H | H | H | NH$_2$ | OPh |
| Me | Me | H | H | 0 | H | H | H | NHMe | OPh |
| Me | Me | H | H | 0 | H | H | H | NMe$_2$ | OPh |
| Me | Me | H | H | 0 | H | H | H | NHEt | OPh |
| Me | Me | H | H | 0 | H | H | H | NEt$_2$ | OPh |
| Me | Me | H | H | 0 | H | H | H | NHPh | OPh |
| Me | Me | H | H | 0 | H | H | H | N(Me)Ph | OPh |
| Me | Me | H | H | 0 | H | H | H | CN | OPh |
| Me | Me | H | H | 0 | H | H | H | F | OCHF$_2$ |
| Me | Me | H | H | 0 | H | H | H | OH | OCHF$_2$ |
| Me | Me | H | H | 0 | H | H | H | OMe | OCHF$_2$ |
| Me | Me | H | H | 0 | H | H | H | OEt | OCHF$_2$ |
| Me | Me | H | H | 0 | H | H | H | OPr-i | OCHF$_2$ |
| Me | Me | H | H | 0 | H | H | H | OPr | OCHF$_2$ |
| Me | Me | H | H | 0 | H | H | H | OBu-t | OCHF$_2$ |
| Me | Me | H | H | 0 | H | H | H | OCH$_2$Pr-c | OCHF$_2$ |
| Me | Me | H | H | 0 | H | H | H | OCH$_2$Bu-c | OCHF$_2$ |
| Me | Me | H | H | 0 | H | H | H | OCH$_2$Pen-c | OCHF$_2$ |
| Me | Me | H | H | 0 | H | H | H | OCH$_2$Hex-c | OCHF$_2$ |
| Me | Me | H | H | 0 | H | H | H | OPen-c | OCHF$_2$ |
| Me | Me | H | H | 0 | H | H | H | OHex-c | OCHF$_2$ |
| Me | Me | H | H | 0 | H | H | H | OCH$_2$Ph | OCHF$_2$ |
| Me | Me | H | H | 0 | H | H | H | OPh | OCHF$_2$ |
| Me | Me | H | H | 0 | H | H | H | OCHF$_2$ | OCHF$_2$ |
| Me | Me | H | H | 0 | H | H | H | SH | OCHF$_2$ |
| Me | Me | H | H | 0 | H | H | H | SMe | OCHF$_2$ |
| Me | Me | H | H | 0 | H | H | H | SO$_2$Me | OCHF$_2$ |
| Me | Me | H | H | 0 | H | H | H | SEt | OCHF$_2$ |
| Me | Me | H | H | 0 | H | H | H | SO$_2$Et | OCHF$_2$ |
| Me | Me | H | H | 0 | H | H | H | SPr-i | OCHF$_2$ |
| Me | Me | H | H | 0 | H | H | H | SO$_2$Pr-i | OCHF$_2$ |
| Me | Me | H | H | 0 | H | H | H | SPh | OCHF$_2$ |
| Me | Me | H | H | 0 | H | H | H | SO$_2$Ph | OCHF$_2$ |
| Me | Me | H | H | 0 | H | H | H | SCHF$_2$ | OCHF$_2$ |
| Me | Me | H | H | 0 | H | H | H | SO$_2$CHF$_2$ | OCHF$_2$ |
| Me | Me | H | H | 0 | H | H | H | NH$_2$ | OCHF$_2$ |
| Me | Me | H | H | 0 | H | H | H | NHMe | OCHF$_2$ |
| Me | Me | H | H | 0 | H | H | H | NMe$_2$ | OCHF$_2$ |
| Me | Me | H | H | 0 | H | H | H | NHEt | OCHF$_2$ |
| Me | Me | H | H | 0 | H | H | H | NEt$_2$ | OCHF$_2$ |
| Me | Me | H | H | 0 | H | H | H | NHPh | OCHF$_2$ |
| Me | Me | H | H | 0 | H | H | H | N(Me)Ph | OCHF$_2$ |
| Me | Me | H | H | 0 | H | H | H | CN | OCHF$_2$ |
| Me | Me | H | H | 0 | H | H | Me | F | CF$_3$ |
| Me | Me | H | H | 0 | H | H | Me | Cl | CF$_3$ |
| Me | Me | H | H | 0 | H | H | Me | OH | CF$_3$ |
| Me | Me | H | H | 0 | H | H | Me | OMe | CF$_3$ |
| Me | Me | H | H | 0 | H | H | Me | OEt | CF$_3$ |
| Me | Me | H | H | 0 | H | H | Me | OPr-i | CF$_3$ |
| Me | Me | H | H | 0 | H | H | Me | OPr | CF$_3$ |
| Me | Me | H | H | 0 | H | H | Me | OBu-t | CF$_3$ |
| Me | Me | H | H | 0 | H | H | Me | OCH$_2$Pr-c | CF$_3$ |
| Me | Me | H | H | 0 | H | H | Me | OCH$_2$Bu-c | CF$_3$ |
| Me | Me | H | H | 0 | H | H | Me | OCH$_2$Pen-c | CF$_3$ |
| Me | Me | H | H | 0 | H | H | Me | OCH$_2$Hex-c | CF$_3$ |
| Me | Me | H | H | 0 | H | H | Me | OPen-c | CF$_3$ |
| Me | Me | H | H | 0 | H | H | Me | OHex-c | CF$_3$ |
| Me | Me | H | H | 0 | H | H | Me | OCH$_2$Ph | CF$_3$ |
| Me | Me | H | H | 0 | H | H | Me | OPh | CF$_3$ |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 0 | H | H | Me | OCHF$_2$ | CF$_3$ |
| Me | Me | H | H | 0 | H | H | Me | SH | CF$_3$ |
| Me | Me | H | H | 0 | H | H | Me | SMe | CF$_3$ |
| Me | Me | H | H | 0 | H | H | Me | SO$_2$Me | CF$_3$ |
| Me | Me | H | H | 0 | H | H | Me | SEt | CF$_3$ |
| Me | Me | H | H | 0 | H | H | Me | SO$_2$Et | CF$_3$ |
| Me | Me | H | H | 0 | H | H | Me | SPr-i | CF$_3$ |
| Me | Me | H | H | 0 | H | H | Me | SO$_2$Pr-i | CF$_3$ |
| Me | Me | H | H | 0 | H | H | Me | SPh | CF$_3$ |
| Me | Me | H | H | 0 | H | H | Me | SO$_2$Ph | CF$_3$ |
| Me | Me | H | H | 0 | H | H | Me | SCHF$_2$ | CF$_3$ |
| Me | Me | H | H | 0 | H | H | Me | SO$_2$CHF$_2$ | CF$_3$ |
| Me | Me | H | H | 0 | H | H | Me | NH$_2$ | CF$_3$ |
| Me | Me | H | H | 0 | H | H | Me | NHMe | CF$_3$ |
| Me | Me | H | H | 0 | H | H | Me | NMe$_2$ | CF$_3$ |
| Me | Me | H | H | 0 | H | H | Me | NHEt | CF$_3$ |
| Me | Me | H | H | 0 | H | H | Me | NEt$_2$ | CF$_3$ |
| Me | Me | H | H | 0 | H | H | Me | NHPh | CF$_3$ |
| Me | Me | H | H | 0 | H | H | Me | N(Me)Ph | CF$_3$ |
| Me | Me | H | H | 0 | H | H | Me | CN | CF$_3$ |
| Me | Me | H | H | 0 | H | H | OMe | F | CF$_3$ |
| Me | Me | H | H | 0 | H | H | OMe | Cl | CF$_3$ |
| Me | Me | H | H | 0 | H | H | OMe | OH | CF$_3$ |
| Me | Me | H | H | 0 | H | H | OMe | OMe | CF$_3$ |
| Me | Me | H | H | 0 | H | H | OMe | OEt | CF$_3$ |
| Me | Me | H | H | 0 | H | H | OMe | OPr-i | CF$_3$ |
| Me | Me | H | H | 0 | H | H | OMe | OPr | CF$_3$ |
| Me | Me | H | H | 0 | H | H | OMe | OBu-t | CF$_3$ |
| Me | Me | H | H | 0 | H | H | OMe | OCH$_2$Pr-c | CF$_3$ |
| Me | Me | H | H | 0 | H | H | OMe | OCH$_2$Bu-c | CF$_3$ |
| Me | Me | H | H | 0 | H | H | OMe | OCH$_2$Pen-c | CF$_3$ |
| Me | Me | H | H | 0 | H | H | OMe | OCH$_2$Hex-c | CF$_3$ |
| Me | Me | H | H | 0 | H | H | OMe | OPen-c | CF$_3$ |
| Me | Me | H | H | 0 | H | H | OMe | OHex-c | CF$_3$ |
| Me | Me | H | H | 0 | H | H | OMe | OCH$_2$Ph | CF$_3$ |
| Me | Me | H | H | 0 | H | H | OMe | OPh | CF$_3$ |
| Me | Me | H | H | 0 | H | H | OMe | OCHF$_2$ | CF$_3$ |
| Me | Me | H | H | 0 | H | H | OMe | SH | CF$_3$ |
| Me | Me | H | H | 0 | H | H | OMe | SMe | CF$_3$ |
| Me | Me | H | H | 0 | H | H | OMe | SO$_2$Me | CF$_3$ |
| Me | Me | H | H | 0 | H | H | OMe | SEt | CF$_3$ |
| Me | Me | H | H | 0 | H | H | OMe | SO$_2$Et | CF$_3$ |
| Me | Me | H | H | 0 | H | H | OMe | SPr-i | CF$_3$ |
| Me | Me | H | H | 0 | H | H | OMe | SO$_2$Pr-i | CF$_3$ |
| Me | Me | H | H | 0 | H | H | OMe | SPh | CF$_3$ |
| Me | Me | H | H | 0 | H | H | OMe | SO$_2$Ph | CF$_3$ |
| Me | Me | H | H | 0 | H | H | OMe | SCHF$_2$ | CF$_3$ |
| Me | Me | H | H | 0 | H | H | OMe | SO$_2$CHF$_2$ | CF$_3$ |
| Me | Me | H | H | 0 | H | H | OMe | NH$_2$ | CF$_3$ |
| Me | Me | H | H | 0 | H | H | OMe | NHMe | CF$_3$ |
| Me | Me | H | H | 0 | H | H | OMe | NMe$_2$ | CF$_3$ |
| Me | Me | H | H | 0 | H | H | OMe | NHEt | CF$_3$ |
| Me | Me | H | H | 0 | H | H | OMe | NEt$_2$ | CF$_3$ |
| Me | Me | H | H | 0 | H | H | OMe | NHPh | CF$_3$ |
| Me | Me | H | H | 0 | H | H | OMe | N(Me)Ph | CF$_3$ |
| Me | Me | H | H | 0 | H | H | OMe | CN | CF$_3$ |
| Me | Me | H | H | 0 | H | H | SMe | F | CF$_3$ |
| Me | Me | H | H | 0 | H | H | SMe | Cl | CF$_3$ |
| Me | Me | H | H | 0 | H | H | SMe | OH | CF$_3$ |
| Me | Me | H | H | 0 | H | H | SMe | OMe | CF$_3$ |
| Me | Me | H | H | 0 | H | H | SMe | OEt | CF$_3$ |
| Me | Me | H | H | 0 | H | H | SMe | OPr-i | CF$_3$ |
| Me | Me | H | H | 0 | H | H | SMe | OPr | CF$_3$ |
| Me | Me | H | H | 0 | H | H | SMe | OBu-t | CF$_3$ |
| Me | Me | H | H | 0 | H | H | SMe | OCH$_2$Pr-c | CF$_3$ |
| Me | Me | H | H | 0 | H | H | SMe | OCH$_2$Bu-c | CF$_3$ |

TABLE 8-continued

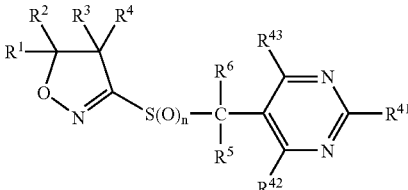

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 0 | H | H | SMe | OCH₂Pen-c | CF₃ |
| Me | Me | H | H | 0 | H | H | SMe | OCH₂Hex-c | CF₃ |
| Me | Me | H | H | 0 | H | H | SMe | OPen-c | CF₃ |
| Me | Me | H | H | 0 | H | H | SMe | OHex-c | CF₃ |
| Me | Me | H | H | 0 | H | H | SMe | OCH₂Ph | CF₃ |
| Me | Me | H | H | 0 | H | H | SMe | OPh | CF₃ |
| Me | Me | H | H | 0 | H | H | SMe | OCHF₂ | CF₃ |
| Me | Me | H | H | 0 | H | H | SMe | SH | CF₃ |
| Me | Me | H | H | 0 | H | H | SMe | SMe | CF₃ |
| Me | Me | H | H | 0 | H | H | SMe | SO₂Me | CF₃ |
| Me | Me | H | H | 0 | H | H | SMe | SEt | CF₃ |
| Me | Me | H | H | 0 | H | H | SMe | SO₂Et | CF₃ |
| Me | Me | H | H | 0 | H | H | SMe | SPr-i | CF₃ |
| Me | Me | H | H | 0 | H | H | SMe | SO₂Pr-i | CF₃ |
| Me | Me | H | H | 0 | H | H | SMe | SPh | CF₃ |
| Me | Me | H | H | 0 | H | H | SMe | SO₂Ph | CF₃ |
| Me | Me | H | H | 0 | H | H | SMe | SCHF₂ | CF₃ |
| Me | Me | H | H | 0 | H | H | SMe | SO₂CHF₂ | CF₃ |
| Me | Me | H | H | 0 | H | H | SMe | NH₂ | CF₃ |
| Me | Me | H | H | 0 | H | H | SMe | NHMe | CF₃ |
| Me | Me | H | H | 0 | H | H | SMe | NMe₂ | CF₃ |
| Me | Me | H | H | 0 | H | H | SMe | NHEt | CF₃ |
| Me | Me | H | H | 0 | H | H | SMe | NEt₂ | CF₃ |
| Me | Me | H | H | 0 | H | H | SMe | NHPh | CF₃ |
| Me | Me | H | H | 0 | H | H | SMe | N(Me)Ph | CF₃ |
| Me | Me | H | H | 0 | H | H | SMe | CN | CF₃ |
| Me | Me | H | H | 0 | H | H | SO₂Me | F | CF₃ |
| Me | Me | H | H | 0 | H | H | SO₂Me | Cl | CF₃ |
| Me | Me | H | H | 0 | H | H | SO₂Me | OH | CF₃ |
| Me | Me | H | H | 0 | H | H | SO₂Me | OMe | CF₃ |
| Me | Me | H | H | 0 | H | H | SO₂Me | OEt | CF₃ |
| Me | Me | H | H | 0 | H | H | SO₂Me | OPr-i | CF₃ |
| Me | Me | H | H | 0 | H | H | SO₂Me | OPr | CF₃ |
| Me | Me | H | H | 0 | H | H | SO₂Me | OBu-t | CF₃ |
| Me | Me | H | H | 0 | H | H | SO₂Me | OCH₂Pr-c | CF₃ |
| Me | Me | H | H | 0 | H | H | SO₂Me | OCH₂Bu-c | CF₃ |
| Me | Me | H | H | 0 | H | H | SO₂Me | OCH₂Pen-c | CF₃ |
| Me | Me | H | H | 0 | H | H | SO₂Me | OCH₂Hex-c | CF₃ |
| Me | Me | H | H | 0 | H | H | SO₂Me | OPen-c | CF₃ |
| Me | Me | H | H | 0 | H | H | SO₂Me | OHex-c | CF₃ |
| Me | Me | H | H | 0 | H | H | SO₂Me | OCH₂Ph | CF₃ |
| Me | Me | H | H | 0 | H | H | SO₂Me | OPh | CF₃ |
| Me | Me | H | H | 0 | H | H | SO₂Me | OCHF₂ | CF₃ |
| Me | Me | H | H | 0 | H | H | SO₂Me | SH | CF₃ |
| Me | Me | H | H | 0 | H | H | SO₂Me | SMe | CF₃ |
| Me | Me | H | H | 0 | H | H | SO₂Me | SO₂Me | CF₃ |
| Me | Me | H | H | 0 | H | H | SO₂Me | SEt | CF₃ |
| Me | Me | H | H | 0 | H | H | SO₂Me | SO₂Et | CF₃ |
| Me | Me | H | H | 0 | H | H | SO₂Me | SPr-i | CF₃ |
| Me | Me | H | H | 0 | H | H | SO₂Me | SO₂Pr-i | CF₃ |
| Me | Me | H | H | 0 | H | H | SO₂Me | SPh | CF₃ |
| Me | Me | H | H | 0 | H | H | SO₂Me | SO₂Ph | CF₃ |
| Me | Me | H | H | 0 | H | H | SO₂Me | SCHF₂ | CF₃ |
| Me | Me | H | H | 0 | H | H | SO₂Me | SO₂CHF₂ | CF₃ |
| Me | Me | H | H | 0 | H | H | SO₂Me | NH₂ | CF₃ |
| Me | Me | H | H | 0 | H | H | SO₂Me | NHMe | CF₃ |
| Me | Me | H | H | 0 | H | H | SO₂Me | NMe₂ | CF₃ |
| Me | Me | H | H | 0 | H | H | SO₂Me | NHEt | CF₃ |
| Me | Me | H | H | 0 | H | H | SO₂Me | NEt₂ | CF₃ |
| Me | Me | H | H | 0 | H | H | SO₂Me | NHPh | CF₃ |
| Me | Me | H | H | 0 | H | H | SO₂Me | N(Me)Ph | CF₃ |
| Me | Me | H | H | 0 | H | H | SO₂Me | CN | CF₃ |
| Me | Me | H | H | 0 | H | H | NH₂ | F | CF₃ |
| Me | Me | H | H | 0 | H | H | NH₂ | Cl | CF₃ |
| Me | Me | H | H | 0 | H | H | NH₂ | OH | CF₃ |
| Me | Me | H | H | 0 | H | H | NH₂ | OMe | CF₃ |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| Me | Me | H | H | 0 | H | H | NH₂ | OEt | CF₃ |
| Me | Me | H | H | 0 | H | H | NH₂ | OPr-i | CF₃ |
| Me | Me | H | H | 0 | H | H | NH₂ | OPr | CF₃ |
| Me | Me | H | H | 0 | H | H | NH₂ | OBu-t | CF₃ |
| Me | Me | H | H | 0 | H | H | NH₂ | OCH₂Pr-c | CF₃ |
| Me | Me | H | H | 0 | H | H | NH₂ | OCH₂Bu-c | CF₃ |
| Me | Me | H | H | 0 | H | H | NH₂ | OCH₂Pen-c | CF₃ |
| Me | Me | H | H | 0 | H | H | NH₂ | OCH₂Hex-c | CF₃ |
| Me | Me | H | H | 0 | H | H | NH₂ | OPen-c | CF₃ |
| Me | Me | H | H | 0 | H | H | NH₂ | OHex-c | CF₃ |
| Me | Me | H | H | 0 | H | H | NH₂ | OCH₂Ph | CF₃ |
| Me | Me | H | H | 0 | H | H | NH₂ | OPh | CF₃ |
| Me | Me | H | H | 0 | H | H | NH₂ | OCHF₂ | CF₃ |
| Me | Me | H | H | 0 | H | H | NH₂ | SH | CF₃ |
| Me | Me | H | H | 0 | H | H | NH₂ | SMe | CF₃ |
| Me | Me | H | H | 0 | H | H | NH₂ | SO₂Me | CF₃ |
| Me | Me | H | H | 0 | H | H | NH₂ | SEt | CF₃ |
| Me | Me | H | H | 0 | H | H | NH₂ | SO₂Et | CF₃ |
| Me | Me | H | H | 0 | H | H | NH₂ | SPr-i | CF₃ |
| Me | Me | H | H | 0 | H | H | NH₂ | SO₂Pr-i | CF₃ |
| Me | Me | H | H | 0 | H | H | NH₂ | SPh | CF₃ |
| Me | Me | H | H | 0 | H | H | NH₂ | SO₂Ph | CF₃ |
| Me | Me | H | H | 0 | H | H | NH₂ | SCHF₂ | CF₃ |
| Me | Me | H | H | 0 | H | H | NH₂ | SO₂CHF₂ | CF₃ |
| Me | Me | H | H | 0 | H | H | NH₂ | NH₂ | CF₃ |
| Me | Me | H | H | 0 | H | H | NH₂ | NHMe | CF₃ |
| Me | Me | H | H | 0 | H | H | NH₂ | NMe₂ | CF₃ |
| Me | Me | H | H | 0 | H | H | NH₂ | NHEt | CF₃ |
| Me | Me | H | H | 0 | H | H | NH₂ | NEt₂ | CF₃ |
| Me | Me | H | H | 0 | H | H | NH₂ | NHPh | CF₃ |
| Me | Me | H | H | 0 | H | H | NH₂ | N(Me)Ph | CF₃ |
| Me | Me | H | H | 0 | H | H | NH₂ | CN | CF₃ |
| H | H | H | H | 0 | H | H | H | OMe | CF₃ |
| H | H | H | H | 0 | H | H | H | OEt | CF₃ |
| Me | H | H | H | 0 | H | H | H | OMe | CF₃ |
| Me | H | H | H | 0 | H | H | H | OEt | CF₃ |
| Me | H | Me | H | 0 | H | H | H | OMe | CF₃ |
| Me | H | Me | H | 0 | H | H | H | OEt | CF₃ |
| Me | Me | H | H | 0 | Me | H | H | OMe | CF₃ |
| Me | Me | H | H | 0 | Me | H | H | OEt | CF₃ |
| Me | Me | H | H | 0 | Et | H | H | OMe | CF₃ |
| Me | Me | H | H | 0 | Et | H | H | OEt | CF₃ |
| Me | Me | H | H | 0 | Pr-i | H | H | H | CF₃ |
| Me | Me | H | H | 0 | Pr-i | H | H | OMe | CF₃ |
| Me | Me | H | H | 0 | Pr-i | H | H | OEt | CF₃ |
| Me | Me | H | H | 0 | Me | Me | H | OMe | CF₃ |
| Me | Me | H | H | 0 | Me | Me | H | OEt | CF₃ |
| Me | Et | H | H | 0 | H | H | H | OMe | CF₃ |
| Me | Et | H | H | 0 | H | H | H | OEt | CF₃ |
| Et | Et | H | H | 0 | H | H | H | OMe | CF₃ |
| Et | Et | H | H | 0 | H | H | H | OEt | CF₃ |
| Me | Pr-i | H | H | 0 | H | H | H | OMe | CF₃ |
| Me | Pr-i | H | H | 0 | H | H | H | OEt | CF₃ |
| Me | Pr | H | H | 0 | H | H | H | OMe | CF₃ |
| Me | Pr | H | H | 0 | H | H | H | OEt | CF₃ |
| Me | Pr-c | H | H | 0 | H | H | H | OMe | CF₃ |
| Me | Pr-c | H | H | 0 | H | H | H | OEt | CF₃ |
| Me | CH₂Pr-c | H | H | 0 | H | H | H | OMe | CF₃ |
| Me | CH₂Pr-c | H | H | 0 | H | H | H | OEt | CF₃ |
| —(CH₂)₂— | | H | H | 0 | H | H | H | OMe | CF₃ |
| —(CH₂)₂— | | H | H | 0 | H | H | H | OEt | CF₃ |
| —(CH₂)₃— | | H | H | 0 | H | H | H | OMe | CF₃ |
| —(CH₂)₃— | | H | H | 0 | H | H | H | OEt | CF₃ |
| —(CH₂)₄— | | H | H | 0 | H | H | H | OMe | CF₃ |
| —(CH₂)₄— | | H | H | 0 | H | H | H | OEt | CF₃ |
| —(CH₂)₅— | | H | H | 0 | H | H | H | OMe | CF₃ |

TABLE 8-continued

| R¹ | R² | R³ | R⁴ | n | R⁵ | R⁶ | R⁴¹ | R⁴² | R⁴³ |
|---|---|---|---|---|---|---|---|---|---|
| —(CH₂)₅— | H | H | H | 0 | H | H | H | OEt | CF₃ |
| H | —(CH₂)₃— | H | H | 0 | H | H | H | OMe | CF₃ |
| H | —(CH₂)₃— | H | H | 0 | H | H | H | OEt | CF₃ |
| H | —(CH₂)₄— | H | H | 0 | H | H | H | OMe | CF₃ |
| H | —(CH₂)₄— | H | H | 0 | H | H | H | OEt | CF₃ |
| H | —(CH₂)₅— | H | H | 0 | H | H | H | OMe | CF₃ |
| H | —(CH₂)₅— | H | H | 0 | H | H | H | OEt | CF₃ |
| H | —(CH₂)₆— | H | H | 0 | H | H | H | OMe | CF₃ |
| H | —(CH₂)₆— | H | H | 0 | H | H | H | OEt | CF₃ |

TABLE 9

| R¹ | R² | R³ | R⁴ | n | R⁵ | R⁶ | Y¹ |
|---|---|---|---|---|---|---|---|
| Me | Me | H | H | 2 | H | H | Pyridin-2-yl |
| Me | Me | H | H | 2 | H | H | Pyridin-2-yl 1-oxide |
| Me | Me | H | H | 2 | H | H | Pyridin-4-yl |
| Me | Me | H | H | 2 | H | H | Pyridin-4-yl 1-oxide |
| Me | Me | H | H | 2 | H | H | 1,2,4-Oxadiazol-3-yl |
| Me | Me | H | H | 2 | H | H | 3-Phenyl-1,2,4-oxadiazol-5-yl |
| Me | Me | H | H | 2 | H | H | 3-Benzyl-1,2,4-oxadiazol-5-yl |
| Me | Me | H | H | 2 | H | H | 2-Chlorothiazol-4-yl |
| Me | Me | H | H | 2 | H | H | 5-Trifluoromethyl-1,3,4-thiadiazol-2-yl |
| Me | Me | H | H | 2 | H | H | 1,4-Dimethylimidazol-5-yl |
| Me | Me | H | H | 2 | H | H | 1-Phenyl-4-methoxycarbonyl-1,2,3-triazol-5-yl |
| Me | Me | H | H | 2 | H | H | 1-Difluoromethyl-1,2,4-triazol-3-yl |
| Me | Me | H | H | 2 | H | H | 1-Difluoromethyl-1,2,4-triazol-5-yl |
| Me | Me | H | H | 2 | H | H | 4-Difluoromethyl-1,2,4-triazol-3-yl |
| Me | Me | H | H | 2 | H | H | 4,6-Dimethoxypyrimidin-2-yl |
| Me | Me | H | H | 2 | H | H | 4,6-Diethoxypyrimidin-2-yl |
| Me | Me | H | H | 2 | H | H | 4,6-Dimethylpyrimidin-2-yl |
| Me | Me | H | H | 2 | H | H | 4-Chloro-6-methylpyrimidin-2-yl |
| Me | Me | H | H | 2 | H | H | 4-Methoxy-6-methylpyrimidin-2-yl |
| Me | Me | H | H | 2 | H | H | 4-Difluoromethoxy-6-metbylpyrimidin-2-yl |
| Me | Me | H | H | 2 | H | H | 4-Phenoxy-6-methylpyrimidin-2-yl |
| Me | Me | H | H | 2 | H | H | 4-Chloro-6-trifluoromethylpyrimidin-2-yl |
| Me | Me | H | H | 2 | H | H | 4-Methoxy-6-trifluoromethylpyrimidin-2-yl |
| Me | Me | H | H | 2 | H | H | 4-Difluoromethoxy-6-trifluoromethylpyrimidin-2-yl |
| Me | Me | H | H | 2 | H | H | 4-Phenoxy-6-trifluoromethylpyrimidin-2-yl |
| H | H | H | H | 2 | H | H | 4,6-Dimethoxypyrimidin-2-yl |
| Me | H | H | H | 2 | H | H | 4,6-Dimethoxypyrimidin-2-yl |
| Me | H | Me | H | 2 | H | H | 4,6-Dimethoxypyrimidin-2-yl |
| Me | Me | H | H | 2 | Me | H | 4,6-Dimethoxypyrimidin-2-yl |
| Me | Me | H | H | 2 | Et | H | 4,6-Dimethoxypyrimidin-2-yl |
| Me | Me | H | H | 2 | Pr-i | H | 4,6-Dimethoxypyrimidin-2-yl |
| Me | Me | H | H | 2 | Me | Me | 4,6-Dirnetboxypyrimidin-2-yl |
| Me | Et | H | H | 2 | H | H | 4,6-Dimethoxypyrimidin-2-yl |
| Et | Et | H | H | 2 | H | H | 4,6-Dimethoxypyrimidin-2-yl |
| Me | Pr-i | H | H | 2 | H | H | 4,6-Dimethoxypyrimidin-2-yl |
| Me | Pr | H | H | 2 | H | H | 4,6-Dimethoxypyrimidin-2-yl |
| Me | Pr-c | H | H | 2 | H | H | 4,6-Dimethoxypyrimidin-2-yl |
| Me | CH₂Pr-c | H | H | 2 | H | H | 4,6-Dimethoxypyrimidin-2-yl |
| —(CH₂)₂— | | H | H | 2 | H | H | 4,6-Dimethoxypyrimidin-2-yl |
| —(CH₂)₃— | | H | H | 2 | H | H | 4,6-Dimethoxypyrimidin-2-yl |
| —(CH₂)₄— | | H | H | 2 | H | H | 4,6-Dimethoxypyrimidin-2-yl |

TABLE 9-continued

Structure: isoxazoline with R¹, R² on C5; R³, R⁴ on C4; S(O)ₙ-C(R⁵)(R⁶)-Y¹ on C3

| R¹ | R² | R³ | R⁴ | n | R⁵ | R⁶ | Y¹ |
|---|---|---|---|---|---|---|---|
| —(CH₂)₅— | | H | H | 2 | H | H | 4,6-Dimethoxypyrimidin-2-yl |
| H | —(CH₂)₃— | H | H | 2 | H | H | 4,6-Dimethoxypyrimidin-2-yl |
| H | —(CH₂)₄— | H | H | 2 | H | H | 4,6-Dimethoxypyrimidin-2-yl |
| H | —(CH₂)₅— | H | H | 2 | H | H | 4,6-Dimethoxypyrimidin-2-yl |
| H | —(CH₂)₆— | H | H | 2 | H | H | 4,6-Dimethoxypyrimidin-2-yl |
| Me | Me | H | H | 1 | H | H | Pyridin-2-yl |
| Me | Me | H | H | 1 | H | H | Pyridin-2-yl 1-oxide |
| Me | Me | H | H | 1 | H | H | Pyridin-4-yl |
| Me | Me | H | H | 1 | H | H | Pyridin-4-yl 1-oxide |
| Me | Me | H | H | 1 | H | H | 1,2,4-Oxadiazol-3-yl |
| Me | Me | H | H | 1 | H | H | 3-Phenyl-1,2,4-oxadiazol-5-yl |
| Me | Me | H | H | 1 | H | H | 3-Benzyl-1,2,4-oxadiazol-5-yl |
| Me | Me | H | H | 1 | H | H | 2-Chlorothiazol-4-yl |
| Me | Me | H | H | 1 | H | H | 5-Trifluoromethyl-1,3,4-thiadiazol-2-yl |
| Me | Me | H | H | 1 | H | H | 1,4-Dimethylimidazol-5-yl |
| Me | Me | H | H | 1 | H | H | 1-Phenyl-4-methoxycarbonyl-1,2,3-triazol-5-yl |
| Me | Me | H | H | 1 | H | H | 1-Difluoromethyl-1,2,4-triazol-3-yl |
| Me | Me | H | H | 1 | H | H | 1-Difluoromethyl-1,2,4-triazol-5-yl |
| Me | Me | H | H | 1 | H | H | 4-Difluoromethyl-1,2,4-triazol-3-yl |
| Me | Me | H | H | 1 | H | H | 4,6-Dimethoxypyrimidin-2-yl |
| Me | Me | H | H | 1 | H | H | 4,6-Diethoxypyrimidin-2-yl |
| Me | Me | H | H | 1 | H | H | 4,6-Dimethylpyrimidin-2-yl |
| Me | Me | H | H | 1 | H | H | 4-Chloro-6-methylpyrimidin-2-yl |
| Me | Me | H | H | 1 | H | H | 4-Methoxy-6-methylpyrimidin-2-yl |
| Me | Me | H | H | 1 | H | H | 4-Difluoromethoxy-6-methylpyrimidin-2-yl |
| Me | Me | H | H | 1 | H | H | 4-Phenoxy-6-methylpyrimidin-2-yl |
| Me | Me | H | H | 1 | H | H | 4-Chloro-6-trifluoromethylpyrimidin-2-yl |
| Me | Me | H | H | 1 | H | H | 4-Methoxy-6-trifluoromethylpyrimidin-2-yl |
| Me | Me | H | H | 1 | H | H | 4-Difluoromethoxy-6-trifluoromethylpyrimidin-2-yl |
| Me | Me | H | H | 1 | H | H | 4-Phenoxy-6-trifluoromethylpyrimidin-2-yl |
| H | H | H | H | 1 | H | H | 4,6-Dimethoxypyrimidin-2-yl |
| Me | H | H | H | 1 | H | H | 4,6-Dimethoxypyrimidin-2-yl |
| Me | H | Me | H | 1 | H | H | 4,6-Dimethoxypyrimidin-2-yl |
| Me | Me | H | H | 1 | Me | H | 4,6-Dimethokypyrimidin-2-yl |
| Me | Me | H | H | 1 | Et | H | 4,6-Dimethoxypyrimidin-2-yl |
| Me | Me | H | H | 1 | Pr-i | H | 4,6-Dimethoxypyrimidin-2-yl |
| Me | Me | H | H | 1 | Me | Me | 4,6-Dimethoxypyrimidin-2-yl |
| Me | Et | H | H | 1 | H | H | 4,6-Dimethoxypyrimidin-2-yl |
| Et | Et | H | H | 1 | H | H | 4,6-Dimethoxypyrimidin-2-yl |
| Me | Pr-i | H | H | 1 | H | H | 4,6-Dimethoxypyrimidin-2-yl |
| Me | Pr | H | H | 1 | H | H | 4,6-Dimethoxypyrimidin-2-yl |
| Me | Pr-c | H | H | 1 | H | H | 4,6-Dimethoxypyrimidin-2-yl |
| Me | CH₂Pr-c | H | H | 1 | H | H | 4,6-Dimethoxypyrimidin-2-yl |
| —(CH₂)₂— | | H | H | 1 | H | H | 4,6-Dimethoxypyrimidin-2-yl |
| —(CH₂)₃— | | H | H | 1 | H | H | 4,6-Dimethoxypyrimidin-2-yl |
| —(CH₂)₄— | | H | H | 1 | H | H | 4,6-Dimethoxypyrimidin-2-yl |
| —(CH₂)₅— | | H | H | 1 | H | H | 4,6-Dimethoxypyrimidin-2-yl |
| H | —(CH₂)₃— | H | H | 1 | H | H | 4,6-Dimethoxypyrimidin-2-yl |
| H | —(CH₂)₄— | H | H | 1 | H | H | 4,6-Dimethoxypyrimidin-2-yl |
| H | —(CH₂)₅— | H | H | 1 | H | H | 4,6-Dimethoxypyrimidin-2-yl |
| H | —(CH₂)₆— | H | H | 1 | H | H | 4,6-Dimethoxypyrimidin-2-yl |
| Me | Me | H | H | 0 | H | H | Pyridin-2-yl |
| Me | Me | H | H | 0 | H | H | Pyridin-2-yl 1-oxide |
| Me | Me | H | H | 0 | H | H | Pyridin-4-yl |
| Me | Me | H | H | 0 | H | H | Pyridin-4-yl 1-oxide |
| Me | Me | H | H | 0 | H | H | 1,2,4-Oxadiazol-3-yl |
| Me | Me | H | H | 0 | H | H | 3-Phenyl-1,2,4-oxadiazol-5-yl |
| Me | Me | H | H | 0 | H | H | 3-Benzyl-1,2,4-oxadiazol-5-yl |
| Me | Me | H | H | 0 | H | H | 2-Chlorothiazol-4-yl |
| Me | Me | H | H | 0 | H | H | 5-Trifluoromethyl-1,3,4-thiadiazol-2-yl |
| Me | Me | H | H | 0 | H | H | 1,4-Dimethylimidazol-5-yl |
| Me | Me | H | H | 0 | H | H | 1-Phenyl-4-methoxycarbonyl-1,2,3-triazol-5-yl |
| Me | Me | H | H | 0 | H | H | 1-Difluoromethyl-1,2,4-triazol-3-yl |
| Me | Me | H | H | 0 | H | H | 1-Difluoromethyl-1,2,4-triazol-5-yl |
| Me | Me | H | H | 0 | H | H | 4-Difluoromethyl-1,2,4-triazol-3-yl |
| Me | Me | H | H | 0 | H | H | 4,6-Dimethoxypyrimidin-2-yl |
| Me | Me | H | H | 0 | H | H | 4,6-Diethoxypyrimidin-2-yl |

TABLE 9-continued

Structure: R¹, R² on C5; R³, R⁴ on C4 of isoxazoline (O-N=C-); C3 bears S(O)ₙ-C(R⁵)(R⁶)-Y¹

| R¹ | R² | R³ | R⁴ | n | R⁵ | R⁶ | Y¹ |
|---|---|---|---|---|---|---|---|
| Me | Me | H | H | 0 | H | H | 4,6-Dimethylpyrimidin-2-yl |
| Me | Me | H | H | 0 | H | H | 4-Chloro-6-methylpyrimidin-2-yl |
| Me | Me | H | H | 0 | H | H | 4-Methoxy-6-methylpyrimidin-2-yl |
| Me | Me | H | H | 0 | H | H | 4-Difluoromethoxy-6-methylpyrimidin-2-yl |
| Me | Me | H | H | 0 | H | H | 4-Phenoxy-6-methylpyrimidin-2-yl |
| Me | Me | H | H | 0 | H | H | 4-Chloro-6-trifluoromethylpyrimidin-2-yl |
| Me | Me | H | H | 0 | H | H | 4-Methoxy-6-trifluoromethylpyrimidin-2-yl |
| Me | Me | H | H | 0 | H | H | 4-Difluoromethoxy-6-trifluoromethylpyrimidin-2-yl |
| Me | Me | H | H | 0 | H | H | 4-Phenoxy-6-trifluoromethylpyrimidin-2-yl |
| H | H | H | H | 0 | H | H | 4,6-Dimethoxypyrimidin-2-yl |
| Me | H | H | H | 0 | H | H | 4,6-Dimethoxypyrimidin-2-yl |
| Me | H | Me | H | 0 | H | H | 4,6-Dimethoxypyrimidin-2-yl |
| Me | Me | H | H | 0 | Me | H | 4,6-Dimethoxypyrimidin-2-yl |
| Me | Me | H | H | 0 | Et | H | 4,6-Dimethoxypyrimidin-2-yl |
| Me | Me | H | H | 0 | Pr-i | H | 4,6-Dimethoxypyrimidin-2-yl |
| Me | Me | H | H | 0 | Me | Me | 4,6-Dimethoxypyrimidin-2-yl |
| Me | Et | H | H | 0 | H | H | 4,6-Dimethoxypyrimidin-2-yl |
| Et | Et | H | H | 0 | H | H | 4,6-Dimethoxypyrimidin-2-yl |
| Me | Pr-i | H | H | 0 | H | H | 4,6-Dimethoxypyrimidin-2-yl |
| Me | Pr | H | H | 0 | H | H | 4,6-Dimethoxypyrimidin-2-yl |
| Me | Pr-c | H | H | 0 | H | H | 4,6-Dimethoxypyrimidin-2-yl |
| Me | CH₂Pr-c | H | H | 0 | H | H | 4,6-Dimethoxypyrimidin-2-yl |
| —(CH₂)₂— | | H | H | 0 | H | H | 4,6-Dimethoxypyrimidin-2-yl |
| —(CH₂)₃— | | H | H | 0 | H | H | 4,6-Dimethoxypyrimidin-2-yl |
| —(CH₂)₄— | | H | H | 0 | H | H | 4,6-Dimethoxypyrimidin-2-yl |
| —(CH₂)₅— | | H | H | 0 | H | H | 4,6-Dimethoxypyrimidin-2-yl |
| H | —(CH₂)₃— | | H | 0 | H | H | 4,6-Dimethoxypyrimidin-2-yl |
| H | —(CH₂)₄— | | H | 0 | H | H | 4,6-Dimethoxypyrimidin-2-yl |
| H | —(CH₂)₅— | | H | 0 | H | H | 4,6-Dimethoxypyrimidin-2-yl |
| H | —(CH₂)₆— | | H | 0 | H | H | 4,6-Dimethoxypyrimidin-2-yl |
| Me | Et | H | H | 2 | H | H | Pirrol-1-yl |
| Me | Et | H | H | 2 | H | H | Oxazol-2-yl |
| Me | Et | H | H | 2 | H | H | Thiazol-2-yl |
| Me | Et | H | H | 2 | H | H | Thiazol-4-yl |
| Me | Et | H | H | 2 | H | H | 1,2,3-Thiadiazol-4-yl |
| Me | Et | H | H | 2 | H | H | 1,2,3-Thiadiazol-5-yl |
| Me | Et | H | H | 2 | H | H | 1,2,4-Thiadiazol-3-yl |
| Me | Et | H | H | 2 | H | H | 1,2,4-Thiadiazol-5-yl |
| Me | Et | H | H | 2 | H | H | 1,3,4-Thiadiazol-2-yl |
| Me | Et | H | H | 2 | H | H | 1,3,4-Thiadiazol-5-yl |
| Me | Et | H | H | 2 | H | H | Pyridin-2-yl |
| Me | Et | H | H | 2 | H | H | Pyridin-3-yl |
| Me | Et | H | H | 2 | H | H | Pyridin-4-yl |
| Me | Et | H | H | 2 | H | H | 1H-Imidazol-2-yl |
| Me | Et | H | H | 2 | H | H | 1H-Imidazol-4-yl |
| Me | Et | H | H | 2 | H | H | 1H-Imidazol-5-yl |
| Me | Et | H | H | 2 | H | H | 1H-1,3,4-Triazol-2-yl |
| Me | Et | H | H | 2 | H | H | 1H-1,3,4-Triazol-5-yl |

TABLE 10

| R¹ | R² | R³ | R⁴ | n | R⁵ | R⁶ | Y¹ |
|---|---|---|---|---|---|---|---|
| Me | Me | H | H | 2 | H | H | Benzimidazol-2-yl |
| Me | Me | H | H | 2 | H | H | Benzothiophen-2-yl |
| Me | Me | H | H | 2 | H | H | 3-Chlorobenzothiophen-2-yl |
| Me | Me | H | H | 2 | H | H | Benzotriazol-1-yl |

TABLE 10-continued

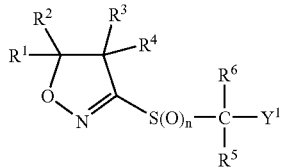

| R¹ | R² | R³ | R⁴ | n | R⁵ | R⁶ | Y¹ |
|----|----|----|----|---|----|----|----|
| Me | Me | H | H | 2 | H | H | 1-Methylindazol-4-yl |
| Me | Me | H | H | 2 | H | H | Benzothiazol-2-yl |
| Me | Me | H | H | 2 | H | H | Benzothiophen-3-yl |
| Me | Me | H | H | 2 | H | H | 5-Chlorobenzothiophen-3-yl |
| Me | Me | H | H | 2 | H | H | Benzoxazol-2-yl |
| Me | Me | H | H | 2 | H | H | 3-Methylbenzothiophen-2-yl |
| Me | Me | H | H | 2 | H | H | 3-Bromobenzothiophen-2-yl |
| Me | Me | H | H | 2 | H | H | Benzofuran-2-yl |
| Me | Me | H | H | 2 | H | H | 2-Methylbenzofuran-7-yl |
| Me | Me | H | H | 2 | H | H | 3-Bromobenzofuran-2-yl |
| Me | Me | H | H | 2 | H | H | Benzothiophen-7-yl |
| Me | Me | H | H | 2 | H | H | 1-Methylindazol-7-yl |
| Me | Me | H | H | 2 | H | H | 1-Difluoromethylindazol-7-yl |
| Me | Me | H | H | 2 | H | H | 3-Methylbenzofuran-2-yl |
| Me | Me | H | H | 2 | H | H | 3-Chloro-1-methylindol-2-yl |
| Me | Me | H | H | 1 | H | H | Benzimidazol-2-yl |
| Me | Me | H | H | 1 | H | H | Benzothiophen-2-yl |
| Me | Me | H | H | 1 | H | H | 3-Chlorobenzothiophen-2-yl |
| Me | Me | H | H | 1 | H | H | Benzotriazol-1-yl |
| Me | Me | H | H | 1 | H | H | 1-Methylindazol-4-yi |
| Me | Me | H | H | 1 | H | H | Benzothiazol-2-yl |
| Me | Me | H | H | 1 | H | H | Benzothiophen-3-yl |
| Me | Me | H | H | 1 | H | H | 5-Chlorobenzothiophen-3-yl |
| Me | Me | H | H | 1 | H | H | Benzoxazol-2-yl |
| Me | Me | H | H | 1 | H | H | 3-Methylbenzothiophen-2-yl |
| Me | Me | H | H | 1 | H | H | 3-Bromobenzothiophen-2-yl |
| Me | Me | H | H | 1 | H | H | Benzofuran-2-yl |
| Me | Me | H | H | 1 | H | H | 2-Methylbenzofuran-7-yl |
| Me | Me | H | H | 1 | H | H | 3-Bromobenzofuran-2-yl |
| Me | Me | H | H | 1 | H | H | Benzothiophen-7-yl |
| Me | Me | H | H | 1 | H | H | 1-Methylindazol-7-yl |
| Me | Me | H | H | 1 | H | H | 3-Methylbenzofuran-2-yl |
| Me | Me | H | H | 1 | H | H | 3-Chloro-1-methylindol-2-yl |
| Me | Me | H | H | 0 | H | H | Benzimidazol-2-yl |
| Me | Me | H | H | 0 | H | H | Benzothiophen-2-yl |
| Me | Me | H | H | 0 | H | H | 3-Chlorobenzothiophen-2-yl |
| Me | Me | H | H | 0 | H | H | Benzotriazol-1-yl |
| Me | Me | H | H | 0 | H | H | 1 -Methylindazol-4-yl |
| Me | Me | H | H | 0 | H | H | Benzothiazol-2-yl |
| Me | Me | H | H | 0 | H | H | Benzothiophen-3-yl |
| Me | Me | H | H | 0 | H | H | 5-Chlorobenzothiophen-3-yl |
| Me | Me | H | H | 0 | H | H | Benzoxazol-2-yl |
| Me | Me | H | H | 0 | H | H | 3-Methylbenzothiophen-2-yl |
| Me | Me | H | H | 0 | H | H | 3-Bromobenzothiophen-2-yl |
| Me | Me | H | H | 0 | H | H | Benzofuran-2-yl |
| Me | Me | H | H | 0 | H | H | 2-Methylbenzofuran-7-yl |
| Me | Me | H | H | 0 | H | H | 3-Bromobenzofuran-2-yl |
| Me | Me | H | H | 0 | H | H | Benzothiophen-7-yl |
| Me | Me | H | H | 0 | H | H | 1-Methylindazol-7-yl |
| Me | Me | H | H | 0 | H | H | 3-Methylbenzofuran-2-yl |
| Me | Me | H | H | 0 | H | H | 3-Chloro-1-methylindol-2-yl |
| Me | Et | H | H | 2 | H | H | Benzoxazol-2-yl |
| Me | Et | H | H | 2 | H | H | 4-Chlorobenzoxazol-2-yl |
| Me | Et | H | H | 2 | H | H | 5-Chlorobenzoxazol-2-yl |
| Me | Et | H | H | 2 | H | H | 6-Chlorobenzoxazol-2-yl |
| Me | Et | H | H | 2 | H | H | 7-Chlorobenzoxazol-2-yl |
| Me | Et | H | H | 2 | H | H | 4-Fluorobenzoxazol-2-yl |

TABLE 10-continued

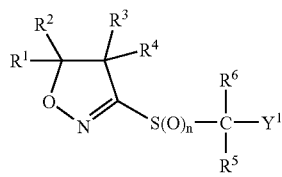

| R¹ | R² | R³ | R⁴ | n | R⁵ | R⁶ | Y¹ |
|----|----|----|----|---|----|----|----|
| Me | Et | H | H | 2 | H | H | 5-Fluorobenzoxazol-2-yl |
| Me | Et | H | H | 2 | H | H | 6-Fluorobenzoxazol-2-yl |
| Me | Et | H | H | 2 | H | H | 7-Fluorobenzoxazol-2-yl |
| Me | Et | H | H | 2 | H | H | 4-Methylbenzoxazol-2-yl |
| Me | Et | H | H | 2 | H | H | 5-Methylbenzoxazol-2-yl |
| Me | Et | H | H | 2 | H | H | 6-Methylbenzoxazol-2-yl |
| Me | Et | H | H | 2 | H | H | 7-Methylbenzoxazol-2-yl |
| Me | Et | H | H | 2 | H | H | 4-Methoxybenzoxazol-2-yl |
| Me | Et | H | H | 2 | H | H | 5-Methoxybenzoxazol-2-yl |
| Me | Et | H | H | 2 | H | H | 6-Methoxybenzoxazol-2-yl |
| Me | Et | H | H | 2 | H | H | 7-Methoxybenzoxazol-2-yl |
| Me | Et | H | H | 2 | H | H | Benzothiazol-2-yl |
| Me | Et | H | H | 2 | H | H | 4-Chlorobenzothiazol-2-yl |
| Me | Et | H | H | 2 | H | H | 5-Chlorobenzothiazol-2-yl |
| Me | Et | H | H | 2 | H | H | 6-Chlorobenzothiazol-2-yl |
| Me | Et | H | H | 2 | H | H | 7-Chlorobenzothiazol-2-yl |
| Me | Et | H | H | 2 | H | H | 4-Fluorobenzothiazol-2-yl |
| Me | Et | H | H | 2 | H | H | 5-Fluorobenzothiazol-2-yl |
| Me | Et | H | H | 2 | H | H | 6-Fluorobenzothiazol-2-yl |
| Me | Et | H | H | 2 | H | H | 7-Fluorobenzothiazol-2-yl |
| Me | Et | H | H | 2 | H | H | 4-Methylbenzothiazol-2-yl |
| Me | Et | H | H | 2 | H | H | 5-Methylbenzothiazol-2-yl |
| Me | Et | H | H | 2 | H | H | 6-Methylbenzothiazol-2-yl |
| Me | Et | H | H | 2 | H | H | 7-Methylbenzothiazol-2-yl |
| Me | Et | H | H | 2 | H | H | 4-Methoxybenzothiazol-2-yl |
| Me | Et | H | H | 2 | H | H | 5-Methoxybenzothiazol-2-yl |
| Me | Et | H | H | 2 | H | H | 6-Methoxybenzothiazol-2-yl |
| Me | Et | H | H | 2 | H | H | 7-Methoxybenzothiazol-2-yl |
| Me | Et | H | H | 2 | H | H | Qnolin-2-yl |
| Me | Et | H | H | 2 | H | H | Qinolin-6-yl |
| Me | Et | H | H | 2 | H | H | Quinoxalin-2-yl |
| Me | Et | H | H | 2 | H | H | Benzofuran-2-yl |
| Me | Et | H | H | 2 | H | H | 3-Chlorobenzofuran-2-yl |
| Me | Et | H | H | 2 | H | H | 4-Chlorobenzofuran-2-yl |
| Me | Et | H | H | 2 | H | H | 5-Chlorobenzofuran-2-yl |
| Me | Et | H | H | 2 | H | H | 6-Chlorobenzofuran-2-yl |
| Me | Et | H | H | 2 | H | H | 7-Chlorobenzofuran-2-yl |
| Me | Et | H | H | 2 | H | H | 3-Methylbenzofuran-2-yl |
| Me | Et | H | H | 2 | H | H | 4-Methylbenzofuran-2-yl |
| Me | Et | H | H | 2 | H | H | 5-Methylbenzofuran-2-yl |
| Me | Et | H | H | 2 | H | H | 6-Methylbenzofuran-2-yl |
| Me | Et | H | H | 2 | H | H | 7-Methylbenzofuran-2-yl |
| Me | Et | H | H | 2 | H | H | 3-Methoxybenzofuran-2-yl |
| Me | Et | H | H | 2 | H | H | 4-Methoxybenzofuran-2-yl |
| Me | Et | H | H | 2 | H | H | 5-Methoxybenzofuran-2-yl |
| Me | Et | H | H | 2 | H | H | 6-Methoxybenzofuran-2-yl |
| Me | Et | H | H | 2 | H | H | 7-Methoxybenzofuran-2-yl |

The present compound represented by the general formula [I] can be produced according to the processes shown below; however, the compound can be produced also by other processes.

<Production Process 1> Step 1 to Step 5

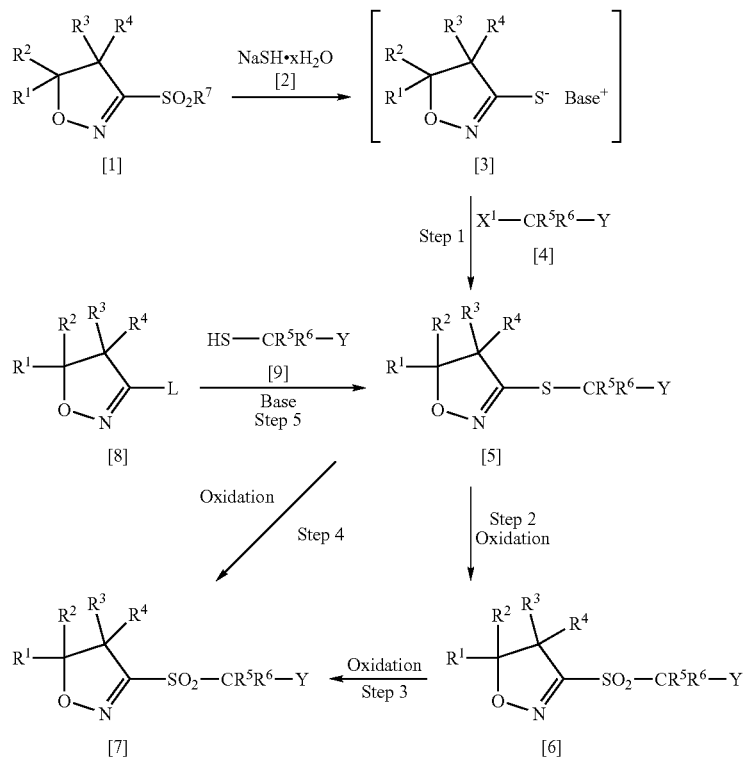

In the above production scheme, $R^1$, $R^2$, $R^3$, $R^4$, $R^5$, $R^6$ and Y have the same definitions as given above; $X^1$ is a halogen atom; $R^7$ is a C1 to C4 alkyl group, an optionally substituted phenyl group or an optionally substituted benzyl group; L is a leaving group such as halogen atom, C1 to C4 alkylsulfonyl group, optionally substituted phenylsulfonyl group, optionally substituted benzylsulfonyl group or the like; and x is an integer of 1 or more.

The above production process is described below in detail on each step.

(Step 1)

A sulfide derivative represented by the general formula [5] can be produced by reacting a compound represented by the general formula [1] with a sodium hydrosulfide hydrate represented by the general formula [2] in the presence or absence of a solvent (preferably in an appropriate solvent) in the presence of a salt to produce a base of a mercaptan, represented by the general formula [3] in the reaction system, and then, without isolating the salt of a mercaptan [3], reacting the salt [3] with a halogen derivative represented by the general formula [4] [in this case, a radical-generating agent, for example, Rongalit (trade name): $CH_2(OH)SO_2Na.2H_2O$ may be added].

The reaction temperature in each reaction is any temperature between 0° C. and the reflux temperature of each reaction system and is preferably 10 to 100° C. The reaction time varies depending upon the compounds used, but is 0.5 to 24 hours.

With respect to the amounts of the reagents used in each reaction, each of the compound represented by the general formula [2] and the compound represented by the general formula [4] is used in an amount of 1 to 3 equivalents relative to one equivalent of the compound represented by the general formula [1] and, when a base is used, the base is used in an amount of 0.5 to 3 equivalents.

As the solvent, there can be mentioned, for example, ethers such as dioxane, tetrahydrofuran (THF) and the like; halogenated hydrocarbons such as dichloroethane, carbon tetrachloride, chlorobenzene, dichlorobenzene and the like; amides such as N,N-dimethylacetamide, N,N-dimethylformamide, N-methyl-2-pyrrolidinone and the like; sulfur compounds such as dimethyl sulfoxide, sulfolane and the like; aromatic hydrocarbons such as benzene, toluene, xylene and the like; alcohols such as methanol, ethanol, propanol, isopropanol, butanol, tert-butanol and the like; ketones such as acetone, 2-butanone and the like; nitriles such as acetonitrile and the like; water; and mixtures thereof.

As the base, there can be mentioned, for example, metal hydrides such as sodium hydride and the like; alkali metal amides such as sodium amide, lithium diisopropylamide and the like; organic bases such as pyridine, triethylamine, 1,8-diazabicyclo[5.4.0]-7-undecene and the like; alkali metal hydroxides such as sodium; hydroxide, potassium hydroxide and the like; alkaline earth metal hydroxides such as calcium hydroxide, magnesium hydroxide and the like; alkali metal carbonates such as sodium carbonate, potassium carbonate and the like; alkali metal hydrogencarbonates such as sodium hydrogencarbonate, potassium hydrogencarbonate and the like; and metal alcholates such as sodium methoxide, potassium tertbutoxide and the like.

(Step 2)

A sulfoxide derivative represented by the general formula [6] can be produced by reacting the sulfide derivative represented by the general formula [5] with an oxidizing agent in an appropriate solvent.

The reaction temperature is any temperature between 0° C. and the reflux temperature of the reaction system and is preferably 0 to 60° C. The reaction time varies depending upon the compounds used, but is 1 to 72 hours.

With respect to the amounts of the reagents used in the reaction, the oxidizing agent is used in an amount of 1 to 3 equivalents per equivalent of the compound represented by the general formula [5].

As the solvent, there can be mentioned, for example, halogenated hydrocarbons such as dichloromethane, chloroform, dichloroethane, carbon tetrachloride, chlorobenzene, dichlorobenzene and the like; ethers such as dioxane, tetrahydrofuran (THF), dimethoxyethane, diethyl ether and the like; amides such as N,N-dimethylacetamide, N,N-dimethylformamide, N-methyl-2-pyrrolidinone and the like; alcohols such as methanol, ethanol, propanol, isopropanol, butanol, tertbutanol and the like; ketones such as acetone, 2-butanone and the like; nitrites such as acetonitrile and the like; acetic acid; water; and mixtures thereof.

As the oxidizing agent, there can be mentioned, for example, organic peroxides such as m-chloroperbenzoic acid, performic acid, peracetic acid and the like; and inorganic peroxides such as hydrogen peroxide, potassium permanganate, sodium periodate and the like.

(Step 3)

A sulfone derivative represented by the general formula [7] can be produced by reacting the sulfoxide derivative represented by the general formula [6] with an oxidizing agent in an appropriate solvent.

The reaction temperature is any temperature between 0° C. and the reflux temperature of the reaction system and is preferably 0 to 60° C. The reaction time varies depending upon the compounds used, but is 1 to 72 hours.

With respect to the amounts of the reagents used in the reaction, the oxidizing agent is used in an amount of 1 to 3 equivalents per equivalent of the compound represented by the general formula [6].

As the solvent and the oxidizing agent, there can be mentioned the same solvents and oxidizing agents as in the step 2.

(Step 4)

The sulfone derivative represented by the general formula [7] can also be produced by reacting the sulfide derivative represented by the general formula [5] with an oxidizing agent of appropriate amount in an appropriate solvent without isolating the sulfoxide derivative represented by the general formula [6].

The reaction temperature is any temperature between 0° C. and the reflux temperature of the reaction system and is preferably 0 to 60° C. The reaction time varies depending upon the compounds used, but is 1 to 72 hours.

With respect to the amounts of the reagents used in the reaction, the oxidizing agent is used in an amount of 1 to 3 equivalents per equivalent of the compound represented by the general formula [5].

As the solvent and the oxidizing agent, there can be mentioned the same solvents and oxidizing agents as in the step 2.

(Step 5)

The sulfide derivative represented by the general formula [5] can also be produced by reacting a compound represented by the general formula [8] with a mercaptan derivative represented by the general formula [9] in the presence or absence of a solvent (preferably in an appropriate solvent) in the presence of a base.

The reaction temperature is any temperature between 0° C. and the reflux temperature of the reaction system and is preferably 10 to 100° C. The reaction time varies depending upon the compounds used, but is 0.5 to 24 hours.

With respect to the amounts of the reagents used in the reaction, the compound represented by the general formula [9] is used in an amount of 1 to 3 equivalents per-equivalent of the compound represented by the general formula [8], and the base is used in an amount of 0.5 to 3 equivalents.

As the solvent, there can be mentioned, for example, ethers such as diethyl ether, dimethoxyethane, dioxane, tetrahydrofuran (THF) and the like; halogenated hydrocarbons such as dichloromethane, chloroform, carbon tetrachloride, dichloroethane, chlorobenzene, dichlorobenzene and the like; amides such as N,N-dimethylacetamide, N,N-dimethylformamide, N-methyl-2-pyrrolidinone and the like; sulfur compounds such as dimethyl sulfoxide, sulfolane and the like; aromatic hydrocarbons such as benzene, toluene, xylene and the like; alcohols such as methanol, ethanol, propanol, isopropanol, butanol, tert-butanol-and the like; ketones such as acetone, 2-butanone and the like; nitriles such as acetonitrile and the like; water; and mixtures thereof.

As the base, there can be mentioned, for example, metal hydrides such as sodium hydride and the like; alkali metal amides such as sodium amide, lithium diisopropylamide and the like; organic bases such as, pyridine, triethylamine, 1,8-diazabicyclo[5.4.0]-7-undecene and the like; alkali metal hydroxides such as sodium hydroxide, potassium hydroxide and the like; alkaline earth metal hydroxides such as calcium hydroxide, magnesium hydroxide and the like; alkali metal carbonates such as sodium carbonate, potassium carbonate and the like; alkali metal hydrogencarbonates such as sodium hydrogencarbonate, potassium hydrogencarbonate and the like; and metal alcholates such as sodium methoxide, potassium tertbutoxide and the like.

A compound of the general formula [8] wherein L is a halogen atom, i.e. a compound [12] can be produced by a process shown by the following step 6. As necessary, a mixture of the compound [12] and a compound [13] is subjected to a separation and purification procedure to isolate the compound [12].

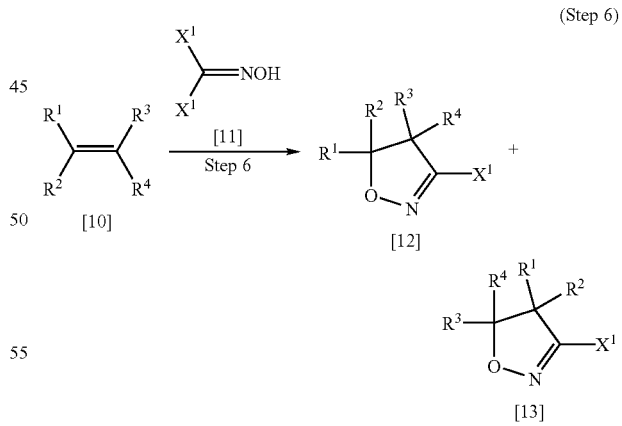

(Step 6)

In the above reaction, $X^1$, $R^1$, $R^2$, $R^3$ and $R^4$ have the same definitions as given above.

The isoxazoline compounds represented by the general formulas [12] and [13] can be produced by reacting an olefin derivative represented by the general formula [10] with an oxime derivative represented by the general formula [11] in the presence or absence of a solvent (preferably in an appropriate solvent) in the presence of a base. When $R^3$ and $R^4$ are each a hydrogen atom, the isoxazoline compound represented by the general formula [12] can be obtained preferentially.

The reaction temperature is any temperature between 0° C. and the reflux temperature of the reaction system and is preferably 10 to 80° C. The reaction time varies depending upon the compounds used, but is 0.5 hours to 2 weeks.

With respect to the amounts of the reagents used in the reaction, the compound represented by the general formula [10] is used in an amount of 1 to 3 equivalents per equivalent of the compound represented by the general formula [11].

As the solvent, there can be mentioned, for example, ethers such as ethylene glycol dimethyl ether, ethylene glycol diethyl ether, diethyl ether, dioxane, tetrahydrofuran and the like; halogenated hydrocarbons such as dichloroethane, carbon tetrachloride, chlorobenzene, dichlorobenzene and the like; aromatic hydrocarbons such as benzene, toluene, xylene and the like; acetic acid esters such as ethyl acetate, butyl acetate and the like; water; and mixtures thereof.

As the base, there can be mentioned, for example, alkali metal hydroxides such as sodium hydroxide, potassium hydroxide and the like; alkaline earth metal hydroxides such as calcium hydroxide, magnesium hydroxide and the like; alkali metal carbonates such as sodium carbonate, potassium carbonate and the like; alkali metal hydrogencarbonates such as sodium hydrogencarbonate, potassium hydrogencarbonate and the like; alkali metal acetates such as sodium acetate, potassium acetate and the like; alkali metal fluorides such as sodium fluoride, potassium fluoride and the like; and organic bases such as pyridine, triethylamine, 1,8-diazabicyclo[5.4.0]-7-undecene and the like.

In the above production process, the compound represented by the general formula [10], used as an intermediate can be a commercial product or can be produced by a known reaction such as Wittig reaction or the like. The compound represented by the general formula [11] can be produced, for example, by a process described in Liebigs Annalen der Chemie, 985 (1989).

The compound represented by the general formula [1] can be produced from the above-shown compound represented by the general formula [12] by the following process.

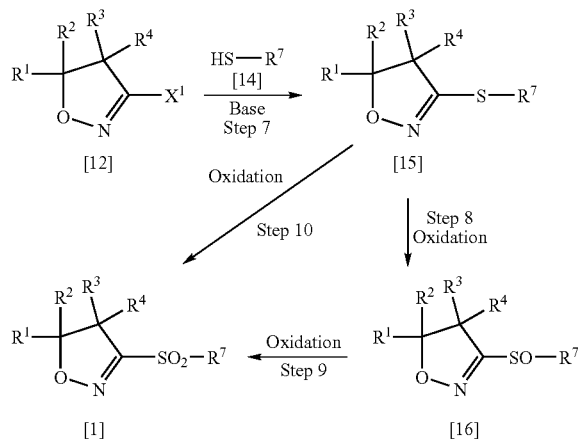

In the above reaction, $X^1$, $R^1$, $R^2$, $R^3$, $R^4$ and $R^7$ have the same definitions as given above.

A compound represented by the general formula [15] can be produced by the above-described step 5; a compound represented by the general formula [16] can be produced by the above-described step 2; and the compound represented by the general formula [1] can be produced from the compound [15] by the above-described step 4 or from the compound [16] by the above-described step 3.

As the solvent, base and oxidizing agent, there can be mentioned the same solvents, bases and oxidizing agents as mentioned in the step 2, 3, 4 or 5.

A compound represented by the general formula [4] wherein $R^6$ is a hydrogen atom, i.e. a compound represented by the general formula [21] can be produced by the following process.

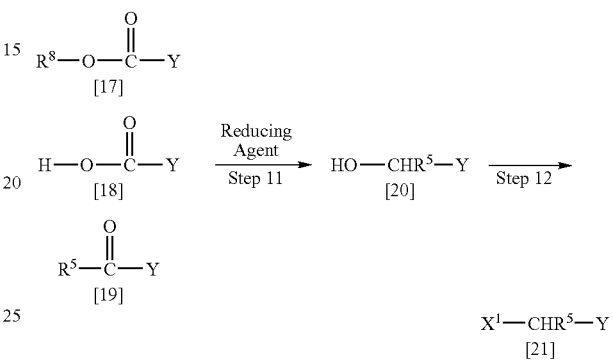

In the above reaction, $R^5$, $X^1$ and Y have the same definitions as given above; and $R^8$ is an alkyl group.

(Step 11)

A compound represented by the general formula [20] can be produced by reacting a compound [17], [18] or [19] with a reducing agent in a solvent.

This reaction is conducted ordinarily at −60 to 150° C. for 10 minutes to 24 hours.

With respect to the amounts of the reagents used in the reaction, the reducing agent is used in an amount of desirably 0.5 to 2 equivalents per equivalent of the compound [17], [18] or [19]; however, the amount can be varied appropriately depending upon the condition of the reaction.

As the reducing agent, there can be mentioned, for example, metal hydrides (e.g. diisobutyl aluminum hydride) and metal hydrogen complex compounds (e.g. sodium borohydride and lithium aluminum hydride) in production of [20] from [17]; and metal hydrides (e.g. diisobutyl aluminum hydride), metal hydrogen complex compounds (e.g. sodium borohydride and lithium aluminum hydride) and diborane in production of [20] from [18] or [19].

As the solvent, there can be mentioned, for example, ethers such as diethyl ether, tetrahydrofuran, dioxane and the like; aromatic hydrocarbons such as benzene, toluene and the like; and alcohols such as methanol, ethanol and the like.

(Step 12)

A compound represented by the general formula [21] can be produced by reacting the compound [20] with a halogenating agent in a solvent.

This reaction is conducted ordinarily at −50 to 100° C. for 10 minutes to 24, hours.

With respect to the amounts of the reagents used in the reaction, the halogenating agent is used in an amount of desirably 1 to 3 equivalents per equivalent of the compound [20]; however, the amount can be varied appropriately depending upon the condition of the reaction.

As the halogenating agent, there can be mentioned, for example, hydrogen chloride, hydrogen bromide, phosphorus trichloride, phosphorus tribromide and thionyl chloride.

As the solvent, there can be mentioned, for example, halogenated hydrocarbons such as dichloroethane, carbon tetrachloride and the like; acids such as acetic acid and the like; and ethers such as tetrahydrofuran and the like.

The compound represented by the general formula [4] can be produced by the following process.

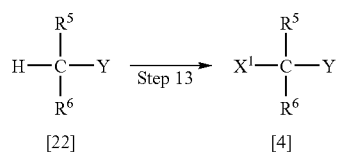

In the above reaction, $R^5$, $R^6$, $X^1$ and Y have the same definitions as given above.

The compound represented by the general formula [4] can be produced by reacting a compound [22] with a halogenating agent in a solvent in the presence or absence of a catalyst.

This reaction is conducted ordinarily at 30 to 150° C. for 10 minutes to 24 hours.

With respect to the amounts of the reagents used in the reaction, the halogenating agent is used in an amount of desirably 1 to 10 equivalents relative to one equivalent of the compound [22]; however, the amount of the halogenating agent can be varied appropriately depending upon the condition of the reaction. The catalyst is used in an amount of 0.01 to 0.5 equivalent.

As the halogenating agent, there can be mentioned, for example, halogens such as bromine, chlorine and the like; N-halosuccinimides such as N-bromosuccinimide and the like; and pyridine salts such as pyridinium perbromide and the like.

As the solvent, there can be mentioned, for example, halogenated hydrocarbons such as dichloroethane, carbon tetrachloride, chlorobenzene, dichlorobenzene and the like; amides such as N,N-dimethylacetamide, N,N-dimethylformamide, N-methyl-2-pyrrolidinone and the like; sulfur compounds such as dimethyl sulfoxide, sulfolane and the like; and carboxylic acids such as formic acid, acetic acid and the like.

As the catalyst, there can be mentioned, for example, benzoyl peroxide, α, α-azobisisobutyronitrile and a mixture thereof.

A compound represented by the general formula [4] wherein $R^5$ and $R^6$ are each a hydrogen atom, i.e. a compound represented by the general formula [24] can be produced by the following process.

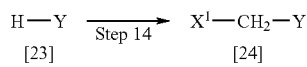

In the above reaction, $X^1$ and Y have the same definitions as given above.

The compound represented by the general formula [24] can be produced by reacting a compound [23], hydrogen halide, and formaldehyde or paraformaldehyde in a solvent in the presence or absence of a Lewis acid according to the method described in Org. Synth., III, 557 (1955) or J. Am. Chem. Soc., 72, 2216 (1950), or by reacting the compound [23] with a halogenomethyl ether in a solvent in the presence of a Lewis acid according to the method described in J. Am. Chem. Soc., 97, 6155 (1975).

This reaction is conducted ordinarily at −40 to 150° C. for 10 minutes to 24 hours.

With respect to the amounts of the reagents used in the reaction, the hydrogen halide, formaldehyde, paraformaldehyde, Lewis acid or halogenomethyl ether is used in an amount of desirably 1 to 2 equivalents per equivalent of the compound [23]; however, the amount of the former can be varied appropriately depending upon the condition of the reaction.

As the Lewis acid, there can be mentioned, for example, titanium tetrachloride, zinc chloride, aluminum chloride and zinc bromide.

As the hydrogen halide, there can be mentioned hydrogen chloride, hydrogen bromide and hydrogen iodide.

As the solvent, there can be mentioned, for example, halogenated hydrocarbons such as dichloroethane, carbon tetrachloride, chloroform and the like; aliphatic hydrocarbons such as hexane, heptane and the like; ethers such as dioxane, tetrahydrofuran and the like; carboxylic acids such as acetic acid and the like; carbon disulfide; and mixtures thereof.

A compound represented by the general formula [19] wherein $R^5$ is a hydrogen atom, i.e. a compound represented by the general formula [25] can be produced by the following process.

In the above reaction, Y has the same definition as given above.

The compound represented by the general formula [25] can be produced by reacting the compound [23] with N,N-dimethylformamide in the presence of phosphoryl chloride, phosgene or thionyl chloride in the presence or absence of a solvent according to the Vilsmeier method described in Org. Synth., IV, 831 (1963), or by reacting the compound [23] with a dihalogenomethyl ether in a solvent in the presence of a Lewis acid and then giving rise to hydrolysis according to the method described in Chem. Ber., 93, 88 (1960).

This reaction is conducted ordinarily at −40 to 150° C. for 10 minutes to 24 hours.

With respect to the amounts of the reagents used in the reaction, the phosphoryl chloride, phosgene, thionyl chloride, N,N-dimethylformamide, Lewis acid or dihalogenomethyl ether is used in an amount of desirably 1 to 2 equivalents per equivalent of the compound [23]; however, the amount of the former can be varied appropriately depending upon the condition of the reaction.

As the Lewis acid, there can be mentioned, for example, titanium tetrachloride, tin tetrachloride, zinc chloride, aluminum chloride and zinc bromide.

As the solvent, there can be mentioned, for example, halogenated hydrocarbons such as dichloroethane, carbon tetrachloride, chloroform and the like; aliphatic hydrocarbons such as hexane, heptane and the like; ethers such as dioxane, tetrahydrofuran and the like; carboxylic acids such as acetic acid and the like; amides such as N,N-dimethylformamide and the like; carbon disulfide; and mixtures thereof.

The compounds represented by the general formulas [17], [18], [19] and [20] can be produced by the following process.

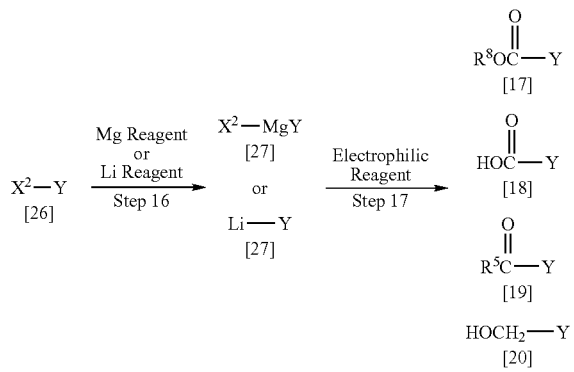

In the above reaction, $R^5$, $R^8$ and Y have the same definitions as given above; and $X^2$ is a chlorine atom, a bromine atom or an iodine atom.

The compounds represented by the general formulas [17], [18], [19] and [20] can be produced by reacting a compound [26] with a magnesium reagent in the presence or absence of a solvent to obtain a compound [27] and then reacting the compound [27] with an electrophilic reagent according to the method described in J. Org. Chem., 65, 4618 (2000), or by reacting the compound [26] with n-butyl lithium in a solvent to obtain a compound [28] and then reacting the compound [28] with an electrophilic reagent according to the method described in Synth. Commun., 24 (2), 253 (1994).

This reaction is conducted ordinarily at −100 to 150° C. for 10 minutes to 24 hours.

With respect to the amounts of the reagents used in the reaction, the amount of the magnesium reagent or the lithium reagent is desirably 1 to 5 equivalents per equivalent of the compound [26], and the amount of the electrophilic reagent is desirably 1 to 5 equivalents; however, these amounts can be varied appropriately depending upon the condition of the reaction.

As the magnesium reagent, there can be mentioned, for example, metal magnesium, isopropyl magnesium bromide and diisopropyl magnesium.

As the lithium reagent, there can be mentioned, for example, n-butyl lithium, sec-butyl lithium and tert-butyl lithium.

As the electrophilic reagent, there can be mentioned, for example, esters such as ethyl formate, ethyl cyanoformate, ethyl acetate and the like; acid halides such as acetyl chloride, methyl chloroformate and the like; amides such as N,N-dimethylformamide and the like; aldehydes such as paraformaldehyde and the like; and carbon dioxide.

As the solvent, there can be mentioned, for example, halogenated hydrocarbons such as dichloroethane, carbon tetrachloride, chloroform and the like; aliphatic hydrocarbons such as hexane, pentane and the like; ethers such as dioxane, tetrahydrofuran and the like; and mixtures thereof.

Among compounds represented by the general formulas [4], [17], [18], [19], [20], [22], [23], [26], [29] or [34], a compound represented by the general formula [31] can be produced by the following process.

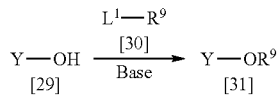

In the above reaction, Y has the same definition as given above; $R^9$ is an alkyl group, a haloalkyl group, a cycloalkyl gorup, a cycloalkylalkyl group, an alkoxycarbonylalkyl group, an optionally substituted, benzyl group, an optionally substituted heterocyclic alkyl group, an alkenyl tionally substituted heterocyclic alkyl group, an alkenyl group, an alkynyl group, an alkylsulfonyl group, a haloalkylsulfonyl group, an optionally substituted aromatic heterocyclic group, an optionally substituted phenylsulfonyl group, an acyl group, a haloalkylcabonyl group, an optionally substituted benzylcarbonyl group or an optionally substituted benzoyl group; and $L^1$ is a leaving group such as halogen atom, C1 to C4 alkylsulfonate group, C1 to C4 alkylsulfonyl group, optionally substituted benzylsulfonyl group, optionally substituted phenylsulfonate group, optionally substituted benzylsulfonate group or the like. When $R^9$ is a haloalkyl group, $L^1$ is a leaving group having a higher reactivity than the halogen atom remaining after haloalkylation. For example, when $R^9$ is a $CHF_2$ group, $L^1$ is a chlorine atom or a bromine atom; and when $R^9$ is a $CH_2CF_3$ group, $L^1$ is a chlorine atom, a bromine atom, a p-toluenesulfonyloxy group or a methylsulfonyloxy group.

The compound represented by the general formula [31] can be produced by reacting a compound [29] with a compound [30] in a solvent in the presence of a base.

This reaction is conducted ordinarily at 0 to 120° C. for 10 minutes to 24 hours.

With respect to the amounts of the reagents used in the reaction, the amount of the compound [30] is 1 to 20 equivalents per equivalent of the compound [29], and the amount of the base is 1 to 3 equivalents.

As the base, there can be mentioned, for example, alkali metal carbonates such as sodium carbonate, potassium carbonate and the like; alkali metal hydroxides such as sodium hydroxide, potassium hydroxide and the like; alkali metal hydrides such as potassium hydride, sodium hydride and the like; alkali metal alcoholates such as sodium ethoxide, sodium methoxide and the like; and organic bases such as 1,8-diazabicyclo[5.4.0]-7-undecene and the like.

As the solvent, there can be mentioned, for example, halogenated hydrocarbons such as dichloromethane, chloroform and the like; ethers such as diethyl ether, tetrahydrofuran and the like; aromatic hydrocarbons such as benzene, toluene and the like; aliphatic hydrocarbons such as hexane, heptane and the like; ketones such as acetone, methyl isobutyl ketone and the like; esters such as ethyl acetate, methyl acetate and the like; amides such as N-methylpyrrolidone, N,N-dimethylformamide and the like; sulfur compounds such as dimethyl sulfoxide, sulfolane and the like; nitriles such as acetonitrile and the like; and mixtures thereof.

Among compounds represented by the general formulas [4], [17], [18], [19], [20], [22], [23], [26], [29] or [31], a compound represented by the general formula [34] can be produced by the following process,

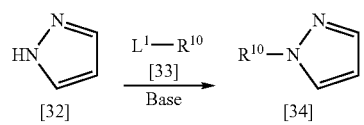

In the above reaction, $L^1$ has the same definition as given above; and $R^{10}$ is an alkyl group, an alkyl group monosubstituted with a group selected from the substituent group β, a haloalkyl group, a cycloalkyl group, an alkenyl group, an alkynyl group, an alkylsulfinyl group, an alkylsulfonyl group, an alkylsulfonyl group mono-substituted with a group selected from the substituent group γ, a haloalkylsulfonyl group, an optionally substituted phenyl group, an optionally substituted aromatic heterocyclic group, an optionally substituted phenylsulfonyl group, an optionally substituted aromatic heterocyclicsulfonyl group, an acyl group, a haloalkylcarbonyl group, an optionally substituted benzylcarbonyl group, an optionally substituted benzoyl group, an alkoxycarbonyl group, an optionally substituted benzyloxycarbonyl group, an optionally substituted phenoxycarbonyl group, or a carbamoyl group (its nitrogen atom may be substituted with same or different groups selected from alkyl groups and optionally substituted phenyl group). The carbon atoms of the pyrazole ring may be substituted with 1 to 2 same or different groups selected from the substituent group α.

The compound represented by the general formula [34] can be produced by reacting a compound [32] with a compound [33] in a solvent in the presence of a base.

This reaction is conducted ordinarily at 0 to 120° C. for 10 minutes to 24 hours.

With respect to the amounts of the reagents used in the reaction, the amount of the compound [33] is 1 to 20 equivalents per equivalent of the compound [32], and the amount of the base is 1 to 3 equivalents.

As the base and the solvent, there can be mentioned, for example, the same bases and solvents as mentioned in production of the compound [31] from the compound [29].

Introduction of a trifluoromethyl group into Y can be conducted according to or based on, for example, the methods described in J. Chem. Soc. Perkin Trans. 1, 8, 2293-2299 (1990); J. Fluorine Chem., 50 (3), 411-426 (1990); J. Chem. Soc. Chem. Commun., 18, 1389-1391 (1993); J. Chem. Soc. Chem. Commun., 1, 53-54 (1992); Chem. Lett., 1719-1720 (1981); Chem. Pharm. Bull., 38 (9), 2446-2458 (1990); J. Chem. Soc. Perkin Trans. 1, 921-926 (1988); Heterocycles, 37 (2), 775-782 (1994); Tetrahedron Lett., 30 (16), 2133-2136 (1989); J. Chem. Soc. Perkin Trans. 1, 2755-2761 (1980); Hetrocycles, 22 (1), 117-124 (1984); Eur. J. Med. Chem. Chim. Ther., 24, 249-258 (1989); Acta Chem. Scand. Ser. B, 38 (6), 505-508 (1984); J. Fluorine Chem., 21, 495-514 (1982); J. Chem. Soc. Chem. Commun., 10, 638-639 (1988); J. Fluorine Chem., 67 (1), 5-6 (1994); J. Heterocycl. Chem., 31 (6), 1413-1416 (1994); Chem. Heterocycl. Compd., 30 (5), 576-578 (1994); J. Fluorine Chem., 78 (2), 177-182 (1996); J. Heterocycl. Chem., 34 (2), 551-556 (1997); Tetrahedron, 55 (52), 15067-15070 (1999); and Synthesis, 11, 932-933 (1980).

The compounds represented by the general formulas [4], [17], [18], [19], [20], [21], [22], [23], [24], [25], [26], [29] and [31] can be produced according to or based on, for example, the methods described in Methoden der Organischen Chemie, E6a, 16-185 (1994) when Y is a furyl group; Methoden der Organischen Chemie, E6a, 186-555 (1994) when Y is a thienyl group; Methoden der Organischen Chemie, E6a, 556-798 (1994) when Y is a pyrrolyl group; Methoden der Organischen Chemie, E8b, 399-763 (1994) and JP-A-2000-219679 when Y is a pyrazolyl group; Methoden der Organischen Chemie, E8a, 45-225 (1993) when Y is an isoxazolyl group; Methoden der Organischen Chemie, E8a, 668-798 (1993) when Y is an isothiazolyl group; Methoden der Organischen Chemie, E8a, 891-1019 (1993) when Y is an oxazolyl group; Methoden der Organischen Chemie, E8b, 1-398 (1994) when Y is a thiazolyl group; Methoden der Organischen Chemie, E8c, 1-215 (1994) when Y is an imidazolyl group; Methoden der Organischen Chemie, E7a, 286-686 (1992) when Y is a pyridyl group; Methoden der Organischen Chemie, E9a, 557-682 (1997) when Y is a pyridazinyl group; Methoden der Organischen Chemie, E9b/1, 1-249 (1998) when Y is a pyrimidinyl group; Methoden der Organischen Chemie, E9b/1, 250-372 (1998) when Y is a pyrazinyl group; Methoden der Organischen Chemie, E9c, 530-796 (1998) when Y is a triazinyl group; Methoden der Organischen Chemie, E8d, 305-405 and 479-598 (1994) when Y is a triazolyl group; Methoden der Organischen Chemie, E8c, 397-818 (1994) when Y is an oxadiazolyl group; Methoden der Organischeh Chemie, E8d, 59-304 (1994) when Y is a thiadiazolyl group; Methoden der Organischen Chemie, E6b1, 33-216 (1994) and Published International Patent Application WO-1997/29105 when Y is a benzofuryl group; Methoden der Organischen Chemie, E6b1, 217-322 (1994) when Y is a benzothienyl group; Methoden der Organischen Chemie, E6b1,546-848 (1994), Methoden der Organischen Chemie, E6b2, 849-1336 (1994) and Published International Patent Application WO-1997/42188-A1 when Y is an indolyl group; Methoden der Organischen Chemie, E8a, 1020-1194 (1993) when Y is a benzoxazolyl group; Methoden der Organischen Chemie, E8b, 865-1062 (1994) when Y is a benzothiazolyl group; Methoden der Organischen Chemie, E8c, 216-391 (1994) when Y is a benzimidazolyl group; Methoden der Organischen Chemie, E8a, 226-348 (1993) when Y is a benzisoxazolyl group; Methoden der Organischen Chemie, E8a, 799-852 (1993) when Y is a benzisothiazolyl group; Methoden der Organischen Chemie, E8b, 764-864 (1994) when Y is an indazolyl group; Methoden der Organischen Chemie, E7a, 290-570 (1991) when Y is a quinolyl group; Methoden der Organischen Chemie, E7a, 571-758 (1991) when Y is an isoquinolyl group; Methoden der Organischen Chemie, E9a, 744-789 (1997) when Y is a phthalazinyl group; Methoden der Organischen Chemie, E9b/2, 93-265 (1998) when Y is a quinoxalinyl group; Methoden der Organischen Chemie, E9b/2, 1-192 (1998) when Y is a quinazolinyl group; Methoden der Organischen Chemie, E9a, 683-743 (1997) when Y is a cinnolinyl group; and Methoden der Organischen Chemie, E8d, 406-478 (1994) when Y is a benzotriazolyl group.

<Production Process 2>

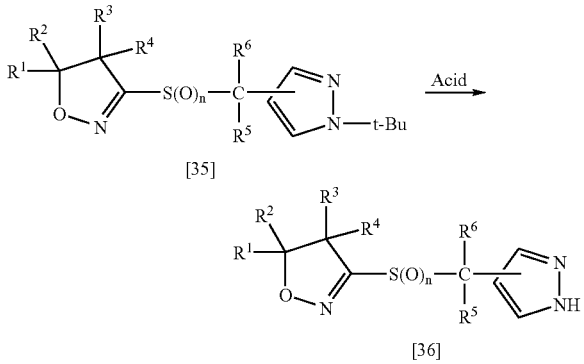

[35]

[36]

In the above reaction, $R^1$, $R^2$, $R^3$, $R^4$, $R^5$ and $R^6$ have the same definitions as given above. The carbon atoms of the pyrazole ring may be substituted with 1 to 2 same or different groups selected from the substituent group α.

A compound of the present invention represented by the general formula [36] can be produced by reacting a compound [35] of the present invention, produced by the Production Process 1, with an acid in a solvent.

This reaction is conducted ordinarily at 0 to 120° C. for 10 minutes to 24 hours.

With respect to the amounts of the reagents used in the reaction, the amount of the acid is 1 to 10 equivalents per equivalent of the compound [35]; however, the amount can be varied appropriately depending upon the condition of the reaction.

As the acid, there can be mentioned, for example, hydrochloric acid, hydrobromic acid and trifluoroacetic acid.

As the solvent, there can be mentioned, for example, halogenated hydrocarbons such as dichloroethane, carbon tetrachloride, chlorobenzene, dichlorobenzene and the like; amides such as N,N-dimethylacetamide, N,N-dimethylformamide, N-methyl-2-pyrrolidinone and the like; sulfur compounds such as dimethyl sulfoxide, sulfolane and the like; carboxylic acids such as formic acid, acetic acid and the like; and water.

<Production Process 3>

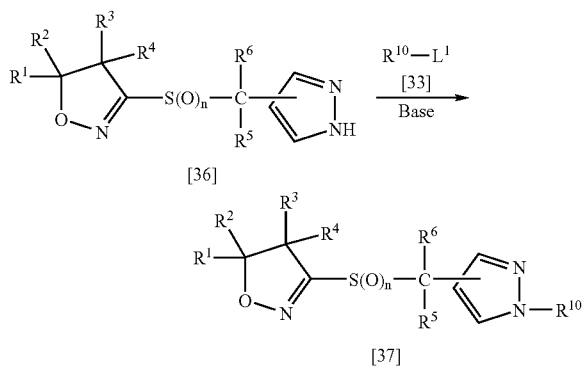

In the above reaction, n, $L^1$, $R^1$, $R^2$, $R^3$, $R^4$, $R^5$, $R^6$ and $R^{10}$ have the same definitions as given above. The carbon atoms of the pyrazole ring may be substituted with 1 to 2 same or different groups selected from the substituent group α.

A compound of the present invention represented by the general formula [37] can be produced by reacting the compound [36] of the present invention with the compound [33] in a solvent in the presence of a base.

With respect to the amounts of the reagents used in the reaction, the amount of the compound [33] is 1 to 3 equivalents per equivalent of the compound represented by the general formula [36] and the amount of the base is 1 to 3 equivalents.

As the solvent, there can be mentioned, for example, ethers such as dioxane, tetrahydrofuran (THF) and the like; halogenated hydrocarbons such as dichloroethane, carbon tetrachloride, chlorobenzene, dichlorobenzene and the like; amides such as N,N-dimethylacetamide, N,N-dimethylformamide, N-methyl-2-pyrrolidinone and the like; sulfur compounds such as dimethyl sulfoxide, sulfolane and the like; aromatic hydrocarbons such as benzene, toluene, xylene and the like; alcohols such as methanol, ethanol propanol, isopropanol, butanol, tert-butanol and the like; ketones such as acetone, 2-butanone and the like; nitrites such as acetonitrile and the like; water; and mixtures thereof.

As the base, there can be mentioned, for example, metal hydrides such as sodium hydride and the like; alkali metal amides such as sodium amide, lithium diisopropylamide and the like; organic bases such as pyridine, triethylamine, 1,8-diazabicyclo[5.4.0]-7-undecene and the like; alkali metal hydroxides such as sodium hydroxide, potassium hydroxide and the like; alkaline earth metal hydroxides such as calcium hydroxide, magnesium hydroxide and the like; alkali metal carbonates such as sodium carbonate, potassium carbonate and the like; alkali metal hydrogencarbonates such as sodium hydrogencarbonate, potassium hydrogencarbonate and the like; and metal alcoholates such as sodium methoxide, potassium tert-butoxide and the like.

<Production Process 4>

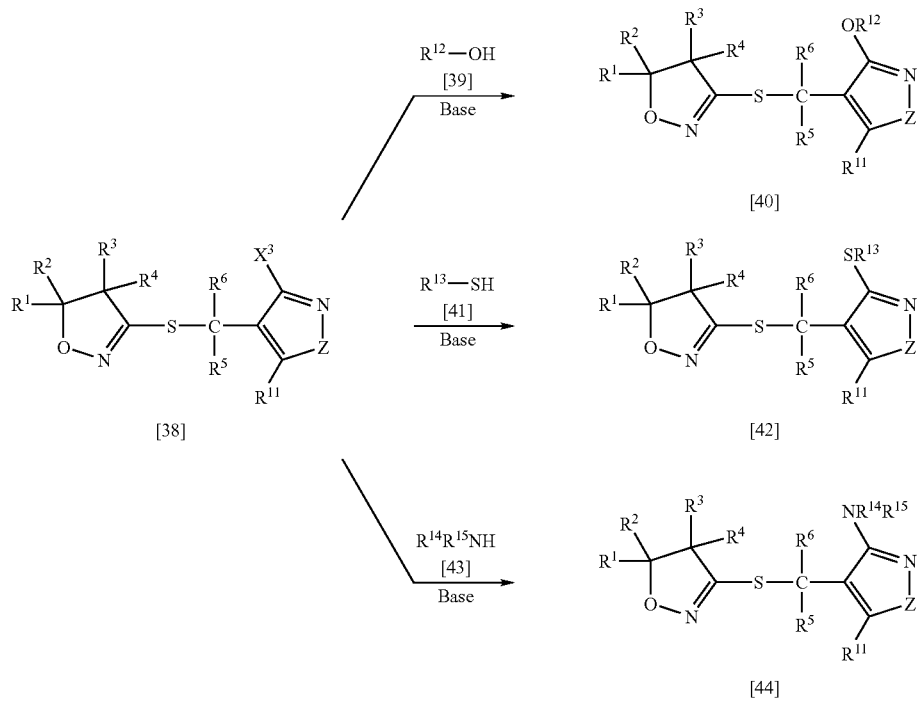

In the above reaction, $R^1$, $R^2$, $R^3$, $R^4$, $R^5$ and $R^6$ have the same definitions as given above; $R^{11}$ is a hydrogen atom or substituent group α as mentioned above; $X^3$ is a chlorine atom, a fluorine atom, an alkylsulfonyl group or an optionally substituted benzylsulfonyl group; $R^{12}$ is an alkyl group, a haloalkyl group, a cycloalkyl group, a cycloalkylalkyl group, an alkenyl group, an alkynyl group, an optionally substituted phenyl group, an optionally substituted aromatic heterocyclic group, an alkoxycarbonylalkyl group, an optionally substituted heterocyclic alkyl group or an optionally substituted benzyl group; $R^{13}$ is an alkyl group, a haloalkyl group, an optionally substituted phenyl group, an optionally substituted aromatic heterocyclic group, an alkoxycarbonylalkyl group or an optionally substituted benzyl group; $R^{14}$ and $R^{15}$ may be the same or different and are each a hydrogen atom, an alkyl group, an optionally substituted phenyl group; an acyl group, a haloalkylcarbonyl group, an optionally substituted benzylcarbonyl group, an optionally substituted benzoyl group, an alkylsulfonyl group, a haloalkylsulfonyl group, an optionally substituted benzylsulfonyl group or an optionally substituted phenylsulfonyl group; and Z is an oxygen atom, a sulfur atom, $N=CR^{11a}$, $CR^{11a}=N$, $CR^{11a}=CR^{11b}$ or $N-R^{16}$ (wherein $R^{16}$ is a hydrogen atom or has the same definition as $R^{10}$, and $R^{11a}$ and $R^{11b}$ have the same definition as $R^{11}$.).

Compounds of the present invention represented by the general formulas [40], [42] and [44] can be produced by reacting a compound of the present invention represented by the general formula [38] with a compound [39], a compound [41] and a compound [43], respectively, in the presence or absence of a solvent and, as necessary, in the presence of a base.

This reaction is conducted ordinarily at 20 to 200° C., preferably 30 to 180° C. for 10 minutes to 48 hours and, as necessary, under pressure.

With respect to the amounts of the reagents used in the reaction, the amount of the compound [39], the compound [41] or the compound [43] is 1 to 20 equivalents per equivalent of the compound [38].

As the base used as necessary, there can be mentioned, for example, alkali metal hydroxides such as potassium hydroxide, sodium hydroxide and the like; alkali metal hydrides such as potassium hydride, sodium hydride and the like; alkali metal alcoholates such as sodium ethoxide, sodium methoxide and the like; and organic bases such as 1,8-diazabicyclo[5.4.0]-7-undecene and the like.

As the solvent, there can be mentioned, for example, halogenated hydrocarbons such as chloroform and the like; ethers such as diethyl ether, tetrahydrofuran and the like; aromatic hydrocarbons such as benzene, toluene and the like; aliphatic hydrocarbons such as hexane, heptane and the like; ketones such as acetone, methyl isobutyl ketone and the like; esters such as ethyl acetate and the like; amides such as N-methylpyrrolidone, N,N-dimethylformamide and the like; sulfur compounds such as dimethyl sulfoxide, sulfolane and the like; acetonitrile; and mixtures thereof.

<Production Process 5>

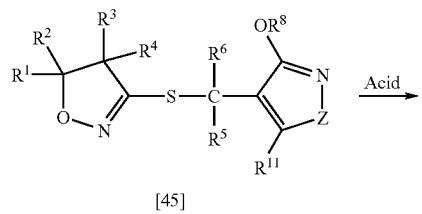

[45]

-continued

[46]

In the above reaction, $R^1$, $R^2$, $R^3$, $R^4$, $R^5$, $R^6$, $R^8$, $R^{11}$ and Z have the same definitions as given above.

A compound of the present invention represented by the general formula [46] can be produced by reacting a compound [45] of the present invention with an acid in a solvent.

This reaction is conducted ordinarily at 0 to 120° C. for 10 minutes to 24 hours.

With respect to the amounts of the reagents used in the reaction, the amount of the acid is desirably 1 to 10 equivalents per equivalent of the compound [45]; however, the amount can be varied appropriately depending upon the condition of the reaction.

As the acid and the solvent, there can be mentioned the same acids and solvents as mentioned in the Production Process 2.

<Production Process 6>

[47]

[48]

In the above reaction, Y, $R^1$, $R^2$, $R^3$, $R^4$, $R^5$, $R^6$, $R^9$ and $L^1$ have the same definitions as given above. Y may be substituted with 1 to 5 same or different groups selected from the substituent group α.

A compound represented by the general formula [48] according to the present invention can be produced by reacting a compound [47] of the present invention with the compound [30] in a solvent in the presence of a base.

This reaction is conducted ordinarily at 0 to 150° C. for 10 minutes to 24 hours.

With respect to the amounts of the reagents used in the reaction, the amount of the acid is desirably 1 to 1.2 equivalents per equivalent of the compound [47]; however, the amount can be varied appropriately depending upon the condition of the reaction.

As the base and the solvent, there can be mentioned the same bases and solvents as mentioned in the Production Process 3.

Production Process 7

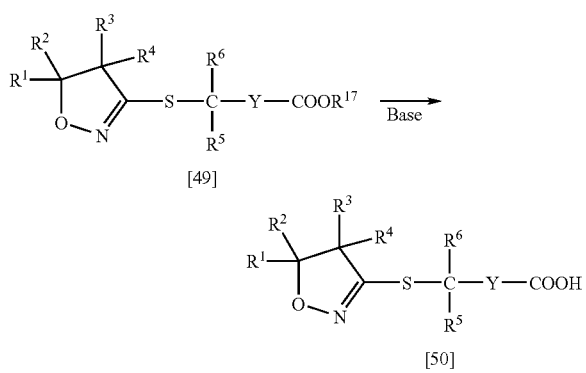

In the above reaction, Y, $R^1$, $R^2$, $R^3$, $R^4$, $R^5$ and $R^6$ have the same definitions as given above; and $R^{17}$ is an alkyl group, an optionally substituted benzyl group or an optionally substituted phenyl group. Y may be substituted with 1 to 5 same or different groups selected from the substituent group α.

A compound represented by the general formula [50] according to the present invention can be produced by hydrolyzing a compound [49] of the present invention in water or a mixed solvent of water and other solvent in the presence or absence of a base.

This reaction is conducted ordinarily at 0 to 100° C. for 10 minutes to 24 hours.

With respect to the amounts of the reagents used in the reaction, the amount of the base, when used, is desirably 1 to 2 equivalents per equivalent of the compound [49]; however, the amount can be varied appropriately depending upon the condition of the reaction.

As the base, there can be mentioned, for example, inorganic bases such as potassium carbonate, sodium hydride, sodium hydroxide and the like; and organic bases such as 1,8-diazabicyclo[5.4.0]-7-undecene and the like.

As the other solvent mixed with water, there can be mentioned, for example, alcohols such as methanol, ethanol and the like; ethers such as tetrahydrofuran and the like; ketones such as acetone, methyl isobutyl ketone and the like; amides such as N,N-dimethylformamide and the like; sulfur compounds such as dimethyl sulfoxide, sulfolane and the like; acetonitrile; and mixtures thereof.

Production Process 8

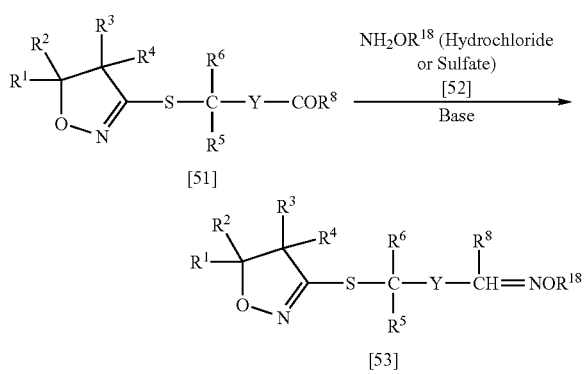

In the above reaction, Y, $R^1$, $R^2$, $R^3$, $R^4$, $R^5$, $R^6$ and $R^8$ have the same definitions as given above; and $R^{18}$ is an alkyl group. Y may be substituted with 1 to 5 same or different groups selected from the substituent group α.

A compound represented by the general formula [53] according to the present invention can be produced by reacting a compound [51] of the present invention with a compound [52] in a solvent in the presence of a base.

This reaction is conducted ordinarily at 0 to 100° C. for 10 minutes to 24 hours.

With respect to the amounts of the reagents used in the reaction, the amount of the hydrochloride or sulfate of the compound [52] is desirably 1 to 5 equivalents per equivalent of the compound [51] and the amount of the base is desirably 1 to 10 equivalents; however, these amounts can be varied, appropriately depending upon the condition of the reaction.

As the base, there can be mentioned, for example, metal carbonates such as potassium carbonate, sodium carbonate and the like; metal acetates such as potassium acetate, sodium acetate and the like; and organic bases such as triethylamine, dimethylamine, 1,8-diazabicyclo[5.4.0]-7-undecene and the like.

As the solvent, there can be mentioned, for example, alcohols such as methanol, ethanol and the like; ethers such as tetrahydrofuran and the like; amides such as N,N-dimethylformamide and the like; water; and mixtures thereof.

Production Process 9

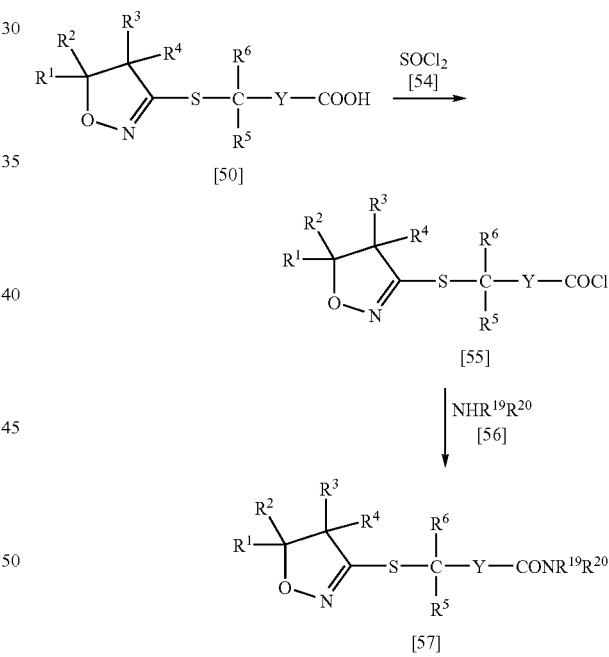

In the above reaction, Y, $R^1$, $R^2$, $R^3$, $R^4$, $R^5$ and $R^6$ have the same definitions as given above; and $R^{19}$ and $R^{20}$ are each a hydrogen atom or an alkyl group. Y may be substituted with 1 to 5 same or different groups selected from the substituent group α.

A compound represented by the general formula [57] according to the present invention can be produced by reacting the compound [50] of the present invention with thionyl chloride in the presence or absence of a solvent to obtain a compound [55] and then reacting the compound [55] with a compound [56] in the presence or absence of a solvent.

The reaction from the compound [50] to the compound [55] is conducted ordinarily at 0 to 100° C. for 10 minutes to 24 hours.

With respect to the amounts of the reagents used in the reaction, the amount of thionyl chloride [54] is desirably 1 to 100 equivalents per equivalent of the compound [50] but it can be varied appropriately depending upon the condition of the reaction.

As the solvent, there can be mentioned, for example, halogenated hydrocarbons such as dichloromethane, chloroform and the like; ethers such as diethyl ether, tetrahydrofuran and the like; and aromatic hydrocarbons such as benzene, toluene and the like.

The reaction from the compound [55] to the compound [57] is conducted ordinarily at 0 to 100° C. for 10 minutes to 24 hours.

With respect to the amounts of the reagents used in the reaction, the amount of the compound [56] is desirably 1 to 100 equivalents per equivalent of the compound [55] but it can be varied appropriately depending upon the condition of the reaction.

As the solvent, there can be mentioned, for example, the same solvents as used in the reaction from the compound [50] to the compound [55].

<Production Process 10>

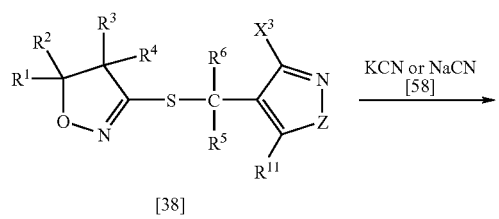

In the above reaction, Z, $R^1$, $R^2$, $R^3$, $R^4$, $R^5$, $R^6$, $R^{11}$ and $X^3$ have the same definitions as given above.

A compound represented by the general formula [59] according to the present invention can be produced by reacting the compound [38] of the present invention with a compound [58] in a solvent.

This reaction is conducted ordinarily at 0 to 100° C. for 10 minutes to 24 hours.

With respect to the amounts of the reagents used in the reaction, the amount of the compound [58] is desirably 1 to 2 equivalents per equivalent of the compound [38] but it can be varied appropriately depending upon the condition of the reaction.

As the solvent, there can be mentioned, for example, ethers such as dioxane, tetrahydrofuran (THF) and the like; halogenated hydrocarbons such as dichloroethane, carbon tetrachloride, chlorobenzene, dichlorobenzene and the like; amides such as N,N-dimethylacetamide, N,N-dimethylformamide, N-methyl-2-pyrrolidinone and the like; sulfur compounds such as dimethyl sulfoxide, sulfolane and the like; ketones such as acetone, 2-butanone and the like; nitriles such as acetonitrile and the like; water; and mixtures thereof.

<Production Process 11>

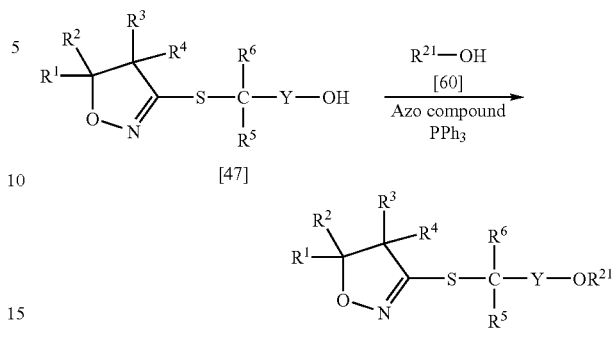

In the above reaction, Y, $R^1$, $R^2$, $R^3$, $R^4$, $R^5$ and $R^6$ have the same definitions as given above; and $R^{21}$ is an alkyl group, a haloalkyl group, a cycloalkyl group, a cycloalkylalkyl group, an alkenyl group, an alkynyl group, an alkoxycarbonylalkyl group, an optionally substituted heteroalkyl group or an optionally substituted benzyl group. Y may be substituted with 1 to 5 same or different groups selected from the substituent group α.

A compound represented by the general formula [61] according to the present invention can be produced by reacting the compound [47] of the present invention with a compound [60] in the presence of an azo compound and triphenylphosphine in a solvent according to a known method [Synthesis, 1-28 (1981)].

This reaction is conducted ordinarily at 0 to 100° C. for 10 minutes to 24 hours.

With respect to the amounts of the reagents used in the reaction, the amounts of the compound [60], the azo compound and triphenylphosphine are desirably each 1 to 1.5 equivalents per equivalent of the compound [47] but the amounts can be varied appropriately depending upon the condition of the reaction.

As the solvent, there can be mentioned, for example, ethers such as dioxane, tetrahydrofuran (THF) and the like; halogenated hydrocarbons such as dichloroethane, carbon tetrachloride, chlorobenzene, dichlorobenzene and the like; amides such as N,N-dimethylacetamide, N,N-dimethylformamide, N-methyl-2-pyrrolidinone and the like; sulfur compounds such as dimethyl sulfoxide, sulfolane and the like; aromatic hydrocarbons such as benzene, toluene, xylene and the like; acetonitrile; and mixtures thereof.

As the azo compound, there can be mentioned, for example, diethyl azodicarboxylate and diisopropyl azodicarboxylate.

<Production Process 12>

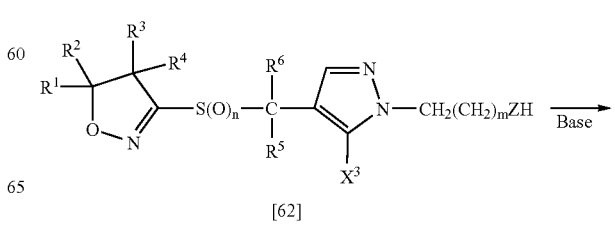

-continued

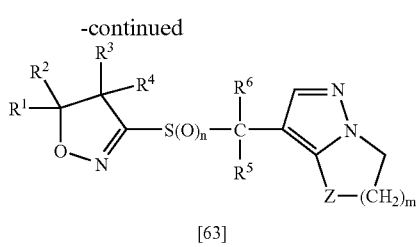

[63]

In the above reaction, $X^3$, n, $R^1$, $R^2$, $R^3$, $R^4$, $R^5$, $R^6$ and Z have the same definitions as given above; and m is an integer of 1 to 4. The carbon atom of the 3-position of the pyrazole ring may be substituted with a group selected from the substituent group α.

A compound represented by the general formula [63] according to the present invention can be produced by reacting a compound [62] of the present invention in the presence of a base in a solvent.

This reaction is conducted ordinarily at 0 to 120° C. for 10 minutes to 24 hours.

With respect to the amounts of the reagents used in the reaction, the amount of the base is desirably 1 to 3 equivalents per equivalent of the compound represented by the general formula [62] but the amount can be varied appropriately depending upon the condition of the reaction.

As the base and the solvent, there can be mentioned the same bases and solvents as mentioned in the Production Process 3.

Incidentally, the sulfide compound mentioned in the Production Process 2 or the Production Processes 4 to 11 can be converted into a sulfoxide compound or a sulfone compound by oxidation according to the method described in the Production Process 1. Furthermore, the sulfide compound mentioned in the Production Process 2 or the Production Processes 4 to 11 wherein substituent Y is substituted by C1 to C10 alkylthio group, C1 to C10 alkylthio group mono-substituted with a group selected from the substituent group γ or C1 to C4 haloalkylthio group, can be converted into a sulfoxide compound or a sulfone compound according to the method described in the Production Process 1, by adding equi-molar to excess amount of an oxidizing agent to the sulfide compound; oxidizing the substituent substituted to substituent Y (C1 to C10 alkylthio group, C1 to C10 alkylthio group mono-substituted with a group selected from the substituent group γ or C1 to C4 haloalkylthio group) at the same time, and convert these substituent into a sulfoxide group or a sulfone group.

Then, specific description is made on the production process of the present compound, the production method of the present herbicide and the application of the present herbicide by way of Examples. Description is also made on the production process of each intermediate of the present compound.

EXAMPLE 1

Production of 3-(5-chloro-1-phenyl-3-trifluoromethyl-1H-pyrazol-4-ylmethylthio)-5,5-dimethyl-2-isoxazoline (present compound No. 3-0001)

2.1 g of sodium hydrosulfide hydrate (purity: 70%, 26.2 mmoles) was added to a solution of 2.3 g (13.1 mmoles) of 5,5-dimethyl-3-methylsulfonyl-2-isoxazoline dissolved in 20 ml of N,N-dimethylformamide. The mixture was stirred for 2 hours. Thereto were added 1.8 g (13.1 mmoles) of anhydrous potassium carbonate, 2.0 g (13.1 mmoles) of Rongalit and 3.6 g (10.5 mmoles) of 4-bromomethyl-5-chloro-1-phenyl-3-trifluoromethyl-1H-pyrazole. The resulting mixture was stirred at room temperature for 15 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 2.7 g (yield: 65.5%) of 3-(5-chloro-1-phenyl-3-trifluoromethyl-1H-pyrazol-4-ylmethylthio)-5,5-dimethyl-2-isoxazoline as white crystals (melting point: 89 to 90° C.).

$^1$H-NMR [CDCl$_3$/TMS, δ (ppm)]: 7.55-7.50 (5H, m), 4.33 (2H, s), 2.83 (2H, s), 1.45 (6H, s)

EXAMPLE 2

Production of 3-(5-chloro-1-phenyl-3-trifluoromethyl-1H-pyrazol-4-ylmethylsulfonyl)-5,5-dimethyl-2-isoxazoline (present compound No. 3-0002)

0.63 g of m-chloroperbenzoic acid (purity: 70%, 2.6 mmoles) was added, with ice-cooling, to a solution of 0.4 g (1.0 mmoles) of 3-(5-chloro-1-phenyl-3-trifluoromethyl-1-H-pyrazol-4-ylmethylthio)-5,5-dimethyl-2-isoxazoline dissolved in 15 ml of chloroform. The mixture was stirred at room temperature for 22 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The resulting crystals were washed with hexane to obtain 0.4 g (yield: 83.2%) of 3-(5-chloro-1-phenyl-3-trifluoromethyl-1H-pyrazol-4-ylmethylsulfonyl)-5,5-dimethyl-2-isoxazoline as white crystals (melting point: 132 to 133° C.).

$^1$H-NMR [CDCl$_3$/TMS, δ (ppm)]: 7.60-7.51 (5H, m), 4.37 (2H, s), 3.14 (2H, s) 1.53 (6H, s)

EXAMPLE 3

Production of 3-(5-chloro-1-methyl-3-phenyl-1H-pyrazol-4-ylmethylsulfonyl)-5,5-dimethyl-2-isoxazoline (present compound No. 3-0003)

0.87 g of m-chloroperbenzoic acid (purity: 70%, 3.54 mmoles) was added, with ice-cooling, to a solution of 0.85 g (2.53 mmoles) of 3-(5-chloro-1-methyl-3-phenyl-1H-pyrazol-4-ylmethylthio)-5,5-dimethyl-2-isoxazoline dissolved in 30 ml of chloroform. The mixture was stirred at room temperature for 1 hour to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein.

The residue was purified by silica gel column chromatography (developing solvent: hexane-ethyl acetate mixed solvent) to obtain 0.48 g (yield: 53.9%) of 3-(5-chloro-1-methyl-3-phenyl-1H-pyrazol-4-ylmethylsulfinyl)-5,5-dimethyl-2-isoxazoline as a transparent viscous substance.

$^1$H-NMR [CDCl$_3$/TMS, δ (ppm)]: 7.63-7.60 (2H, m), 7.48-7.37 (3H, m), 4.29 (2H, q), 3.91 (3H, s), 3.12 (1H, d), 2.79 (1H, d), 1.41 (3H, s), 1.35 (3H, s)

EXAMPLE 4

Production of 5,5-dimethyl-3-(5-fluoro-1-phenyl-3-trifluoromethyl-1H-pyrazol-4-ylmethylthio)-2-isoxazoline (present compound No. 3-0021)

9.3 g of sodium hydrosulfide hydrate (purity: 70%, 116.3 mmoles) was added to a solution of 18.7 g (105.7 mmoles) of 5,5-dimethyl-3-methylsulfonyl-2-isoxazoline (present compound No. 2-1) dissolved in 300 ml of N,N-dimethylformamide. The mixture was stirred for 2 hours. The reaction system was ice-cooled. Thereto was added a solution of 30.3 g (93.8 mmoles) of 4-bromomethyl-5-fluoro-1-phenyl-3-trifluoromethyl-1H-pyrazole dissolved in 200 ml of N,N-dimethylformamide. The mixture was stirred at 0° C. for 30 minutes to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 13.11 g (yield: 37.4%) of 5,5-dimethyl-3-(5-fluoro-1-phenyl-3-trifluoromethyl-1H-pyrazol-4-ylmethylthio)-2-isoxazoline as a yellow oily substance.

$^1$H-NMR [CDCl$_3$/TMS, δ (ppm)]: 7.65-7.39 (5H, m), 4.24 (2H, s), 2.81 (2H, s), 1.43 (6H, s)

EXAMPLE 5

Production of 5,5-dimethyl-3-(5-ehtylthio-1-phenyl-3-trifluoromethyl-1H-pyrazol-4-ylmethylthio)-2-isoxazoline (present compound No. 3-0022)

0.2 g (4.0 mmoles) of sodium hydroxide and 1 ml of water were added to a solution of 0.25 g (4.0 mmoles) of ethanethiol dissolved in 10 ml of N,N-dimethylformamide. The mixture was stirred at room temperature for 30 minutes. Thereto was added a solution of 0.5 g (1.4 mmoles) of 5,5-dimethyl-3-(5-fluoro-1-phenyl-3-trifluoromethyl-1H-pyrazol-4-ylmethylthio)-2-isoxazoline dissolved in 5 ml of N,N-dimethylformamide. The resulting mixture was stirred for 1 hour to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 0.6 g (yield: 100%) of 5,5-dimethyl-3-(5-ethylthio-1-phenyl-3-trifluoromethyl-1H-pyrazol-4-ylmethylthio)-2-isoxazoline.

$^1$H-NMR [CDCl$_3$/TMS, δ (ppm)]: 7.62-7.47 (5H, m), 4.44 (2H, s), 2.83 (2H, s), 2.50 (2H, q), 1.45 (6H, s), 1.02 (3H, t)

EXAMPLE 6

Production of 5,5-dimethyl-3-(5-ethylsulfonyl-1-phenyl-3-trifluoromethyl-1H-pyrazol-4-ylmethylsulfonyl)-2-isoxazoline (present compound No. 3-0004)

1.7 g of m-chloroperbenzoic acid (purity: 70%, 6.7 mmoles) was added, with ice-cooling, to a solution of 0.6 g (1.3 mmoles) of 5,5-dimethyl-3-(5-ethylthio-1-phenyl-3-trifluoromethyl-1H-pyrazol-4-ylmethylthio)-2-isoxazoline dissolved in 10 ml of chloroform. The mixture was stirred at room temperature for 16 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The resulting crystals were washed with hexane to obtain 0.6 g (yield: 93.0%) of 5,5-dimethyl-3-(5-ethylsulfonyl-1-phenyl-3-trifluoromethyl-1H-pyrazol-4-ylmethylsulfonyl)-2-isoxazoline as light yellow crystals (melting point: 158 to 160° C.).

$^1$H-NMR [CDCl$_3$/TMS, δ (ppm)]: 7.58-7.54 (5H, m), 5.16 (2H, s), 3.18 (2H, s), 3.15 (2H, q), 1.55 (6H, s), 1.24 (3H, t)

EXAMPLE 7

Production of 5,5-dimethyl-3-(5-dimethylamino-1-phenyl-3-trifluoromethyl-1H-pyrazol-4-ylmethylthio)-2-isoxazoline (present compound 3-0023)

0.8 g (6.7 mmoles) of a 40% aqueous dimethylamine solution was added to a solution of 0.5 g (1.3 mmoles) of 5,5-dimethyl-3-(5-fluoro-1-phenyl-3-trifluoromethyl-1H-pyrazol-4-ylmethylthio)-2-isoxazoline dissolved in 10 ml of N,N-dimethylformamide. The mixture was stirred at 100° C. for 9 hours in a sealed tube. Thereto was added 3.0 g (26.6 mmoles) of a 40% aqueous dimethylamine solution, and the resulting mixture was stirred for 9 hours to give rise to a reaction. After the completion of the reaction, the reaction mixture was poured into water, followed by extraction with ethyl acetate. The resulting organic layer was washed with an aqueous sodium chloride solution and then dried over anhydrous sodium sulfate. The resulting solution was subjected to vacuum distillation to remove the solvent contained therein. The residue was purified by silica gel column chromatography (developing solvent: hexane-ethyl acetate mixed solvent) to obtain 0.4 g (yield: 80.6%) of 5,5-dimethyl-3-(5-dimethylamino-1-phenyl-3-trifluoromethyl-1H-pyrazol-4-ylmethylthio)-2-isoxazoline.

$^1$H-NMR [CDCl$_3$/TMS, δ (ppm)]: 7.58-7.38 (5H, m), 4.35 (2H, s), 2.82 (2H, s), 2.77 (6H, s), 1.45 (6H, s)

EXAMPLE 8

Production of 5,5-dimethyl-3-(5-dimethylamino-1-phenyl-3-trifluoromethyl-1H-pyrazol-4-ylmethylsulfonyl)-2-isoxazoline (present compound 3-0005)

0.7 g of m-chloroperbenzoic acid (purity: 70%, 2.7 mmoles) was added, with ice-cooling, to a solution of 0.4 g (1.1 mmoles) of 5,5-dimethyl-3-(5-dimethylamino-1-phenyl-3-trifluoromethyl-1H-pyrazol-4-ylmethylthio)-2-isoxazoline dissolved in 10 ml of chloroform. The mixture was stirred at room temperature for 20 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The resulting crystals were washed with hexane to obtain 0.2 g (yield: 52.0%) of 5,5-dimethyl-3-(5-dimethylamino-1-phenyl-3-trifluoromethyl-1H-pyrazol-4-ylmethylsulfonyl)-2-isoxazoline as a white powder (melting point: 150 to 151° C.).

$^1$H-NMR [CDCl$_3$/TMS, δ (ppm)]: 7.61-7.38 (5H, m), 4.75 (2H, s), 3.13 (2H, s), 2.76 (6H, s), 1.53 (6H, s)

EXAMPLE 9

Production of 3-(1-tert-butyl-5-chloro-3-trifluoromethyl-1H-pyrazol-4-ylmethylthio)-5,5-dimethyl-2-isoxazoline (present compound No. 3-0006)

21.8 g of sodium hydrosulfide (purity: 70%, 272.5 mmoles) was added to a solution of 24.1 g (136.0 mmoles) of 5,5-dimethyl-3-methylsulfonyl-2-isoxazoline dissolved in 200 ml of N,N-dimethylformamide. The mixture was stirred for 1 hour. Thereto were added 18.8 g (136.2 mmoles) of anhydrous potassium carbonate and 21.0 g (136.2 mmoles) of Rongalit. The resulting mixture was stirred for 2 hours. Thereto was added, with ice-cooling, 40 g (125 mmoles) of 4-bromomethyl-1-tert-butyl-5-chloro-3-trifluoromethyl-1H-pyrazole. The resulting mixture was stirred at room temperature for 2 hours to give rise to a reaction. After the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 23.0 g (yield: 57.1%) of 3-(1-tert-butyl-5-chloro-3-trifluoromethyl-1H-pyrazol-4-ylmethylthio)-5,5-dimethyl-2-isoxazoline as light pink crystals (melting point: 79.0 to 81.0° C.).

$^1$H-NMR [CDCl$_3$/TMS, δ (ppm)]: 4.24 (2H, s), 2.80 (2H, s), 1.71 (9H, s), 1.43 (6H, s)

EXAMPLE 10

Production of 3-(5-chloro-3-trifluoromethyl-1H-pyrazol-4-ylmethylthio)-5,5-dimethyl-2-isoxazoline (present compound No. 3-0007)

19.8 g (53.4 mmoles) of 3-(1-tert-butyl-5-chloro-3-trifluoromethyl-1H-pyrazol-4-ylmethylthio)-5,5-dimethyl-2-isoxazoline was added to 170 ml of a 25% hydrogen bromide-acetic acid solution. The mixture was stirred at 40 to 50° C. for 2 hours to give rise to a reaction. After the completion of the reaction was confirmed, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 12.0 g (yield: 60.6%) of 3-(5-chloro-3-trifluoromethyl-1H-pyrazol-4-ylmethylthio)-5,5-dimethyl-2-isoxazoline as light yellow crystals (melting point: 120.0 to 122.0° C.)

$^1$H-NMR [CDCl$_3$/TMS, δ (ppm)]: 4.26 (2H, s), 2.81 (2H, s), 1.44 (6H, s)

EXAMPLE 11

Production of 3-(5-chloro-1-difluoromethyl-3-trifluoromethyl-1H-pyrazol-4-ylmethylthio)-5,5-dimethyl-2-isoxazoline (present compound No. 3-0008) and 3-(3-chloro-1-difluoromethyl-5-trifluoromethyl-1H-pyrazol-4-ylmethylthio)-5,5-dimethyl-2-isoxazoline (present compound 3-0009)

3.1 g (22.5 mmoles) of anhydrous potassium carbonate was added to a solution of 2.3 g (7.3 mmoles) of 3-(5-chloro-3-trifluoromethyl-1H-pyrazol-4-ylmethylthio)-5,5-dimethyl-2-isoxazoline dissolved in 50 ml of N,N-dimethylformamide. Thereinto was blown chlorodifluoromethane. The resulting mixture was stirred at 130 to 140° C. for 3 hours to give rise to a reaction. After confirmation of the completion of the reaction, the reaction mixture was pored into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.69 g (yield: 25.8%) of 3-(5-chloro-1-difluoromethyl-3-trifluoromethyl-1H-pyrazol-4-ylmethylthio)-5,5-dimethyl-2-isoxazoline as light yellow crystals (melting point: 41.0 to 42.0° C.) and 0.54 g (yield: 20.2%) of 3-(3-chloro-1-difluoromethyl-5-trifluoromethyl-1H-pyrazol-4-ylmethylthio)-5,5-dimethyl-2-isoxazoline as a white powder (melting point: 89.0 to 90.0° C.). 3-(5-Chloro-1-difluoromethyl-3-trifluoromethyl-1H-pyrazol-4-ylmethylthio)-5,5-dimethyl-2-isoxazoline $^1$H-NMR [CDCl$_3$/TMS, δ (ppm)]: 7.22 (1H, t), 4.25 (2H, s), 2.80 (2H, s), 0.44 (6H, s) 3-(3-Chloro-1-difluoromethyl-5-trifluoromethyl-1H-pyrazol-4-ylmethylthio)-5,5-dimethyl-2-isoxazoline $^1$H-NMR [CDCl$_3$/TMS, δ (ppm)]: 7.19 (1H, t), 4.28 (2H, s), 2.80 (2H, s), 1.44 (6H, s)

EXAMPLE 12

Production of 3-(5-chloro-1-difluoromethyl-3-trifluoromethyl-1H-pyrazol-4-ylmethylsulfonyl)-5,5-dimethyl-2-isoxazoline (present compound No. 3-0010)

1.4 g of m-chloroperbenzoic acid (purity: 70%, 8.1 mmoles) was added, with ice-cooling, to a solution of 0.69 g (1.9 mmoles) of 3-(5-chloro-1-difluoromethyl-3-trifluoromethyl-1H-pyrazol-4-ylmethylthio)-5,5-dimethyl-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed with n-hexane to obtain 0.4 g (yield: 53.3%) of 3-(5-chloro-1-difluoromethyl-3-trifluoromethyl-1H-pyrazol-4-ylmethylsulfonyl)-5,5-dimethyl-2-isoxazoline as a white powder (melting point: 126.0 to 127.0° C.).

$^1$H-NMR [CDCl$_3$/TMS, δ (ppm)]: 7.26 (1H, t), 4.68 (2H, s), 3.11 (2H, s), 1.53 (6H, s)

EXAMPLE 13

Production of 3-(3-chloro-1-difluoromethyl-5-trifluoromethyl-1H-pyrazol-4-ylmethylsulfonyl)-5,5-dimethyl-2-isoxazoline (present compound No. 3-0011)

1.1 g of m-chloroperbenzoic acid (purity: 70%, 6.4 mmoles) was added, with ice-cooling, to a solution of 0.54 g (1.5 mmoles) of 3-(3-chloro-1-difluoromethyl-5-trifluoromethyl-1H-pyrazol-4-ylmethylthio)-5,5-dimethyl-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed, with n-hexane to obtain 0.47 g (yield: 79.7%) of 3-(3-chloro-1-difluoromethyl-5-trifluoromethyl-1H-pyrazol-4-ylmethylsulfonyl)-5,5-dimethyl-2-isoxazoline as a white powder (melting point: 136.0 to 137.0° C.).

$^1$H-NMR [CDCl$_3$/TMS, δ (ppm)]: 7.23 (1H, t), 4.71 (2H, s), 3.11 (2H, s), 1.53 (6H, s)

EXAMPLE 14

Production of 5,5-dimethyl-3-(3-methoxy-1-methyl-5-trifluoromethyl-1H-pyrazol-4-ylmethylthio)-2-isoxazoline (present compound No. 3-0024)

3.1 g of sodium hydrosulfide hydrate (purity: 70%, 22.0 mmoles) was added to a solution of 3.3 g (17.3 mmoles) of 5,5-dimethyl-3-ethylsulfonyl-2-isoxazoline dissolved in 10 ml of N,N-dimethylformamide. The mixture was stirred for 2 hours. Thereto were added 3.1 g (22.0 mmoles) of anhydrous potassium carbonate, 2.7 g (17.5 mmoles) of Rongalit and 4.0 g (17.5 mmoles) of 4-chloromethyl-3-methoxy-1-methyl-5-trifluoromethyl-1H-pyrazole. The resulting mixture was stirred at room temperature for 2 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 2.8 g (yield: 52.0%) of 5,5-dimethyl-3-(3-methoxy-1-methyl-5-trifluoromethyl-1H-pyrazol-4-ylmethylthio)-2-isoxazoline.

EXAMPLE 15

Production of 5,5-dimethyl-3-(3-hydroxy-1-methyl-5-trifluoromethyl-1H-pyrazol-4-ylmethylthio)-2-isoxazoline (present compound No. 3-0025)

To 20 ml of a 25% hydrogen bromide acetic acid solution was added 3.3 g (10.6 mmoles) of 5,5-dimethyl-3-(3-methoxy-1-methyl-5-trifluoromethyl-1H-pyrazol-4-ylmethylthio)-2-isoxazoline. The mixture was stirred at 50° C. for 3 hours to give rise to a reaction. After the completion of the reaction, the reaction mixture was subjected to vacuum distillation to remove the solvent contained therein. The residue was poured into water. The resulting crystals were collected by filtration, washed with water and dried to obtain 3.1 g (yield: 96.0%) of intended 5,5-dimethyl-3-(3-hydroxy-1-methyl-.5-trifluoromethyl-1H-pyrazol-4-ylmethylthio)-2-isoxazoline.

EXAMPLE 16

Production of 5,5-dimethyl-3-(3-ethoxy-1-methyl-5-trifluoromethyl-1H-pyrazol-4-ylmethylthio)-2-isoxazoline (present compound No. 3-0026)

0.20 g (1.3 mmoles) of anhydrous potassium carbonate and 0.20 g (1.5 mmoles) of ethyl iodide were added to a solution of 0.30 g (1.0 mmoles) of 5,5-dimethyl-3-(3-hydroxy-1-methyl-5-trifluoromethyl-1H-pyrazol-4-ylmethylthio)-2-isoxazoline dissolved in 10 ml of N,N-dimethylformamide. The mixture was stirred at 50° C. for 3 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 0.30 g (yield: 92.0%) of intended 5,5-dimethyl-3-(3-ethoxy-1-methyl-5-trifluoromethyl-1H-pyrazol-4-ylmethylthio)-2-isoxazoline.

EXAMPLE 17

Production of 5,5-dimethyl-3-(3-ethoxy-1-methyl-5-trifluoromethyl-1H-pyrazol-4-ylmethylsulfonyl)-2-isoxazoline (present compound No. 3-0012)

0.68 g of m-chloroperbenzoic acid (purity: 70%, 2.76 mmoles) was added, with ice-cooling, to a solution of 0.30 g (0.92 mmoles) of 5,5-dimethyl-3-(3-ethoxy-1-methyl-5-trifluoromethyl-1H-pyrazol-4-ylmethylthio)-2-isoxazoline dissolved in 10 ml of chloroform. The mixture was stirred at room temperature for 5 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The resulting crystals were washed with hexane to obtain 0.24 g (yield: 73.0%) of 5,5-dimethyl-3-(3-ethoxy-1-methyl-5-trifluoromethyl-1H-pyrazol-4-ylmethylsulfonyl)-2-isoxazoline as white crystals (melting point: 124 to 125° C.).

$^1$H-NMR [CDCl$_3$/TMS, δ (ppm)]: 4.50 (2H, s), 4.27 (2H, q), 3.86 (3H, s), 3.04 (2H, s), 1.49 (6H, s), 1.39 (3H, t)

EXAMPLE 18

Production of 5,5-dimethyl-3-(5-fluoro-1-methyl-3-trifluoromethyl-1H-pyrazol-4-ylmethylthio)-2-isoxazoline (present compound No. 3-0027)

19.3 g of sodium hydrosulfide (purity: 70%, 344.6 mmoles) was added to a solution of 21.3 g (120.3 mmoles) of 5,5-dimethyl-3-methylsulfonyl-2-isoxazoline dissolved in 200 ml of N,N-dimethyl-formamide. The mixture was stirred for 1 hour. Thereto were added 16.7 g (121.0 mmoles) of anhydrous potassium carbonate and 18.6 g (120.7 mmoles) of Rongalit. The resulting mixture was stirred for 2 hours. Thereto was added, with ice-cooling, 31.4 g (120.3 mmoles) of 4-bromomethyl-5-fluoro-1-methyl-3-trifluoromethyl-1H-pyrazole. The resulting mixture was stirred at room temperature for 2 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 29.0 g (yield: 90.3%) of 5,5-dimethyl-3-(5-fluoro-1-methyl-3-trifluoromethyl-1H-pyrazol-4-ylmethylyhio)-2-isoxazoline as a yellow oily substance.

$^1$H-NMR [CDCl$_3$/TMS, δ (ppm)]: 4.24 (2H, s), 3.90 (3H, s), 2.78 (2H, s), 1.42 (6H, s)

EXAMPLE 19

Production of 5,5-dimethyl-3-(5-methoxy-1-methyl-3-trifluoromethyl-1H-pyrazol-4-ylmethylthio)-2-isoxazoline (present compound No. 3-0028)

0.77 g (4.0 mmoles) of sodium methoxide (a 28% methanol solution) was added to a solution of 0.5 g (1.6 mmoles) of 5,5-dimethyl-3-(5-fluoro-1-methyl-3-trifluoromethyl-1H-pyrazol-4-ylmethylthio)-2-isoxazoline dissolved in 20 ml of methanol. The mixture was stirred for 4 hours under refluxing, to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 0.5 g (yield: 96.7%) of 5,5-dimethyl-3-(5-methoxy-2-methyl-3-trifluoromethyl-1H-pyrazol-4-ylmethylthio)-2-isoxazoline as a yellow oily substance.

$^1$H-NMR [CDCl$_3$/TMS, δ (ppm)]: 4.26 (2H, s), 4.07 (3H, s), 3.72 (3H, s), 2.80 (2H, s), 1.43 (6H, s)

EXAMPLE 20

Production of 5,5-dimethyl-3-(5-methoxy-1-methyl-3-trifluoromethyl-1H-pyrazol-4-ylmethylsulfonyl)-2-isoxazoline (present compound No. 3-0013)

1.3 g of m-chloroperbenzoic acid (purity: 70%, 7.5 mmoles) was added, with ice-cooling, to a solution of 0.5 g (1.5 mmoles) of 5,5-dimethyl-3-(5-methoxy-1-methyl-3-trifluoromethyl-1H-pyrazol-4-ylmethylthio)-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed with n-hexane to obtain 0.31 g (yield: 58.2%). of 5,5-dimethyl-3-(5-methoxy-1-methyl-3-trifluoromethyl-1H-pyrazol-4-ylmethylsulfonyl)-2-isoxazoline as a white powder (melting point: 113.0 to 114.0° C.).

$^1$H-NMR [CDCl$_3$/TMS, δ (ppm)]: 4.60 (2H, s), 4.11 (3H, s), 3.79 (3H, s), 3.10 (2H, s), 1.51 (6H, s)

EXAMPLE 21

Production of 3-(5-(2-chlorophenoxy)-1-methyl-3-trifluoromethyl-1H-pyraxzol-4-ylmethylthio)-5,5-dimethyl-2-isoxazoline (present compound No. 3-0029)

0.2 g (8.3 mmoles) of sodium hydride (purity: 60%) was added, with ice-cooling, to a solution of 0.44 g (3.4 mmoles) of 2-chlorophenol dissolved in 30 ml of N,N-dimethylformamide. The mixture was stirred for 1 hour. Thereto was added 0.7 g (2.2 mmoles) of 5,5-dimethyl-3-(5-fluoro-1-methyl-3-trifluoromethyl-1H-pyrazol-4-ylmethylthio)-2-isoxazoline The resulting mixture was stirred at 120 to 130° C. for 5 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.63 g (yield: 66.7%) of 3-(5-(2-chlorophenoxy)-1-methyl-3-trifluoromethyl-1H-pyraxzol-4-ylmethylthio)-2-isoxazoline-5,5-dimethyl-2-isoxazoline as a yellow oily substance.

EXAMPLE 22

Production of 3-(5-(2-chlorophenoxy)-17-methyl-3trifluoromethyl-1H-pyraxzol-4-ylmethylsulfonyl)-5,5-dimethyl-2-isoxazoline (present compound No. 3-0014)

1.0 g of m-chloroperbenzoic acid (purity: 70%, 5.8 mmoles) was added, with ice-cooling, to a solution of 0.63 g (1.5 mmoles) of 3-(5-(2-chlorophenoxy)-1-methyl-3-trifluoromethyl-1H-pyrazol-4-ylmethylthio)-5,5-dimethyl-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride:

solution in this order and then dried over anhydrous magnesium sulfate. The resulting solution was subjected to vacuum distillation to remove the solvent contained therein. The resulting solid was washed with n-hexane to obtain 0.31 g (yield: 45.7%) of 3-(5-(2-chlorophenoxy)-1-methyl-3-trifluoromethyl-1H-pyrazol-4-ylmethylsulfonyl)-5,5-dimethyl-2-isoxazoline as a white powder (melting point: 67.0 to 70.0° C.).

$^1$H-NMR [CDCl$_3$/TMS, δ (ppm)]: 7.50-6.91 (4H, m), 4.45 (2H, s), 3.71 (3H, s), 3.03 (2H, s), 1.47 (6H, s)

EXAMPLE 23

Production of 3-(5-cyclopentyloxy-1-methyl-3-trifluoromethyl-1H-pyrazol-4-ylmethylthio)-5,5-dimethyl-2-isoxazoline (present compound No. 3-0030)

To a solution of 0.43 g (1.6 mmoles) of triphenylphosphine dissolved in 10 ml of benzene were added 0.14 g (1.6 mmoles) of cyclopentanol, 0.5 g (1.6 mmoles) of 5,5dimethyl-3-(5-hydroxy-1-methyl-3-trifluoromethyl-1H-pyrazol-4-ylmethylthio)-2-isoxazoline and 0.7 g (1.6 mmoles) of di-ethyl azodicarboxylate (a 40%, toluene solution). The mixture was stirred at room temperature for 12 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting organic layer was subjected to vacuum distillation to remove the solvent contained therein. The residue was purified by silica, gel column chromatography (developing solvent: hexane-ethyl acetate mixed solvent) to obtain 0.52 g (yield: 85.2%) of 3-(5-cyclopentyloxy-1-methyl-3-trifluoromethyl-1H-pyrazol-4-ylmethylthio)-5,5-dimethyl-2-isoxazoline as a colorless transparent oily substance.

EXAMPLE 24

Production of 3-(5-cyclopentyloxy-1-methyl-3-trifluoromethyl-1H-pyrazol-4-ylmethylsulfonyl)-5,5-dimethyl-2-isoxazoline (present compound No. 3-0015)

0.85 g of m-chloroperbenzoic acid (purity: 70%, 4.9 mmoles) was added, with ice-cooling, to a solution of 0.52 g (1.4 mmoles) of 3-(5-(cyclopentyloxy-1-methyl-3trifluoromethyl-1H-pyrazol-4-ylmethylthio)-5,5-dimethyl-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed with n-hexane to obtain 0.2 g (yield: 35.5%) of 3-(5-cyclopentyloxy-1-methyl-3-trifluoromethyl-1H-pyrazol-4-ylmethylsulfonyl)-5,5-dimethyl-2-isoxazoline as a white powder (melting point: 113.0 to 114.0° C.).

$^1$H-NMR [CDCl$_3$/TMS, δ (ppm)]: 5.03 (1H, br), 4.60 (2H, s), 3.73 (3H, s), 3.05 (2H, s), 1.88-1.70 (8H, m), 1.50 (6H, s)

EXAMPLE 25

Production of 3-(5-cyano-1-methyl-3-trifluoromethyl-1H-pyrazol-4-ylmethylthio)-5,5-dimethyl-2-isoxazoline (present compound No. 3-0031)

0.2 g (4.0 mmoles) of sodium cyanide was added to a solution of 0.5 g (1.6 mmoles) of 5,5-dimethyl-3-(5-fluoro-1-methyl-3-trifluoromethyl-1H-pyrazol-4-ylmethylthio)-2-isoxazoline dissolved in 30 ml of N,N-dimethylformamide. The mixture was stirred at 40° C. for 1 hour to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 0.9 g of crude 3-(5cyano-1-methyl-3-trifluoromethyl-1H-pyrazol-4-ylmethylthio)-5,5-dimethyl-2-isoxazoline as a yellow oily substance.

$^1$H-NMR [CDCl$_3$/TMS, δ (ppm)]: 4.30 (2H, s), 4.08 (3H, s), 2.81 (2H, s), 1.43 (6H, s)

EXAMPLE 26

Production of 3-(5-cyano-1-methyl-3-trifluoromethyl-1H-pyrazol-4-ylmethylsulfonyl)-5,5-dimethyl-2-isoxazoline (present compound No. 3-0016)

2.1 g of m-chloroperbenzoic acid (purity: 70%, 12.2 mmoles) was added, with ice-cooling, to a solution of 0.9 g of 3-(5-cyano-1-methyl-3-trifluoromethyl-1H-pyrazol-4ylmethylthio)-5,5-dimethyl-2-isoxazoline (crude compound) dissolved in 50 ml of chloroform. The mixture was stirred for 1 hour and then-at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed with n-hexane to obtain 0.43 g (yield: 76.4%) of 3-(5-cyano-1-methyl-3-trifluoromethyl-1H-pyrazol-4-ylmethylsulfonyl)-5,5-dimethyl-2-isoxazoline as a white, powder (melting point: 105.0 to 108.0° C.).

$^1$H-NMR [CDCl$_3$/TMS, δ (ppm)]: 4.73 (2H, s), 4.16 (3H, s), 3.14 (2H, s), 1.53 (6H, s)

EXAMPLE 27

Production of 3-(3,5-dichloro-1-ethyl-1H-pyrazol-4ylmethylthio)-5,5-dimethyl-2-isoxazoline (present compound No. 3-0032)

0.6 g of sodium hydrosulfide (purity: 70%, 10.7 mmoles) was added to a solution of 0.7 g (3.7 mmoles) of 5,5-dimethyl-3-ethylsulfonyl-2-isoxazoline dissolved in 30 ml of N,N-dimethylformamide. The mixture was stirred for 1 hour. Thereto were added 0.51 g (3.7 mmoles) of anhydrous potassium carbonate and 0.56 g (3.6 mmoles) of Rongalit. The resulting mixture was stirred for 2 hours. Thereto was added, with ice-cooling, 0.9 g (3.5 mmoles) of 4-bromomethyl-3,5-dichloro-1-ethyl-1H-pyrazole. The resulting mixture was stirred at room temperature for 2 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.8 g (yield: 70.8%) of 3-(3,5-dichloro-1-ethyl-1H-pyrazol-4-ylmethylthio)-5,5-dimethyl-2-isoxazoline as a colorless transparent oily substance.

$^1$H-NMR [CDCl$_3$/TMS, δ (ppm)]: 4.14 (2H, s), 4.14 (2H, q), 2.81 (2H, s), 1.43 (6H, s), 1.42 (3H, t)

EXAMPLE 28

Production of 3-(3,5-dichloro-1-ethyl-1H-pyrazol-4-ylmethylsulfonyl)-5,5-dimethyl-2-isoxazoline (present compound No. 3-0017)

2.0 g of m-chloroperbenzoic acid (purity: 70%, 11.6 mmoles) was added, with ice-cooling, to a solution of 0.8 g (2.6 mmoles) of 3-(3,5-dichloro-1-ethyl1H-pyrazol-4ylmethylthio)-5,5-dimethyl-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed with n-hexane to obtain 0.41 g (yield: 46.6%) of 3-(3,5-dichloro-1-ethyl-1H-pyrazol-4-ylmethylsulfonyl)-5,5-dimethyl-2-isoxazoline as a white powder (melting point: 105.0 to 107.0° C.)

$^1$H-NMR [CDCl$_3$/TMS, δ (ppm)]: 4.48 (2H, s), 4.19 (2H, q), 3.05 (2H, s), 1.51 (6H, s), 1.45 (3H, t)

EXAMPLE 29

Production of 3-(5-chloro-3-difluoromethyl-1-methyl-1H-pyrazol-4-ylmethylthio)-5,5-dimethyl-2-isoxazoline (present compound No. 3-0020)

1.2 g of sodium hydrosulfide hydrate (purity: 70%, 15.0 mmoles) was added to a solution of 1.9 g (10.0 mmoles) of 5,5-dimethyl-3-ethylsulfonyl-2-isoxazoline dissolved in 30 ml of N,N-dimethylformamide. The mixture was stirred for 2 hours. Thereto were added 2.1 g (15.0 mmoles) of anhydrous potassium carbonate, 2.3 g (15.0 mmoles) of Rongalit and 2.6 g (10.0 mmoles) of 4-bromomethyl-5-chloro-3-difluoromethyl-1-methyl-1H-pyrazole. The resulting mixture was stirred at room temperature for 15 hours to give, rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 2.1 g (yield: 68.0%) of 3-(5-chloro-3-difluoromethyl-1-methyl-1H-pyrazol-4-ylmethylthio)-5,5-dimethyl-2-isoxazoline as a colorless viscous liquid ($n_D^{20}$ =1.5183).

$^1$H-NMR [CDCl$_3$/TMS, δ (ppm)]: 6.70 (1H, t, J=54.2 Hz), 4.24 (2H, s), 3.86 (3H, s) 2.80 (2H, s), 1.42 (6H, s)

EXAMPLE 30

Production of 3-(5-chloro-3-difluoromethyl-1-methyl-1H-pyrazol-4-ylmethylsulfonyl)-5,5-dimethyl-2-isoxazoline (present compound No. 3-0018)

3.6 g of m-chloroperbenzoic acid (purity:, 70%, 14.5 mmoles) was added, with ice-cooling, to a solution of 1.8 g (5.8 mmoles) of 3-(5-chloro-3-difluoromethyl-1-methyl-1H-pyrazol-4-ylmethylthio)-5,5-dimethyl-2-isoxazoline dissolved 30 in 15 ml of chloroform. The mixture was stirred at room temperature for 22 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The resulting crystals were washed with hexane to obtain 1.7 g (yield: 85.9%) of 3-(5-chloro-3-difluoromethyl-1-methyl-1H-pyrazol-4-ylmethylsulfonyl)-5,5-dimethyl-2-isoxazoline as white crystals (melting point: 78 to 79° C.).

$^1$H-NMR [CDCl$_3$/TMS, δ (ppm)]: 6.80 (1H, t, J=54.8 Hz), 4.60 (2H, s), 3.91 (3H, s), 3.08 (2H, s), 1.51 (6H, s)

EXAMPLE 31

Production of 5,5-dimethyl-3-(5-methyl-3-trifluoromethylisoxazol-4-ylmethylthio)-2-isoxazoline (present compound No. 4-0003)

0.4 g of sodium hydrosulfide hydrate (purity: 70%, 4.6 mmoles) was added to a solution of 0.4 g (2.3 mmoles) of 5,5-dimethyl-3-methylsulfonyl-2-isoxazline dissolved in 10 ml of N,N-dimethylformamide. The mixture was stirred for 2 hours. Thereto were added 0.3 g (2.3 mmoles) of potassium carbonate, 0.4 g (2.3 mmoles) of Rongalit and 0.5 g (1.8 mmoles) of 4bromomethyl-5-methyl-3-trifluoromethylisoxazole. The resulting mixture was stirred at room temperature for 14 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.4 g (yield: 70.0%) of 5,5-dimethyl-3-(5-methyl-3-trifluoromethylisoxazol-4-ylmethylthio)-2-isoxazoline.

$^1$H-NMR [CDCl$_3$/TMS, δ (ppm)]: 4.11 (2H, s), 2.77 (2H, s), 2.54 (3H, s), 1.42 (6H, s)

EXAMPLE 32

Production of 5,5-dimethyl-3-(5-methyl-3trifluoromethylisoxazol-4-ylmehtylsulfonyl)-2-isoxazoline (present compound No. 4-0001)

0.8 g of m-chloroperbenzoic acid (purity: 70%, 3.2 mmoles) was added, with ice-cooling, to a solution of 0.4 g (1.3 mmoles) of 5,5-dimethyl-3-(5-methyl-3-trifluoromethylisoxazol-4-ylmehtylthio)-2-isoxazoline dissolved in 10 ml of chloroform. The mixture was stirred at room temperature for 4 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous-sodium chloride solution in this order and then dried over anhydrous magnesium sulfate. The resulting solution was subjected to vacuum distillation to remove the solvent contained therein. The resulting crystals were washed with hexane to obtain 0.4 g (yield: 95.0%) of 5,5-dimethyl-3-(5-methyl-3-trifluoromethylisoxazol-4-ylmehtylsulfonyl)-2-isoxazoline as white crystals (melting point: 135 to 136° C.).

$^1$H-NMR [CDCl$_3$/TMS, δ (ppm)]: 4.54 (2H, s), 3.11 (2H, s), 2.61 (3H, s), 1.52 (6H, s)

EXAMPLE 33

Production of [(5-chloro-3-methyl-isothiazol-4-yl)methylthio]-5,5-dimethyl-2-isoxazoline (present compound No. 4-0004)

0.82 g of sodium hydrosulfide (purity: 70%, 10.00 mmoles) was added at the room temperature to a solution of 0.89 g (5.00 mmoles) of 5,5-dimethyl-3-methylsulfonyl-2-isoxazoline dissolved in 10 ml of N,N-dimethylformamide. The mixture was stirred for 2 hours. Thereto were added 0.70 g (5.00 mmoles) of anhydrous potassium carbonate, 0.78 g (5.00 mmoles) of Rongalit and 0.91 g (5.00 mmoles) of 5-chloro-4-chloromethyl-3-methylisothiazole. The resulting mixture was stirred at room temperature overnight to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography to obtain 1.38 g (yield: quantitative) of [(5-chloro-3-methyl-isothiazol-4-yl)methylthio]-5,5-dimethyl-2-isoxazoline.

EXAMPLE 34

Production of [(5-chloro-3-methyl-isothiazol-4-yl)-methylsulfonyl]-5,5-dimethyl-2-isoxazoline (present compound No. 4-0002)

2.96 g of m-chloroperbenzoic acid (purity: 70%, 12.00 mmoles) was added, with ice-cooling, to a solution of 1.38 g (5.00 mmoles) of [(5-chloro-3-methyl-isothiazol-4-yl)-methylthio]-5,5-dimethyl-2-isoxazoline dissolved in 20 ml of chloroform. The mixture was stirred for 1 hour and then at room temperature for overnight to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The reside was purified by silica gel column chromatography to obtain 0.65 g (yield: 47.0%) of [(5-chloro-3-methyl-isothiazol-4-yl)-methylsulfonyl]-5,5-dimethyl-2-isoxazoline as a light yellow powder (melting point: 113 to 114° C.)

$^1$H-NMR [CDCl$_3$/TMS, δ (ppm)]: 8.89 (1H, s), 4.67 (2H, s), 3.05 (2H, s), 2.59 (3H, s) 1.51 (6H, s)

EXAMPLE 35

Production of 5,5-dimethyl-3-[2,5-dimethyl-4-(1-methoxyiminoethyl)-thiophen-3-ylmethylthio]-2-isoxazoline (present compound No. 2-0002)

0.57 g (6.8 mmoles) of O-methylhydroxylamine hydrochloride and 0.56 g (6.8 mmoles) of sodium acetate were added to a solution of 1.0 g (3.4 mmoles) of 3-(4-acetyl-2,5-dimethylthiophen-3-ylmethylthio)-5,5-dimethyl-2-isoxazoline dissolved in 50 ml of ethanol. The mixture was stirred for 5 hours under refluxing, to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.4 g (36.4%) of 5,5-dimethyl-3-[2,5-dimethyl-4-(1-methoxyiminoethyl)-thiophen-2-ylmethylthio]-2-isoxazoline as a yellow oily substance.

$^1$H-NMR [CDCl$_3$/TMS, (ppm)]: 4.21 (2H, s), 3.95 (3H, s), 2.76 (2H, s), 2.38 (3H, s), 2.34 (3H, s), 2.13 (3H, s), 1.42 (6H, s)

EXAMPLE 36

Production of 5,5-dimethyl-3-[2,5-dimethyl-4-(1-methoxyiminoethyl)-thiophen-3-ylmethylsulfonyl]-2-isoxazoline (present compound No. 2-0001)

0.61 g of m-chloroperbenzoic acid (purity: 70%, 3.5 mmoles) was added, with ice-cooling, to a solution of 0.4 g (1.2 mmoles) of 5,5-dimethyl-3-[2,5-dimethyl-4-(1-methoxyiminoethyl)-thiophen-3-ylmethylthio]-2-isoxazoline dissolved in 30 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.35 g (80%) of 5,5-dimethyl-3-[2,5-dimethyl-4-(1-methoxyiminoethyl)-thiophen-3-ylmethylsulfonyl]-2-isoxazoline as white crystals (melting point: 95.0 to 96.0° C.).

¹H-NMR [CDCl₃/TMS, δ (ppm)]: 4.79 (2H, s), 3.95 (3H, s), 2.93 (2H, s), 2.42 (3H, s), 2.37 (3H, s), 2.17 (3H, s), 1.47 (6H, s)

EXAMPLE 37

Production of 5,5-dimethyl-3-(4-trifluoromethyl-pyridin-3-ylmethylthio)-2-isoxazoline (present compound No. 7-0003)

0.26 g of sodium hydrosulfide (purity: 70%, 4.6 mmoles) was added to a solution of 0.3 g (1.6 mmoles) of 5,5-dimethyl-3-ethylsulfonyl-2-isoxazoline dissolved in 20 ml of N,N-dimethylformamide. The mixture was stirred for 1 hour. Thereto were added 0.22 g (1.6 mmoles) of anhydrous potassium carbonate and 0.25 g (1.6 mmoles) of Rongalit. The resulting mixture was stirred for 2 hours. Thereto was added, with ice-cooling, 0.3 g (1.3 mmoles) of 3-bromomethyl-4-trifluoromethyl-pyridine. The resulting mixture was stirred at room temperature for 2 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.45 g (yield: 98.9%) of 5,5-dimethyl-3-(4-trifluoromethyl-pyridin-3-ylmethylthio)-2isoxazoline as a yellow oily substance.

¹H-NMR [CDCl₃/TMS, δ (ppm)]: 8.98 (1H, s), 8.70 (1H, d), 7.51 (1H, d), 4.47 (2H, s), 2.79 (2H, s), 1.43 (6H, s)

EXAMPLE 38

Production of 5,5-dimethyl-3-(4-trifluoromethyl-pyridin-3-ylmethylsulfonyl)-2-isoxazoline (present compound No. 7-0001) and 5,5-dimethyl-3-(4-trifluoromethyl-pyridine-N-oxide-3-ylmethylsulfonyl)-2-isoxazoline (present compound No. 7-0002)

0.77 g of m-chloroperbenzoic acid (purity: 70%, 4.5 mmoles) was added, with ice-cooling, to a solution of 0.45 g (1.6 mmoles) of 5,5-dimethyl-3-(4-trifluoromethyl-pyridin-3-ylmethylthio)-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.06 g (yield: 12.0%) of 5,5-dimethyl-3-(4-trifluoromethyl-pyridin-3-ylmethylsulfonyl)-2-isoxazoline as light yellow crystals (melting point: 77.0 to 80.0° C.) and 0.12 g (yield: 23.1%) of 5,5-dimethyl-3-(4-trifluoromethyl-pyridin-N-oxide-3-ylmethylsulfonyl)-2-isoxazoline as white crystals (melting point: 114.0 to 116.0° C.).

5,5-Dimethyl-3-(4-trifluoromethyl-pyridin-3-ylmethylsulfonyl)-2-isoxazoline

¹H-NMR [CDCl₃/TMS, δ (ppm)]: 8.98 (1H, s), 8.84 (1H, d), 7.64 (1H, d), 4.92 (2H, s), 3.09 (2H, s), 1.52 (6H, s)

5,5-Dimethyl-3-(4-trifluoromethyl-pyridin-N-oxide-3ylmethylsulfonyl)-2-isoxazoline ¹H-NMR [CDCl₃/TMS, δ (ppm)]: 8.50 (1H, s), 8.25 (1H, d), 7.59 (1H, d), 4.81 (2H, s), 3.12 (2H, s), 1.53 (6H, s)

EXAMPLE 39

Production of 5,5-dimethyl-[(4-methoxy-6-trifluoromethylpyrimidin-5-yl)-methylthio]-2-isoxazoline (present compound No. 8-0002)

0.32 g of sodium hydrosulfide (purity: 70%, 4.00 mmoles) was added, at room temperature, to a solution of 0.35 g (2.00 mmoles) of 5,5-dimethyl-3-methylsulfonyl-2-isoxazoline dissolved in 10 ml of dimethylformamide. The mixture was stirred for 2 hours. To the reaction mixture were added 0.28 g (2.00 mmoles) of anhydrous potassium carbonate, 0.31 g (2.00 mmoles) of Rongalit and 0.45 g (2.00 mmoles) of 5-chloromethyl-4-methoxy-6-trifluoromethylpyrimidine. The resulting mixture was stirred at room temperature for 2 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography to obtain 0.55 g (yield: 85.9%) of 5,5-dimethyl-[(4-methoxy-6-trifluoromethylpyrimidin-5-yl)-methylthio]-2-isoxazoline.

¹H-NMR [CDCl₃/TMS, δ (ppm)]: 8.81 (1H, s), 4.44 (2H, d), 4.12 (3H, s), 2.81 (2H, s), 1.45 (6H, s)

EXAMPLE 40

Production of 5,5-dimethyl-[(4-methoxy-6-trifluoromethylpyrimidin-5-yl)-methylsulfonyl]-2-isoxazoline (present compound No. 8-0001)

1.05 g of m-chloroperbenzoic acid (purity: 70%, 4.28 mmoles) was added, with ice-cooling, to a solution of 0.55 g (1.71 mmoles) of 5,5-dimethyl-[(4-methoxy-6-trifluoromethylpyrimidin-5-yl)-methylthio]-2-isoxazoline dissolved in 20 ml of chloroform. The mixture was stirred for 1 hour and then at room temperature for 4 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The residue was purified by silica gel column chromatography to obtain 0.45 g (yield: 75.0%) of 5,5-dimethyl-[(4-methoxy-6-trifluoromethylpyrimidin-5-yl)-methylsulfonyl]-2-isoxazoline as white feather-like crystals (melting point: 175 to 176° C.).

$^1$H-NMR [CDCl$_3$/TMS, δ (ppm)]: 8.89 (1H, s), 5.00 (2H, d), 4.11 (3H, s), 3.11 (2H, s), 1.53 (6H, s)

EXAMPLE 41

Production of 3-(5,5-dimethyl-2-isoxazolin-3-ylthiomethyl)-2-trifluoromethyl-6,7-dihydro-5H-pyrazolo[5,1-b][1,3]oxazine (present compound No. 3-0033)

A solution of 0.82 g (2.3 mmoles) of 3-[5-chloro-1-(3-hydroxypropyl)-3-trifluoromethyl-1H-pyrazol-4-ylmethylthio]-5,5-dimethyl-2-isoxazole dissolved in 5 ml of N,N-dimethylformamide was dropwise added to a suspension of 0.11 g (2.8 mmoles) of sodium hydride in 15 ml of N,N-dimethylformamide. After the completion of the dropwise addition, the resulting mixture was stirred at room temperature for 30 minutes, then heated to 100° C., and stirred for 1 hour to give rise to a reaction. After confirmation of the completion of the reaction, the reaction mixture was poured into water, followed by extraction with ethyl acetate. The resulting organic layer was washed with an aqueous citric acid solution and an aqueous sodium chloride solution, and then dried over magnesium sulfate. The resulting solution was subjected to vacuum distillation to obtain 0.77 g (yield: 100%) of 3-(5,5-dimethyl-2-isoxazolin-3-ylthiomethyl)-2-trifluoromethyl-6,7-dihydro-5H-pyrazolo[5,1-b][1,3]oxazine.

$^1$H-NMR [CDCl$_3$/TMS, δ (ppm)]: 4.37 (2H, t), 4.19 (2H, t), 4.15 (2H, s), 2.80 (2H, s), 2.31 (2H, m), 1.42 (6H, s)

EXAMPLE 42

Production of 3-(5,5-dimethyl-2-isoxazolin-3-ylsulfonylmethyl)-2-trifluoromethyl-6,7-dihydro-5H-pyrazolo[5,1-b][1,3]oxazine (present compound No. 3-0019)

1.25 g of m-chloroperbenzoic acid (purity: 70%, 5.1 mmoles) was added, with ice-cooling, to a solution of 0.77 g (2.3 mmoles) of 3-(6,7-dihydro-3-trifluoromethyl-5H-pyrazolo[5,1-b][1,3]oxazin-4yl-methylthio)-5,5-dimethyl-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The residue was purified by silica gel column chromatography to obtain 0.36 g (yield: 43%) of 3-(5,5-dimethyl-2-isoxazolin-3-ylsulfonylmethyl)-2-trifluoromethyl-6,7-dihydro-5H-pyrazolo[5,1-b][1,3]oxazine as a white powder (melting point: 151.0 to 152.0° C.).

$^1$H-NMR [CDCl$_3$/TMS, δ (ppm)]: 4.47 (2H, s), 4.40 (2H, t), 4.23 (2H, t), 3.09 (2H, s), 2.34 (2H, m), 1.50 (6H, s)

Compound numbers shown in Tables 11 to 20 are referred to in the Examples.

TABLE 11

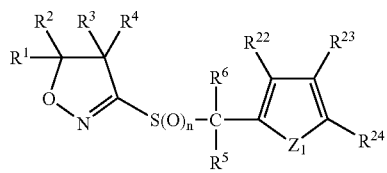

| Compound No. | R$^1$ | R$^2$ | R$^3$ | R$^4$ | n | R$^5$ | R$^6$ | Z$_1$ | R$^{22}$ | R$^{23}$ | R$^{24}$ | Melting point(° C.) or refractive index (n$_D^{20}$) |
|---|---|---|---|---|---|---|---|---|---|---|---|---|
| 1-0001 | Me | Me | H | H | 2 | H | H | S | Me | H | H | 66–68 |
| 1-0002 | Me | Me | H | H | 2 | H | H | S | Cl | Me | H | 87–88 |
| 1-0003 | Me | Me | H | H | 2 | H | H | S | H | H | Me | 95–97 |
| 1-0004 | Me | Me | H | H | 2 | H | H | S | Cl | H | H | 70–72 |
| 1-0005 | Me | Me | H | H | 2 | H | H | S | H | H | Cl | 118–119 |
| 1-0006 | Me | Me | H | H | 2 | H | H | O | H | H | H | Impossible to measure |
| 1-0007 | Me | Me | H | H | 2 | H | H | O | H | H | C(=O)OMe | 124–125 |

TABLE 12

| Compound No. | $R^1$ | $R^2$ | $R^3$ | $R^4$ | n | $R^5$ | $R^6$ | $Z^2$ | $R^{25}$ | $R^{26}$ | $R^{27}$ | Melting point(° C.) or refractive index ($n_D^{20}$) |
|---|---|---|---|---|---|---|---|---|---|---|---|---|
| 2-0001 | Me | Me | H | H | 2 | H | H | S | Me | C(=NOMe)Me | Me | 95–96 |
| 2-0002 | Me | Me | H | H | 0 | H | H | S | Me | C(=NOMe)Me | Me | |
| 2-0003 | Me | Me | H | H | 2 | H | H | S | H | H | H | 99–101 |
| 2-0004 | Me | Me | H | H | 2 | H | H | S | H | Ome | H | 96–97 |
| 2-0005 | Me | Me | H | H | 2 | H | H | S | Cl | H | Cl | 125–127 |
| 2-0006 | Me | Me | H | H | 2 | H | H | S | Cl | Cl | Cl | 158–160 |
| 2-0007 | Me | Me | H | H | 2 | H | H | S | Me | Me | Me | 117–117 |
| 2-0008 | Me | Me | H | H | 2 | H | H | S | Me | C(=O)Me | Me | 146–148 |
| 2-0009 | Me | Me | H | H | 2 | H | H | S | Ph | C(=O)Me | Me | 1.5730 |
| 2-0010 | Me | Me | H | H | 2 | H | H | S | Ph | C(=NOMe)Me | Me | 129–131 |
| 2-0011 | Me | Me | H | H | 2 | H | H | S | Cl | C(=O)Ome | Cl | 157–158 |
| 2-0012 | Me | Me | H | H | 2 | H | H | S | Cl | C(=O)NHMe | Cl | 178–180 |
| 2-0013 | Me | Me | H | H | 2 | H | H | O | H | H | H | 58–61 |
| 2-0014 | Me | Me | H | H | 2 | H | H | O | Me | H | Cl | 180–181 |

TABLE 13

| Compound No. | $R^1$ | $R^2$ | $R^3$ | $R^4$ | n | $R^5$ | $R^6$ | $R^{29}$ | $R^{28}$ | $R^{30}$ | Melting point(° C.) or refractive index ($n_D^{20}$) |
|---|---|---|---|---|---|---|---|---|---|---|---|
| 3-0001 | Me | Me | H | H | 0 | H | H | CF₃ | Ph | Cl | 89–90 |
| 3-0002 | Me | Me | H | H | 2 | H | H | CF₃ | Ph | Cl | 132–133 |
| 3-0003 | Me | Me | H | H | 1 | H | H | Ph | Me | Cl | Impossible to measure |
| 3-0004 | Me | Me | H | H | 2 | H | H | CF₃ | Ph | SO₂Et | 158–160 |
| 3-0005 | Me | Me | H | H | 2 | H | H | CF₃ | Ph | N(Me)₂ | 150–151 |
| 3-0006 | Me | Me | H | H | 0 | H | H | CF₃ | Bu-t | Cl | 79-81 |
| 3-0007 | Me | Me | H | H | 0 | H | H | CF₃ | H | Cl | 120–122 |
| 3-0008 | Me | Me | H | H | 0 | H | H | CF₃ | CHF₂ | Cl | 41-42 |
| 3-0009 | Me | Me | H | H | 0 | H | H | Cl | CHF₂ | CF₃ | 89–90 |
| 3-0010 | Me | Me | H | H | 2 | H | H | CF₃ | CHF₂ | Cl | 126–127 |
| 3-0011 | Me | Me | H | H | 2 | H | H | Cl | CHF₂ | CF₃ | 136–137 |
| 3-0012 | Me | Me | H | H | 2 | H | H | OEt | Me | CF₃ | 124–125 |
| 3-0013 | Me | Me | H | H | 2 | H | H | CF₃ | Me | OMe | 113–114 |
| 3-0014 | Me | Me | H | H | 2 | H | H | CF₃ | Me | O(2-Cl)Ph | 67–70 |
| 3-0015 | Me | Me | H | H | 2 | H | H | CF₃ | Me | OPen-c | 113–114 |
| 3-0016 | Me | Me | H | H | 2 | H | H | CF₃ | Me | CN | 105–108 |
| 3-0017 | Me | Me | H | H | 2 | H | H | Cl | Et | Cl | 105–107 |
| 3-0018 | Me | Me | H | H | 2 | H | H | CHF₂ | Me | Cl | 78–79 |
| 3-0019 | Me | Me | H | H | 2 | H | H | CF₃ | —(CH₂)₃O— | | 151–152 |
| 3-0020 | Me | Me | H | H | 0 | H | H | CHF₂ | Me | Cl | 1.5183 |
| 3-0021 | Me | Me | H | H | 0 | H | H | CF₃ | Ph | F | |
| 3-0022 | Me | Me | H | H | 0 | H | H | CF₃ | Ph | SEt | |
| 3-0023 | Me | Me | H | H | 0 | H | H | CF₃ | Ph | N(Me)₂ | |
| 3-0024 | Me | Me | H | H | 0 | H | H | OMe | Me | CF₃ | |
| 3-0025 | Me | Me | H | H | 0 | H | H | OH | Me | CF₃ | |
| 3-0026 | Me | Me | H | H | 0 | H | H | OEt | Me | CF₃ | |

TABLE 13-continued

| Compound No. | R¹ | R² | R³ | R⁴ | n | R⁵ | R⁶ | R²⁹ | R²⁸ | R³⁰ | Melting point(° C.) or refractive index ($n_D^{20}$) |
|---|---|---|---|---|---|---|---|---|---|---|---|
| 3-0027 | Me | Me | H | H | 0 | H | H | $CF_3$ | Me | F | |
| 3-0028 | Me | Me | H | H | 0 | H | H | $CF_3$ | Me | OMe | |
| 3-0029 | Me | Me | H | H | 0 | H | H | $CF_3$ | Me | O(2-Cl)Ph | |
| 3-0030 | Me | Me | H | H | 0 | H | H | $CF_3$ | Me | OPen-c | |
| 3-0031 | Me | Me | H | H | 0 | H | H | $CF_3$ | Me | CN | |
| 3-0032 | Me | Me | H | H | 0 | H | H | Cl | Et | Cl | |
| 3-0033 | Me | Me | H | H | 0 | H | H | $CF_3$ | —(CH₂)₃O— | | |
| 3-0034 | Me | Me | H | H | 2 | H | H | $CF_3$ | H | Cl | 138–140 |
| 3-0035 | Me | Me | H | H | 2 | H | H | H | Me | Cl | 105–106 |
| 3-0036 | Me | Me | H | H | 2 | H | H | Me | Me | Me | 148–150 |
| 3-0037 | Me | Me | H | H | 2 | H | H | Me | Me | Cl | 99–101 |
| 3-0038 | Me | Me | H | H | 2 | H | H | Cl | Me | Cl | 143–145 |
| 3-0039 | Me | Me | H | H | 2 | H | H | $CF_3$ | Me | Cl | 115–116 |
| 3-0040 | Me | Me | H | H | 2 | H | H | Cl | Me | $CF_3$ | 120–122 |
| 3-0041 | Me | Me | H | H | 2 | H | H | $CF_3$ | Me | F | 79–82 |
| 3-0042 | Me | Me | H | H | 2 | H | H | $CF_3$ | Me | OH | 90–92 |
| 3-0043 | Me | Me | H | H | 2 | H | H | OMe | Me | $CF_3$ | 125–126 |
| 3-0044 | Me | Me | H | H | 2 | H | H | $CF_3$ | Me | OEt | 92–94 |
| 3-0045 | Me | Me | H | H | 2 | H | H | $CF_3$ | Me | OPr-i | 69–71 |
| 3-0046 | Me | Me | H | H | 2 | H | H | $CF_3$ | Me | OPr | 82–83 |
| 3-0047 | Me | Me | H | H | 2 | H | H | $CF_3$ | Me | OBu-t | 86–89 |
| 3-0048 | Me | Me | H | H | 2 | H | H | $CF_3$ | Me | OBu | 61–62 |
| 3-0049 | Me | Me | H | H | 2 | H | H | $CF_3$ | Me | OHex-c | 124–125 |
| 3-0050 | Me | Me | H | H | 2 | H | H | $CF_3$ | Me | OCH₂Pr-c | 93–94 |
| 3-0051 | Me | Me | H | H | 2 | H | H | $CF_3$ | Me | OCH₂Pen-c | 112–113 |
| 3-0052 | Me | Me | H | H | 2 | H | H | $CF_3$ | Me | OCH₂Hex-c | 56–59 |
| 3-0053 | Me | Me | H | H | 2 | H | H | $CF_3$ | Me | OCH₂C≡CH | 92–93 |
| 3-0054 | Me | Me | H | H | 2 | H | H | $CF_3$ | Me | OCHF₂ | 129–130 |
| 3-0055 | Me | Me | H | H | 2 | H | H | OCHF₂ | Me | $CF_3$ | Impossible to measure |
| 3-0056 | Me | Me | H | H | 2 | H | H | $CF_3$ | Me | OCH₂CHF₂ | 89–91 |
| 3-0057 | Me | Me | H | H | 2 | H | H | $CF_3$ | Me | OCH₂CF₃ | 93–95 |
| 3-0058 | Me | Me | H | H | 2 | H | H | $CF_3$ | Me | OCH₂CN | 1.4872 |
| 3-0059 | Me | Me | H | H | 2 | H | H | $CF_3$ | Me | OCH₂Ph | 79–81 |
| 3-0060 | Me | Me | H | H | 2 | H | H | $CF_3$ | Me | OPh | 122–123 |
| 3-0061 | Me | Me | H | H | 2 | H | H | $CF_3$ | Me | O(3-Cl)Ph | Impossible to measure |
| 3-0062 | Me | Me | H | H | 2 | H | H | $CF_3$ | Me | O(3-OMe)Ph | 1.5059 |
| 3-0063 | Me | Me | H | H | 2 | H | H | $CF_3$ | Me | O(4-Cl)Ph | 68–69 |
| 3-0064 | Me | Me | H | H | 2 | H | H | $CF_3$ | Me | O(4-Me)Ph | 132–133 |
| 3-0065 | Me | Me | H | H | 2 | H | H | $CF_3$ | Me | O(4-OMe)Ph | 115–117 |
| 3-0066 | Me | Me | H | H | 2 | H | H | $CF_3$ | Me | OC(=O)Me | 130–131 |
| 3-0067 | Me | Me | H | H | 2 | H | H | $CF_3$ | Me | SO₂Me | 168–169 |
| 3-0068 | Me | Me | H | H | 2 | H | H | $CF_3$ | Me | SEt | 100–102 |
| 3-0069 | Me | Me | H | H | 2 | H | H | $CF_3$ | Me | SO₂Et | 107–108 |
| 3-0070 | Me | Me | H | H | 2 | H | H | $CF_3$ | Me | SO₂Ph | 166–168 |
| 3-0071 | Me | Me | H | H | 2 | H | H | $CF_3$ | Me | Me | 105–107 |
| 3-0072 | Me | Me | H | H | 2 | H | H | Ph | Me | Cl | 127–129 |
| 3-0073 | Me | Me | H | H | 2 | H | H | $CF_3$ | Et | Cl | 111–112 |
| 3-0074 | Me | Me | H | H | 2 | H | H | Cl | Et | $CF_3$ | 112–114 |
| 3-0075 | Me | Me | H | H | 2 | H | H | $CF_3$ | Pr-i | Cl | 157–158 |
| 3-0076 | Me | Me | H | H | 2 | H | H | Cl | Pr-i | $CF_3$ | 135–136 |
| 3-0077 | Me | Me | H | H | 2 | H | H | $CF_3$ | Pr | Cl | 89–90 |
| 3-0078 | Me | Me | H | H | 2 | H | H | Cl | Pr | $CF_3$ | 111–113 |
| 3-0079 | Me | Me | H | H | 2 | H | H | $CF_3$ | Bu-t | H | 101–103 |
| 3-0080 | Me | Me | H | H | 2 | H | H | $CF_3$ | Bu-t | Cl | 118–119 |

TABLE 13-continued

| Compound No. | R¹ | R² | R³ | R⁴ | n | R⁵ | R⁶ | R²⁹ | R²⁸ | R³⁰ | Melting point(° C.) or refractive index ($n_D^{20}$) |
|---|---|---|---|---|---|---|---|---|---|---|---|
| 3-0081 | Me | Me | H | H | 2 | H | H | CF₃ | Bu-s | Cl | 110–112 |
| 3-0082 | Me | Me | H | H | 2 | H | H | Cl | Bu-s | CF₃ | 110–111 |
| 3-0083 | Me | Me | H | H | 2 | H | H | CF₃ | Bu-i | Cl | 96–98 |
| 3-0084 | Me | Me | H | H | 2 | H | H | Cl | Bu-i | CF₃ | 140–141 |
| 3-0085 | Me | Me | H | H | 2 | H | H | CF₃ | Bu | Cl | 89–90 |
| 3-0086 | Me | Me | H | H | 2 | H | H | Cl | Bu | CF₃ | 108–110 |
| 3-0087 | Me | Me | H | H | 2 | H | H | CF₃ | CH₂Ph | Cl | 132–133 |
| 3-0088 | Me | Me | H | H | 2 | H | H | Cl | CH₂Ph | CF₃ | 118–120 |
| 3-0089 | Me | Me | H | H | 2 | H | H | CF₃ | Pen-c | Cl | 130–131 |
| 3-0090 | Me | Me | H | H | 2 | H | H | Cl | Pen-c | CF₃ | 147–148 |
| 3-0091 | Me | Me | H | H | 2 | H | H | CF₃ | Hex-c | Cl | 151–152 |
| 3-0092 | Me | Me | H | H | 2 | H | H | CF₃ | CH₂Pr-c | Cl | 93–95 |
| 3-0093 | Me | Me | H | H | 2 | H | H | Cl | CH₂Pr-c | CF₃ | 129–130 |
| 3-0094 | Me | Me | H | H | 2 | H | H | CF₃ | 1-cyclopropylethyl | Cl | 87–89 |
| 3-0095 | Me | Me | H | H | 2 | H | H | Cl | 1-cyclopropylethyl | CF₃ | 121–123 |
| 3-0096 | Me | Me | H | H | 2 | H | H | CF₃ | CH₂(2-Methylcyclopropyl) | Cl | 102–103 |
| 3-0097 | Me | Me | H | H | 2 | H | H | Cl | CH₂(2-Methylcyclopropyl) | CF₃ | 118–119 |
| 3-0098 | Me | Me | H | H | 2 | H | H | CF₃ | CH₂Bu-c | Cl | 94–96 |
| 3-0099 | Me | Me | H | H | 2 | H | H | Cl | CH₂Bu-c | CF₃ | 141–142 |
| 3-0100 | Me | Me | H | H | 2 | H | H | CF₃ | CH₂Pen-c | Cl | 127–129 |
| 3-0101 | Me | Me | H | H | 2 | H | H | Cl | CH₂Pen-c | CF₃ | 146–149 |
| 3-0102 | Me | Me | H | H | 2 | H | H | CF₃ | CH₂Hex-c | Cl | 152–154 |
| 3-0103 | Me | Me | H | H | 2 | H | H | Cl | CH₂Hex-c | CF₃ | 115–117 |
| 3-0104 | Me | Me | H | H | 2 | H | H | CF₃ | CH₂CH=CH₂ | Cl | 78–80 |
| 3-0105 | Me | Me | H | H | 2 | H | H | Cl | CH₂CH=CH₂ | CF₃ | 105–106 |
| 3-0106 | Me | Me | H | H | 2 | H | H | CF₃ | CH₂C≡CH | Cl | 73–74 |
| 3-0107 | Me | Me | H | H | 2 | H | H | Cl | CH₂C≡CH | CF₃ | 108–109 |
| 3-0108 | Me | Me | H | H | 2 | H | H | CF₃ | CHMeC≡CH | Cl | 95–96 |
| 3-0109 | Me | Me | H | H | 2 | H | H | Cl | CHMeC≡CH | CF₃ | 116–118 |
| 3-0110 | Me | Me | H | H | 2 | H | H | CF₃ | CH₂C≡CMe | Cl | 114–115 |
| 3-0111 | Me | Me | H | H | 2 | H | H | Cl | CH₂C≡CMe | CF₃ | 115–116 |
| 3-0112 | Me | Me | H | H | 2 | H | H | CF₃ | CHF₂ | OMe | 72–74 |
| 3-0113 | Me | Me | H | H | 2 | H | H | OMe | CHF₂ | CF₃ | 108–109 |
| 3-0114 | Me | Me | H | H | 2 | H | H | CF₃ | CH₂CHF₂ | Cl | 99–100 |
| 3-0115 | Me | Me | H | H | 2 | H | H | Cl | CH₂CHF₂ | CF₃ | 107–109 |
| 3-0116 | Me | Me | H | H | 2 | H | H | CF₃ | CH₂CF₃ | Cl | 135–136 |
| 3-0117 | Me | Me | H | H | 2 | H | H | Cl | CH₂CF₃ | CF₃ | 112–115 |
| 3-0118 | Me | Me | H | H | 2 | H | H | CF₃ | CH₂OMe | Cl | 87–89 |
| 3-0119 | Me | Me | H | H | 2 | H | H | Cl | CH₂OMe | CF₃ | 125–128 |
| 3-0120 | Me | Me | H | H | 2 | H | H | CF₃ | CH₂OEt | Cl | 97–98 |
| 3-0121 | Me | Me | H | H | 2 | H | H | Cl | CH₂OEt | CF₃ | 128–129 |
| 3-0122 | Me | Me | H | H | 2 | H | H | CF₃ | CH₂CH₂OH | Cl | 79–81 |
| 3-0123 | Me | Me | H | H | 2 | H | H | Cl | CH₂CH₂OH | CF₃ | 93–94 |
| 3-0124 | Me | Me | H | H | 2 | H | H | CF₃ | CH₂CH₂OMe | Cl | 102–104 |
| 3-0125 | Me | Me | H | H | 2 | H | H | Cl | CH₂CH₂OMe | CF₃ | 118–119 |
| 3-0126 | Me | Me | H | H | 2 | H | H | CF₃ | CH₂CH₂OEt | Cl | 56–59 |
| 3-0127 | Me | Me | H | H | 2 | H | H | Cl | CH₂CH₂OEt | CF₃ | 118–119 |
| 3-0128 | Me | Me | H | H | 2 | H | H | CF₃ | CH₂SMe | Cl | 103–105 |
| 3-0129 | Me | Me | H | H | 2 | H | H | Cl | CH₂SMe | CF₃ | 128–129 |
| 3-0130 | Me | Me | H | H | 2 | H | H | CF₃ | CH₂SO₂Me | Cl | 157–159 |
| 3-0131 | Me | Me | H | H | 2 | H | H | Cl | CH₂SO₂Me | CF₃ | 165–166 |
| 3-0132 | Me | Me | H | H | 2 | H | H | CF₃ | CH₂CH₂SO₂Me | Cl | 155–157 |
| 3-0133 | Me | Me | H | H | 2 | H | H | Cl | CH₂CH₂SO₂Me | CF₃ | 166–168 |
| 3-0134 | Me | Me | H | H | 2 | H | H | CF₃ | CH₂CN | Cl | 128–129 |
| 3-0135 | Me | Me | H | H | 2 | H | H | Cl | CH₂CN | CF₃ | 117–118 |

TABLE 13-continued

| Compound No. | R¹ | R² | R³ | R⁴ | n | R⁵ | R⁶ | R²⁹ | R²⁸ | R³⁰ | Melting point(° C.) or refractive index ($n_D^{20}$) |
|---|---|---|---|---|---|---|---|---|---|---|---|
| 3-0136 | Me | Me | H | H | 2 | H | H | CF₃ | CH₂C(=O)OEt | Cl | 127–129 |
| 3-0137 | Me | Me | H | H | 2 | H | H | Cl | CH₂C(=O)OEt | CF₃ | 143–145 |
| 3-0138 | Me | Me | H | H | 2 | H | H | CF₃ | CH₂C(=O)NH₂ | Cl | 173–174 |
| 3-0139 | Me | Me | H | H | 2 | H | H | Cl | CH₂C(=O)NH₂ | CF₃ | 182–183 |
| 3-0140 | Me | Me | H | H | 2 | H | H | CF₃ | CH₂C(=O)N(Me)₂ | Cl | 142–143 |
| 3-0141 | Me | Me | H | H | 2 | H | H | Cl | CH₂C(=O)N(Me)₂ | CF₃ | 181–182 |
| 3-0142 | Me | Me | H | H | 2 | H | H | CF₃ | CH₂C(=O)Me | Cl | 148–149 |
| 3-0143 | Me | Me | H | H | 2 | H | H | Cl | CH₂C(=O)Me | CF₃ | 163–164 |
| 3-0144 | Me | Me | H | H | 2 | H | H | CF₃ | CH₂CH₂C(=O)Me | Cl | 89–91 |
| 3-0145 | Me | Me | H | H | 2 | H | H | Me | Ph | Me | 140–141 |
| 3-0146 | Me | Me | H | H | 2 | H | H | Me | Ph | Cl | 124–125 |
| 3-0147 | Me | Me | H | H | 2 | H | H | Et | Ph | Cl | 112–113 |
| 3-0148 | Me | Me | H | H | 2 | H | H | Pr | Ph | Cl | 122–123 |
| 3-0149 | Me | Me | H | H | 2 | H | H | Pr-i | Ph | Cl | 116–117 |
| 3-0150 | Me | Me | H | H | 2 | H | H | Bu-t | Ph | Cl | 100–102 |
| 3-0151 | Me | Me | H | H | 2 | H | H | CF₃ | Ph | H | 111–112 |
| 3-0152 | Me | Me | H | H | 2 | H | H | CF₃ | Ph | Me | 129–132 |
| 3-0153 | Me | Me | H | H | 2 | H | H | CF₃ | Ph | CF₃ | 112–113 |
| 3-9154 | Me | Me | H | H | 2 | H | H | CF₃ | Ph | F | 90–91 |
| 3-0155 | Me | Me | H | H | 2 | H | H | CF₃ | Ph | OMe | 104–106 |
| 3-0156 | Me | Me | H | H | 2 | H | H | CF₃ | Ph | OEt | 129–131 |
| 3-0157 | Me | Me | H | H | 2 | H | H | CF₃ | Ph | OPr-i | 86–88 |
| 3-0158 | Me | Me | H | H | 2 | H | H | CF₃ | Ph | OPr | 117–118 |
| 3-0159 | Me | Me | H | H | 2 | H | H | CF₃ | Ph | OBu-t | 105–108 |
| 3-0160 | Me | Me | H | H | 2 | H | H | CF₃ | Ph | OCHF₂ | 90–92 |
| 3-0161 | Me | Me | H | H | 2 | H | H | CF₃ | Ph | SO₂Me | 167–168 |
| 3-0162 | Me | Me | H | H | 2 | H | H | CF₃ | Ph | CN | 113–115 |
| 3-0163 | Me | Me | H | H | 2 | H | H | CF₃ | (2-Cl)Ph | Cl | 153–154 |
| 3-0164 | Me | Me | H | H | 2 | H | H | CF₃ | (3-Cl)Ph | Cl | 106–107 |
| 3-0165 | Me | Me | H | H | 2 | H | H | CF₃ | (4-Cl)Ph | Cl | 142–143 |
| 3-0166 | Me | Me | H | H | 2 | H | H | CF₃ | (4-F)Ph | Cl | 135–138 |
| 3-0167 | Me | Me | H | H | 2 | H | H | CF₃ | (4-OMe)Ph | Cl | 136–138 |
| 3-0168 | Me | Me | H | H | 2 | H | H | CF₃ | (4-Me)Ph | Cl | 129–130 |
| 3-0169 | Me | Me | H | H | 2 | H | H | CF₃ | (4-NO₂)Ph | Cl | 145–147 |
| 3-0170 | Me | Me | H | H | 2 | H | H | CF₃ | (4-CN)Ph | Cl | 91–93 |
| 3-0171 | Me | Me | H | H | 2 | H | H | CF₃ | (4-C(=O)Me)Ph | Cl | 133–135 |
| 3-0172 | Me | Me | H | H | 2 | H | H | CF₃ | (4-C(=O)OMe)Ph | Cl | 121–124 |
| 3-0173 | Me | Me | H | H | 2 | H | H | CF₃ | Pyrmidin-2-yl | Cl | 148–150 |
| 3-0174 | Me | Me | H | H | 2 | H | H | CF₃ | 4,6-Dimethoxypyrmidin-2-yl | Cl | 117–118 |
| 3-0175 | Me | Me | H | H | 2 | H | H | CF₃ | SO₂Me | Cl | 146–148 |
| 3-0176 | Me | Me | H | H | 2 | H | H | CF₃ | SO₂Ph | Cl | 145–148 |
| 3-0177 | Me | Me | H | H | 2 | H | H | CF₃ | C(=O)Me | Cl | 130–131 |
| 3-0178 | Me | Me | H | H | 2 | H | H | CF₃ | C(=O)Ph | Cl | 114–117 |
| 3-0179 | Me | Me | H | H | 2 | H | H | CF₃ | C(=O)OMe | Cl | 104–106 |
| 3-0180 | Me | Et | H | H | 2 | H | H | CF₃ | Me | Cl | 108–110 |
| 3-0181 | Me | Me | H | H | 0 | H | H | CHF₂ | Me | Cl | 1.5183 |
| 3-0182 | Me | Me | H | H | 0 | H | H | Ph | Me | Cl | 76–77 |
| 3-0183 | Me | Me | H | H | 0 | H | H | CF₃ | Bu-t | OMe | 1.4831 |
| 3-0184 | Me | Me | H | H | 0 | H | H | CF₃ | CH₂C(=O)NH₂ | Cl | 179–180 |
| 3-0185 | Me | Me | H | H | 0 | H | H | Me | Ph | Cl | 58–60 |

TABLE 14

| R² | R³ | R⁴ | n | R⁵ | R⁶ | Z³ | R³¹ | R³² | Melting point(° C.) or refractive index ($n_D^{20}$) |
|---|---|---|---|---|---|---|---|---|---|
| Me | H | H | 2 | H | H | O | CF₃ | Me | 135–136 |
| Me | H | H | 2 | H | H | S | Me | Cl | 113–114 |
| Me | H | H | 0 | H | H | O | CF₃ | Me | |
| Me | H | H | 0 | H | H | S | Me | Cl | |

TABLE 14-continued

| R² | R³ | R⁴ | n | R⁵ | R⁶ | Z³ | R³¹ | R³² | Melting point(° C.) or refractive index ($n_D^{20}$) |
|---|---|---|---|---|---|---|---|---|---|
| Me | H | H | 2 | H | H | O | Me | Me | 178–179 |
| Me | H | H | 2 | H | H | O | CF₃ | OEt | 89–91 |
| Me | H | H | 2 | H | H | O | Ph | Me | 81–83 |
| Me | H | H | 2 | H | H | S | Me | OEt | 109–111 |

TABLE 15

| Compound No. | R¹ | R² | R³ | R⁴ | n | R⁵ | R⁶ | Z⁴ | R³³ | R³⁴ | Melting point(° C.) or refractive index ($n_D^{20}$) |
|---|---|---|---|---|---|---|---|---|---|---|---|
| 5-0001 | Me | Me | H | H | 2 | H | H | NMe | Cl | Me | 114–115 |
| 5-0002 | Me | Me | H | H | 2 | H | H | NMe | Cl | Et | 107–108 |
| 5-0003 | Me | Me | H | H | 2 | H | H | NMe | CF₃ | H | 142–143 |
| 5-0004 | Me | Me | H | H | 2 | H | H | NCHF₂ | —(CH₂)₄— | | 123–125 |
| 5-0005 | Me | Me | H | H | 2 | H | H | NPh | OEt | Me | 1.5397 |
| 5-0006 | Me | Me | H | H | 2 | H | H | NPh | OCHF₂ | Me | 1.5339 |
| 5-0007 | Me | Me | H | H | 2 | H | H | NPh | CF₃ | H | 99–101 |
| 5-0008 | Me | Me | H | H | 2 | H | H | NPh | OCH₂CH=CH₂ | Me | 87–90 |
| 5-0009 | Me | Me | H | H | 1 | H | H | NPh | OCH₂CH=CH₂ | Me | 1.5702 |

TABLE 16

| Compound No. | R¹ | R² | R³ | R⁴ | n | R⁵ | R⁶ | Z⁵ | R³⁵ | R³⁶ | Melting point(° C.) or refractive index ($n_D^{20}$) |
|---|---|---|---|---|---|---|---|---|---|---|---|
| 6-0001 | Me | Me | H | H | 2 | H | H | NCHF₂ | —(CH₂)₄— | | Impossible to measure |
| 6-0002 | Me | Me | H | H | 2 | H | H | NPh | H | OEt | 107–108 |
| 6-0003 | Me | Me | H | H | 2 | H | H | NPh | H | OCHF₂ | 1.5383 |
| 6-0004 | Me | Me | H | H | 2 | H | H | O | Me | H | 100–102 |
| 6-0005 | Me | Me | H | H | 0 | H | H | NCHF₂ | —(CH₂)₄— | | 1.5264 |

TABLE 17

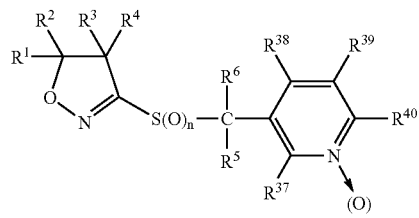

| Compound No. | R¹ | R² | R³ | R⁴ | n | R⁵ | R⁶ | R³⁷ | R³⁸ | R³⁹ | R⁴⁰ | | Melting point(° C.) or refractive index ($n_D^{20}$) |
|---|---|---|---|---|---|---|---|---|---|---|---|---|---|
| 7-0001 | Me | Me | H | H | 2 | H | H | H | CF₃ | H | H | — | 77–80 |
| 7-0002 | Me | Me | H | H | 2 | H | H | H | CF₃ | H | H | N-oxide | 114–116 |
| 7-0003 | Me | Me | H | H | 0 | H | H | H | CF₃ | H | H | — | |
| 7-0004 | Me | Me | H | H | 2 | H | H | H | H | H | H | — | 130–131 |
| 7-0005 | Me | Me | H | H | 2 | H | H | H | H | H | H | N-oxide | 166–168 |
| 7-0006 | Me | Me | H | H | 2 | H | H | Cl | Ph | H | H | — | 118–120 |
| 7-0007 | Me | Me | H | H | 2 | H | H | OMe | Ph | H | H | — | 105–106 |
| 7-0008 | Me | Me | H | H | 2 | H | H | Cl | Me | H | H | — | 115–116 |
| 7-0009 | Me | Me | H | H | 2 | H | H | OMe | Me | H | H | — | 134–135 |
| 7-0010 | Me | Me | H | H | 2 | H | H | Me | Me | H | H | N-oxide | 198–199 |
| 7-0011 | Me | Me | H | H | 2 | H | H | Ph | Ph | H | H | — | 161–162 |
| 7-0012 | Me | Me | H | H | 1 | H | H | H | H | H | H | — | 97–99 |
| 7-0013 | Me | Me | H | H | 0 | H | H | (2-Chloropyridin-3-yl)methylthio | H | H | H | — | 154–155 |

TABLE 18

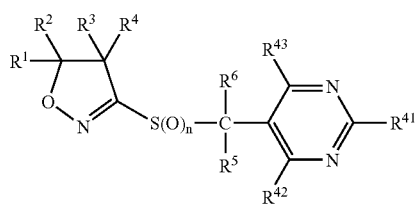

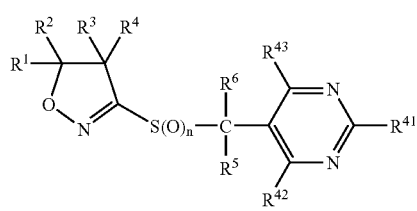

| R¹ | R² | R³ | R⁴ | n | R⁵ | R⁶ | R⁴¹ | R⁴² | R⁴³ | Melting point(° C.) or refractive index ($n_D^{20}$) |
|---|---|---|---|---|---|---|---|---|---|---|
| Me | Me | H | H | 2 | H | H | H | OMe | CF₃ | 175–176 |
| Me | Me | H | H | 0 | H | H | H | OMe | CF₃ | |
| Me | Me | H | H | 2 | H | H | Cl | Cl | | 119–120 |
| Me | Me | H | H | 2 | H | H | OEt | CF₃ | | 94–95 |
| Me | Me | H | H | 2 | H | H | OMe | OMe | | 186–187 |
| Me | Me | H | H | 2 | H | Me | OMe | CF₃ | | 143–144 |
| Me | Me | H | H | 2 | H | H | OMe | OMe | CF₃ | 144–145 |
| Me | Me | H | H | 2 | H | H | SMe | OMe | CF₃ | 160–162 |
| Me | Me | H | H | 2 | H | H | SO₂Me | OMe | CF₃ | 144–146 |
| Me | Me | H | H | 2 | H | H | NH₂ | OMe | CF₃ | 208–209 |
| Me | Me | H | H | 2 | Pr-i | H | H | H | CF₃ | 112–113 |
| Me | Me | H | H | 0 | Pr-i | H | H | H | CF₃ | 1.4986 |

TABLE 19

[Structure: isoxazoline ring with R¹, R², R³, R⁴ substituents and S(O)ₙ-C(R⁵)(R⁶)-Y¹ group]

| Compound No. | R¹ | R² | R³ | R⁴ | n | R⁵ | R⁶ | Y¹ | Melting point(° C.) or refractive index ($n_D^{20}$) |
|---|---|---|---|---|---|---|---|---|---|
| 9-0001 | Me | Me | H | H | 2 | H | H | Pyridin-2-yl | 116–118 |
| 9-0002 | Me | Me | H | H | 2 | H | H | Pyridin-2-yl 1-oxide | 140–143 |
| 9-0003 | Me | Me | H | H | 2 | H | H | Pyridin-4-yl | 133–136 |
| 9-0004 | Me | Me | H | H | 2 | H | H | Pyridin-4-yl 1-oxide | 110–113 |
| 9-0005 | Me | Me | H | H | 2 | H | H | 1,2,4-Oxadiazol-3-yl | Impossible to measure |
| 9-0006 | Me | Me | H | H | 2 | H | H | 3-Phenyl-1,2,4-oxadiazol-5-yl | 153–454 |
| 9-0007 | Me | Me | H | H | 2 | H | H | 3-Benzyl-1,2,4-oxadiazol-5-yl | 108–109 |
| 9-0008 | Me | Me | H | H | 2 | H | H | 2-Chlorothiazol-4-yl | 110–112 |
| 9-0009 | Me | Me | H | H | 2 | H | H | 1,4-Dimethylimidazol-5-yl | 163–164 |
| 9-0010 | Me | Me | H | H | 1 | H | H | Pyridin-2-yl | 81–82 |
| 9-0011 | Me | Me | H | H | 1 | H | H | Pyridin-4-yl | 94–96 |
| 9-0012 | Me | Me | H | H | 1 | H | H | 1,4-Dimethylimidazol-5-yl | 138–140 |
| 9-0013 | Me | Me | H | H | 0 | H | H | 1,4-Dimethylimidazol-5-yl | 1.5427 |

TABLE 20

[Structure: isoxazoline ring with R¹, R², R³, R⁴ substituents and S(O)ₙ-C(R⁵)(R⁶)-Y¹ group]

| Compound No. | R¹ | R² | R³ | R⁴ | n | R⁵ | R⁶ | Y¹ | Melting point(° C.) or refractive index ($n_D^{20}$) |
|---|---|---|---|---|---|---|---|---|---|
| 10-0001 | Me | Me | H | H | 2 | H | H | Benzimidazol-2-yl | 171–174 |
| 10-0002 | Me | Me | H | H | 2 | H | H | Benzothiophen-2-yl | 181–183 |
| 10-0003 | Me | Me | H | H | 2 | H | H | 3-Chlorobenzothiophen-2-yl | 109–112 |
| 10-0004 | Me | Me | H | H | 2 | H | H | Benzotriazol-1-yl | 206–207 |
| 10-0005 | Me | Me | H | H | 2 | H | H | 1-Methylindazol-4-yl | 128–130 |
| 10-0006 | Me | Me | H | H | 2 | H | H | Benzothiazol-2-yl | 142–143 |
| 10-0007 | Me | Me | H | H | 2 | H | H | Benzothiophen-3-yl | 188–191 |
| 10-0008 | Me | Me | H | H | 2 | H | H | 5-Chlorobenzothiophen-3-yl | 129–130 |
| 10-0009 | Me | Me | H | H | 2 | H | H | Benzoxazol-2-yl | 127–129 |
| 10-0010 | Me | Me | H | H | 2 | H | H | 3-Methylbenzothiophen-2-yl | 161–163 |
| 10-0011 | Me | Me | H | H | 2 | H | H | 3-Bromobenzothiophen-2-yl | 118–119 |
| 10-0012 | Me | Me | H | H | 2 | H | H | Benzofuran-2-yl | 123–124 |
| 10-0013 | Me | Me | H | H | 2 | H | H | 2-Methylbenzofuran-7-yl | 135–137 |
| 10-0014 | Me | Me | H | H | 2 | H | H | 3-Bromobenzofuran-2-yl | 107–108 |
| 10-0015 | Me | Me | H | H | 2 | H | H | Benzothiophen-7-yl | 95–97 |
| 10-0016 | Me | Me | H | H | 2 | H | H | 1-Methylindazol-7-yl | 89–90 |
| 10-0017 | Me | Me | H | H | 2 | H | H | 3-Methylbenzofuran-2-yl | 111–112 |
| 10-0018 | Me | Me | H | H | 2 | H | H | 3-Chloro-1-methylindol-2-yl | 162–165 |

PRODUCTION EXAMPLES OF INTERMEDIATES

Reference Example 1

Production of 3-chloro-5,5-7dimethyl-2-isoxazoline 534.0 g (4.0 moles) of N-chlorosuccinimide was gradually added, at 65 to 70° C., to a solution of 182.7 g (2.05 moles) of glyoxylic acid aldoxime dissolved in 2 liters of 1,2-dimethoxyethane. The mixture was refluxed for 1 hour with heating. Thereto were added, with ice-cooling, 1,440.0 g (14.4 moles) of potassium hydrogencarbonate and 10 ml of water. Then, 360.0 g (6.4 moles) of 2-methylpropene was added. The resulting mixture was stirred at room temperature for 24 hours to give rise to a reaction. The reaction mixture was poured into water, followed by extraction with diisopropyl ether. The resulting organic layer was washed with water and an aqueous sodium chloride solution in this order and then dried over anhydrous magnesium sulfate. The resulting solution was subjected to vacuum distillation to remove the solvent contained therein, to obtain 107.7 g (yield: 40.0%) of 3-chloro-5,5-dimethyl-2-isoxazoline as a yellow viscous liquid.

$^1$H-NMR [CDCl$_3$/TMS, δ (ppm)]: 2.93 (2H, s), 1.47 (6H, s)

Reference Example 2

Production of 3-chloro-5-ethyl-5-methyl-2-isoxazoline 61.9 g (463.4 mmoles) of N-chlorosuccinimide was gradually added, at 60° C., to a solution of 20.6 g (231.7 mmoles) of glyoxylic acid aldoxime dissolved in 500 ml of 1,2-dimethoxyethane. After the addition, the mixture was refluxed for 10 minutes with heating. Thereto were added, with ice-cooling, 50 ml (463.4 mmoles) of 2-methyl-1-butene, 98.9 g (1,622 mmoles) of potassium hydrogencarbonate and 10 ml of water. The resulting mixture was stirred for 12 hours to give rise to a reaction. The reaction mixture was poured into water, followed by extraction with n-hexane. The resulting organic layer was washed with water and an aqueous sodium chloride solution in this order and then dried over anhydrous magnesium sulfate. The resulting solution was subjected to vacuum-distillation to remove the solvent contained therein, to obtain 13.9 g (yield: 40.6%) of 3-chloro-5-ethyl-5-methyl-2-isoxazoline as a yellow viscous liquid.

$^1$H-NMR [CDCl$_3$/TMS, δ (ppm)]: 2.91 (2H, ABq, J=17.0, Δv=46.1 Hz), 1.73 (2H, q) 1.42 (3H, s), 0.96 (3H, t)

Reference Example 3

Production of 3-benzylthio-5,5-dimethyl-2-isoxazoline 3.2 g (23.2 mmoles) of anhydrous potassium carbonate and 3.0 g (22.5 mmoles) of 3-chloro-5,5-dimethyl-2-isoxazoline were added, in a nitrogen atmosphere, to a solution of 2.8 g (22.5 mmoles) of benzylmercaptan dissolved in 50 ml of N,N-dimethylformamide. The mixture was stirred at 100° C. for 2 hours to give rise to a reaction. After the completion of the reaction, the reaction mixture was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 3.1 g (yield: 62.0%) of 3-benzylthio-5,5-dimethyl-2-isoxazoline as a yellow oily substance ($n_D^{20}$=1.5521).

$^1$H-NMR [CDCl$_3$/TMS, δ (ppm)]: 7.24-7.39 (5H, m), 4.26 (2H, s), 2.77 (2H, s), 1.40 (6H, s)

Reference Example 4

Production of 3-(2,6-difluorobenzylsulfinyl)-5-ethyl-5-methyl-2-isoxazoline 4.6 g of m-chloroperbenzoic acid (purity: 70%, 18.8 mmoles) was added, with ice-cooling, to a solution of 4.1 g (15.0 mmoles) of 3-(2,6-difluorobenzylthio)-5-ethyl-5-methyl-2-isoxazoline dissolved in 50 ml of chloroform. The mixture was stirred for 1 hour and then at room temperature for 12 hours to give rise to a reaction. After the completion of the reaction the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 1.5 g (yield: 34.8%) of 3-(2,6-difluorobenzylsulfinyl)-5-ethyl-5-methyl-2-isoxazoline as a white powder (melting point: 30° C. or less).

$^1$H-NMR [CDCl$_3$/TMS, δ (ppm)]: 7.39-7.28 (1H, m), 7.03-6.94 (2H, m), 4.38 (2H, s), 3.04 (1H, ABq, J=17.2, Δv=85.7 Hz), 3.12 (1H, s), 1.75 (2H, m), 1.44 (3H, S)+1.41 (3H, s), 0.97 (3H, m)

Reference Example 5

Production of 3-(2,6-difluorobenzylsulfonyl)-5-ethyl-5-methyl-2-isoxazoline 1.0 g of m-chloroperbenzoic acid (purity: 70%, 4.1 mmoles) was added, with ice-cooling, to a solution of 0.8 g (2.8 mmoles) of 3-(2,6-difluorobenzylsulfinyl)-5-ethyl-5-methyl-2-isoxazoline dissolved in 50 ml of chloroform. The mixture was stirred for 1 hour and then at room temperature for 12 hours to give rise to a reaction. After the completion of the reaction the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.6 g (yield: 75.0%) of 3-(2,6-difluorobenzylsulfonyl)-5-ethyl-5-methyl-2-isoxazoline as a white powder (melting point: 64 to 65° C.).

$^1$H-NMR [CDCl$_3$/TMS, δ (ppm)]: 7.36-7.46 (1H, m), 6.98-7.04 (2H, m), 4.73 (2H, s) 3.04 (2H, ABq, J=17.2, Δv=51.1 Hz), 1.77 (2H, q) 1.46 (3H, s), 0.97 (3H, t).

Reference Example 6

Production of
5,5-dimethyl-3-methylsulfonyl-2-isoxazoline 1.0 kg of an aqueous sodium methanethiolate solution (content: 15%, 2.14 mmoles) was dropwise added, with ice-cooling, to a solution of 143.0 g (1.07 moles) of 3-chloro-5,5-dimethyl-2-isoxazoline dissolved in 500 ml of N,N-dimethylformamide. The mixture was stirred at room temperature for 12 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 115.0 g (yield: 74.1%) of 5,5-dimethyl-3-methylthio-2-isoxazoline. This residue (741.2 mmoles) was dissolved in 1 liter of chloroform. Thereto was added, with ice-cooling, 392.0 g of m-chloroperbenzoic acid (purity: 70%, 1.59 moles). The resulting mixture was stirred for 1 hour and then at room temperature for 12 hours to give rise to a reaction. After the completion of the reaction, the separated m-chloroperbenzoic acid was removed by filtration. The resulting filtrate was washed with an aqueous sodium hydrogensulfite solution, water, an aqueous sodium hydrogencarbonate solution and an aqueous sodium chloride solution in this order and then dried over anhydrous magnesium sulfate. The resulting solution was subjected to vacuum distillation to remove the solvent contained therein. The residue was washed with diisopropyl ether to obtain 77.6 g (yield: 59.1%) of 5,5-dimethyl-3-methylsulfonyl-2-isoxazoline as a white powder (melting point: 82 to 84° C.).

$^1$H-NMR [CDCl$_3$/TMS, δ (ppm)]: 3.26 (3H, s), 3.12 (2H, s), 1.51 (6H, s)

Reference Example 7

Production of
5,5-dimethyl-3-ethylthio-2-isoxazoline 1,500 ml of an aqueous solution containing 560.0 g (9.0 moles) of ethyl mercaptan and 360.0 g (9.0 moles) of sodium hydroxide was added to a solution containing 3-chloro-5,5dimethyl-2-isoxazoline. The mixture was stirred at 60 to 70° C. for 16 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 270.0 g of crude 5,5-dimethyl-3-ethylthio-2-isoxazoline as a dark red oily substance.

Reference Example 8

Production of
5,5-dimethyl-3-ethylsulfonyl-2-isoxazoline 270.0 g (1.7 moles) of crude oily 5,5-dimethyl-3-ethylthio-2-isoxazoline was dissolved in 1.0 liter of chloroform. Thereto was added, with ice-cooling, 1,050 g of m-chloroperbenzoic acid (purity: 70%, 6.1 moles). The resulting mixture was stirred for 1 hour and then at room temperature for 12 hours to give rise to a reaction. After confirmation of the completion of the reaction, the separated m-chloroperbenzoic acid was removed by filtration. The resulting filtrate was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The residue was washed with n-hexane to obtain 133.6 g (yield: 65.4%) of 5,5-dimethyl-3-ethylsulfonyl-2-isoxazoline as a white powder.

Reference Example 9

Production of
1-phenyl-3-trifluoromethyl-1H-pyrazol-5-ol 20 g (184.9 mmoles) of phenylhydrazine and 4 ml of concentrated hydrochloric acid were added to a solution of 34.1 g (184.9 mmoles) of ethyl trifluoroacetoacetate dissolved in 500 ml of ethanol. The mixture was refluxed for 1 hour with heating, to give rise to a reaction. After the completion of the reaction, the reaction mixture was subjected to vacuum distillation to remove the most part of the solvent contained therein. The residue was mixed with water to precipitate crystals. The crystals were collected by filtration, washed with water until the filtrate became neutral, and dried to obtain 37.1 g (yield: 87.9%) of 1-phenyl-3-trifluoromethyl-1H-pyrazol-5-ol as ocherous crystals.

$^1$H-NMR [CDCl$_3$/TMS, δ (ppm)]: 7.68-7.41 (5H, m), 5.86 (1H, s), 3.71 (1H, s)

Reference Example 10

Production of 5-chloro-1-phenyl-3-trifluoromethyl-1H-pyrazole-4-carboaldehyde 33.6 g (219.1 mmoles) of phosphorus oxychloride was added to 7.7 g (105.2 mmoles) of N,N-dimethylformamide with ice-cooling. Thereto was added, at room temperature, 20 g (87.7 mmoles) of 1-phenyl-3-trifluoromethyl-1H-pyrazol-5-ol. The resulting mixture was refluxed for: 1 hour with heating, to give rise to a reaction. After the completion of the reaction, the reaction mixture was poured into water with ice-cooling, followed by extraction with chloroform. The resulting organic layer was washed with an aqueous sodium hydrogencarbonate solution and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 19.1 g (yield: 79.1%) of 5-chloro-1-phenyl-3-trifluoromethyl-1H-pyrazole-4-carboaldehyde as white crystals.

$^1$H-NMR [CDCl$_3$/TMS, δ (ppm)]: 10.06 (1H, s), 7.57 (5H, s)

Reference Example 11

Production of (5-chloro-1-phenyl-3-trifluoromethyl-1H-pyrazol-4-yl)-methanol

A solution of 0.21 g (5.5 mmoles) of lithium aluminum hydride dissolved in 70 ml of THF was cooled to -30° C. Thereto was gradually added a solution of 3 g (10.9 mmoles) of 5-chloro-1-phenyl-3-trifluoromethyl-1H-pyrazole-4carboaldehyde dissolved in 30 ml of tetrahydrofuran. The resulting mixture was stirred at −30° C. for 30 minutes to give rise to a reaction. After the completion of the reaction, ethyl acetate was added, followed by stirring. Then, water was added, followed by stirring for a while. The reaction mixture was filtered under vacuum. The filtrate was extracted with ethyl acetate. The resulting organic layer was washed with an aqueous sodium chloride solution and then dried over anhydrous magnesium sulfate. The resulting solution was subjected to vacuum distillation to remove the solvent contained therein, to obtain 3.0 g (yield: 99.9%) of (5-chloro-1-phenyl-3-trifluoromethyl-1H-pyrazol-4-yl)-methanol as white crystals.

$^1$H-NMR [CDCl$_3$/TMS, δ (ppm)]: 7.54-7.51 (5H, m), 4-71 (2H, d) 1.79 (1H, b)

Reference Example 12

Production of 4-bromomethyl-5-chloro-1-phenyl-3-trifluoromethyl-1H-pyrazole

A solution of 3.0 g (10.9 mmoles) of (5-chloro-1-phenyl-3-trifluoromethyl-1H-pyrazol-4-yl)-methanol dissolved in 60 ml of diethyl ether was cooled to −10° C. Thereto was added 1.0 g (3.8 mmoles) of phosphorus tribromide. The mixture was stirred at room temperature for 1 hour to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 3.6 g (yield: 95.8%) of 4-bromomethyl-5-chloro-1-phenyl-3-trifluoromethyl-1H-pyrazole as white crystals.

$^1$H-NMR [CDCl$_3$/TMS, δ (ppm)]: 7.58-7.48 (5H, m), 4.48 (2H, s)

Reference Example 13

Production of 5-fluoro-1-phenyl-3-trifluoromethyl-1H-pyrazole-4-carboaldehyde 10.5 g (180.2 mmoles) of potassium fluoride was added to a solution of 33.0 g (120.1 mmoles) of 5-chloro1-phenyl-3-trifluoromethyl-1H-pyrazole-4-carboaldehyde dissolved in 500 ml of dimethyl sulfoxide. The mixture was stirred at 100° C. for 2 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 26.5 g (yield: 85.0%) of 5-fluoro-1-phenyl-3-trifluoromethyl-1H-pyrazole-4-carboaldehyde.

$^1$H-NMR [CDCl$_3$/TMS, δ (ppm)]: 9.96 (1H, s), 7.68-7.51 (5H, m)

Reference Example 14

Production of (5-fluoro-1-phenyl-3-trifluoromethyl-1H-pyrazol-4-yl)-methanol

To a solution of 1.6 g (41.0 mmoles) of sodium borohydride dissolved in 300 ml of methanol was added, with ice-cooling, a solution of 26.5 g (102.5 mmoles) of 5-fluoro-1-phenyl-3-trifluoromethyl-1H-pyrazole-4-carboaldehyde dissolved in 200 ml of methanol. The resulting mixture was stirred at 0° C. for 30 minutes to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 28.5 g (yield: 100%) of (5-fluoro-1-phenyl-3-trifluoromethyl-1H-pyrazol-4-yl)-methanol.

$^1$H-NMR [CDCl$_3$/TMS, δ (ppm)]: 7.65-7.41-(5H, m), 4.68 (2H, d), 1.73 (1H, t)

Reference Example 15

Production of 4-bromomethyl-5-fluoro-1-phenyl-3-trifluoromethyl-1H-pyrazole

A solution of 27.5 g (105.7 mmoles) of (5-fluoro-1-phenyl-3-trifluoromethyl-1H-pyrazol-4-yl)-methanol dissolved in 300 ml of diethyl ether was cooled to 0° C. Thereto was added 10.0 g (37.0 mmoles) of phosphorus tribromide. The mixture was stirred at room temperature for 2 hours to give rise to a reaction. After the completion of the reaction, the reaction mixture was poured into water, followed by extraction with diethyl ether. The resulting organic layer was washed with an aqueous sodium chloride solution and then dried over anhydrous magnesium sulfate. The resulting solution was subjected to vacuum distillation to remove the solvent contained therein, to obtain 30.3 g (yield: 88.8%) of 4-bromomethyl-5-fluoro-1-phenyl-3-trifluoromethyl-1H-pyrazole.

$^1$H-NMR [CDCl$_3$/TMS, δ (ppm)]: 7.66-7.42 (5H, m), 4.44 (2H, s)

Reference Example 16

Production of 1-tert-butyl-3-trifluoromethyl-1H-pyrazol-5-ol 373.8 g (3.0 moles) of tert-butylhydrazine hydrochloride and 50 ml of concentrated hydrochloric acid were added to a solution of 552.3 g (3.0 moles) of ethyl trifluoroacetoacetate dissolved in 1,500 ml of ethanol. The mixture was refluxed for 2 days with heating, to give rise to a reaction. After the completion of the reaction, the reaction mixture was subjected to vacuum distillation to remove the most part of the solvent contained therein. The residue was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was washed with n-hexane to obtain 369.0 g (yield: 59.1%) of 1-tert-butyl-3-trifluoromethyl-1H-pyrazol-5-ol as a white powder.

Reference Example 17

Production of 1-tert-butyl-5-chloro-3-trifluoromethyl-1H-pyrazole-4-carboaldehyde 462.0 g (3.0 moles) of phosphorus oxychloride was added to 87.7 g (1.2 moles) of N,N-dimethylformamide with ice-cooling. Thereto was added, at room temperature, 208.2 g (1.0 moles) of 1-tert-butyl-3-trifluoromethyl-1H-pyrazol- 5-ol. The resulting mixture was refluxed for 10 hours with heating, to give rise to a reaction. After the completion of the reaction, the reaction mixture was poured into water, followed by extraction with chloroform. The resulting organic layer was washed with water, a 5% aqueous sodium hydroxide solution and water in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 131.5 g (yield: 21.7%) of 1-tert-butyl-5-chloro-3-trifluoromethyl-1H-pyrazole-4-carboaldehyde as white crystals.

$^1$H-NMR [CDCl$_3$/TMS, δ (ppm)]: 9.97 (1H, d), 1.76 (9H, s)

Reference Example 18

Production of (1-tert-butyl-5-chloro-3-trifluoromethyl-1H-pyrazol-4-yl)-methanol A solution of 39.9 g (156.9 mmoles) of (1-tert-butyl-5chloro-3-trifluoromethyl-1H-pyrazole-4-carboaldehyde dissolved in 300 ml of methanol was cooled to 0° C. Thereto was gradually added 6.5 g (172.6 mmoles) of sodium borohydride. The mixture was stirred at room temperature for 3 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 37.7 g (yield: 93.6%) of (1-tert-butyl-5-chloro-3-trifluoromethyl-1H-pyrazol-4-yl)-methanol.

$^1$H-NMR [CDCl$_3$/TMS, δ (ppm)]: 4.60 (2H, d), 1.72 (9H, s), 1.58 (1H, t)

Reference Example 19

Production of 4-bromomethyl-1-tert-butyl-5-chloro-3-trifluoromethyl-1H-pyrazole

A solution of 9.2 g (35.7 mmoles) of (1-tert-butyl-5-chloro-3-trifluoromethyl-1H-pyrazol-4-yl)-methanol dissolved in 100 ml of diethyl ether was cooled to −10° C. Thereto was added 11.6 g (42.9 mmoles) of phosphorus tribromide. The mixture was stirred at room temperature overnight to give rise to a reaction. After the completion of the reaction, the reaction mixture was poured into water, followed by extraction with diethyl ether. The resulting organic layer was washed with an aqueous sodium chloride solution and then dried over anhydrous magnesium sulfate. The resulting solution was subjected to vacuum distillation to remove the solvent contained therein, to obtain 10.0 g (yield: 87.3%) of 4-bromomethyl-1-tert-butyl-5-chloro-3-trifluoromethyl-1H-pyrazole.

Reference Example 20

Production of (1-tert-butyl-5-chloro-3-trifluoromethyl-1H-pyrazol-4-yl)-methanethiol 43.5 g (136.1 mmoles) of 4-bromomethyl-1-tert-butyl-5-chloro-3-trifluoromethyl-1H-pyrazole was added to a solution of 21.8 g of sodium hydrosulfide hydrate (purity: 70%, 272.2 mmoles) dissolved in 300 ml of N,N-dimethylformamide. The mixture was stirred at room temperature overnight to give rise to a reaction. After the completion of the reaction, the reaction mixture was poured into water, followed by extraction with diethyl ether. The resulting organic layer was washed with an aqueous sodium chloride solution and then dried over anhydrous magnesium sulfate. The resulting solution was subjected to vacuum distillation to remove the solvent contained therein, to obtain 32.3 g (yield: 87.0%) of (1-tert-butyl-5-chloro-3-trifluoromethyl-1H-pyrazol-4-yl)-methanethiol.

$^1$H-NMR [CDCl$_3$/TMS, δ (ppm)]: 3.65 (2H, d), 1.90 (1H, t), 1.70 (9H, s)

Reference Example 21

Production of 1-tert-butyl-5-methoxy-3-trifluoromethyl-1H-pyrazole 15.0 g (108.4 mmoles) of anhydrous potassium carbonate and 19.3 g (135.5 mmoles) of methyl iodide were added, at room temperature, to a solution of 18.8 g (90.3 mmoles) of 1-tert-butyl-3-trifluoromethyl-1H-pyrazol-5-ol dissolved in 100 ml of N,N-dimethylformamide. The mixture was stirred for 15 hours to give rise to a reaction. After the completion of the reaction, the reaction mixture was poured into water, followed by extraction with diethyl ether. The resulting organic layer was washed with water and an aqueous sodium chloride solution in this order and then dried over anhydrous magnesium sulfate. The resulting solution was subjected to vacuum distillation to remove the solvent contained therein, to obtain 20.0 g (yield: 99.8%) of 1-tert-butyl-5-methoxy-3-trifluoromethyl-1H-pyrazole.

Reference Example 22

Production of 1-tert-butyl-4-chloromethyl-5-methoxy-3-trifluoromethyl-1H-pyrazole 5.4 g of paraformaldehyde (180.2 mmoles in terms of formaldehyde) and 20 ml of concentrated hydrochloric acid were added to a solution of 20.0 g (90.1 mmoles) of 1-tert-butyl-5-methoxy-3-trifluoromethyl-1H-pyrazole dissolved in 90 ml of acetic acid. The mixture was stirred at 60° C. for 30 minutes to give rise to a reaction. After the completion of the reaction, the reaction mixture was poured into water, followed by extraction with diisopropyl ether. The resulting organic layer was washed with water and then dried over anhydrous magnesium sulfate. The resulting solution was subjected to vacuum distillation to remove the solvent contained therein, to obtain 21.7 g (yield: 89.0%) of 1-tert-butyl-4-chloromethyl-5-methoxy-3-trifluoromethyl-1H-pyrazole.

Reference Example 23

Production of 3-methoxy-1-methyl-5-trifluoromethyl-1H-pyrazole 10.0 g (72.3 mmoles) of anhydrous potassium carbonate and 12.8 g (90.3 mmoles) of methyl iodide were added, at room temperature, to a solution of 10.0 g (60.2 mmoles) of 3-hydroxy-1-methyl-5-trifluoromethyl-1H-pyrazole dissolved in 50 ml of N,N-dimethylformamide. The mixture was stirred for 15 hours to give rise to a reaction. After the completion of the reaction, the reaction mixture was poured into water, followed by extraction with diethyl ether. The resulting organic layer was washed with water and an aqueous sodium chloride solution in this order and then dried over anhydrous magnesium sulfate. The resulting solution was subjected to vacuum distillation to remove the solvent contained therein, to obtain 9.8 g (yield: 90.7%) of 3-methoxy-1-methyl-5-trifluoromethyl-1H-pyrazole.

Reference Example 24

Production of 4-chloromethyl-3-methoxy-1-methyl-5-trifluoromethyl-1H-pyrazole 0.45 g of paraformaldehyde (15.0 mmoles in terms of formaldehyde) and 5 ml of concentrated hydrochloric acid were added to a solution of 1.00 g (5.6 mmoles) of 3-methoxy-1-methyl-5-trifluoromethyl-1H-pyrazole dissolved in 25 ml of acetic acid. The mixture was stirred at 80° C. for 2 hours to give rise to a reaction. After the completion of the reaction, the reaction mixture was poured into water and neutralized with potassium carbonate, followed by extraction with ethyl acetate. The resulting organic layer was washed with water and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.83 g (yield: 65.0%) of 4-chloromethyl-3-methoxy-1-methyl-5-trifluoromethyl-1H-pyrazole.

Reference Example 25

Production of 5-fluoro-1-methyl-3-trifluoromethyl-1H-pyrazole-4-carboaldehyde 42.0 g (711.9 mmoles) of potassium fluoride was added to a solution of 60.4 g (282.7 mmoles) of 5-chloro-1-methyl-3-trifluoromethyl-1H-pyrazole-4-carboaldehyde dissolved in 700 ml of dimethyl sulfoxide. The mixture was stirred at 120 to 140° C. for 5 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 36.8 g (yield: 66.0%) of 5-fluoro-1-methyl-3-trifluoromethyl-1H-pyrazole-4-carboaldehyde.

Reference Example 26

Production of (5-fluoro-1-methyl-3-trifluoromethyl-1H-pyrazol-4-yl)-methanol

To a solution of 3.9 g (102.6 mmoles) of sodium borohydride dissolved in 500 ml of methanol was added, with ice-cooling, a solution of 36.8 g (187.6 mmoles) of 5-fluoro-1-methyl-3-trifluoromethyl-1H-pyrazole-4-carboaldehyde dissolved in 200 ml of methanol. The resulting mixture was stirred at 0° C. for 30 minutes to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 35.4 g (yield: 95.4%) of (5-fluoro-1-methyl-3-trifluoromethyl-1H-pyrazol-4-yl)-methanol.

Reference Example 27

Production of 4-bromomethyl-5-fluoro-1-methyl-3-trifluoromethyl-1H-pyrazole

A solution of 35.4 g (178.7 mmoles) of 5-fluoro-1-methyl-3-trifluoromethyl-1H-pyrazole-4-methanol dissolved in 500 ml of diethyl ether was cooled to −30° C. Thereto was added 54.0 g (199.5 mmoles) of phosphorus tribromide. The mixture was stirred at room temperature for 12 hours to give rise to a reaction. After confirmation of the completion of the reaction, the reaction mixture was poured into water, followed by extraction with diethyl ether. The resulting organic layer was washed with water and an aqueous sodium chloride solution and then dried over anhydrous magnesium sulfate. The resulting solution was subjected to vacuum distillation to remove the solvent contained therein, to obtain 31.4 g (yield: 80.8%) of 4-bromomethyl-5-fluoro1-methyl-3-trifluoromethyl-1H-pyrazole.

Reference Example 28

Production of (ethoxycarbonyl)malondialdehyde 12.6 g of sodium hydride (purity: 60%, 525.0 mmoles) was washed with diethyl ether by decantation several times and then made into a solution; in 500 ml of diethyl ether. Thereto were added, in a nitrogen current at 0 to 10° C., 194 g (2.6 moles) of ethyl formate and 50 g (262.0 mmoles) of ethyl 3,3-diethoxy-propionate. The resulting mixture was stirred at room temperature for 15 hours to give rise to a reaction. After confirmation of the completion of the reaction, the reaction mixture was poured into water, followed by washing with diethyl ether. The resulting aqueous layer was allowed to have a pH of 1 with hydrochloric acid, followed by extraction with dichloromethane. The resulting organic layer was washed with an aqueous sodium chloride solution and then dried over anhydrous magnesium sulfate. The resulting solution was subjected to vacuum distillation to remove the solvent contained therein, to obtain 37.6 g (yield: 100%) of crude (ethoxycarbonyl)malondialdehyde as a dark red oily substance.

$^1$H-NMR [CDCl$_3$/TMS, δ (ppm)]: 9.09 (2H, s), 5.26 (1H, s), 4.27 (2H, q), 1.28 (3H, t)

Reference Example 29

Production of ethyl 1H-pyrazole-4-carboxylate 6.2 g (193 mmoles) of hydrazine was added, with ice-cooling, to a solution of 27.6 g (192 mmoles) of (ethoxycarbonyl)malondialdehyde dissolved in 150 ml of ethanol. The mixture was stirred at room temperature for 17 hours to give rise to a reaction. The reaction mixture was subjected to vacuum distillation to remove the ethanol contained therein. The residue was purified by silica gel column chromatography (developing solvent: dichloromethane-ethyl acetate mixed solvent) to obtain 19.4 g (72.4%) of ethyl 1H-pyrazole-4-carboxylate as yellow crystals.

$^1$H-NMR [CDCl$_3$/TMS, δ (ppm)]: 8.08 (2H, s), 5.30 (1H s), 4.31 (2H, q), 1.36 (3H, t)

Reference Example 30

Production of ethyl 1-ethyl-1H-pyrazole-4-carboxylate 3.7 g (26.8 mmoles) of anhydrous potassium carbonate and 4.2 g (26.6 mmoles) of ethyl iodide were added to a solution of 1.5 g (10.7 mmoles) of ethyl 1H-pyrazole-4-carboxylate dissolved in 50 ml of N,N-dimethylformamide. The mixture was stirred at room temperature for 20 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 1.6 g (yield: 88.9%) of ethyl 1-ethyl-1H-pyrazole-4-carboxylate as a yellow oily substance.

$^1$H-NMR [CDCl$_3$/TMS, $\delta$ (ppm)]: 7.90 (2H, s), 4.28 (2H, q), 4.18 (2H, q), 1.51 (3H, t), 1.35 (3H, t)

Reference Example 31

Production of ethyl 3,5-dichloro-1-ethyl-1H-pyrazole-4-carboxylate

In a glass sealed tube were placed 1.6 g (9.5 mmoles) of ethyl 1-ethyl-1H-pyrazole-4-carboxylate and 5.1 g (38.3 mmoles) of N-chlorosuccinimide. There were allowed to react at 160° C. for 6 hours. After the completion of the reaction, the reaction mixture was cooled to room temperature, washed with carbon tetrachloride and chloroform, and filtered under vacuum. The resulting filtrate (organic layer) was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 1.0 g (yield: 44.2%) of ethyl 3,5-dichloro-1-ethyl-1H-pyrazole-4-carboxylate as a yellow oily substance.

$^1$H-NMR [CDCl$_3$/TMS, $\delta$ (ppm)]: 4.36 (2H, q), 4.21 (2H, q), 1.44 (3H, t), 1.38 (3H, t)

Reference Example 32

Production of (3,5-dichloro-1-ethyl-1H-pyrazol-4-yl)methanol

A solution of 0.16 g (4.2 mmoles) of lithium aluminum hydride dissolved in 70 ml of tetrahydrofuran was cooled to −50° C. Thereto was gradually added dropwise a solution of 1.0 g (4.2 mmoles) of ethyl 3,5-dichloro-1-ethyl-1H-pyrazole-4-carboxylate dissolved in 30 ml of tetrahydrofuran. The mixture was stirred at −50° C. for 3 hours to give rise to a reaction. After confirmation of the completion of the reaction, ethyl acetate was added, followed by stirring for a while. Water was added, followed by stirring for a while. The resulting mixture was filtered under vacuum. The filtrate was extracted with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 0.82 g (yield: 100%) of (3,5-dichloro-1-ethyl-1H-pyrazol-4-yl)methanol as a brown oily substance.

$^1$H-NMR [CDCl$_3$/TMS, $\delta$ (ppm)]: 4.52 (2H, s), 4.16 (2H, q), 1.43, (3H, t)

Reference Example 33

Production of 4-bromomethyl-3,5-dichloro-1-ethyl-1H-pyrazole

A solution of 0.82 g (4.2 mmoles) of (3,5-dichloro-1-ethyl-1H-pyrazol-4-yl)methanol dissolved in 50 ml of diethyl ether was cooled to −30° C. Thereto was added 1.3 g (4.8 mmoles) of phosphorus tribromide. The mixture was stirred at room temperature for 12 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 0.9 g (yield: 81.8%) of 4-bromomethyl-3,5-dichloro-1-ethyl-1H-pyrazole as a yellow oily substance.

$^1$H-NMR [CDCl$_3$/TMS, $\delta$ (ppm)]: 4.33 (2H, s), 4.13 (2H, q), 1.43 (3H, t)

Reference Example 34

Production of 3-difluoromethyl-1-methyl-1H-pyrazol-5-ol 8.3 g (180.6 mmoles) of methylhydrazine and 5 ml of concentrated hydrochloric acid were added to a solution of 30.0 g (180.6 mmoles) of ethyl difluoroacetoacetate dissolved in 200 ml of ethanol. The mixture was refluxed for 2 days with heating, to give rise to a reaction. After the completion of the reaction, the reaction mixture was subjected to vacuum distillation to remove the most part of the solvent contained therein. The residue was poured into water. The mixture was allowed to have a pH of 4 using citric acid and extracted with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 8.9 g (yield: 33.3) of 3-difluoromethyl-1-methyl-1H-pyrazol-5-ol.

Reference Example 35

Production of 5-chloro-3-difluoromethyl-1-methyl-1H-pyrazole-4-carboaldehyde 41.6 g (270.1 mmoles) of phosphorus oxychloride was added, with ice-cooling, to 7.9 g (108.0 mmoles) of N,N-dimethylformamide. Thereto was added, at room temperature, 8.0 g (54.0 mmoles) of 3-difluoromethyl-1-methyl-1H-pyrazol-5-ol. The mixture was refluxed for 4 hours with heating, to give rise to a reaction. After the completion of the reaction, the reaction mixture was poured into water, followed by extraction with chloroform. The resulting organic layer was washed with water, a 5% aqueous sodium hydroxide solution and water in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 7.7 g (yield: 73.3%) of 5-chloro-3-difluoromethyl-1-methyl-1H-pyrazole-4-carboaldehyde as white crystals.

$^1$H-NMR [CDCl$_3$/TMS, δ (ppm)]: 9.96 (1H, s), 6.90 (1H, t, J=53.6 Hz), 3.93 (3H, s)

Reference Example 36

Production of (5-chloro-3-difluoromethyl-1-methyl-1H-pyrazol-4-yl)-methanol

A solution of 7.2 g (37.0 mmoles) of 5-chloro-3-difluoromethyl-1-methyl-1H-pyrazole-4-carboaldehyde dissolved in 100 ml of methanol was cooled to 0° C. Thereto was gradually added 2.1 g (55.5 mmoles) of sodium borohydride. The mixture was stirred at room temperature for 3 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 3.8 g (yield: 52.1%) of (5-chloro-3-difluoromethyl-1-methyl-1H-pyrazol-4-yl)-methanol.

$^1$H-NMR [CDCl$_3$/TMS, δ (ppm)]: 6.70 (1H, t, J=40.8 Hz), 4.63 (2H, s), 3.86 (3H, s), 1.79 (1H, br)

Reference Example 37

Production of 4-bromomethyl-5-chloro-3-difluoromethyl-1-methyl-1H-pyrazole

A solution of 2.0 g (10.0 mmoles) of (5-chloro-3-difluoromethyl-1-methyl-1H-pyrazol-4-yl)-methanol dissolved in 50 ml of diethyl ether was cooled to −10° C. Thereto was added 1.0 g (3.5 mmoles) of phosphorus tribromide. The mixture was stirred at room temperature overnight to give rise to a reaction. After the completion of the reaction, the reaction mixture was poured into ice water, followed by extraction with diethyl ether. The resulting organic layer was washed with an aqueous sodium chloride solution and then dried over anhydrous magnesium sulfate. The resulting solution was subjected to vacuum distillation to remove the solvent contained therein, to obtain 2.6 g (yield: 100.0%) of 4-bromomethyl-5-chloro-3-difluoromethyl-1-methyl-1H-pyrazole.

Reference Example 38

Production of Trifluoroacetaldehyde Oxime Etherate 24.1 g (347.0 mmoles) of hydroxylamine hydrochloride and 160 ml of water were added to a solution of 50.0 g (347.0 mmoles) of trifluoroacetaldehyde hemiethyl acetal dissolved in 80ml of methanol. Thereto was dropwise added, with ice-cooling, 80.0 g of a 50% aqueous sodium hydroxide solution (1.7 moles). After the completion of the dropwise addition, the resulting mixture was stirred at room temperature for 6 hours to give rise to a reaction. After the completion of the reaction, 10% hydrochloric acid was added for pH adjustment to 6. The resulting mixture was extracted with diethyl ether. The extract was subjected to vacuum distillation to remove the solvent contained therein. The residue was subjected to distillation to obtain 24.7 g (yield: 38.0%) of trifluoroacetaldehyde oxime etherate.

Reference Example 39

Production of Trifluoroacetohydroximoyl Bromide Etherate

A solution of 38.8 g (218.0 mmoles) of N-bromosuccinimide dissolved in 125 ml of N,N-dimethylformamide was added, with ice-cooling, to a solution of.24.7 g (131.7 mmoles) of trifluoroacetaldehyde oxime etherate dissolved in 50 ml of N,N-dimethylformamide. The mixture was stirred at room temperature for 3 hours to give rise to a reaction. After the completion of the reaction, the reaction mixture was poured into water, followed by extraction with diethyl ether. The resulting organic layer was washed with an aqueous sodium chloride solution, and then dried over anhydrous magnesium sulfate. The resulting solution was subjected to vacuum distillation to remove the solvent contained therein. The residue was subjected to distillation to obtain 33.3 g (yield: 95.0%) of trifluoroacetohydroximoyl bromide etherate as a brown oily substance.

$^1$H-NMR [CDCl$_3$/TMS, δ (ppm)]: 9.30 (1H, s)

Reference Example 40

Production of 4-ethoxycarbonyl-5-methyl-3-trifluoromethylisoxazole 2.8 g (51.3 mmoles) of sodium methoxide was added to a solution of 6.7 g (51.3 mmoles) of ethyl acetoacetate dissolved in 80 ml of methanol. Thereto was added, with ice-cooling, a solution of 5.0 g (18.8 mmoles) of trifluorohydroximoyl bromide etherate dissolved in 20 ml of methanol. The resulting mixture was stirred at room temperature for 3 hours to give rise to a reaction. After the completion of the reaction, the reaction mixture was subjected to vacuum distillation to remove the solvent contained therein. Water was added to the residue, followed by extraction with chloroform. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 2.9 g (yield: 69.0%) of 4-ethoxycarbonyl-5-methyl-3-trifluoromethylisoxazole as a colorless oily substance.

$^1$H-NMR [CDCl$_3$/TMS, δ (ppm)]: 4.36 (2H, q), 2;77 (3H,s), 1.37 (3H, t)

Reference Example 41

Production of (5-methyl-3-trifluoromethylisoxazol-4-yl)-methanol

A solution of 0. 16 g (4.2 mmoles) of lithium aluminum hydride dissolved in 15 ml of THF was cooled to 0° C. Thereto was gradually added a solution of 0.93 g (4.2 mmoles) of 4-ethoxycarbonyl-5-methyl-3-trifluoromethylisoxazole dissolved in 15 ml of THF. The mixture was stirred at 0° C. for 1 hour to give rise to a reaction. After the completion of the reaction, ethyl acetate was added, followed by stirring for a while. Water was added, followed by stirring for a while. The reaction mixture was filtered under vacuum. The filtrate was extracted with diethyl ether. The resulting organic layer was washed with an aqueous sodium chloride solution and then dried over anhydrous magnesium sulfate. The resulting solution was subjected to vacuum distillation to remove the solvent contained therein, to obtain 0.5 g (yield: 60.0%) of (5-methyl-3-trifluoromethylisoxazol-4-yl)-methanol.

$^1$H-NMR [CDCl$_3$/TMS, δ (ppm)]: 4.60 (2H, d), 2.54 (3H, s), 1.66 (1H, br)

Reference Example 42

Production of 4-bromomethyl-5-methyl-3-trifluoromethylisoxazole

A solution of 0.45 g (2.5 mmoles) of (5-methyl-3-trifluoromethylisoxazol-4-yl)-methanol dissolved in 10 ml of diethyl ether was cooed to 0° C. Thereto was added 0.2 g (8.9 mmoles) of phosphorus tribromide. The mixture was stirred at room temperature for 1 hour to give rise to a reaction. After the completion of the reaction, the reaction mixture was poured into water, followed by extraction with diethyl ether. The resulting organic layer was washed with an aqueous sodium chloride solution and then dried over anhydrous magnesium sulfate. The resulting solution was subjected to vacuum distillation to remove the solvent contained therein, to obtain 0.5 g (yield: 74.0%) of 4-bromomethyl-5-methyl-3-trifluoromethylisoxazole.

$^1$H-NMR [CDCl$_3$/TMS, δ (ppm)]: 4.31 (2H, d), 2.51 (3H, s)

Reference Example 43

Production of (5-chloro-3-methyl-isothiazol-4-yl)-methanol

A solution of 2.06 g (10.0 mmoles) of ethyl 5-chloro-3-methyl-isothiazole-4-carboxylate dissolved in 10 ml of THF was dropwise added at −30° C., to. a solution of 0.42 g (11.0 mmoles) of lithium aluminum hydride dissolved in 10 ml of THF. The mixture was stirred at the same temperature for 1 hour to give rise to a reaction. After confirmation of the completion of the reaction, ethyl acetate was added to the reaction mixture. The resulting mixture was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 1.50 g (yield: 91.5%) of (5-chloro-3-methyl-isothiazol-4-yl)-methanol.

Reference Example 44

Production of 4-chloromethyl-5-chloro-3-methylisothiazole 3.26 g (27.44 mmoles) of thionyl chloride was added, at room temperature, to a solution of 1.50 g (9.15 mmoles) of (5-chloro-3-methyl-isothiazol-4-yl)-methanol dissolved in 10 ml of chloroform. The mixture was stirred for 3 hours to give rise to a reaction. After confirmation of the completion of the reaction, the reaction mixture was subjected to vacuum distillation to remove the solvent contained therein, to obtain 1.67 g (yield: quantitative) of 4-chloromethyl-5-chloro-3-methylisothiazole.

Reference Example 45

Production of Methyl 4-trifluoromethylnicotinate 6.7 g (48.6 mmoles) of anhydrous potassium carbonate and 6.9 g (48.6 mmoles) of methyl iodide were added to a solution of 4.6 g (24.1 mmoles) of 4-trifluoromethylnicotinic acid dissolved in 70 ml of N,N-dimethylformamide. The mixture was stirred at room temperature for 12 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 2.77 g (yield: 56.1%) of methyl 4-trifluoromethylnicotinate as a yellow oily substance.

$^1$H-NMR [CDCl$_3$/TMS, δ (ppm)]: 9.11 (1H, s), 8.92 (1H, d), 7.64 (1H, d), 3.99 (3H, s)

Reference Example 46

Production of (4 trifluoromethylpyridin-3-yl)-methanol

A solution of 0.37 g (9.7 mmoles) of lithium aluminum hydride dissolved in 100 ml of THF was cooled to −50° C. Thereto was gradually added dropwise a solution of 2.0 g (9.8 mmoles) of methyl 4-trifluoromethylnicotinate dissolved in 30 ml of THF. The mixture was stirred at −50° C. for 3 hours to give rise to a reaction. After confirmation of the completion of the reaction, ethyl acetate was added, followed by stirring for a while. Water was added, followed by stirring for a while. The reaction mixture was filtered under vacuum. The filtrate was extracted with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.6 g (yield: 35.3%) of (4-trifluoromethylpyridin-3-yl)-methanol as a yellow oily substance.

$^1$H-NMR [CDCl$_3$/TMS, δ (ppm)]: 9.00 (1H, s), 8.73 (1H, d), 7.51 (1H, d), 4.95 (2H, s)

Reference Example 47

Production of 3-bromomethyl-4-trifluoromethylpyridine

A solution of 0.6 g (3.4. mmoles) of (4-trifluoromethylpyridin-3-yl)-methanol dissolved in 50 ml of diethyl ether was cooed to −30° C. Thereto was added 1.4 g (5.2 mmoles) of phosphorus tribromide. The mixture was stirred at room temperature for 12 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 0.61 g (yield: 75.3%) of 3-bromomethyl-4-trifluoromethylpyridine as a yellow oily substance.

¹H-NMR [CDCl₃/TMS, δ (ppm)]: 8.88 (1H, s), 8.73 (1H, d), 7.54 (1H, d), 4.63 (2H, s)

Reference Example 48

Production of
5-bromo-4-hydroxy-6-trifluoromethylpyrimidine 77.5 g (945.0 mmoles) of anhydrous sodium acetate was added, at room temperature, to a solution of 49.2 g (300.0 mmoles) of 4-hydroxy-6-trifluoromethylpyrimidine dissolved in 600 ml of acetic acid. Thereto was gradually added 50.3 g (315 mmoles) of bromine at 45° C. The resulting mixture was stirred at the same temperature for 3 hours to give rise to a reaction. After confirmation of the completion of the reaction, the reaction mixture was subjected to vacuum distillation to remove the solvent contained therein. The residue was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was washed with n-hexane to obtain 38.9 g (yield: 53.4%) of 5-bromo-4-hydroxy-6-trifluoromethylpyrimidine.

Reference Example 49

Production of
5-bromo-4-chloro-6-trifluoromethylpyrimidine 24.3 g (100.0 mmoles) of 5-bromo-4-hydroxy-6-trifluoromethylpyrimidine was suspended in 18.5 g (120.0 mmoles) of phosphorus oxychloride. The mixture was stirred at 100° C. for 2 hours to give rise to a reaction. After confirmation of the completion of the reaction, the reaction mixture was poured into water gradually, followed by extraction with chloroform. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 21.5 g (yield: 82.4%) of 5-bromo-4-chloro-6-trifluoromethylpyrimidine.

Reference Example 50

Production of
5-bromo-4-methoxy-6-trifluoromethylpyrimidine 16.7 ml of sodium methoxide (a 28% methanol solution, 86.4 mmoles) was added, at room temperature, to a solution of 21.5 g (82.2 mmoles) of 5-bromo-4-chloro-6-trifluoromethylpyrimidine dissolved in 100 ml of methanol. The mixture was stirred to give rise to a reaction. After confirmation of the completion of the reaction, the reaction mixture was subjected to vacuum distillation to remove the solvent contained therein. The residue was poured into water, followed by extraction with chloroform. The resulting organic layer was washed with water and an aqueous sodium chloride solution in this order and then dried over anhydrous magnesium sulfate. The resulting solution was subjected to vacuum distillation to remove the solvent contained therein. The residue was washed with n-hexane to obtain 19.2 g (yield: 91.0%) of 5-bromo-4-methoxy-6-trifluoromethylpyrimidine.

Reference Example 51

Production of
5-bromo-4-ethoxy-6-trifluoromethylpyrimidine 0.94 g (13.77 mmoles) of sodium ethoxide was added, at room temperature, to a solution of 3.00 g (11.48 mmoles) of 5-bromo-4-chloro-6-trifluoromethylpyrimidine dissolved in 50 ml of ethanol. The mixture was stirred to give rise to a reaction. After confirmation of the completion of the reaction, the reaction mixture was subjected to vacuum distillation to remove the solvent contained therein. The residue was poured into water, followed by extraction with chloroform. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 2.44 g (yield: 82.9%) of 5-bromo-4-ethoxy-6-trifluoromethylpyrimidine.

Reference Example 52

Production of 4-methoxy-6-trifluoromethylpyrimidine-5-carboaldehyde 30.0 ml of n-butyllithium (a 1.6 moles/liter n-hexane solution, 48.0 mmoles) was gradually added, at −65 to −60° C., to a solution of 10.3 g (40.0 mmoles) of 5-bromo-4-methoxy-6-trifluoromethylpyrimidine dissolved in 100 ml of tetrahydrofuran. The mixture was stirred for 30 minutes. Thereto was added 3.6 g (48.0 mmoles) of ethyl formate at the same temperature. The resulting mixture was stirred at the same temperature for 3 hours to give rise to a reaction. The reaction mixture was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 1.3 g (yield: 15.8%) of 4-methoxy-6-trifluoromethylpyrimidine-5-carboaldehyde.

¹H-NMR [CDCl₃/TMS, δ (ppm)]: 10.41 (1H, q), 8.91 (1H, s), 4.18 (3H, s)

Reference Example 53

Production of 4-ethoxy-6-trifluoromethylpyrimidine-5-carboaldehyde

A solution of 5.76 g (21.3 mmoles) of 5-bromo-4-ethoxy-6-trifluoromethylpyrimidine dissolved in 250 ml of THF was cooled to −78° C. Thereto was dropwise added 22.6 ml of n-butyllithium (a 1.6 moles/liter n-hexane solution, 36.1 mmoles). The mixture was stirred for 40 minutes. Thereto was added 2.7 g (45.1 mmoles) of methyl formate. The resulting mixture was stirred for 1.5 hours to give rise to a reaction. After the completion of the reaction, an aqueous ammonium chloride solution was added. The mixture was extracted with diethyl ether. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 3.82 g (yield:. 81.6%) of 4-ethoxy-6-trifluoromethylpyrimidine-5-carboaldehyde.

$^1$H-NMR [CDCl$_3$/TMS, δ (ppm)]: 10.41 (1H, s), 8.95 (1H, s), 4.63 (2H, q), 1.48 (3H, t)

Reference Example 54

Production of (4-methoxy-6-trifluoromethylpyrimidin-5-yl)-methanol 0.24 g (6.3 mmoles) of sodium borohydride was gradually added, at room temperature, to a solution of 1.3 g (6.3 mmoles) of 4-methoxy-6-trifluoromethylpyrimidine-5-carboaldehyde dissolved in 30 ml of methanol. The mixture was stirred for 3 hours to give rise to a reaction. After confirmation of the completion of the reaction, the reaction mixture was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 0.42 g (yield: 32.1%) of (4-methoxy-6-trifluoromethylpyrimidin-5-yl)-methanol $^1$H-NMR [CDCl$_3$/TMS, δ (ppm)]: 8.93 (1H, s), 4.81 (2H, s), 4.13 (3H, s), 2.26 (1H, br)

Reference Example 55

Production of (4-ethoxy-6-trifluoromethylpyrimidin-5-yl)-methanol

A solution of 3.82 g (17.2 mmoles) of 4-ethoxy-6-trifluoromethylpyrimidine-5-carboaldehyde dissolved in 50 ml of methanol was added, with ice-cooling, to a solution of 1.7 g (45.7 mmoles) of sodium borohydride dissolved in 50 ml of methanol. The mixture was stirred at 0° C. for 1 hour to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 3.77 g (yield: 97.8%) of (4-ethoxy-6-trifluoromethylpyrimidin-5-yl)-methanol $^1$H-NMR [CDCl$_3$/TMS, δ (ppm)]: 8.80 (1H, s), 4.81 (2H, s), 4.59 (2H, q), 2.28 (1H, b), 1.48 (3H, t)

Reference Example 56

Production of 5-chloromethyl-4-methoxy-6-trifluoromethylpyrimidine 1.19 g (10.1 mmoles) of thionyl chloride was added, at room temperature, to a solution of 0.42 g (2.02 mmoles) of (4-methoxy-6-trifluoromethylpyrimidin-5-yl)-methanol. The mixture was stirred for 3 hours to give rise to a reaction. After confirmation of the completion of the reaction, the reaction mixture was subjected to vacuum distillation to remove the solvent contained therein, to obtain 0.45 g (yield: quantitative) of 5-chloromethyl-4-methoxy-6-trifluoromethylpyrimidine.

Reference Example 57

Production of 5-bromomethyl-4-ethoxy-6-trifluoromethylpyrimidine

A solution of 3.77 g (17.0 mmoles) of (4-ethoxy-6-trifluoromethylpyrimidine-5-yl)-methanol dissolved in 50 ml of diethyl ether was cooled to 0° C. Thereto was added 2.0 g (7.2 mmoles) of phosphorus tribromide. The mixture was stirred at room temperature for 1 hour. The resulting salt was dissolved using methanol. The resulting mixture was stirred for 1 hour to give rise to a reaction. The reaction mixture was poured into water, followed by extraction with diethyl ether. The resulting organic layer was washed with an aqueous sodium chloride solution and then dried over anhydrous magnesium sulfate. The resulting solution was subjected to vacuum distillation to remove the solvent contained therein, to obtain crude 5-bromomethyl-4-ethoxy-6-trifluoromethylpyrimidine.

$^1$H-NMR [CDCl$_3$/TMS, δ (ppm)]: 8.79 (1H, s), 4.61 (2H, q), 4.55 (2H, s), 1.49 (3H, t)

Reference Example 58

Production of (2-chloro-4-methylpyridin-3-yl)methanol

A solution of 1.9 g (10.0 mmoles) of methyl 2-chloro-4-methylnicotinate dissolved in 5.0 ml of THF was gradually added, at −65 to −60° C., to a suspension of 0.4 g (10.0 mmoles) of lithium aluminum hydride in 30 ml of tetrahydrofuran. The mixture was stirred for 30 minutes and at −20° C. for 1 hour to give rise to a reaction. The reaction mixture was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 0.6 g (yield: 38.2%) of (2-chloro-4-methylpyridin-3-yl)methanol.

$^1$H-NMR [CDCl$_3$/TMS, δ (ppm)]: 8.19 (1H, d), 7.08 (1h, d), 4.85 (2H, s), 2.49 (3H, s)

Reference Example 59

Production of 3-acetyl-4-chloromethyl-2,5-dichlorothiophene 33 ml of titanium tetrachloride (a 2 moles/liter dichloromethane solution, 66.0 mmoles) was dropwise added, at 10° C. with ice-cooling, to a solution of 5.0 g (32;4 mmoles) of 3-acetyl-2,5-dichlorothiophene dissolved in 26 ml (323.0 mmoles) of chloromethyl methyl ether. The mixture was stirred at room temperature for 2 hours to give rise to a reaction. After the completion of the reaction, the reaction action. After the completion of the reaction, the reaction mixture was poured into ice water, followed by extraction with chloroform. The resulting organic layer was washed with sodium bicarbonate, water and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane/ethyl acetate=9/1) to obtain 2.6 g (yield: 39.7%) of 3-acetyl-4-chloromethyl-2,5-dichlorothiophene as yellow crystals.

$^1$H-NMR [CDCl$_3$/TMS, δ (ppm)]: 4.70 (2H, s), 2.56 (3H, s), 2.54 (3H, s), 2.39 (3H, s)

Reference Example 60

Production of 3-bromo-2-bromomethylbenzofuran 2.7 g (15.3 mmoles) of N-bromosuccinimide and 0.4 g (2.7 mmoles) of azobisisobutyronitrile were added to a solution of 2.8 g (13.3 mmoles) of 3-bromo-2-mehtylbenzofuran dissolved in 30 ml of monochlorobenzene. The mixture was stirred at 80° C. for 30 minutes to give rise to a reaction. After confirmation of the disappearance of the raw materials, the reaction mixture was cooled to room temperature. The insolubles were removed by filtration. The filtrate was subjected to vacuum distillation to remove the solvent contained therein. The residue was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein, to obtain 3.0 g (yield: 79.0%) of 3-bromo-2-bromomethylbenzofuran.

Reference Example 61

Production of ethyl 1-difluoromethyl-1H-pyrazole-4-carboxylate 6.0 g (43.5 mmoles) of anhydrous potassium carbonate was added to a solution of 3.0 g (21.4 mmoles) of ethyl 1H-pyrazole-4-carboxylate dissolved in 100 ml of N,N-dimethylformamide. Thereinto was blown chlorodifluoromethane. The resulting mixture was stirred at 130 to 140° C. for 3 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 1.67 g (yield: 41.0%) of ethyl 1-difluoromethyl-1H-pyrazole-4-carboxylate as a colorless transparent oily substance.

$^1$H-NMR [CDCl$_3$/TMS, δ (ppm)]: 8.32 (1H, s), 8.04 (1H, s), 7.20 (1H, t), 4.32 (2H, q), 1.37 (3H, t)

The herbicide of the present invention contains, as the active ingredient, an isoxazoline derivative represented by the genera formula [I] or a salt thereof.

In using the compound of the present invention as a herbicide, the present compound may be used by itself. It can also be used in the form of a powder, a wettable powder, an emulsifiable concentrate, a flowable, fine granules, granules, etc. by mixing with a carrier, a surfactant, a dispersant, a adjuvant, etc. all generally used in formulation.

As the carrier used in formulation, there can be mentioned, for example, solid carriers such as talc, bentonite, clay, kaolin, diatomaceous earth, white carbon, vermiculite, calcium carbonate, slaked lime, siliceous sand, ammonium sulfate, urea and the like; and liquid carriers such as isopropyl alcohol, xylene, cyclohexane, methylnaphthalene and the like.

As the surfactant and the dispersant, there can be mentioned, for example, metal salts of alkylbenzenesulfonic acids, metal salts of dinaphthylmethanedisulfonic acid, salts of alcohol sulfates, alkylarylsulfonic acid salts, ligninsulfonic acid salts, polyoxyethylene glycol ether, polyoxyethylene alkyl aryl ethers, monoalkylates of polyoxyethylene sorbitan and the like. As the adjuvant, there can be mentioned, for example, carboxymethyl cellulose, polyethylene glycol and gum arabic. The present herbicide, when used, is diluted to an appropriate concentration and sprayed or applied directly.

The herbicide of the present invention can be used by spraying on foliage, application to soil, application on water surface, etc. The amount of the active ingredient used is determined appropriately so as to meet the application purpose. The content of the active ingredient is appropriately determined according to the purpose. When the present compound is formulated as a powder or granules, the content is in a range of 0.01% to 10% by weight, preferably 0.05% to 5% by weight. When the present compound is made into an emulsifiable concentrate or a wettable powder, the amount is appropriately determined in a range of 1 to 50% by weight, 5 to 30% by weight. When the present compound is made into a flowable, the amount is appropriately determined in a range of 1 to 40% by weight, preferably 5 to 30% by weight.

The amount of the present herbicide used varies depending upon the kind of the compound used, the target weed, the tendency of weed emergence, the environmental conditions, the type of the herbicide used, etc. When the present herbicide is used per se as in the case of a powder or granules, the amount is appropriately selected in a range of 1 g to 50 kg, preferably 10 g to 10 kg per 1 hectare in terms of the active ingredient. When the present herbicide is used in a liquid form as in the case of an emulsifiable concentrate, a wettable powder or a flowable, the amount is appropriately selected in a range of 0.1 to 50,000 ppm, preferably 10 to 10,000 ppm.

The compound of the present invention may be mixed as necessary with an insecticide, a fungicide, other herbicide, a plant growth-regulating agent, a fertilizer, etc.

Next, formulation from the present compound is described specifically by showing typical examples of formulation. The kinds of compounds and additives and their compounding ratios are not restricted to those shown below and can be varied widely. In the following description, "parts" refer to parts by weight.

<Formulation 1> Wettable Powder 10 parts of a compound (3-0006) were mixed with 0.5 part of polyoxyethylene octylphenyl ether, 0.5 part of a sodium salt of a β-naphthalenesulfonic acid-formalin condensate, 20 parts of diatomaceous earth and 69 parts of clay. The mixture was mixed and pulverlized to obtain a wettable powder.

<Formulation 2> Flowable 20 parts of a coarsely ground compound (3-0006) were dispersed in 69 parts of water. Thereto were added 4 parts of a polyoxyethylene styryl phenylether sulfate, 7 parts of ethylene glycol and 200 ppm, relative to the herbicide produced, of Silicone AF-118N (a product of Asahi Chemical Industry, Co. Ltd.). The resulting mixture was stirred for 30 minutes using a high-speed stirrer and then ground using a wet grinder to obtain a flowable.

<Formulation 3> Emulsion

To 30 parts of a compound (3-0006) were added 60 parts of an equal volume mixture of xylene and isophorone and 10 parts of a surfactant mixture of a polyoxyethylene sorbitan alkylate, a polyoxyethylene alkylaryl polymer and an alkylaryl sulfonate. The resulting mixture was stirred sufficiently to obtain an emulsifiable concentrate.

<Formulation 4> Granules

There were mixed 10 parts of a compound (3-0006), 80 parts of an extender which was a 1:3 mixture of talc and bentonite, 5 parts of white carbon and 5 parts of a surfactant mixture of a polyoxyethylene sorbitan alkylate, a polyoxyethylene alkylaryl polymer and an alkylaryl sulfonate. To the mixture were added 10 parts of water. The resulting mixture was kneaded sufficiently to form a paste. The paste was extruded through the eyes (diameter: 0.7 mm) of a sieve. The extrudate was dried and cut into a length of 0.5 to 1 mm to obtain granules.

Next, Application Examples of the present compound are described to show the effect of the present compound.

Application Example 1

Test for Herbicidal Effect by Paddy Field Soil Treatment

A paddy field soil was filled in a plastic pot of 100 cm$^2$ and subjected to puddling. Then, seeds of *Echinochloa oryzicola* Vasing and *Monochoria vaginalis* (Murm. f.) Presl var. *plantaginea* (Roxb.) *Solms-Laub.* were sowed and water was filled in a depth of 3 cm. Next day, wettable powders produced in accordance with the Formulation 1 were diluted with water and dropped on the water surface. The application amount of each wettable powder was 1,000 g per 1 hectare in terms of the active ingredient. Then, breeding was made in a greenhouse, and the herbicidal effect of each wettable powder was examined at the 21st day from the treatment in accordance with the standard shown in Table 21. The results are shown in Table 22.

TABLE 21

| Index | Herbicidal effect (extent of growth inhibition) or phytotoxicity |
|---|---|
| 5 | A herbicidal effect or phytotoxicity of 90% |
| 4 | A herbicidal effect or phytotoxicity of 70% to less than 90% |
| 3 | A herbicidal effect or phytotoxicity of 50% to less than 70% |
| 2 | A herbicidal effect or phytotoxicity of 30% to less than 50% |
| 1 | A herbicidal effect or phytotoxicity of 10% to less than 30% |
| 0 | A herbicidal effect or phytotoxicity of 0% to less than 10% |

TABLE 22

| Compound No. | Active ingredient (g/ha) | *Echinochloa oryzicola* Vasing | *Monochoria vaginalis* (Burm. F.) Presl var. plantaginea (Roxb.) Solms-Laub. |
|---|---|---|---|
| 1-0001 | 1000 | 5 | 5 |
| 1-0002 | 1000 | 5 | 5 |
| 1-0003 | 1000 | 5 | 5 |
| 1-0004 | 1000 | 5 | 5 |
| 1-0005 | 1000 | 5 | 5 |
| 2-0001 | 1000 | 5 | 5 |
| 2-0003 | 1000 | 5 | 5 |
| 2-0004 | 1000 | 5 | 5 |
| 2-0005 | 1000 | 5 | 5 |
| 2-0006 | 1000 | 5 | 5 |
| 2-0008 | 1000 | 5 | 5 |
| 2-0011 | 1000 | 5 | 5 |
| 2-0012 | 1000 | 5 | 5 |
| 3-0002 | 1000 | 5 | 5 |
| 3-0004 | 1000 | 5 | 5 |
| 3-0009 | 1000 | 5 | 5 |
| 3-0013 | 1000 | 5 | 5 |
| 3-0014 | 1000 | 5 | 5 |
| 3-0015 | 1000 | 5 | 5 |
| 3-0016 | 1000 | 5 | 5 |
| 3-0034 | 1000 | 5 | 5 |
| 3-0035 | 1000 | 5 | 5 |
| 3-0037 | 1000 | 5 | 5 |
| 3-0038 | 1000 | 5 | 5 |
| 3-0039 | 1000 | 5 | 5 |
| 3-0040 | 1000 | 5 | 5 |
| 3-0041 | 1000 | 5 | 5 |
| 3-0044 | 1000 | 5 | 5 |
| 3-0047 | 1000 | 5 | 5 |
| 3-0049 | 1000 | 5 | 5 |
| 3-0051 | 1000 | 5 | 5 |
| 3-0054 | 1000 | 5 | 5 |
| 3-0059 | 1000 | 5 | 5 |
| 3-0060 | 1000 | 5 | 5 |
| 3-0061 | 1000 | 5 | 5 |
| 3-0070 | 1000 | 5 | 5 |
| 3-0072 | 1000 | 5 | 5 |
| 3-0073 | 1000 | 5 | 5 |
| 3-0074 | 1000 | 5 | 5 |
| 3-0081 | 1000 | 5 | 5 |
| 3-0082 | 1000 | 5 | 5 |
| 3-0083 | 1000 | 5 | 5 |
| 3-0084 | 1000 | 5 | 5 |
| 3-0085 | 1000 | 5 | 5 |
| 3-0086 | 1000 | 5 | 5 |
| 3-0087 | 1000 | 5 | 5 |
| 3-0088 | 1000 | 5 | 5 |
| 3-0089 | 1000 | 5 | 5 |
| 3-0090 | 1000 | 5 | 5 |
| 3-0091 | 1000 | 5 | 5 |
| 3-0100 | 1000 | 5 | 5 |
| 3-0101 | 1000 | 5 | 5 |
| 3-0102 | 1000 | 5 | 5 |
| 3-0103 | 1000 | 5 | 5 |
| 3-0114 | 1000 | 5 | 5 |
| 3-0115 | 1000 | 5 | 5 |
| 3-0117 | 1000 | 5 | 5 |
| 3-0118 | 1000 | 5 | 5 |
| 3-0119 | 1000 | 5 | 5 |
| 3-0120 | 1000 | 5 | 5 |
| 3-0121 | 1000 | 5 | 5 |
| 3-0124 | 1000 | 5 | 5 |
| 3-0125 | 1000 | 5 | 5 |
| 3-0126 | 1000 | 5 | 5 |
| 3-0127 | 1000 | 5 | 5 |
| 3-0128 | 1000 | 5 | 5 |
| 3-0129 | 1000 | 5 | 5 |
| 3-0130 | 1000 | 5 | 5 |
| 3-0131 | 1000 | 5 | 5 |
| 3-0134 | 1000 | 5 | 5 |
| 3-0135 | 1000 | 5 | 5 |
| 3-0137 | 1000 | 5 | 5 |
| 3-0139 | 1000 | 5 | 5 |
| 3-0144 | 1000 | 5 | 5 |
| 3-0153 | 1000 | 5 | 5 |
| 3-0156 | 1000 | 5 | 5 |
| 3-0160 | 1000 | 5 | 5 |
| 3-0173 | 1000 | 5 | 5 |
| 3-0174 | 1000 | 5 | 5 |
| 3-0176 | 1000 | 5 | 5 |
| 3-0177 | 1000 | 5 | 5 |
| 3-0178 | 1000 | 5 | 5 |
| 3-0180 | 1000 | 5 | 5 |
| 4-0001 | 1000 | 5 | 5 |
| 4-0002 | 1000 | 5 | 5 |

TABLE 22-continued

| Compound No. | Active ingredient (g/ha) | Echinochloa oryzicola Vasing | Monochoria vaginalis (Burm. F.) Presl var. plantaginea (Roxb.) Solms-Laub. |
|---|---|---|---|
| 4-0005 | 1000 | 5 | 5 |
| 4-0007 | 1000 | 5 | 5 |
| 4-0008 | 1000 | 5 | 5 |
| 5-0001 | 1000 | 5 | 5 |
| 5-0002 | 1000 | 5 | 5 |
| 5-0003 | 1000 | 5 | 5 |
| 5-0005 | 1000 | 5 | 5 |
| 5-0006 | 1000 | 5 | 5 |
| 5-0007 | 1000 | 5 | 5 |
| 6-0003 | 1000 | 5 | 5 |
| 6-0004 | 1000 | 5 | 5 |
| 7-0004 | 1000 | 5 | 5 |
| 7-0006 | 1000 | 5 | 5 |
| 7-0008 | 1000 | 5 | 5 |
| 7-0009 | 1000 | 5 | 5 |
| 8-0001 | 1000 | 5 | 5 |
| 8-0012 | 1000 | 5 | 5 |
| 9-0001 | 1000 | 5 | 5 |
| 9-0003 | 1000 | 5 | 5 |
| 9-0005 | 1000 | 5 | 5 |
| 9-0006 | 1000 | 5 | 5 |
| 9-0008 | 1000 | 5 | 5 |
| 10-0002 | 1000 | 5 | 4 |
| 10-0003 | 1000 | 5 | 5 |
| 10-0004 | 1000 | 5 | 5 |
| 10-0005 | 1000 | 5 | 5 |
| 10-0006 | 1000 | 5 | 5 |
| 10-0008 | 1000 | 5 | 5 |
| 10-0009 | 1000 | 5 | 5 |
| 10-0011 | 1000 | 5 | 5 |
| 10-0012 | 1000 | 5 | 5 |
| 10-0013 | 1000 | 5 | 5 |
| 10-0014 | 1000 | 5 | 5 |
| 10-0015 | 1000 | 5 | 5 |
| 10-0016 | 1000 | 5 | 5 |
| 10-0017 | 1000 | 5 | 5 |
| 10-0018 | 1000 | 5 | 5 |

Application Example 2

Test for Herbicidal Effect by Upland Field Soil Treatment

An upland field soil was filled in a plastic pot of 80 cm². Seeds of *Echinochloa crus-galli* (L.) Beauv. var. *crusgalli* and *Setaria viridis* (L.) Beauv. were sowed, followed by covering with the same soil. Wettable powders produced in accordance with the Formulation 1 were diluted with water and sprayed uniformly on the soil surface using a small sprayer, in an amount of 1,000 liters per 1 hectare so that the amount of each active ingredient became 1,000 g per 1 hectare. Then, breeding was made in a greenhouse, and the herbicidal effect of each wettable powder was examined at the 21st day from the treatment in accordance with the standard shown in Table 21. The results are shown in Table 23.

TABLE 23

| Compound No. | Active ingredient (g/ha) | Echinochloa curs-galli (L.) Beauv. Var. crus-galli | Setaria viridis (L.) Beauv. |
|---|---|---|---|
| 1-0001 | 1000 | 5 | 5 |
| 1-0002 | 1000 | 5 | 5 |
| 1-0003 | 1000 | 5 | 5 |
| 1-0004 | 1000 | 5 | 5 |
| 1-0005 | 1000 | 5 | 5 |
| 1-0006 | 1000 | 5 | 4 |
| 2-0001 | 1000 | 5 | 5 |
| 2-0003 | 1000 | 5 | 5 |
| 2-0004 | 1000 | 5 | 5 |
| 2-0005 | 1000 | 5 | 5 |
| 2-0006 | 1000 | 5 | 4 |
| 2-0007 | 1000 | 4 | 4 |
| 2-0008 | 1000 | 5 | 5 |
| 2-0011 | 1000 | 5 | 4 |
| 2-0012 | 1000 | 5 | 5 |
| 3-0002 | 1000 | 5 | 5 |
| 3-0004 | 1000 | 5 | 5 |
| 3-0006 | 1000 | 4 | 4 |
| 3-0008 | 1000 | 5 | 5 |
| 3-0009 | 1000 | 5 | 5 |
| 3-0012 | 1000 | 5 | 5 |
| 3-0013 | 1000 | 5 | 5 |
| 3-0015 | 1000 | 5 | 5 |
| 3-0016 | 1000 | 5 | 5 |
| 3-0017 | 1000 | 5 | 5 |
| 3-0018 | 1000 | 5 | 5 |
| 3-0019 | 1000 | 5 | 5 |
| 3-0020 | 1000 | 5 | 5 |
| 3-0034 | 1000 | 5 | 5 |
| 3-0035 | 1000 | 5 | 5 |
| 3-0036 | 1000 | 5 | 5 |
| 3-0037 | 1000 | 5 | 5 |
| 3-0038 | 1000 | 5 | 5 |
| 3-0039 | 1000 | 5 | 5 |
| 3-0040 | 1000 | 5 | 5 |
| 3-0041 | 1000 | 5 | 5 |
| 3-0043 | 1000 | 5 | 5 |
| 3-0044 | 1000 | 5 | 5 |
| 3-0047 | 1000 | 5 | 5 |
| 3-0048 | 1000 | 5 | 5 |
| 3-0049 | 1000 | 5 | 5 |
| 3-0050 | 1000 | 5 | 5 |
| 3-0053 | 1000 | 5 | 5 |
| 3-0054 | 1000 | 5 | 5 |
| 3-0054 | 1000 | 5 | 5 |
| 3-0056 | 1000 | 5 | 5 |
| 3-0059 | 1000 | 5 | 5 |
| 3-0060 | 1000 | 5 | 5 |
| 3-0063 | 1000 | 5 | 5 |
| 3-0070 | 1000 | 4 | 4 |
| 3-0072 | 1000 | 5 | 5 |
| 3-0073 | 1000 | 5 | 5 |
| 3-0074 | 1000 | 5 | 5 |
| 3-0081 | 1000 | 5 | 5 |
| 3-0082 | 1000 | 5 | 5 |
| 3-0083 | 1000 | 5 | 5 |
| 3-0084 | 1000 | 5 | 5 |
| 3-0085 | 1000 | 5 | 5 |
| 3-0086 | 1000 | 5 | 5 |
| 3-0087 | 1000 | 5 | 5 |
| 3-0088 | 1000 | 5 | 4 |
| 3-0091 | 1000 | 5 | 5 |
| 3-0114 | 1000 | 5 | 5 |
| 3-0115 | 1000 | 5 | 5 |
| 3-0117 | 1000 | 5 | 5 |
| 3-0118 | 1000 | 5 | 5 |
| 3-0119 | 1000 | 5 | 5 |
| 3-0120 | 1000 | 5 | 5 |
| 3-0121 | 1000 | 5 | 5 |
| 3-0124 | 1000 | 5 | 5 |
| 3-0125 | 1000 | 5 | 5 |
| 3-0126 | 1000 | 5 | 5 |
| 3-0127 | 1000 | 5 | 5 |
| 3-0128 | 1000 | 5 | 5 |
| 3-0129 | 1000 | 5 | 5 |
| 3-0130 | 1000 | 5 | 5 |
| 3-0131 | 1000 | 5 | 5 |

TABLE 23-continued

| Compound No. | Active ingredient (g/ha) | Echinochloa curs-galli (L.) Beauv. Var. crus-galli | Setaria viridis (L.) Beauv. |
|---|---|---|---|
| 3-0134 | 1000 | 5 | 5 |
| 3-0135 | 1000 | 5 | 5 |
| 3-0136 | 1000 | 5 | 5 |
| 3-0137 | 1000 | 5 | 5 |
| 3-0138 | 1000 | 4 | 5 |
| 3-0139 | 1000 | 5 | 5 |
| 3-0142 | 1000 | 5 | 5 |
| 3-0143 | 1000 | 5 | 5 |
| 3-0144 | 1000 | 5 | 5 |
| 3-0153 | 1000 | 5 | 5 |
| 3-0156 | 1000 | 5 | 5 |
| 3-0173 | 1000 | 5 | 5 |
| 3-0174 | 1000 | 5 | 5 |
| 3-0180 | 1000 | 5 | 5 |
| 4-0001 | 1000 | 5 | 5 |
| 4-0001 | 1000 | 4 | 3 |
| 4-0002 | 1000 | 5 | 5 |
| 4-0005 | 1000 | 5 | 5 |
| 4-0006 | 1000 | 5 | 5 |
| 4-0007 | 1000 | 5 | 5 |
| 4-0008 | 1000 | 5 | 5 |
| 5-0001 | 1000 | 5 | 5 |
| 5-0002 | 1000 | 5 | 5 |
| 5-0003 | 1000 | 5 | 5 |
| 5-0005 | 1000 | 5 | 4 |
| 5-0006 | 1000 | 5 | 5 |
| 5-0007 | 1000 | 5 | 5 |
| 6-0001 | 1000 | 5 | 5 |
| 6-0003 | 1000 | 5 | 5 |
| 6-0004 | 1000 | 5 | 5 |
| 7-0002 | 1000 | 5 | 5 |
| 7-0004 | 1000 | 5 | 4 |
| 7-0006 | 1000 | 5 | 5 |
| 7-0007 | 1000 | 5 | 4 |
| 7-0008 | 1000 | 5 | 5 |
| 7-0009 | 1000 | 5 | 5 |
| 8-0001 | 1000 | 5 | 5 |
| 8-0004 | 1000 | 5 | 5 |
| 8-0005 | 1000 | 5 | 4 |
| 8-0007 | 1000 | 5 | 5 |
| 9-0001 | 1000 | 5 | 5 |
| 9-0005 | 1000 | 5 | 4 |
| 9-0006 | 1000 | 5 | 4 |
| 9-0007 | 1000 | 4 | 4 |
| 9-0008 | 1000 | 5 | 5 |
| 10-0003 | 1000 | 5 | 5 |
| 10-0004 | 1000 | 5 | 5 |
| 10-0005 | 1000 | 5 | 5 |
| 10-0006 | 1000 | 5 | 4 |
| 10-0009 | 1000 | 5 | 5 |
| 10-0012 | 1000 | 5 | 4 |
| 10-0013 | 1000 | 5 | 5 |
| 10-0014 | 1000 | 5 | 5 |
| 10-0015 | 1000 | 5 | 5 |
| 10-0016 | 1000 | 5 | 4 |
| 10-0017 | 1000 | 5 | 5 |
| 10-0018 | 1000 | 5 | 5 |

Application Example 3

Test for Herbicidal Effect by Upland Foliage Treatment

A sand was filled in a plastic pot of 80 cm². Seeds of *Echinochloa crus-galli* (L.) *Beauv.* var. *crus-galli* and *Setaria viridis* (L.) *Beauv.* were sowed. Breeding was made in a greenhouse for 2 weeks. Wettable powders produced in accordance with the Formulation 1 were diluted with water and sprayed on the whole foliage of plants from above the plants using a small sprayer in an amount of 1,000 liters per 1 hectare so that the amount of each active ingredient became 1,000 g per 1 hectare. Then, breeding was made in the greenhouse, and the herbicidal effect of each wettable powder was examined at the 14th day from the treatment in accordance with the standard shown in Table 21. The results are shown in Table 24.

TABLE 24

| Compound No. | Active ingredient (g/ha) | Echinochloa curs-galli (L.) Beauv. Var. crus-galli | Setaria viridis (L.) Beauv. |
|---|---|---|---|
| 1-0001 | 1000 | 5 | 4 |
| 1-0004 | 1000 | 5 | 4 |
| 2-0001 | 1000 | 5 | 4 |
| 2-0003 | 1000 | 5 | 4 |
| 2-0004 | 1000 | 5 | 4 |
| 2-0008 | 1000 | 5 | 5 |
| 2-0011 | 1000 | 5 | 4 |
| 3-0008 | 1000 | 4 | 4 |
| 3-0010 | 1000 | 5 | 4 |
| 3-0011 | 1000 | 5 | 4 |
| 3-0013 | 1000 | 5 | 5 |
| 3-0015 | 1000 | 5 | 4 |
| 3-0035 | 1000 | 4 | 4 |
| 3-0036 | 1000 | 4 | 4 |
| 3-0037 | 1000 | 5 | 4 |
| 3-0038 | 1000 | 5 | 5 |
| 3-0039 | 1000 | 5 | 5 |
| 3-0044 | 1000 | 5 | 4 |
| 3-0049 | 1000 | 4 | 4 |
| 3-0073 | 1000 | 5 | 4 |
| 3-0074 | 1000 | 5 | 4 |
| 3-0076 | 1000 | 5 | 4 |
| 3-0077 | 1000 | 5 | 4 |
| 3-0081 | 1000 | 4 | 4 |
| 3-0082 | 1000 | 4 | 4 |
| 3-0083 | 1000 | 4 | 4 |
| 3-0084 | 1000 | 4 | 4 |
| 3-0085 | 1000 | 4 | 4 |
| 3-0086 | 1000 | 4 | 4 |
| 3-0092 | 1000 | 4 | 4 |
| 3-0104 | 1000 | 5 | 4 |
| 3-0105 | 1000 | 5 | 4 |
| 3-0106 | 1000 | 5 | 4 |
| 3-0107 | 1000 | 5 | 5 |
| 3-0115 | 1000 | 5 | 4 |
| 3-0118 | 1000 | 5 | 4 |
| 3-0119 | 1000 | 5 | 4 |
| 3-0120 | 1000 | 5 | 5 |
| 3-0144 | 1000 | 5 | 5 |
| 4-0002 | 1000 | 5 | 4 |
| 4-0005 | 1000 | 5 | 4 |
| 5-0001 | 1000 | 5 | 4 |
| 5-0002 | 1000 | 5 | 5 |
| 5-0003 | 1000 | 5 | 4 |
| 5-0007 | 1000 | 5 | 5 |
| 6-0004 | 1000 | 5 | 4 |
| 7-0008 | 1000 | 5 | 5 |
| 7-0009 | 1000 | 4 | 4 |
| 8-0001 | 1000 | 5 | 4 |
| 9-0001 | 1000 | 4 | 4 |
| 9-0005 | 1000 | 4 | 4 |
| 9-0008 | 1000 | 4 | 4 |

INDUSTRIAL APPLICABILITY

The compound represented by the general formula [I] according to the present invention shows an excellent herbicidal effect over a wide period from before germination to growth, to various weeds causing problems in upland fields, for example, broadleaf weeds [e.g. *Polygonum lapathifolium L.* subsp. *nodosum* (Pers.) *Kitam.*, *Amaranthus viridis L.*, *Chenopodium album L.*, *Stellaria media* (L.) *Villars*, *Abutilon theophrasti Medik.*, *Sida spinosa*, *Sesbaria exal-* tata, ipomoea spp. and *Xanthium strumarium* L.], perennial or annual cyperaceous weeds [e.g. *Cyperus rotundus* L., *Cyperus esculentus, Kyllinga brevifolia* Rottb. subsp. *leiolepis (Fraxch.* et *Savat.) T. Koyama, Cyperus microiria* Steud., and *Cyperus iria* L.], and Gramineae weeds [e.g. *Echinochloa crus-galli* (L.) *Beauv.* var. *crus-galli, Digitaria ciliaris (Retz.) Koeler, Setaria viridis* (L.) *Beauv., Poa annua* L., *Sorghum halepense* (L.) *Pers., Alopecurus aequalis Sobol.* var. *amurensis (Komar.) Ohwi,* and *Avena fatua* L.]. Further, the present compound shows a herbicidal effect also to weeds emerging in paddy fields, i.e. annual weeds [e.g. *Echinochloa oryzicola Vasing., Cyperus difformis L., Mohochoria vaginalis (Burm. f.) Presl.* var. *plantaginea (Roxb.) Solms-Laub.,* and *Lindernia procumbens*] and perennial weeds [e.g. *Sagittaria trifolia L., Sagittaria pygmaea Miq., Cyperus serotinus Rottb., Eleocharis kuroguwai Ohwi,* and *Scirpus juncoides Roxb.* subsp. *hotarui (Ohwi) T. Koyama, Alisma canaliculatum*].

The herbicide of the present invention has high safety to crops, particularly to rice, wheat, barley, corn, grain sorghum, soybean, cotton, sugar beat, etc.

What is claimed is:

1. An isoxazoline derivative represented by the following general formula [I] or a pharmaceutically acceptable salt thereof:

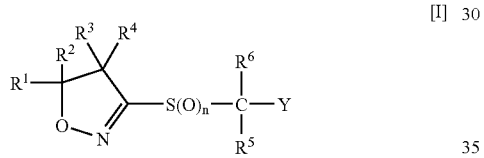

wherein $R^1$ and $R^2$ may be the same or different and are each a hydrogen atom, a C1 to C10 alkyl group, a C3 to C8 cycloalkyl group or a C3 to C8 cycloalkyl C1 to C3 alkyl group; or $R^1$ and $R^2$ may be bonded to each other to form a C3 to C7 spiro ring together with the carbon atoms to which they bond;

$R^3$ and $R^4$ may be the same or different and are each a hydrogen atom, a C1 to C10 alkyl group or a C3 to C8 cycloalkyl group; or $R^3$ and $R^4$ may be bonded to each other to form a C3 to C7 spiro ring together with the carbon atoms to which they bond; or $R^1$, $R^2$, $R^3$ and $R^4$ may form a 5- to 8-membered ring together with the carbon atoms to which they bond;

$R^5$ and $R^6$ may be the same or different and are each a hydrogen atom or a C1 to C10 alkyl group;

Y is a 5- to 6-membered aromatic heterocyclic group or condensed aromatic heterocyclic group having one or more hetero atoms selected from a nitrogen atom, an oxygen atom and a sulfur atom; the heterocyclic group may be substituted with 0 to 6 same or different groups selected from the following substituent group α; when the heterocyclic group is substituted at the two adjacent positions with two alkyl groups, two alkoxy groups, an alkyl group and an alkoxy group, an alkyl group and an alkylthio group, an alkyl group and an alkylsulfonyl group, an alkyl group and a monoalkylamino group, or an alkyl group and a dialkylamino group, all selected from the substituent group α, the two groups may form, together with the atoms to which they bond, a 5- to 8-membered ring which may be substituted with 1 to 4 halogen atoms; the hetero atom of the heterocyclic group, when it is a nitrogen atom, may be oxidized to become N-oxide;

wherein n is an integer of 0 to 2;

wherein Substituent group α is at least one member selected from the group consisting of:

hydroxyl group; thiol group; halogen atoms; C1 to C10 alkyl groups; C1 to C10 alkyl groups each mono-substituted with a group selected from the following substituent group β, C1 to C4 haloalkyl groups; C3 to C8 cycloalkyl groups; C1 to C10 alkoxy groups; C1 to C10 alkoxy groups each mono-substituted with a group selected from the following substituent group γ; C1 to C4 haloalkoxy groups; C3 to C8 cycloalkyloxy groups; C3 to C8 cycloalkyl C1 to C3 alkyloxy groups; C1 to C10 alkylthio groups; C1 to C10 alkylthio groups each mono-substituted with a group selected from the substituent group γ; C1 to C4 haloalkylthio groups; C2 to C6 alkenyl groups; C2 to C6 alkenyloxy groups; C2 to C6 alkynyl groups; C2 to C6 alkynyloxy groups; C1 to C10 alkylsulfinyl groups; C1 to C10 alkylsulfinyl groups each mono-substituted with a group selected from the substituent group γ; C1 to C10 alkylsulfonyl groups; C1 to C10 alkylsulfonyl groups each mono-substituted with a group selected from the substituent group γ; C1 to C4 haloalkylsulfinyl groups; C1 to C10 alkylsulfonyloxy groups each mono-substituted with a group selected from the substituent group γ; C1 to C4 haloalkylsulfonyl groups; C1 to C10 alkylsulfonyloxy groups; C1 to C4 haloalkylsulfonyloxy groups; optionally substituted phenyl group; optionally substituted phenoxy group; optionally substituted phenylthio group; optionally substituted aromatic heterocyclic groups; optionally substituted aromatic heterocyclic oxy groups; optionally substituted aromatic heterocyclic thio groups; optionally substituted phenylsulfinyl groups; optionally substituted phenylsulfonyl groups; optionally substituted aromatic heterocyclic sulfonyl groups; optionally substituted phenylsulfonyloxy groups; acyl groups; C1 to C4 haloalkylcarbonyl groups; optionally substituted benzylcarbonyl group; optionally substituted benzoyl group; carboxyl group; C1 to C10 alkoxycarbonyl groups; optionally substituted benzyloxycarbonyl group; optionally substituted phenoxycarbonyl group; cyano group; carbamoyl group (its nitrogen atom may be substituted with same or different groups selected from C1 to C10 alkyl groups and optionally substituted phenyl group); C1 to C6 acyloxy groups; C1 to C4 haloalkylcarbonyloxy groups; optionally substituted benzylcarbonyloxy group; optionally substituted benzoyloxy group; nitro group; and amino group (its nitrogen atom may be substituted with same or different groups selected from C1 to C10 alkyl groups, optionally substituted phenyl group, C1 to C6 acyl groups, C1 to C4 haloalkylcarbonyl groups, optionally substituted benzylcarbonyl group, optionally substituted benzoyl group, C1 to C10 alkylsulfonyl group, C1 to C4 haloalkylsulfonyl groups, optionally substituted benzylsulfonyl group, and optionally substituted phenylsulfonyl group);

wherein Substituent group β is at least one member selected from the group consisting of:

hydroxyl group; C3 to C8 cycloalkyl groups (which may be substituted with halogen atom or alkyl group); C1 to C10 alkoxy groups; C1 to C10 alkylthio groups; C1 to C10 alkylsulfonyl groups; C1 to C10 alkoxycarbonyl groups; C2 to C6 haloalkenyl groups; amino group (its nitrogen atom may be substituted with same or different groups selected from C1 to C10 alkyl groups, C1 to C6 acyl groups; C1 to C4 haloalkylcarbonyl groups, C1 to C10 alkylsulfonyl groups and C1 to C4 haloalkylsulfonyl groups); carbamoyl group (its nitrogen atom may be substituted with same or different C1 to C10 alkyl groups); C1 to C6 acyl groups; C1 to C4 haloalkylcarbonyl groups; C1 to C10 alkoxyimino groups; cyano group; optionally substituted phenyl group; and optionally substituted phenoxy group; and wherein Substituent group γ is at least one member selected from the group consisting of:

C1 to C10 alkoxycarbonyl groups; optionally substituted phenyl group; optionally substituted aromatic heterocyclic groups; cyano group; and carbamoyl group (its nitrogen atom may be substituted with same or different C1 to C10 alkyl groups).

2. An isoxazoline derivative according to claim 1, wherein the substituent group α consists of hydroxyl group; halogen atoms; C1 to C10 alkyl groups; C1 to C10 alkyl groups each mono-substituted with a group selected from the substituent group β, C1 to C4 haloalkyl groups; C3 to C8 cycloalkyl groups; C1 to C10 alkoxy groups; C1 to C10 alkoxy groups each mono-substituted with a group selected from the substituent group γ; C1 to C4 haloalkoxy groups; C3 to C8 cycloalkyloxy groups; C3 to C8 cycloalkyl C1 to C3 alkyloxy groups; C1 to C10 alkylthio groups; C1 to C10 alkylthio groups each mono-substituted with a group selected from the substituent group γ; C1 to C4 haloalkylthio groups; C2 to C6 alkenyl groups; C2 to C6 alkenyloxy groups; C2 to C6 alkynyl groups; C2 to C6 alkynyloxy groups; C1 to C10 alkylsulfonyl groups; C1 to C4 haloalkylsulfonyl groups; optionally substituted phenyl group; optionally substituted phenoxy group; optionally substituted phenylthio group; optionally substituted aromatic heterocyclic groups; optionally substituted aromatic heterocyclic oxy groups; optionally substituted aromatic heterocyclic thio groups; optionally substituted phenylsulfonyl groups; optionally substituted aromatic heterocyclic sulfonyl groups; C1 to C6 acyl groups; C1 to C4 haloalkylcarbonyl groups; optionally substituted benzylcarbonyl group; optionally substituted benzoyl group; carboxyl group; C1 to C10 alkoxycarbonyl groups; cyano group; carbamoyl group (its nitrogen atom may be substituted with same or different groups selected from C1 to C10 alkyl groups and optionally substituted phenyl group); nitro group; and amino group (its nitrogen atom may be substituted with same or different groups selected from C1 to C10 alkyl groups, optionally substituted phenyl group, C1 to C6 acyl groups, C1 to C4 haloalkylcarbonyl groups, optionally substituted benzylcarbonyl group, optionally substituted benzoyl group, C1 to C10 alkylsulfonyl groups, C1 to C4 haloalkylsulfonyl groups, optionally substituted benzylsulfonyl group, and optionally substituted phenylsulfonyl group); when the heterocyclic group is substituted at the two adjacent positions with two alkyl groups, two alkoxy groups, an alkyl group and an alkoxy group, an alkyl group and an alkylthio group, an alkyl group and an alkylsulfonyl group, an alkyl group and a monoalkylamino group, or an alkyl group and a dialkylamino group, all selected from the substituent group α, the two groups may form, together with the atoms to which they bond, a 5- to 8-membered ring which may be substituted with 1 to 4 halogen atoms.

3. An isoxazoline derivative according to claim 2, wherein the substituent group α consists of halogen atoms; C1 to C10 alkyl groups; C1 to C4 haloalkyl groups; C1 to C10 alkoxy C1 to C3 alkyl groups; C3 to C8 cycloalkyl groups (which may be substituted with halogen atom or alkyl group); C1 to C10 alkoxy groups; C1 to C4 haloalkoxy groups; C3 to C8 cycloalkyl C1 to C3 alkyloxy groups; optionally substituted phenoxy group; C1 to C10 alkylthio groups; C1 to C10 alkylsulfonyl groups; acyl groups; C1 to C4 haloalkylcarbonyl groups; C1 to C10 alkoxycarbonyl groups; cyano group and carbamoyl group (its nitrogen atom may be substituted with same or different C1 to C10 alkyl groups).

4. An isoxazoline derivative according to claim 1, wherein $R^1$ and $R^2$ are the same or different and are each a methyl group or an ethyl group; and $R^3$, $R^4$, $R^5$ and $R^6$ are each a hydrogen atom.

5. An isoxazoline derivative according to claim 1, wherein Y is a 5- or 6-membered aromatic heterocyclic group having a hetero atom selected from a nitrogen atom, an oxygen atom and a sulfur atom.

6. An isoxazoline derivative according to claim 5, wherein Y is a thienyl group, a pyrazolyl group, an isoxazolyl group, an isothiazolyl group, a pyridyl group or a pyrimidinyl group.

7. An isoxazoline derivative according to claim 6, wherein Y is a thiophen-3-yl group, a pyrazol-4-yl group, a pyrazol-5-yl group, an isoxazol-4-yl group, an isothiazol-4-yl group, a pyridyn-3-yl group or a pyrimidin-5-yl group.

8. An isoxazoline derivative according to claim 7, wherein Y is a thiophen-3-yl group and the thiophene ring is substituted with the substituent group α at the 2- and 4-positions.

9. An isoxazoline derivative according to claim 7, wherein Y is a pyrazol-4-yl group and the pyrazole ring is substituted at the 3- and 5-positions with the substituent group α and at the 1-position with a hydrogen atom, a C1 to C10 alkyl group, a C1 to C10 alkyl group mono-substituted with a group selected from the substituent group β, a C1 to C4 haloalkyl group, a C3 to C8 cycloalkyl group, a C2 to C6 alkenyl group, a C2 to C6 alkynyl group, a C1 to C10 alkylsulfinyl group, a C1 to C10 alkylsulfonyl group, a C1 to C10 alkylsulfonyl group mono-substituted with a group selected from the substituent group γ, a C1 to C4 haloalkylsulfonyl group, an optionally substituted phenyl group, an optionally substituted aromatic heterocyclic group, an optionally substituted phenylsulfonyl group, an optionally substituted aromatic heterocyclic sulfonyl group, an acyl group, a C1 to C4 haloalkylcarbonyl group, an optionally substituted benzylcarbonyl group, an optionally substituted benzoyl group, a C1 to C10 alkoxycarbonyl group, an optionally substituted benzyloxycarbonyl group, an optionally substituted phenoxycarbonyl group, a carbamoyl group (its nitrogen atom may be substituted with same or different groups selected from C1 to C10 alkyl groups and optionally substituted phenyl group), an amino group or an amino group having its nitrogen atom substituted with same or different groups selected from C1 to C10 alkyl groups, optionally substituted phenyl group, acyl groups, C1 to C4 haloalkylcarbonyl groups, optionally substituted benzylcarbonyl group, optionally substituted benzoyl group, C1 to C10 alkylsulfonyl groups, C1 to C4 haloalkylsulfonyl groups, optionally substituted benzylsulfonyl group and optionally substituted phenylsulfonyl group.

10. An isoxazoline derivative according to claim 7, wherein Y is a pyrazol-5-yl group and the pyrazole ring is substituted at the 4-position with the substituent group α and at the 1-position with a hydrogen atom, a C1 to C10 alkyl group, a C1 to C10 alkyl group mono-substituted with a group selected from the substituent group β, a C1 to C4 haloalkyl group, a C3 to C8 cycloalkyl group, a C2 to C6 alkenyl group, a C2 to C6 alkynyl group, a C1 to C10 alkylsulfinyl group, a C1 to C10 alkylsulfonyl group, a C1 to C10 alkylsulfonyl group mono-substituted with a group selected from the substituent group γ, a C1 to C4 haloalkylsulfonyl group, an optionally substituted phenyl group, an optionally substituted aromatic heterocyclic group, an optionally substituted phenylsulfonyl group, an optionally substituted aromatic heterocyclic sulfonyl group, an acyl group, a C1 to C4 haloalkylcarbonyl group, an optionally substituted benzylcarbonyl group, an optionally substituted benzoyl group, a C1 to C10 alkoxycarbonyl group, an optionally substituted benzyloxycarbonyl group, an optionally substituted phenoxycarbonyl group, a carbamoyl group (its nitrogen atom may be substituted with same or different groups selected from C1 to C10 alkyl groups and optionally substituted phenyl group), or an amino group (its nitrogen atom may be substituted with same or different groups selected from C1 to C10 alkyl groups, optionally substituted phenyl group, acyl groups, C1 to C4 haloalkylcarbonyl groups, optionally substituted benzylcarbonyl group, optionally substituted benzoyl group, C1 to C10 alkylsulfonyl groups, C1 to C4 haloalkylsulfonyl groups, optionally substituted benzylsulfonyl group and optionally substituted phenylsulfonyl group).

11. An isoxazoline derivative according to claim 7, wherein Y is an isoxazol-4-yl group and the isoxazole ring is substituted with the substituent group α at the 3- and 5-positions.

12. An isoxazoline derivative according to claim 7, wherein Y is an isothiazol-4-yl group and the isothiazole ring is substituted with the substituent group α at the 3- and 5-positions.

13. An isoxazoline derivative according to claim 7, wherein Y is a pyridin-3-yl group and the pyridine ring is substituted with the substituent group α at the 2- and 4-positions.

14. An isoxazoline derivative according to claim 7, wherein Y is a pyrimidin-5-yl group and the pyrimidine ring is substituted with the substituent group α at the 4- and 6-positions.

15. An isoxazoline derivative according to claim 1, wherein n is an integer of 2.

16. An isoxazoline derivative according to claim 1, wherein n is an integer of 1.

17. An isoxazoline derivative according to claim 1, wherein n is an integer of 0.

18. A herbicide containing, as the active ingredient, an isoxazoline derivative set forth in claim 1 or a pharmaceutically acceptable salt thereof.

* * * * *

UNITED STATES PATENT AND TRADEMARK OFFICE
CERTIFICATE OF CORRECTION

PATENT NO. : 7,238,689 B2 Page 1 of 1
APPLICATION NO. : 10/250937
DATED : July 3, 2007
INVENTOR(S) : Nakatani et al.

It is certified that error appears in the above-identified patent and that said Letters Patent is hereby corrected as shown below:

On the title page change the name of the "Assignee" item [73] to:

"Japan and Kumiai Chemical Industry Co., Ltd." should read -- Kumiai Chemical Industry Co., Ltd. --.

Signed and Sealed this

Nineteenth Day of February, 2008

JON W. DUDAS
*Director of the United States Patent and Trademark Office*